Figure 1A:
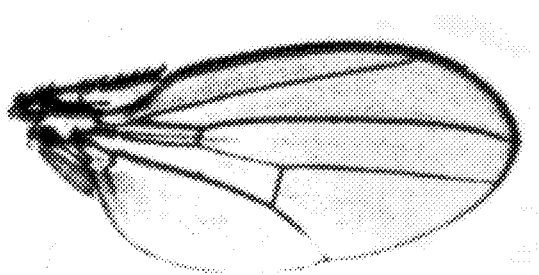
Figure 1B:
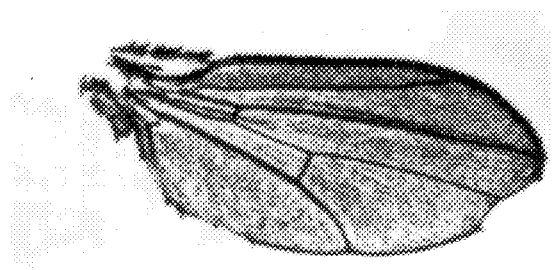
Figure 1C:
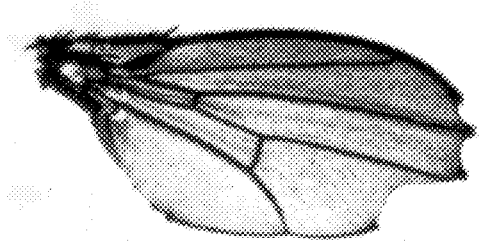

United States Patent [19]

Ish-Horowicz et al.

[11] Patent Number: 5,869,282

[45] Date of Patent: Feb. 9, 1999

[54] NUCLEOTIDE AND PROTEIN SEQUENCES OF THE SERRATE GENE AND METHODS BASED THEREON

[75] Inventors: David Ish-Horowicz; Domingos Manuel Pinto Henrique; Julian Hart Lewis; Anna Mary Myat, all of Oxford, England; Robert J. Fleming, Rochester, N.Y.; Spyridon Artavanis-Tsakonas; Robert S. Mann, both of Hamden, Conn.; Grace E. Gray, New Haven, Conn.

[73] Assignees: Imperial Cancer Research Technology, Ltd., London, England; Yale University, Haven, Conn.

[21] Appl. No.: 400,159

[22] Filed: Mar. 7, 1995

Related U.S. Application Data

[63] Continuation-in-part of Ser. No. 255,102, Jun. 7, 1994, abandoned, which is a continuation of Ser. No. 121,979, Sep. 14, 1993, abandoned, which is a continuation of Ser. No. 808,458, Dec. 11, 1991, abandoned.

[51] Int. Cl.$^6$ .......................... C12P 21/00; C12N 15/00; C07H 17/00; C07K 14/00
[52] U.S. Cl. ..................... 435/69.1; 435/325; 435/252.3; 435/320.1; 536/23.1; 536/24.3; 530/300; 530/350
[58] Field of Search ............................... 536/23.1, 24.3; 435/69.1, 320.1, 240.1, 252.3, 325; 530/300, 350

[56] References Cited

U.S. PATENT DOCUMENTS 4,981,784  1/1991  Evans et al. ................................ 435/6

FOREIGN PATENT DOCUMENTS

WO 97/45143  12/1997  WIPO .

OTHER PUBLICATIONS

Thomas et al 1991 Development 111:749–761.
Wosnick et al 1987 Gene 60:115–127.
Coffman et al 1990. Science 249:1438–1441.
Krapp et al 1989 Mol. Biochem. Parasit. 32:73–84.
Thomas et al., 1991, "The Drosophila gene serrate encodes an EGF–like transmembrane protein with a complex expression pattern in embryos and wing discs," Development 111(3):749–761.
Anson et al., 1984, "The gene structure of human anti–haemophilic factor IX," EMBO J. 3:1053–1060.
Appella et al., 1987, "The receptor–binding sequence of Urokinase," J. Biol. Chem. 242:4437–4440.
Artavanis–Tsakonas, 1988, "The molecular biology of the Notch locus and the fine tuning of differentiation in Drosophila," Trends Genet. 4:95–100.
Artavanis–Tsakonas et al., 1991, "The Notch locus and the cell biology of neuroblast segregation," Ann. Rev. Cell Biol. 7:427–452.

Beachy et al., 1985, "Segmental distribution of bithorax complex proteins during Drosophila development," Nature 313:545–550.
Belt, 1971, Research notes, Drosophila Inf. Serv. 46:116.
Benton and Davis, 1977, Screening lambda gt10 recombinant clones by hybridizing to single plaques in situ, Science 196:180–182.
Cagan and Ready, 1989, "Notch is required for successive cell decisions in the developing Drosophila retina," Genes Dev. 3:1099–1112.
Campos–Ortega and Hartenstein, 1985, "The embryonic development of Drosophila melanogaster," Springer–Verlag, Berlin, pp. 1–8.
Carpenter, 1987, "Receptors for epidermal growth factor and other polypeptide mitogens," Annu. Rev. Biochem. 56:881–914.
Cavener, 1987, Comparison of the consensus sequence flanking translational start sites in Drosophila and vertebrates, Nucleic Acids Res. 15:1353–1361.
Clifford and Schüpbach, 1989, "Coordinately and differentially mutable activities of torpedo, the *Drosophila melanogaster* homolog of the vertebrate EGF receptor gene," Genetics 123:771–787.
de la Concha et al., 1988, "Functional interactions of neurogenic genes in *Drosophila melanogaster*," Genetics 118:499–508.
Doe and Goodman, 1985, "Early events in insect neurogenesis. II. The role of cell interactions and cell lineage in the determination of neuronal precursor cells," Dev. Biol. 111:206–219.
Engel, 1989, "EGF–like domains in extracellar matrix proteins: Localized signals for growth and differentiation?" FEBS 251:1–7.
Fehon et al., 1990, Molecular interactions between the protein products of the neurogenic loci Notch and Delta, two EGF–homologous genes in Drosophila, Cell 61:523–534.

(List continued on next page.)

*Primary Examiner*—Karen Cochrane Carlson
*Attorney, Agent, or Firm*—Pennie & Edmonds LLP

[57] ABSTRACT

The present invention relates to nucleotide sequences of Serrate genes, and amino acid sequences of their encoded proteins, as well as derivatives (e.g., fragments) and analogs thereof. In a specific embodiment, the Serrate protein is a human protein. The invention further relates to fragments (and derivatives and analogs thereof) of Serrate which comprise one or more domains of the Serrate protein, including but not limited to the intracellular domain, extracellular domain, DSL domain, cysteine rich domain, transmembrane region, membrane-associated region, or one or more EGF-like repeats of a Serrate protein, or any combination of the foregoing. Antibodies to Serrate, its derivatives and analogs, are additionally provided. Methods of production of the Serrate proteins, derivatives and analogs, e.g., by recombinant means, are also provided. Therapeutic and diagnostic methods and pharmaceutical compositions are provided. In specific examples, isolated Serrate genes, from Drosophila, chick, mouse, Xenopus and human, are provided.

109 Claims, 36 Drawing Sheets

Fleming et al., 1990, "The gene Serrate encodes a putative EGF–like transmembrane protein essential for proper ectodermal development in *Drosophila melanogaster*," Genes Dev. 4:2188–2201.

Furie and Furie, 1988, "The molecular basis of blood coagulation," Cell 53:505–518.

Fryberg et al., 1983, "Transcripts of the six Drosophila genes accumulate in a stage– and tissue–specific manner," Cell 33:115–123.

Gottschewski, 1935, "New mutants: report of G. Gottschewski," Dros. Inf. Serv. 4:14, 16.

Gribshov et al., 1984, "The codon preference plot: Graphic analysis of protein coding sequences and prediction of gene expression," Nucleic Acids Res. 12:539–549.

Jan and Jan, 1982, "Antibodies to horseradish peroxidase as specific neuronal markers in Drosophila and in grasshopper embryos," Proc. Natl. Acad. Sci. USA 79:2700–2704.

Jürgens et al., 1984, "Mutations affecting the pattern of larval cuticle in *Drosophila melanogaster*, II. Zygotic loci ont the third chromosome," Wilhelm Roux's Arch. Dev. Biol. 193:283–295.

Kidd et al., 1986, "Sequence of Notch locus of *Drosophila melanogaster*: relationship of the encoded protein to mammalian clotting and growth factors," Mol. Cell. Biol. 6:3094–3108.

King, 1988, "Cellular organization and peritrophic membrane formation in the cardia (proventriculus) of *Drosophila melanogaster*," J. Morphol. 196:253–282.

Kopczynski et al., 1988, Delta, a Drosophila neurogenic gene, is transcriptionally complex and encodes a protein related to blood coagulation factors and epidermal growth factor of vertebrates, Genes Dev. 2:1723–1735.

Lehmann et al., 1983, "On the phenotype and development of mutants of early neurogenesis in *Drosophila melanogaster*," Wilhelm Roux's Arch. Dev. Biol. 192:62–74.

Lindsley and Zimm, 1992, in The Genome of *Drosophila melanogaster*, Academic Press Inc.

Lindsley et al., 1972, "Segmental aneuploidy and the genetic gross structure of the Drosophila genome," Genetics 71:157–184.

Livneh et al., 1985, "The Drosophila EGF receptor gene homolog: conservation of both hormone binding and kinase domains," Cell 40:599–607.

Nüsslein–Volhard et al., 1984, "Mutations affecting the pattern of larval cuticle in *Drosophila melanogaster*. I. Zygotic loci on the second chromosone," Wilhelm Roux's Arch. Dev. Biol. 193:267–282.

Olson et al., 1990, "Glutactin, a novel Drosophila basement membrane–related glycoprotein with sequence similarity to serine esterases," EMBO J. 9:1219–1227.

Pirrotta et al., 1983, "Microdissection and cloning of the white locus and the 3B1–3C2 region of the Drosophila X chromosome," EMBO J. 2:927–934.

Poole et al., 1985, "The engrailed locus of Drosophila: structural analysis of an embryonic transcript," Cell 40:37–43.

Poulson, 1937, "Chromosomal deficiencies and embryonic development of Drosophila melanogaster," Proc. Natl. Acad. Sci. USA 23:133–137.

Preiss et al., 1985, "Molecular genetics of Krüppel, a gene required for segmentation of the Drosophila embryo," Nature 313:27–32.

Price et al., 1989, "The maternal ventralizing locus torpedo is allelic to faint little ball, an embryonic lethal, and encodes the Drosophila EGF receptor homolog," Cell 56:1085–1092.

Ramos et al., 1989, "Physical and functional definition of the Drosophila Notch locus by P element transformation," Genetics 123:337–348.

Rebay et al., 1991, "Specific EGF repeats of Notch mediate interactions with Delta and Serrate: Implications for Notch as a multifunctional receptor," Cell 67:687–699.

Rothberg et al., 1988, "slit: an EGF–homologous locus in *D. melanogaster* involved in the development of the embryonic central nervous system," Cell 55:1047–1059.

Schejter and Shilo, 1989, "The Drosophila EGF receptor homolog (DER) gene is allelic to faint little ball, a locus essential for embyronic development," Cell 56:1093–1104.

Siegelman et al., 1990, "The mouse lymph node homing receptor is identical with the lymphocute cell surface marker Ly–22: Role of the EGF domain in endothelial binding," Cell 61:611–622.

Tautz and Pfeifle, 1989, "A non–radioactive in situ hybridization method for the localization of specific RNAs in Drosophila embryos reveals translational control of the segmentation gene hunchback," Chromosoma 98:81–85.

Tepass et al., 1990, "crumbus encodes and EGF–like protein expressed on apical membranes of Drosophila epithelial cells and required for organization of epithalia," Cell 61:787–799.

Vässin et al., 1985, Genetic interactions in early neurogenesis of *Drosophila melanogaster*, J. Neurogenet. 2:291–308.

Vässin et al., 1987, "The neurogenic gene Delta of *Drosophila melanogaster* is expressed in neurogenic territories and encodes a putative transmembrane protein with EGF–like repeats," EMBO J. 6:3431–3440.

Wharton et al., 1985, "Nucleotide sequence from the neurogenic locus Notch implies a gene product that shares homology with proteins containing EGF–like repeats," Cell 43:567–581.

Wieschaus et al., 1984, "Mutations affecting the pattern of larval cuticle in *Drosophila melanogaster*. II. Zygotic loci on the X–chromosome and fourth chromosome," Wilhelm Roux's Arch. Dev. Biol. 193:296–307.

Xie et al., 1990, "Extracellular domain of lutropin/choriogonadotropin receptor expressed in transfected cells binds choriogonadotropin with high affinity," J. Biol. Chem. 265(35):21411–21414.

Xu et al., 1990, "The Notch locus and the genetic circuitry involved in early Drosophila neurogenesis," Genes Dev. 4:464–475.

Yochem et al., 1988, "The Caenorhabditis elegans lin–12 gene encodes a transmembrane protein with overall similarity to *Drosophila Notch*," Nature 335:547–550.

Zak et al., 1990, "Localization of the DER/fib protein in embryos: Implications on the faint little ball lethal phenotype," Development 109:865–874.

S. Artavanis–Tsakonas, 1997, "Alagille syndrome—a notch up for the Notch receptor", *Nature Genetics* 16:212–213.

Li et al., 1997, "Alagille syndrome is caused by mutations in human Jagged1, which encodes a ligand for Notch 1", *Nature Genetics* 16:243–251.

Oda et al., 1997, "Mutations in the human Jagged1 gene are responsible for Alagille syndrome", *Nature Genetics* 16:235–242.

```
2521  GGTCACTGCCTCAACACGCCGAAGGATACTACTGCCATTGTCCACCGGATCGGGCCGGAAAGCACTGCCGAGCAACTGGTCCGCTCCTTGCTCCTCAGCCGCCCTGCAACGAGGCTGCTTC
      GlyHisCysLeuAsnThrProGluGlyTyrTyrCysHisCysProProAspArgAlaGlyLysHisCysGlyGlnLeuArgProLeuCysSerGlnProProCysAsnGluGlyCysPhe  733

2641  GCCAATGTCAGCTAGGAGTCAGCGACGAGCAACGACGACGACAACCACCACCACCACTAACTAATAACTAACTACTACTACTACACGGACAAGGAAGATGCCTGCAGCGGACACGGCAGCTGCGAG
      AlaAsnValSerLeuAlaThrSerAlaThrThrThrThrThrThrThrThrAlaThrThrThrAlaThrThrArgLysMetAlaLysProCysSerGlyHisGlyLeuProCysSerCysGlu 773

2761  ATGAGCGACGTGGGCACCTTCTGCAAATGCCATGTGGGCCACACCTCTGCGAGCACAATCTCAACGAATGTCGCCGAATCCTTGTCGAAATGGGGAATTTGCCTTGACGGC
      MetSerAspValGlyThrPheCysLysCysHisValGlyHisThrGlyThrPheCysGluHisAsnLeuAsnGluCysSerProAsnProCysSerArgAsnGlyGlyIleCysLeuAspGly 813

2881  GACGGCGATTTTACATGCGAGTGCATGTCGGGCTGGACAGGTAAACGCTGCTCGGAGAGCGCGCTACAGGTTGTTATGCCGGTCAGTGCCAGAATGGTGGTACCGGTACGGGTTACTGCATGCCTGGAGCCCCG
      AspGlyAspPheThrCysGluCysMetSerGlyTrpThrGlyLysArgCysSerGlyGluArgAlaTyrArgGlyGlnAsnGlyGlyThrGlyThrCysMetProGlyAlaPro 853

3001  GACAAGGCTCTGCAGCCGGCATTGCCGCTGTCCTGGTCTGTTTTGCCGCAGCCTATTGACGAGGCTATTGCCGAGAGCTGTCCGGGGCAGCCGCTGCCACAATGGCGAACGTGCCGAGTCGGGA
      AspLysAlaLeuGlnProHisCysArgArgCysAlaGlyCysSerAlaGlyLeuAlaIleAspGlnCysHisAsnGlyGlyThrCysGluSerGly 893

3121  GCGGCTGGTTCCGCTGGCTCTGCCTGCCTGCAGGGATTCTCTGCTTGTCCAGAGACTGCCGCATCAATGTGAACGTGAATGTGACTGCCAGGGGCGGTGCCACTGCCACACTCGACGGAATCGGT
      AlaGlyTrpPheArgCysValCysAlaGlnGlyPheSerGlyProAspCysArgIleAsnValAsnGluCysSerProGlnProCysGlnGlyGlyAlaThrCysIleAspGlyIleGly 933

3241  GGATACAGCTGCATCTGCCACCAGGAGGCATGGATTGCGGTGTGAAATTTGCTCTCCGATCCAAGTCCCAAGTCCCAGGAACGCAAGCAACACTATCTCCGTATACAGCTCTAAAC
      GlyTyrSerCysIleCysHisGlnGluGlyTrpIleCysGlyValArgHisGlyLeuArgCysGluIleLeuLeuSerAspProLysSerAlaCysGlnAsnAlaSerAsnThrIleSerProTyrThrAlaLeuAsn 973
```

```
SERRATE  TCATTAAAGTCTGCCTGCAACTTAATTGCTTTAATTTAATACTGTTAGTCCATAAG

DELTA    ATGCATTGGATTAAATGTTTATTAACAGCATTCATTGCTTCACAGTCATCGTGCAG

SERRATE  ATATCCGCAGCTGGTAACTTCGAGCTGGAAATATTAGAAATCTCAAATACCAACAGC

DELTA    GTTCACAGTTCCGGCAGCTTTGAGTTGCGCCTGAAGTACTTCAGCAACGATCACGGG

SERRATE  CATCTACTCAACGGCTATTGCTGCGGCATGCCAGCGAACTTAGGGCCACCAAGACG

DELTA    CGGGACAACGAGGGTCGCTGCTGCAGCGAGTCGACGGAGCGGACGGGCAAGTGC

FLE1
                                                    ──────▶
SERRATE  ATAGGCTGCTGCGCCATGCAACGACCATTCCCGCTGTCCCTGAAGCAGTACCAGACC
                                                    ◀──────
                                                    FLE1R

DELTA    CTGGGC------AGCTGCAAGACGCGGTTTCGGTCTGCCTAAAGCACTACCAGGCC
```

FIG. 8A

```
              10          20         30         40         50         60
       GAATTCCCCT CCCCCCTTTT TCCATGCAGC TGATCTAAAA GGGAATAAAA GGCTGCGCAT
              70          80         90        100        110        120
       AATCATAATA ATAAAAGAAG GGGAGCGCGA GAGAAGGAAA GAAAGCCGGG AGGTGGAAGA
             130         140        150        160        170        180
       GGAGGGGGAG CGTCTCAAAG AAGCGATCAG AATAATAAAA GGAGGCCGGG CTCTTTGCCT
             190         200        210        220        230        240
       TCTGGAAGGG GCCGCTCTTG AAAGGGCTTT TGAAAAGTGG TGTTGTTTTC CAGTCGTGCA
             250         260        270        280        290        300
       TGCTCCAATC GGCGGAGTAT ATTAGAGCCG GGACGCGGCC GCAGGGGCAG CGGCGACGGC
             310         320        330        340        350        360
       AGCACCGGCG GCAGCACCAG CGCGAACAGC AGCGGCGGCG TCCCGAGTGC CCGCGGCGGC
             370         380        390        400        410        420
       GCGCGCAGCG ATGCGTTCCC CACGGACACG CGGCCGGTCC GGGCGCCCCC TAAGCCTCCT
                     M   R   S   P   R   T   R   G   R   S   G   R   P   L   S   L   L>
             430         440        450        460        470        480
       GCTCGCCCTG CTCTGTGCCC TGCGAGCCAA GGTGTGTGGG GCCTCGGGTC AGTTCGAGTT
        L   A   L   L   C   A   L   R   A   K   V   C   G   A   S   G   Q   F   E   L>
             490         500        510        520        530        540
       GGAGATCCTG TCCATGCAGA ACGTGAACGG GGAGCTGCAG AACGGGAACT GCTGCGGCGG
        E   I   L   S   M   Q   N   V   N   G   E   L   Q   N   G   N   C   C   G   G>
             550         560        570        580        590        600
       CGCCCGGAAC CCGGGAGACC GCAAGTGCAC CCGCGACGAG TGTGACACAT ACTTCAAAGT
        A   R   N   P   G   D   R   K   C   T   R   D   E   C   D   T   Y   F   K   V>
             610         620        630        640        650        660
       GTGCCTCAAG GAGTATCAGT CCCGCGTCAC GGCCGGGGGG CCCTGCAGCT TCGGCTCAGG
        C   L   K   E   Y   Q   S   R   V   T   A   G   G   P   C   S   F   G   S   G>
             670         680        690        700        710        720
       GTCCACGCCT GTCATCGGGG GCAACACCTT CAACCTCAAG GCCAGCCGCG GCAACGACCC
        S   T   P   V   I   G   G   N   T   F   N   L   K   A   S   P   G   N   D   P>
             730         740        750        760        770        780
       GAACCGCATC GTGCTGCCTT TCAGTTTCGC CTGGCCGAGG TCCTATACGT TGCTTGTGGA
        N   R   I   V   L   P   F   S   F   A   W   P   R   S   Y   T   L   L   V   E>
             790         800        810        820        830        840
       GGCGTGGGAT TCCAGTAATG ACACCGTTCA ACCTGACAGT ATTATTGAAA AGGCTTCTCA
        A   W   D   S   S   N   D   T   V   Q   P   D   S   I   I   E   K   A   S   H>
             850         860        870        880        890        900
       CTCGGGCATG ATCAACCCCA GCCGGCAGTG GCAGACGCTG AAGCAGAACA CGGGCGTTGC
        S   G   M   I   N   P   S   R   Q   W   Q   T   L   K   Q   N   T   G   V   A>
```

FIG. 9A

```
     910        920        930        940        950        960
CCACTTTGAG TATCAGATCC GCGTGACCTG TGATGACTAC TACTATGGCT TTGGCTGTAA
 H  F  E    Y  Q  I    R  V  T    C  D  D  Y   Y  Y  G   F  G  C  N>
     970        980        990       1000       1010       1020
TAAGTTCTGC CGCCCCAGAG ATGACTTCTT TGGACACTAT GCCTGTGACC AGAATGGCAA
 K  F  C    R  P  R    D  D  F  F   G  H  Y    A  C  D    Q  N  G  N>
    1030       1040       1050       1060       1070       1080
CAAAACTTGC ATGGAAGGCT GGATGGGCCC CGAATGTAAC AGAGCTATTT GCCGACAAGG
 K  T  C    M  E  G    W  M  G  P   E  C  N    R  A  I    C  R  Q  G>
    1090       1100       1110       1120       1130       1140
CTGCAGTCCT AAGCATGGGT CTTGCAAACT CCCAGGTGAC TGCAGGTGCC AGTACGGCTG
 C  S  P    K  H  G    S  C  K  L   P  G  D    C  R  C    Q  Y  G  W>
    1150       1160       1170       1180       1190       1200
GCAAGGCCTG TACTGTGATA AGTGCATCCC ACACCCGGGA TGCGTCCACG GCATCTGTAA
 Q  G  L    Y  C  D    K  C  I  P   H  P  G    C  V  H    G  I  C  N>
    1210       1220       1230       1240       1250       1260
TGAGCCCTGG CAGTGCCTCT GTGAGACCAA CTGGGGCGGC CAGCTCTGTG ACAAAGATCT
 E  P  W    Q  C  L    C  E  T  N   W  G  G    Q  L  C    D  K  D  L>
    1270       1280       1290       1300       1310       1320
CAATTACTGT GGGACTCATC AGCCGTGTCT CAACGGGGGA ACTTGTAGCA ACACAGGCCC
 N  Y  C    G  T  H    Q  P  C  L   N  G  G    T  C  S    N  T  G  P>
    1330       1340       1350       1360       1370       1380
TGACAAATAT CAGTGTTCCT GCCCTGAGGG GTATTCAGGA CCCAACTGTG AAATTGCTGA
 D  K  Y    Q  C  S    C  P  E  G   Y  S  G    P  N  C    E  I  A  E>
    1390       1400       1410       1420       1430       1440
GCACGCCTGC CTCTCTGATC CCTGTCACAA CAGAGGCAGC TGTAAGGAGA CCTCCCTGGG
 H  A  C    L  S  D    P  C  H  N   R  G  S    C  K  E    T  S  L  G>
    1450       1460       1470       1480       1490       1500
CTTTGAGTGT GAGTGTTCCC CAGGCTGGAC CGGCCCCACA TGCTCTACAA ACATTGATGA
 F  E  C    E  C  S    P  G  W  T   G  P  T    C  S  T    N  I  D  D>
    1510       1520       1530       1540       1550       1560
CTGTTCTCCT AATAACTGTT CCCACGGGGG CACCTGCCAG GACCTGGTTA ACGGATTTAA
 C  S  P    N  N  C    S  H  G  G   T  C  Q    D  L  V    N  G  F  K>
    1570       1580       1590       1600       1610       1620
GTGTGTGTGC CCCCCACAGT GGACTGGGAA AACGTGCCAG TTAGATGCAA ATGAATGTGA
 C  V  C    P  P  Q    W  T  G  K   T  C  Q    L  D  A    N  E  C  E>
    1630       1640       1650       1660       1670       1680
GGCCAAACCT TGTGTAAACG CCAAATCCTG TAAGAATCTC ATTGCCAGCT ACTACTGCGA
 A  K  P    C  V  N    A  K  S  C   K  N  L    I  A  S    Y  Y  C  D>
```

FIG. 9B

```
      1690       1700       1710       1720       1730       1740
CTGTCTTCCC GGCTGGATGG GTCAGAATTG TGACATAAAT ATTAATGACT GCCTTGGCCA
  C  L  P    G  W  M    G  Q  N    C  D  I    I  N  D    C  L  G  Q>
      1750       1760       1770       1780       1790       1800
GTGTCAGAAT GACGCCTCCT GTCGGGATTT GGTTAATGGT TATCGCTGTA TCTGTCCACC
  C  Q  N    D  A  S    C  R  D    L  V  N  G  Y  R  C    I  C  P  P>
      1810       1820       1830       1840       1850       1860
TGGCTATGCA GGCGATCACT GTGAGAGAGA CATCGATGAA TGTGCCAGCA ACCCCTGTTT
  G  Y  A    G  D  H    C  E  R  D  I  D  E    C  A  S    N  P  C  L>
      1870       1880       1890       1900       1910       1920
GAATGGGGGT CACTGTCAGA ATGAAATCAA CAGATTCCAG TGTCTGTGTC CCACTGGTTT
  N  G  G    H  C  Q    N  E  I  N  R  F  Q    C  L  C    P  T  G  F>
      1930       1940       1950       1960       1970       1980
CTCTGGAAAC CTCTGTCAGC TGGACATCGA TTATTGTGAG CCTAATCCCT GCCAGAACGG
  S  G  N    L  C  Q    L  D  I  D  Y  C  E    P  N  P    C  Q  N  G>
      1990       2000       2010       2020       2030       2040
TGCCCAGTGC TACAACCGTG CCAGTGACTA TTTCTGCAAG TGCCCCGAGG ACTATGAGGG
  A  Q  C    Y  N  R    A  S  D  Y  F  C  K    C  P  E    D  Y  E  G>
      2050       2060       2070       2080       2090       2100
CAAGAACTGC TCACACCTGA AAGACCACTG CCGCACGACC CCCTGTGAAG TGATTGACAG
  K  N  C    S  H  L    K  D  H  C  R  T  T    P  C  E    V  I  D  S>
      2110       2120       2130       2140       2150       2160
CTGCACAGTG GCCATGGCTT CCAACGACAC ACCTGAAGGG GTGCGGTATA TTTCCTCCAA
  C  T  V    A  M  A    S  N  D  T  P  E  G    V  R  Y    I  S  S  N>
      2170       2180       2190       2200       2210       2220
CGTCTGTGGT CCTCACGGGA AGTGCAAGAG TCAGTCGGGA GGCAAATTCA CCTGTGACTG
  V  C  G    P  H  G    K  C  K  S  Q  S  G    G  K  F    T  C  D  C>
      2230       2240       2250       2260       2270       2280
TAACAAAGGC TTCACGGGAA CATACTGCCA TGAAAATATT AATGACTGTG AGAGCAACCC
  N  K  G    F  T  G    T  Y  C  H  E  N  I    N  D  C    E  S  N  P>
      2290       2300       2310       2320       2330       2340
TTGTAGAAAC GGTGGCACTT GCATCGATGG TGTCAACTCC TACAAGTGCA TCTGTAGTGA
  C  R  N    G  G  T    C  I  D  G  V  N  S    Y  K  C    I  C  S  D>
      2350       2360       2370       2380       2390       2400
CGGCTGGGAG GGGGCCTACT GTGAAACCAA TATTAATGAC TGCAGCCAGA ACCCCTGCCA
  G  W  E    G  A  Y    C  E  T  N  I  N  D    C  S  Q    N  P  C  H>
      2410       2420       2430       2440       2450       2460
CAATGGGGGC ACGTGTCGCG ACCTGGTCAA TGACTTCTAC TGTGACTGTA AAAATGGGTG
  N  G  G    T  C  R    D  L  V  N  D  F  Y    C  D  C    K  N  G  W>
```

FIG. 9C

```
              2470       2480       2490       2500       2510       2520
         GAAAGGAAAG ACCTGCCACT CACGTGACAG TCAGTGTGAT GAGGCCACGT GCAACAACGG
           K  G  K    T  C  H    S  R  D  S  Q  C  D    E  A  T    C  N  N  G>
              2530       2540       2550       2560       2570       2580
         TGGCACCTGC TATGATGAGG GGGATGCTTT TAAGTGCATG TGTCCTGGCG GCTGGGAAGG
           G  T  C    Y  D  E    G  D  A  F  K  C  M    C  P  G    G  W  E  G>
              2590       2600       2610       2620       2630       2640
         AACAACCTGT AACATAGCCC GAAACAGTAG CTGCCTGCCC AACCCCTGCC ATAATGGGGG
           T  T  C    N  I  A    R  N  S  S  C  L  P    N  P  C    H  N  G  G>
              2650       2660       2670       2680       2690       2700
         CACATGTGTG GTCAACGGCG AGTCCTTTAC GTGCGTCTGC AAGGAAGGCT GGGAGGGGCC
           T  C  V    V  N  G    E  S  F  T  C  V  C    K  E  G    W  E  G  P>
              2710       2720       2730       2740       2750       2760
         CATCTGTGCT CAGAATACCA ATGACTGCAG CCCTCATCCC TGTTACAACA GCGGCACCTG
           I  C  A    Q  N  T    N  D  C  S  P  H  P    C  Y  N    S  G  T  C>
              2770       2780       2790       2800       2810       2820
         TGTGGATGGA GACAACTGGT ACCGGTGCGA ATGTGCCCCG GGTTTTGCTG GGCCCGACTG
           V  D  G    D  N  W    Y  R  C  E  C  A  P    G  F  A    G  P  D  C>
              2830       2840       2850       2860       2870       2880
         CAGAATAAAC ATCAATGAAT GCCAGTCTTC ACCTTGTGCC TTTGGAGCGA CCTGTGTGGA
           R  I  N    I  N  E    C  Q  S  S  P  C  A    F  G  A    T  C  V  D>
              2890       2900       2910       2920       2930       2940
         TGAGATCAAT GGCTACCGGT GTGTCTGCCC TCCAGGGCAC AGTGGTGCCA AGTGCCAGGA
           E  I  N    G  Y  R    C  V  C  P  P  G  H    S  G  A    K  C  Q  E>
              2950       2960       2970       2980       2990       3000
         AGTTTCAGGG AGACCTTGCA TCACCATGGG GAGTGTGATA CCAGATGGGG CCAAATGGGA
           V  S  G    R  P  C    I  T  M  G  S  V  I    P  D  G    A  K  W  D>
              3010       3020       3030       3040       3050       3060
         TGATGACTGT AATACCTGCC AGTGCCTGAA TGGACGGATC GCCTGCTCAA AGGTCTGGTG
           D  D  C    N  T  C    Q  C  L  N  G  R  I    A  C  S    K  V  W  C>
              3070       3080       3090       3100       3110       3120
         TGGCCCTCGA CCTTGCCTGC TCCACAAAGG GCACAGCGAG TGCCCCAGCG GGCAGAGCTG
           G  P  R    P  C  L    L  H  K  G  H  S  E    C  P  S    G  Q  S  C>
              3130       3140       3150       3160       3170       3180
         CATCCCCATC CTGGACGACC AGTGCTTCGT CCACCCCTGC ACTGGTGTGG GCGAGTGTCG
           I  P  I    L  D  D    Q  C  F  V  H  P  C    T  G  V    G  E  C  R>
              3190       3200       3210       3220       3230       3240
         GTCTTCCAGT CTCCAGCCGG TGAAGACAAA GTGCACCTCT GACTCCTATT ACCAGGATAA
           S  S  S    L  Q  P    V  K  T  K  C  T  S    D  S  Y    Y  Q  D  N>
              3250       3260       3270       3280       3290       3300
         CTGTGCGAAC ATCACATTTA CCTTTAACAA GGAGATGATG TCACCAGGTC TTACTACGGA
           C  A  N    I  T  F    T  F  N  K  E  M  M    S  P  G    L  T  T  E>
```

FIG. 9D

```
      3310       3320       3330       3340       3350       3360
GCACATTTGC AGTGAATTGA GGAATTTGAA TATTTTGAAG AATGTTTCCG CTGAATATTC
   H I C    S E L      R N L      I L K      N V S      A E Y  S>
      3370       3380       3390       3400       3410       3420
AATCTACATC GCTTGCGAGC CTTCCCCTTC AGCGAACAAT GAAATACATG TGGCCATTTC
   I Y I    A C E      P S P S    A N N      E I H      V A I  S>
      3430       3440       3450       3460       3470       3480
TGCTGAAGAT ATACGGGATG ATGGGAACCC GATCAAGGAA ATCACTGACA AAATAATCGA
   A E D    I R D      D G N P    I K E      I T D      K I I  D>
      3490       3500       3510       3520       3530       3540
TCTTGTTACT AAACGTGATG GAAACAGCTC GCTGATTGCT GCCGTTGAAG AAGTAAGAGT
   L V T    K R D      G N S S    L I A      A V E      E V R  V>
      3550       3560       3570       3580       3590       3600
TCAGAGGCGG CCTCTGAAGA ACAGAACAGA TTTCCTTGTT CCCTTGCTGA GCTCTGTCTT
   Q R R    P L K      N R T D    F L V      P L L      S S V  L>
      3610       3620       3630       3640       3650       3660
AACTGTGGCT TGGATCTGTT GCTTGGTGAC GGCCTTCTAC TGGTGCCTGC GGAAGCGGCG
   T V A    W I C      C L V T    A F Y      W C L      R K R  R>
      3670       3680       3690       3700       3710       3720
GAAGCCGGGC AGCCACACAC ACTCAGCCTC TGAGGACAAC ACCACCAACA ACGTGCGGGA
   K P G    S H T      H S A S    E D N      T T N      N V R  E>
      3730       3740       3750       3760       3770       3780
GCAGCTGAAC CAGATCAAAA ACCCCATTGA GAAACATGGG GCCAACACGG TCCCCATCAA
   Q L N    Q I K      N P I E    K H G      A N T      V P I  K>
      3790       3800       3810       3820       3830       3840
GGATTACGAG AACAAGAACT CCAAAATGTC TAAAATAAGG ACACACAATT CTGAAGTAGA
   D Y E    N K N      S K M S    K I R      T H N      S E V  E>
      3850       3860       3870       3880       3890       3900
AGAGGACGAC ATGGACAAAC ACCAGCAGAA AGCCCGGTTT GCCAAGCAGC CGGCGTACAC
   E D D    M D K      H Q Q K    A R F      A K Q      P A Y  T>
      3910       3920       3930       3940       3950       3960
GCTGGTAGAC AGAGAAGAGA AGCCCCCCAA CGGCACGCCG ACAAAACACC CAAACTGGAC
   L V D    R E E      K P P N    G T P      T K H      P N W  T>
      3970       3980       3990       4000       4010       4020
AAACAAACAG GACAACAGAG ACTTGGAAAG TGCCCAGAGC TTAAACCGAA TGGAGTACAT
   N K Q    D N R      D L E S    A Q S      L N R      M E Y  I>
      4030       4040       4050       4060       4070       4080
CGTATAGCAG ACCGCGGGCA CTGCCGCCGC TAGGTAGAGT CTGAGGGCTT GTAGTTCTTT
   V  >
```

FIG. 9E

```
          4090       4100       4110       4120       4130       4140
     AAACTGTCGT GTCATACTCG AGTCTGAGGC CGTTGCTGAC TTAGAATCCC TGTGTTAATT
          4150       4160       4170       4180       4190       4200
     TAGTTTGACA AGCTGGCTTA CACTGGCAAT GGTAGTTCTG TGGTTGGCTG GGAAATCGAG
          4210       4220       4230       4240       4250       4260
     TGGCGCATCT CACAGCTATG CAAAAAGCTA GTCAACAGTA CCCCTGGTTG TGTGTCCCCT
          4270       4280       4290       4300       4310       4320
     TGCAGCCGAC ACGGTCTCGG ATCAGGCTCC CAGGAGCTGC CCAGCCCCCT GGTACTTTGA
          4330       4340       4350       4360       4370       4380
     GCTCCCACTT CTGCCAGATG TCTAATGGTG ATGCAGTCTT AGATCATAGT TTTATTTATA
          4390       4400       4410       4420       4430       4440
     TTTATTGACT CTTGAGTTGT TTTTGTATAT TGGTTTTATG ATGACGTACA AGTAGTTCTG
          4450       4460       4470       4480       4490       4500
     TATTTGAAAG TGCCTTTGCA GCTCAGAACC ACAGCAACGA TCACAAATGA CTTTATTATT
          4510       4520       4530       4540       4550       4560
     TATTTTTTTT AATTGTATTT TTGTTGTTGG GGGAGGGGAG ACTTTGATGT CAGCAGTTGC
          4570       4580       4590       4600       4610       4620
     TGGTAAAATG AAGAATTTAA AGAAAAAATG TCCAAAAGTA GAACTTTGTA TAGTTATGTA
          4630       4640       4650       4660       4670       4680
     AATAATTCTT TTTTATTAAT CACTGTGTAT ATTTGATTTA TTAACTTAAT AATCAAGAGC
          4690       4700       4710       4720       4730       4740
     CTTAAAACAT CATTCCTTTT TATTTATATG TATGTGTTTA GAATTGAAGG TTTTTGATAG
          4750       4760       4770       4780       4790       4800
     CATTGTAAGC GTATGGCTTT ATTTTTTTGA ACTCTTCTCA TTACTTGTTG CCTATAAGCC
          4810       4820       4830       4840       4850       4860
     AAAAAGGAAA GGGTGTTTTG AAAATAGTTT ATTTTAAAAC AATAGGATGG GCTACACGTA
          4870       4880       4890       4900       4910       4920
     CATAGGTAAA TAATAGCACC GTACTGGTTA TGATGATGAA AATAACTGGA AACTTGAAAG
          4930       4940       4950       4960       4970       4980
     CTTGTGGTAA TGGCAGATAA AGATGGTTCA CCTGGGAAAT TAAAACTTGA ATGGTTGTAC
          4990       5000       5010       5020       5030       5040
     AGAAAAGCAC AGAGTGGAAT GCACATCAAT GACAGTAAGG GAGTTAGTTC TAGGAACAGC
          5050       5060       5070       5080       5090       5100
     TCCTGAACAG TAAGATTCCC GCAATAGTCT CCGCCTCGTT CGTCTATGGT ATGCATCCCA
          5110       5120       5130       5140       5150       5160
     TTCATTTTCT TCTTCTGATT ATTGTCATCT TTCCCTTTGC CAAATGGGCA GTTATTGTTT
          5170       5180       5190       5200       5210       5220
     CAGGGAGAGA AGCTGCTCAT TGGCCAATCA TTCTGGTGTG CAGTGCTCCA TCGGATTCTA
          5230       5240       5250       5260       5270       5280
     CATGTCCAAC AAGGCATGTC TGGATGATGC AATGTCTGTC TGACCCCCGG AATTCCGTGC
```

FIG. 9F

```
      5290       5300       5310       5320       5330       5340
AGAGACAACA TTCTAGACAG ATATACACTT TTTATTATTA ACAAACTTTG GCCACAACCT
      5350       5360       5370       5380       5390       5400
TTGATGTATA AATTGCCGGA TTTCCCCAGT CCTTTCATTG TGGCTTTGGA CAGGAGCAGG
      5410       5420       5430       5440       5450       5460
CTCACTTGTC TGCTTCAGGC TGCCTTTCTC TTGGGTTGCA CCTCAGTTCT TACTTATTTA
      5470       5480       5490       5500       5510       5520
TTTATTTTGA GTGGAGCATA GGGGCCTCTT CCAAAATGGG TAGAGCTCAG GGGCTTTCTT
      5530       5540       5550       5560       5570       5580
ATTGAAATGG TCACATGATA AAAACGGGCT GAAAAGGAG AGTTCCAGGA GAAAAGCCCA
      5590       5600       5610       5620       5630       5640
GAAAAGGCCC CTCCTCAGAA GACAGCCTTT AAGCCTCTTG CTTACTGAAG GAAGCCCCAC
      5650       5660       5670       5680       5690       5700
CTTCTAGCAC TGAGGCCGGG TCTGATCTTC CAGAGGAGTT GGAGGAGTCC ATGAGAATGG
      5710       5720       5730       5740       5750       5760
CCACCATTCT TGCTTGCTGC TGCTGATGTT GCAGTTTTGA GAGAACAGCG GGATCCTTGT
      5770       5780       5790       5800       5810       5820
TGTCCTCTAG AGACTTGAGT CTGTCACTGA CATTTTTTCA GTTCCTTTGC TCATAGACCA
      5830       5840       5850       5860       5870       5880
TACGAGGAAT TAGTGATGTG TCAGTTGAGA GTTCACAATC TCATTGTTCA TTTAATTCAC
      5890       5900       5910       5920       5930       5940
TTTAAAGTTG TCAATTTCTG TGTGAGTAAC CTGTAAAAGA CACCTTTCCA GAAGAGTTTT
      5950       5960       5970       5980       5990       6000
GCCGTCTGTT TGAAAAAAAA ATCTTTATAA ACTTTCCTAA GTATCTGGAT TTGGATTCCT
      6010       6020       6030       6040       6050       6060
TATTTGGAGA GAAAATGTAC CCTGTCTCCA CCAAAAATAC AAAAATTAGC CAGGCTTGGT
      6070       6080       6090       6100       6110       6120
GGTGCACACC GGTAATCCCA GCAACTCTGG AGACTAAGGC AGGAAGAATC GCTTGACCCA
      6130       6140       6150       6160       6170       6180
GGAGGGTCGA GGCTACAATG AGTTGAAACC GCGCCACTGC ACTCCAGCCT GGGCGACAGT
      6190       6200       6210       6220       6230       6240
GCGAGGCCCT GTCTCAAAAA TAAAATAAAA TAAATAAATA AATTAGCCAG ATACTGTGTG
      6250       6260       6270       6280       6290       6300
CACGCCTGCA GTCCCAGCTA TTCTGGAAGC TGAGGTGGGA AGATGGTTAA GCCTGAGAGG
      6310       6320       6330       6340       6350       6360
ACAAAGCTGC AGTGAGTCAT GTTTGCATCA CTGCACTCCA GCCTGGGTGA CAGAGCAAGA
      6370       6380       6390       6400       6410       6420
CCCTGTCTAA AAAACAAAAA CAGGCCGGGT GTGGTGGCTC ATGCCTGCCA TCCCAGTGCT
      6430       6440       6450       6460
TTGGGAGGCA GAGGTTGGCA TAATCCCAGC GCTCTGGGAA TTCC
```

FIG. 9G

```
GGCCGGGGCC GGGCGGGCGG GTCGCGGGGG CAATGCGGGC GCAGGGCCGG GGGCGCCTTC    60

CCCGGCGGCT GCTGCTGCTG CTGGCGCTCT GGGTGCAGGC GGCGCGGCCC ATGGGCTATT   120

TCGAGCTGCA GCTGAGCGCG CTGCGGAACG TGAACGGGGA GCTGCTGAGC GGCGCCTGCT   180

GTGACGGCGA CGGCCGGACA ACGCGCGCGG GGGCTGCGG CCACGACGAG TGCGACACCG    240

CTCCTTTACC CTCATCGTGG AGGCCTGGGA CTGGGACAAC GATACCACCC CGAATGAGGA   300

GCTGCTGATC GAGCGAGTGT CGCATGCCGG CATGATCAAC CCGGAGGACC GCTGGAAGAG   360

CCTGCACTTC AGCGGCCACG TGGCGCACCT GGAGCTGCAG ATCCGCGTGC GCTGCGACGA   420

GAACTACTAC AGCGCCACTT GCAACAAGTT CTGCCGGCCC CGCAATGACT TTTTCGGCCA   480

CTACACCTGC GACCAGTACG GCAACAAGGC CTGCATGGAC GGCTGGATGG GCAAGGAGTG   540

CAAGGAAGCT GTGTGTAAAC AAGGGTGTAA TTTGCTCCAC GGGGGATGCA CCGTGCCTGG   600

GGAGTGCAGG TGCAGCTACG GCTGGCAAGG GAGGTTCTGC GATGAGTGTG TCCCCTACCC   660

CGGCTGCGTG CATGGCAGTT GTGTGGAGCC CTGGCAGTGC AACTGTGAGA CCAACTGGGG   720

CGGCCTGCTC TGTGACAAAG ACCTGAACTA CTGTGGCAGC CACCACCCCT GCACCAACGG   780

AGCACGTGC ATCAACGCCG AGCCTGACCA GTACCGCTGC ACCTGCCCTG ACGGCTACTC    840

GGGCAGGAAC TGTGAGAAGG CTGAGCACGC CTGCACCTCC AACCCGTGTG CCAACGGGGG   900

CTCTTGCCAT GAGGTGCCGT CCGGCTTCGA ATGCCACTGC CCATCGGGCT GGAGCGGGCC   960

CACCTGTGCC CTTGACATCG ATGAGTGTGC TTCGAACCCG TGTGCGGCCG GTGGCACCTG  1020

TGTGGACCAG GTGGACGGCT TTGAGTGCAT CTGCCCCGAG CAGTGGGTGG GGCCACCTG   1080

CCAGCTGGAC GCCAATGAGT GTGAAGGGAA GCCATGCCTT AACGCTTTTT CTTGCAAAAA  1140

CCTGATTGGC GGCTATTACT GTGATTGCAT CCCGGGCTGG AAGGGCATCA ACTGCCATAT  1200

CAACGTCAAC GACTGTCGCG GGCAGTGTCA GCATGGGGGC ACCTGCAAGG ACCTGGTGAA  1260
```

FIG.10A

```
CGGGTACCAG TGTGTGTGCC CACGGGGCTT CGGAGGCCGG CATTGCGAGC TGGAACGAGA    1320

CAAGTGTGCC AGCAGCCCCT GCCACAGCGG CGGCCTCTGC GAGGACCTGG CCGACGGCTT    1380

CCACTGCCAC TGCCCCCAGG GCTTCTCCGG GCCTCTCTGT GAGGTGGATG TCGACCTTTG    1440

TGAGCCAAGC CCCTGCCGGA ACGGCGCTCG CTGCTATAAC CTGGAGGGTG ACTATTACTG    1500

CGCCTGCCCT GATGACTTTG GTGGCAAGAA CTGCTCCGTG CCCCGCGAGC CGTGCCCTGG    1560

CGGGGCCTGC AGAGTGATCG ATGGCTGCGG GTCAGACGCG GGGCCTGGGA TGCCTGGCAC    1620

AGCAGCCTCC GGCGTGTGTG GCCCCCATGG ACGCTGCGTC AGCCAGCCAG GGGGCAACTT    1680

TTCCTGCATC TGTGACAGTG GCTTTACTGG CACCTACTGC CATGAGAACA TTGACGACTG    1740

CCTGGGCCAG CCCTGCCGCA ATGGGGGCAC ATGCATCGAT GAGGTGGACG CCTTCCGCTG    1800

CTTCTGCCCC AGCGGTTGGG AGGGCGAGCT CTGCCACACC AATCCCAACG ACTGCCTTCC    1860

CGATCCCTGC CACAGCCGCG GCCGCTGCTA CGACCTGGTC AATGACTTCT ACTGTGCGTG    1920

CGACGACGGC TGGAAGGGCA AGACCTGCCA CTCACGCGAG TTCCAGTGCG ATGCCTACAC    1980

CTGCAGCAAC GGTGGCACCT GCTACGACAG CGGCGACACC TTCCGCTGCG CCTGCCCCCC    2040

CGGCTGGAAG GGCAGCACCT GCGCCGTCGC CAAGAACAGC AGCTGCCTGC CCAACCCCTG    2100

TGTGAATGGT GGCACCTGCG TGGGCAGCGG GGCCTCCTTC TCCTGCATCT GCCGGGACGG    2160

CTGGGAGGGT CGTACTTGCA CTCACAATAC CAACGACTGC AACCCTCTGC CTTGCTACAA    2220

TGGTGGCATC TGTGTTGACG GCGTCAACTG GTTCCGCTGC GAGTGTGCAC CTGGCTTCGC    2280

GGGGCCTGAC TGCCGCATCA ACATCGACGA GTGCCAGTCC TCGCCCTGTG CCTACGGGGC    2340

CACGTGTGTG GATGAGATCA ACGGGTATCG CTGTAGCTGC CCACCCGGCC GAGCCGGCCC    2400

CCGGTGCCAG GAAGTGATCG GGTTCGGGAG ATCCTGCTGG TCCCGGGGCA CTCCGTTCCC    2460

ACACGGAAGC TCCTGGGTGG AAGACTGCAA CAGCTGCCGC TGCCTGGATG GCCGCCGTGA    2520
```

FIG.10B

```
CTGCAGCAAG GTGTGGTGCG GATGGAAGCC TTGTCTGCTG GCCGGCCAGC CCGAGGCCCT      2580

GAGCGCCCAG TGCCCACTGG GGCAAAGGTG CCTGGAGAAG GCCCCAGGCC AGTGTCTGCG      2640

ACCACCCTGT GAGGCCTGGG GGGAGTGCGG CGCAGAAGAG CCACCGAGCA CCCCCTGCCT      2700

GCCACGCTCC GGCCACCTGG ACAATAACTG TGCCCGCCTC ACCTTGCATT TCAACCGTGA      2760

CCACGTGCCC CAGGGCACCA CGGTGGGCGC CATTTGCTCC GGGATCCGCT CCCTGCCAGC      2820

CACAAGGGCT GTGGCACGGG ACCGCCTGCT GGTGTTGCTT TGCGACCGGG CGTCCTCGGG      2880

GGCCAGTGCT GTGGAGGTGG CCGTGTCCTT CAGCCCTGCC AGGGACCTGC CTGACAGCAG      2940

CCTGATCCAG GGCGCGGCCC ACGCCATCGT GGCCGCCATC ACCCAGCGGG GGAACAGCTC      3000

ACTGCTCCTG GCTGTCACCG AGGTCAAGGT GGAGACGGTT GTTACGGGCG GCTCTTCCAC      3060

AGGTCTGCTG GTGCCTGTGC TGTGTGGTGC CTTCAGCGTG CTGTGGCTGG CGTGCGTGGT      3120

CCTGTGCGTG TGGTGGACAC AAGCGCAGGA AAGAGCGGGA GAGGAGCCGG CTGCCGCGGG      3180

AGGAGAGCGC CAACAACCAG TGGGCCCCGC TCAACCCCAT CCGCAACCCC ATTGAGCNNC      3240

CGGGGGCACA AGGACGTGCT CTACCAGTGC AAGAACTTCA CNCCGCCGCC GCGCAGGNCG      3300

AGGNCTNCCG GNCCGNCNGC ACNCNNCAGG GAGGATGAGG AGGACGGGAT CTGGGCCNCN      3360

GTGAGGAGGA CTCCTGGAGG CNNAGAAGTT CCTCTCACAC AAATTCACCA AGATCCTGG      3420

CCGCTCGCCG GGAGNCGNCC ACTGCNCAGG CCAAAGTGGA CAACCGCNCN GTCAGGAGCA      3480

TCAATGAGGC CCGCTACNCG CAAGGGAAGT AGGGCGGCTG CAGCTGGGCC GGGACCCAGG      3540

GCCTCGGTGG GAGCCATGCC GTCTGCCGGN CCCGAGCCGA GGCATGTGCA TAGTTTCTTT      3600

ATTTTGTGTA AAAAAACCAC CAAAAACAAA AACCAAATGT TTATTTTCTA CGTTTCTTTA      3660

ACCTTGTATA AATTATTCAG TAACTGTCAG GCTGAAACAA TGGAGTATTC TCGGATAGTT      3720
```

FIG.10C

```
GCTATTTTTG TTAAAGTTTC TCTCGCGTGG CACTCGCTGT ATGGAAAGGA GAGAGCAAAA    3780

GGGTGTCTGA CGTCGTCACC AAATCGTAGC GTTTGTTACC AGAGGTTGTG CACTGTTTAC    3840

AGAATGTTGG TTTTATTCCT CACTCGGGTT TCTCTGTGCT CCAGGCCAAA GTGCCGGTGA    3900

GACCCATGGC TGTGTTGGTG TGGCCCATGG CTGTTGGTGG GACCCTGTGG CTGATGGTGT    3960

GGCCTGTGGC TGTCGGTGGG ACTCGTGGCT GTCAATGGGA CCTGTGGCTG TCGGTGGGAC    4020

CTACGGTGGT CGGTGGGACC CTGGTTATTG ATGTGGCCCT GGCTGCCCGGC ACGGCCCGTG    4080

GCTGTTGACG CACCTGTGGT TGTTAGTGGG GCCTGAGGTC ATCGGCGTGG CCCAAGGCCG    4140

GCAGGTCAAC CTCGCGCTTG CTGGCCAGTC CACCCTGCCT GCCGTCTGTG CTTCCTCCTG    4200

CCCAGAACGC CGCTCCAGCG TACTCTCCAC TGTGCTTTCA GAAGTGCCCT TCCTGCTGNG    4260

CAGTTCTCCC ATCCTGGACG GCGGCAGTAT TGAAGCTCGT GACAAGTGCC TTCACACAGA    4320

CCCCTCGCAA CTGTCCACGC GTGCCGTGGC ACCAGGCGCT GCCCACCTGC CGGCCCCGGC    4380

CGCCCCTCCT CGTGAAAGTG CATTTTTGTA AATGTGTACA TATTAAAGGA AGCACTCTGT    4440

ATAAAAAAAA AAAACCGGAA TTCC                                          4464
```

FIG.10D

| | | | | | |
|---|---|---|---|---|---|
| MINPEDRWKS | LHFSGHVAHL | ELQIRVRCDE | NYYSATCNKF | CRPRNDFFGH | 50 |
| YTCDQYGNKA | CMDGWMGKEC | KEAVCKQGCN | LLHGGCTVPG | ECRCSYGWQG | 100 |
| RFCDECVPYP | GCVHGSCVEP | WQCNCETNWG | GLLCDKDLNY | CGSHHPCTNG | 150 |
| GTCINAEPDQ | YRCTCPDGYS | GRNCEKAEHA | CTSNPCANGG | SCHEVPSGFE | 200 |
| CHCPSGWSGP | TCALDIDECA | SNPCAAGGTC | VDQVDGFECI | CPEQWVGATC | 250 |
| QLDANECEGK | PCLNAFSCKN | LIGGYYCDCI | PGWKGINCHI | NVNDCRGQCQ | 300 |
| HGGTCKDLVN | GYQCVCPRGF | GGRHCELERD | KCASSPCHSG | GLCEDLADGF | 350 |
| HCHCPQGFSG | PLCEVDVDLC | EPSPCRNGAR | CYNLEGDYYC | ACPDDFGGKN | 400 |
| CSVHREPCPG | GACRVIDGCG | SDAGPGMPGT | AASGVCGPHG | RCVSQPGGNF | 450 |
| SCICDSGFTG | TYCHENIDDC | LGQPCRNGGT | CIDEVDAFRC | FCPSGWEGEL | 500 |
| CDTNPNDCLP | DPCHSRGRCY | DLVNDFYCAC | DDGWKGKTCH | SREFQCDAYT | 550 |
| CSNGGTCYDS | GDTFRCACPP | GWKGSTCAVA | KNSSCLPNPC | VNGGTCVGSG | 600 |
| ASFSCICRDG | WEGRTCTHNT | NDCNPLPCYN | GGICVDGVNW | FRCECAPGFA | 650 |
| GPDCRINIDE | CQSSPCAYGA | TCVDEINGYR | CSCPPGRAGP | RCQEVIGFGR | 700 |
| SCWSRGTPFP | HGSSWVEDCN | SCRCLDGRRD | CSKVWCGWKP | CLLAGQPEAL | 750 |
| SAQCPLGQRC | LEKAPGQCLR | PPCEAWGECG | AEEPPSTPCL | PRSGHLDNNC | 800 |
| ARLTLHFNRD | HVPQGTTVGA | ICSGIRSLPA | TRAVARDRLL | VLLCDRASSG | 850 |
| ASAVEVAVSF | SPARDLPDSS | LIQDAAHAIV | AAITQRGNSS | LLLAVTEVKV | 900 |
| ETVVTGGSST | GLLVPVLCGA | FSVLWLACVV | LCVWWTQAQE | RAGEEPAAAG | 950 |
| GERQQPVGPA | QPHPQPHHAA | GGTRTCSTSA | RTSSRRRAGR | GLPPRRHHHG | 1000 |
| RMRRTGSGPP | PGGLLEAAKF | LSHKFTKDPG | RSPGGHCCG | QSGQPPPQEH | 1050 |
| QQGPLLARSR | RRAAG | | | | 1065 |

FIG.10E

```
CAGGTGGCGTCAGCATCGGGACAGTTCGAGCTGGAGATCTTATCCGTGCAGAATGTGAACGGCGTGCT
GCAGAACGGGAACTGCTGCGACGGCACTCGAAACCCCGGAGATAAAAAGTGCACCAGAGATGAGTGTG
ACACCTACTTTAAAGTTTGCCTGAAGGAGTACCAGTCGCGGGTCACTGCTGGCGGCCCTTGCAGCTTC
GGATCCAAATCCACCCCTGTCATCGGCGGGAATACCTTCAATTTAAAGTACAGCCGGAATAATGAAAA
GAACCGGATTGTTATCCCTTTCACGTTCGCCTGGCCGAGATCCTACACGTTGCTTGTTGAGGCATGGG
ATTACAATGATAACTCTACTAATCCCGATCGCATAATTGAGAAGGCATCCCACTCTGGCATGATCAAT
CCAAGCCGTCAGTGGCAGACGTTGAAACATAACACAGGAGCTGCCCACTTTGAGTATCAAATCCGTGT
GACTTGCGCAGAACATTACTATGGCTTTGGATGCAACAAGTTTTGTCGACCGAGAGATGACTTCTTCA
CTCACCATACCTGTGACCAGAATGGCAACAAAACCTGCTTGGAAGGCTGGACGGGACCAGAATGCAAC
AAAGCTATTTGTCGTCAGGGATGTAGCCCCAAGCATGGTTCTTGCACAGTTCCAGGAGAGTGCAGGTG
TCAGTATGGATGGCAAGGCCAGTACTGTGATAAGTGCATTCCACACCCGGGATGTGTCCATGGCACTT
GCATTGAACCATGGCAGTGCCTCTGTGAAACCAACTGGGGTGGTCAGCTCTGTGACAAAGACCTGAAC
TACTGTGGAACCCACCCACCCTGTTTGAATGGTGGTACCTGCAGCAACACTGGCCCCGATAAATACCA
GTGTTCCTGCCCTGAGGGTTACTCAGGACAGAACTGTGAAATAGCGGAGCATGCGTGCCTCTCTGATC
CGTGCCACAACGGAGGAAGCTGCCTAGAAACGTCTACAGGATTTGAATGTGTGTGTGCACCTGGCTGG
GCTGGACCAACTTGCACTGATAATATTGATGATTGTTCTCCAAATCCCTGTGGTCATGGAGGAACTTG
CCAAGATCTAGTTGATGGATTTAAGTGTATTTGCCCACCTCAGTGGACTGGCAAAACATGCCAGCTAG
ATGCGAATGAATGTGAGGGCAAACCCTGTGTCAATGCCAACTCCTGCAGGAACTTGATTGGCAGCTAC
TATTGTGACTGCATTACTGGCTGGTCTGGCCACAACTGTGATATAAATATTAATGATTGTCGTGGACA
ATGTCAGAATGGAGGATCCTGTCGGGACTTGGTTAATGGTTATCGGTGCATCTGTTCACCTGGCTATG
CAGGAGATCACTGTGAGAAAGACATCAATGAATGTGCAAGTAACCCTTGCATGAATGGGGGTCACTGC
CAGGATGAAATCAATGGATTCCAATGTCTGTGTCCTGCTGGTTTCTCAGGAAACCTCTGTCAGCTGGA
TATAGACTACTGTGAGCCAAACCCTTGCCAGAACGGTGCCCAGTGCTTCAATCTTGCTATGGACTATT
TCTGTAACTGCCCTGAAGATTACGAAGGCAAGAACTGCTCCCACCTGAAAGATCACTGCCGCACAACT
CCTTGTGAAGTAATCGACAGCTGTACAGTGGCAGTGGCTTCTAACAGCACACCAGAAGGAGTTCGTTA
CATTTCTTCAAATGTCTGTGGTCCTCATGGAAAATGCAAGAGCCAAGCAGGTGGAAAATTCACCTGTG
AATGCAACAAAGGATTCACTGGCACCTACTGTCATGAGAATATCAATGACTGTGAGAGCAACCCCTGT
AAAAATGGTGGCACTTGTATTGACGGTGTAAACTCCTACAAATGTATTTGTAGTGATGGATGGGAAGG
AACATATTGTGAAACAAATATTAATGACTGCAGTAAAAACCCCTGCCACAATGGAGGAACTTGCCGAG
ACTTGGTCAATGACTTCTTCTGTGAATGTAAAAATGGGTGGAAAGGAAAAACTTGCCACTCTCGTGAC
AGCCAGTGTGATGAGGCAACATGCAATAATGGAGGAACATGTTATGATGAGGGGGACACTTTCAAGTG
CATGTGTCCTGCAGGATGGGAAGGAGCCACTTGTAATATAGCAAGGAACAGCAGCTGCCTGCCAAACC
CCTGTCACAATGGTGGTACCTGTGTAGTTAGTGGGGATTCTTTCACTTGTGTCTGCAAGGAGGGCTGG
GAAGGACCGACATGTACTCAGAACACAAATGACTGCAGTCCTCATCCTTGTTACAACAGTGGTACTTG
TGTGGATGGAGACAACTGGTACCGCTGTGAGTGCGCTCCCGGCTTCGCAGGTCCCGACTGTAGGATCA
ACATCAATGAATGTCAGTCTTCACCCTGTGCCTTTGGGGCTACTTGTGTGGATGAAATTAATGGGTAC
CGTTGCATTTGTCCACCGGGTCGCAGTGGTCCAGGATGCCAGGAAGTTACAGGGAGGCCTTGCTTTAC
CAGTATTCGAGTAATGCCAGACGGTGCTAAGTGGGATGATGACTGTAATACTTGTCAGTGTTTGAATG
GAAAAGTCACCTGTTCTAAGGTTTGGTGTGGTCCTCGACCTTGTATAATACATGCCAAAGGTCATAAT
GAATGCCCAGCTGGACACGCTTGTGTTCCTGTTAAAGAAGACCATTGTTTCACTCATCCTTGTGCTGC
```

FIG. 11A

```
AGTGGGTGAATGCTGGCCTTCTAATCAGCAGCCTGTGAAGACCAAATGCAATTCTGATTCTTATTACC
AAGATAATTGTGCCAACATCACCTTCACCTTTAATAAGGAAATGATGGCACCAGGCCTTACCACGGAG
CACATTTGCAGTGAATTGAGGAATCTGAATATCCTGAAGAATGTTTCTGCTGAATATTCCATCTATAT
TACCTGTGAGCCTTCACACTTGGCAAATAATGAAATACATGTTGCTATTTCTGCTGAAGATATAGGAG
AAGATGAAAACCCAATCAAGGAAATCACAGATAAGATTATTGACCTTGTCAGTAAGCGTGATGGAAAC
AACACACTAATTGCTGCAGTCGCAGAAGTCAGAGTACAAAGGCGACCAGTTAAGAACAAAACAGATTT
CTTGGTGCCATTACTGAGCTCAGTCTTAACAGTAGCCTGGATCTGCTGTCTGGTAACTGTTTTCTATT
GGTGCATTCAAAAGCGCAGAAAGCAGAGCAGCCATACTCACACAGCATCTGATGACAACACCACCAAC
AACGTAAGGGAGCAGCTGAATCAGATTAAAAACCCCATAGAGAAACACGGAGCAAATACTGTTCCAAT
TAAAGACTATGAAAACAAAAACTCTAAAATCGCCAAAATAAGGACGCACAATTCAGAAGTGGAGGAAG
ATGACATGGACAAACACCAGCAAAAGGCCCGGTTTGCCAAGCAGCCAGCGTACACTTTGGTAGACAGA
GATGAAAAGCCACCCAACAGCACACCCACAAAACACCCAAACTGGACAAATAAACAGGACAACAGAGA
CTTGGAAAGTGCACAAAGTTTAAATAGAATGGAGTACATTGTATAG
```

FIG. 11B

```
QVASASGQFE LEILSVQNVN GVLQNGNCCD GTRNPGDKKC TRDECDTYFK   50
           ^
VCLKEYQSRV TAGGPCSFGS KSTPVIGGNT FNLKYSRNNE KNRIVIPFSF  100

AWPRSYTLLV EAWDYNDNST NPDRIIEKAS HSGMINPSRQ WQTLKHNTGA  150

AHFEYQIRVT CAEHYYGFGC NKFCRPRDDF FTEHTCDQNG NKTCLEGWTG  200
           *******************DSL DOMAIN***************
PECNKAICRQ GCSPKHGSCT VPGECRCQYG WQGQYCDKCI PHPGCVHGTC  250
***        <---------------EGF 1-------------><------------
IEPWQCLCET NWGGQLCDKD LNYCGTHPPC LNGGTCSNTG PDKYQCSCPE  300
-----EGF 2----------------><-------------------EGF 3----
GYSGQNCEIA EHACLSDPCH NGGSCLETST GFECVCAPGW AGPTCTDNID  350
-------------><-------------------EGF 4----------------
DCSPNPCGHG GTCQDLVDGF KCICPPQWTG KTCQLDANEC EGKPCVNANS  400
><----------------------EFG 5----------------><----------
CRNLIGSYYC DCITGWSGHN CDININDCRG QCQNGGSCRD LVNGYRCICS  450
-------EFG 6----------------><-----------------EFG 7---
PGYAGDHCEK DINECASNPC MNGGHCQDEI NGFQCLCPAG FSGNLCQLDI  500
--------------><-------------------EFG 8---------------
DYCEPNPCQN GAQCFNLAMD YFCNCPEDYE GKNCSHLKDH CRTTPCEVID  550
-><------------------EFG 9------------------><---------
SCTVAVASNS TPEGVRYISS NVCGPHGKCK SQAGGKFTCE CNKGFTGTYC  600
---------------------EFG 10-----------------------
HENINDCESN PCKNGGTCID GVNSYKCICS DGWEGTYCET NINDCSKNPC  650
------><-------------------EFG 11----------------><-----
HNGGTCRDLV NDFFCECKNG WKGKTCHSRD SQCDEATCNN GGTCYDEGDT  700
--------------EFG 12------------------><---------------
FKCMCPAGWE GATCNIARNS SCLPNPCHNG GTCVVSGDSF TCVCKEGWEG  750
EGF 13-------------------><-----------------EGF 14-------
PTCTQNTNDC SPHPCYNSGT CVDGDNWYRC ECAPGFAGPD CRININECQS  800
---------><-------------------EGF 15----------------><--
SPCAFGATCV DEINGYRCIC PPGRSGPGCQ EVTGRPCFTS IRVMPDGAKW  850
-----------------EGF 16----------------->
DDDCNTCQCL NGKVTCSKVW CGPRPCIIHA KGHNECPAGH ACVPVKEDHC  900
         <-                            CYSTEINE-RICH REGION
FTHPCAAVGE CWPSNQQPVK TKCNSDSYYQ DNCANITFTF NKEMMAPGLT  950
              ->
TEHICSELRN LNILKNVSAE YSIYITCEPS HLANNEIHVA ISAEDIGEDE 1000
```

FIG. 12A

```
NPIKEITDKI IDLVSKRDGN NTLIAAVAEV RVQRRPVKNK TDFLVPLLSS 1050

VLTVAWICCL VTVFYWCIQK RRKQSSHTHT ASDDNTTNNV REQLNQIKNP 1100

IEKHGANTVP IKDYENKNSK IAKIRTHNSE VEEDDMDKHQ QKARFAKQPA 1150

YTLVDRDEKP PNSTPTKHPN WTNKQDNRDL ESAQSLNRME YIV        1193
```

FIG. 12B

```
DmDelta   SGSFELRLKY  FSNDHGRDNE  GRCCS-GESD  GATGKCL-GS  CKTRFRLCLK    48
CSer      SGQFELEILS  VQNVNGVLQN  GNCCD-GTRN  PGDKKCTRDE  CDTYFKVCLK    49
DmSer     AGNFELEILE  ISNTNSHLLN  GYCCGMPAEL  RATKTIGCSP  CTTAFRLCLK    50

DmDelta   HYQATIDTTS  QCTYGDVITP  ILGENSVNLT  DAQRFQNKGF  TNPIQFPFSP    98
CSer      EYQSRVTAGG  PCSFGSKSTP  VIGGNTFNL-  ——KYSRNNE   KNRIVIPFSF    95
DmSer     EYQTTEQGAS  ISTGCSFGNA  TTKILGGSS-  ——FVLSDPG   VGAIVLPFTF    96

DmDelta   SWPGTFSLIV  EAWHDTNNSG  NARTNKLLIQ  RLLVQQVLEV  SSEWKTNKSE   148
CSer      AWPRSYTLLV  EAWDYNDNS-  -TNPDR-IIE  KASHSGMINP  SRQWQTLKHN   142
DmSer     RWTKSFTLIL  QALDMYNTS-  YPDAER-LIE  ETSYSGVILP  SPEWKTLDHI   144

DmDelta   SQYTSLEYDF  RVTCDLNYYG  SGCAKFCRPR  DDSFGHSTCS  ETGEIICLTG   198
CSer      TGAAHFEYQI  RVTCAEHYYG  FGCNKFCRPR  DDFFTHHTCD  QNGNKTCLEG   192
DmSer     GRNARITYRV  RVQCAVTYYN  TTCTTFCRPR  DDQFGHYACG  SEGQKLCLNG   194
                                              ========== D S L DOMAIN ===

DmDelta   WQGDYC                                                       204
CSer      WTGPEC                                                       198
DmSer     WQGVNC                                                       200
          ======
```

FIG.13

NUCLEOTIDE AND PROTEIN SEQUENCES OF THE SERRATE GENE AND METHODS BASED THEREON

This application is a continuation-in-part of application Ser. No. 08/255,102 filed Jun. 7, 1994, now abandoned, which is a continuation of application Ser. No. 08/121,979 filed Sep. 14, 1993, now abandoned, which is a continuation of Ser. No. 07/808,458 filed Dec. 11, 1991, now abandoned, each of which is incorporated by reference herein in its entirety.

This invention was made in part with government support under Grant numbers GM 29093 and NS 26084 awarded by the Department of Health and Human Services. The government has certain rights in the invention.

1. INTRODUCTION

The present invention relates to Serrate genes and their encoded protein products, as well as derivatives and analogs thereof. Production of Serrate proteins, derivatives, and antibodies is also provided. The invention further relates to therapeutic compositions and methods of diagnosis and therapy.

2. BACKGROUND OF THE INVENTION

Genetic analyses in Drosophila have been extremely useful in dissecting the complexity of developmental pathways and identifying interacting loci. However, understanding the precise nature of the processes that underlie genetic interactions requires a knowledge of the protein products of the genes in question.

Embryological, genetic and molecular evidence indicates that the early steps of ectodermal differentiation in Drosophila depend on cell interactions (Doe and Goodman, 1985, Dev. Biol. 111:206–219; Technau and Campos-Ortega, 1986, Dev. Biol. 195:445–454; Vassin et al., 1985, J. Neurogenet. 2:291–308; de la Concha et al., 1988, Genetics 118:499–508; Xu et al., 1990, Genes Dev. 4:464–475; Artavanis-Tsakonas, 1988, Trends Genet. 4:95–100). Mutational analyses reveal a small group of zygotically-acting genes, the so called neurogenic loci, which affect the choice of ectodermal cells between epidermal and neural pathways (Poulson, 1937, Proc. Natl. Acad. Sci. 23:133–137; Lehmann et al., 1983, Wilhelm Roux's Arch. Dev. Biol. 192:62–74; Jürgens et al., 1984, Wilhelm Roux's Arch. Dev. Biol. 193:283–295; Wieschaus et al., 1984, Wilhelm Roux's Arch. Dev. Biol. 193:296–307; Nusslein-Volhard et al., 1984, Wilhelm Roux's Arch. Dev. Biol. 193:267–282). Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate. Serrate has been identified as a genetic unit capable of interacting with the Notch locus (Xu et al., 1990, Genes Dev. 4:464–475). These genetic and developmental observations have led to the hypothesis that the protein products of the neurogenic loci function as components of a cellular interaction mechanism necessary for proper epidermal development (Artavanis-Tsakonas, S., 1988, Trends Genet. 4:95–100).

Mutational analyses also reveal that the action of the neurogenic genes is pleiotropic and is not limited solely to embryogenesis. For example, ommatidial, bristle and wing formation, which are known also to depend upon cell interactions, are affected by neurogenic mutations (Morgan et al., 1925, Bibliogr. Genet. 2:1–226; Welshons, 1956, Dros. Inf. Serv. 30:157–158; Preiss et al., 1988, EMBO J. 7:3917–3927; Shellenbarger and Mohler, 1978, Dev. Biol. 62:432–446; Technau and Campos-Ortega, 1986, Wilhelm Roux's Dev. Biol. 35 195:445–454; Tomlison and Ready, 1987, Dev. Biol. 120:366–376; Cagan and Ready, 1989, Genes Dev. 3:1099–1112).

Sequence analyses (Wharton et al., 1985, Cell 43:567–581; Kidd and Young, 1986, Mol. Cell. Biol. 6:3094–3108; Vassin, et al., 1987, EMBO J. 6:3431–3440; Kopczynski, et al., 1988, Genes Dev. 2:1723–1735) have shown that two of the neurogenic loci, Notch and Delta, appear to encode transmembrane proteins that span the membrane a single time. The Notch gene encodes a -300 kd protein (we use "Notch" to denote this protein) with a large N-terminal extracellular domain that includes 36 epidermal growth factor (EGF)-like tandem repeats followed by three other cysteine-rich repeats, designated Notch/lin-12 repeats (Wharton, et al., 1985, Cell 43:567–581; Kidd and Young, 1986, Mol. Cell. Biol. 6:3094–3108; Yochem, et al., 1988, Nature 335:547–550). Delta encodes a ~100 kd protein (we use "Delta" to denote DLZM, the protein product of the predominant zygotic and maternal transcripts; Kopczynski, et al., 1988, Genes Dev. 2:1723–1735) that has nine EGF-like repeats within its extracellular domain (Vässin, et al., 1987, EMBO J. 6:3431–3440; Kopczynski, et al., 1988, Genes Dev. 2:1723–1735). Molecular studies have lead to the suggestion that Notch and Delta constitute biochemically interacting elements of a cell communication mechanism involved in early developmental decisions (Fehon et al., 1990, Cell 61:523–534).

The EGF-like motif has been found in a variety of proteins, including those involved in the blood clotting cascade (Furie and Furie, 1988, Cell 53: 505–518). In particular, this motif has been found in extracellular proteins such as the blood clotting factors IX and X (Rees et al., 1988, EMBO J. 7:2053–2061; Furie and Furie, 1988, Cell 30 53: 505–518), in other Drosophila genes (Knust et al., 1987 EMBO J. 761–766; Rothberg et al., 1988, Cell 55:1047–1059), and in some cell-surface receptor proteins, such as thrombomodulin (Suzuki et al., 1987, EMBO J. 6:1891–1897) and LDL receptor (Sudhof et al., 1985, Science 228:815–822). A protein binding site has been mapped to the EGF repeat domain in thrombomodulin and urokinase (Kurosawa et al., 1988, J. Biol. Chem 263:5993–5996; Appella et al., 1987, J. Biol. Chem. 262:4437–4440).

Citation of references hereinabove shall not be construed as an admission that such references are prior art to the present invention.

3. SUMMARY OF THE INVENTION

The present invention relates to nucleotide sequences of Serrate genes (Drosophila Serrate and related genes of other species), and amino acid sequences of their encoded proteins, as well as derivatives (e.g., fragments) and analogs thereof. Nucleic acids hybridizable to or complementary to the foregoing nucleotide sequences are also provided. In a specific embodiment, the Serrate protein is a human protein.

The invention relates to Serrate derivatives and analogs of the invention which are functionally active, i.e., they are capable of displaying one or more known functional activities associated with a full-length (wild-type) Serrate protein. Such functional activities include but are not limited to antigenicity [ability to bind (or compete with Serrate for binding) to an anti-Serrate antibody], immunogenicity (ability to generate antibody which binds to Serrate), ability to bind (or compete with Serrate for binding) to Notch or other toporythmic proteins or fragments thereof ("adhesiveness"), ability to bind (or compete with Serrate for binding) to a receptor for Serrate. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Serrate which comprise one or more domains of the Serrate protein, including but not limited to the intracellular domain, extracellular domain, transmembrane domain, membrane-associated region, or one or more EGF-like (homologous) repeats of a Serrate protein, or any combination of the foregoing.

Antibodies to Serrate, its derivatives and analogs, are additionally provided.

Methods of production of the Serrate proteins, derivatives and analogs, e.g., by recombinant means, are also provided.

The present invention also relates to therapeutic and diagnostic methods and compositions based on Serrate proteins and nucleic acids. The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof; antibodies thereto; nucleic acids encoding the Serrate proteins, analogs, or derivatives; and Serrate antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch and/or Serrate function (hereinafter "Antagonist Therapeutics") are administered for therapeutic effect. In another embodiment, Therapeutics which promote Notch and/or Serrate function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Serrate protein can be diagnosed by detecting such levels, as described more fully infra.

In a preferred aspect, a Therapeutic of the invention is a protein consisting of at least a fragment (termed herein "adhesive fragment") of Serrate which mediates binding to a Notch protein or a fragment thereof.

3.1. DEFINITIONS

As used herein, underscoring or italicizing the name of a gene shall indicate the gene, in contrast to its encoded protein product which is indicated by the name of the gene in the absence of any underscoring. For example, "Serrate" shall mean the Serrate gene, whereas "Serrate" shall indicate the protein product of the Serrate gene.

4. DESCRIPTION OF THE FIGURES

FIGS. 1A–1F. Phenotypic interactions between Notch and Serrate. (a) $w^a$ spl wing blade showing characteristic wild-type symmetry, venation, and marginal wing bristles and hairs. (b) nd/Y male. Distal wing notches and loss of posterior hairs are evident. (c) $Ser^D/+$ heterozygote. Note similarity to nd/Y wing blade in FIG. 1b. (d) nd/Y; $Ser^D/+$ transheterozygote wing blade. Mutant wing shows typical "fig leaf" shape, distorted wing veins, and loss of the majority of marginal bristles and hairs, with the exception of the anterodistal wing margin. (e) +/Y; $Ser^D/Dp(3R)$ CosP479BE (N$^+$) male. The extra N$^+$ copy suppresses the heterozygous $Ser^D$ dominant phenotype (compare to FIG. 1c). Also note suppression of the Confluens phenotype (see text). (f) $Ser^D/Ser^D$ homozygote. Note the increased severity of the phenotype relative to $Ser^D/+$(compare to FIG. 1c).

Figure 2:
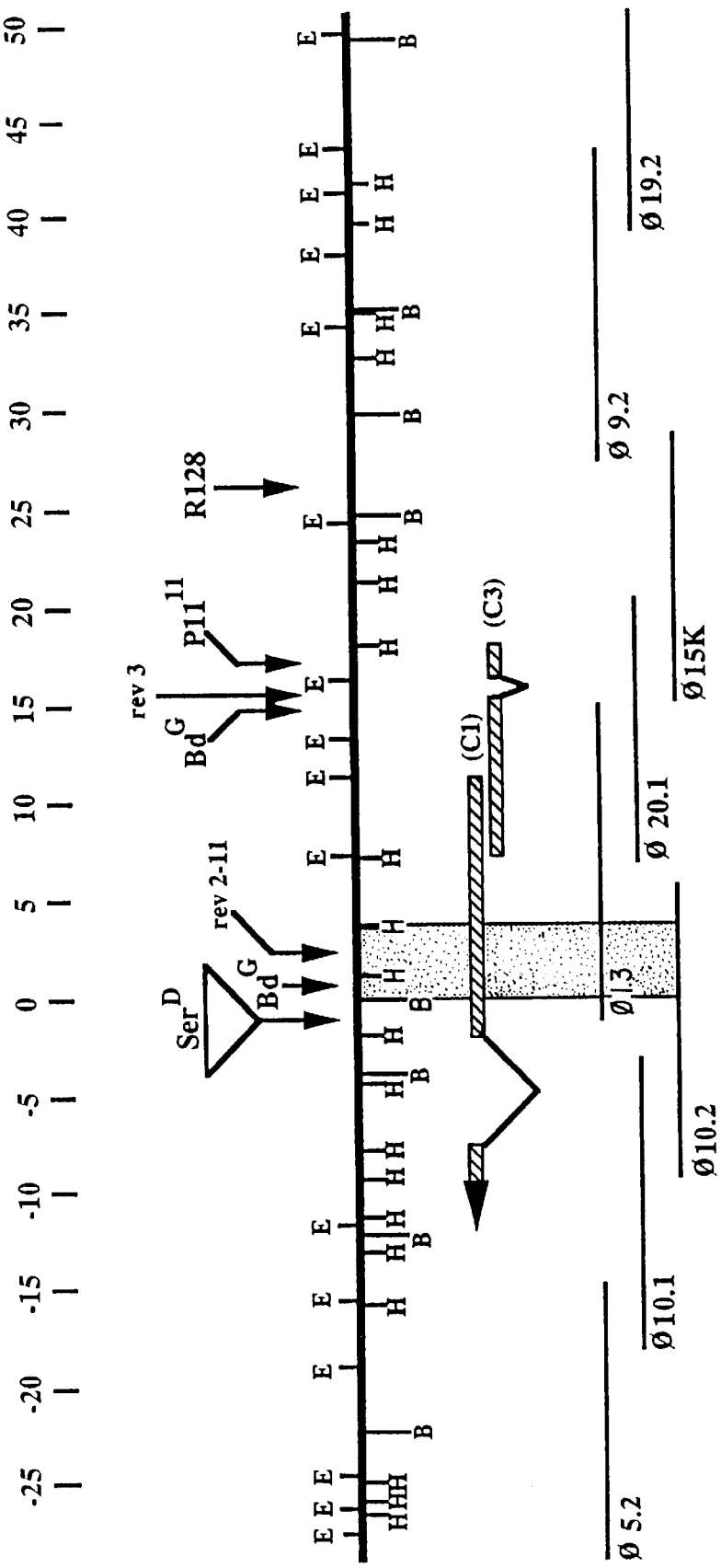

FIG. 2. Molecular map of the Serrate-encoding region. Approximately 85 kb of cloned genomic DNA from the 97 F chromosomal region are presented along with the restriction sites of three enzymes [(B) BamHI; (E) EcoRI; (H) HindIII]. The locations of individual DNA alterations associated with Serrate allelic breakpoints are displayed above the genomic DNA (for descriptions of mutant alleles, see Section 6, infra; (rev 3 and rev 2–11) $Ser^{rev\ 3}$ and $Ser^{2-11}$, respectively; (R128) T(Y:3)R128. The shaded box from coordinates 0 to +3 represents the region of EGF homology detectable by Southern hybridization. The BamHI site adjacent to the EGF homology was arbitrarily chosen as position 0. Map orientation is with the centromere to the left. At the bottom of the figure are shown the individual recombinant phage isolates. The C1 and C3 cDNAs together constitute the larger of the two Serrate messages (~5.6 kb). Intron positions and coding capacities have been approximated solely upon cross hybridization of the cDNAs with the genomic DNA regions.

Figure 3A:
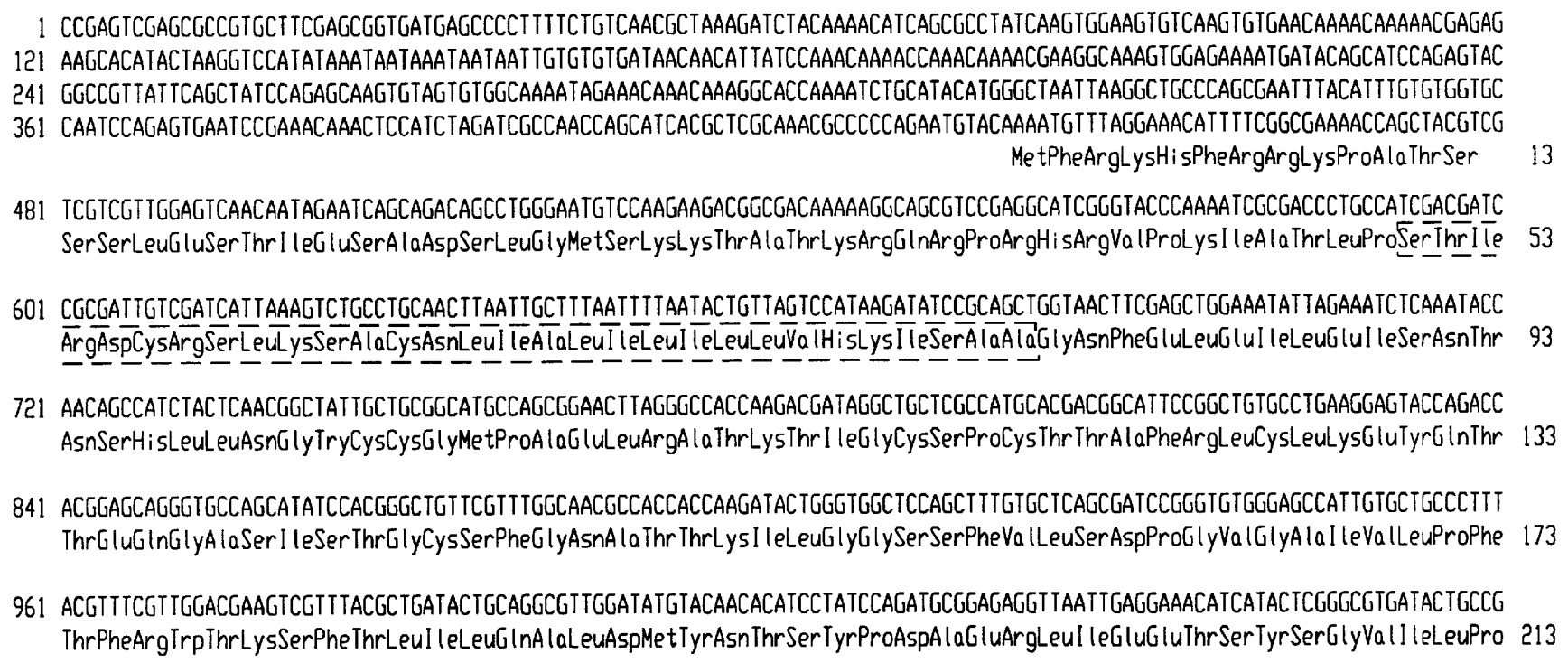
Figure 3B:
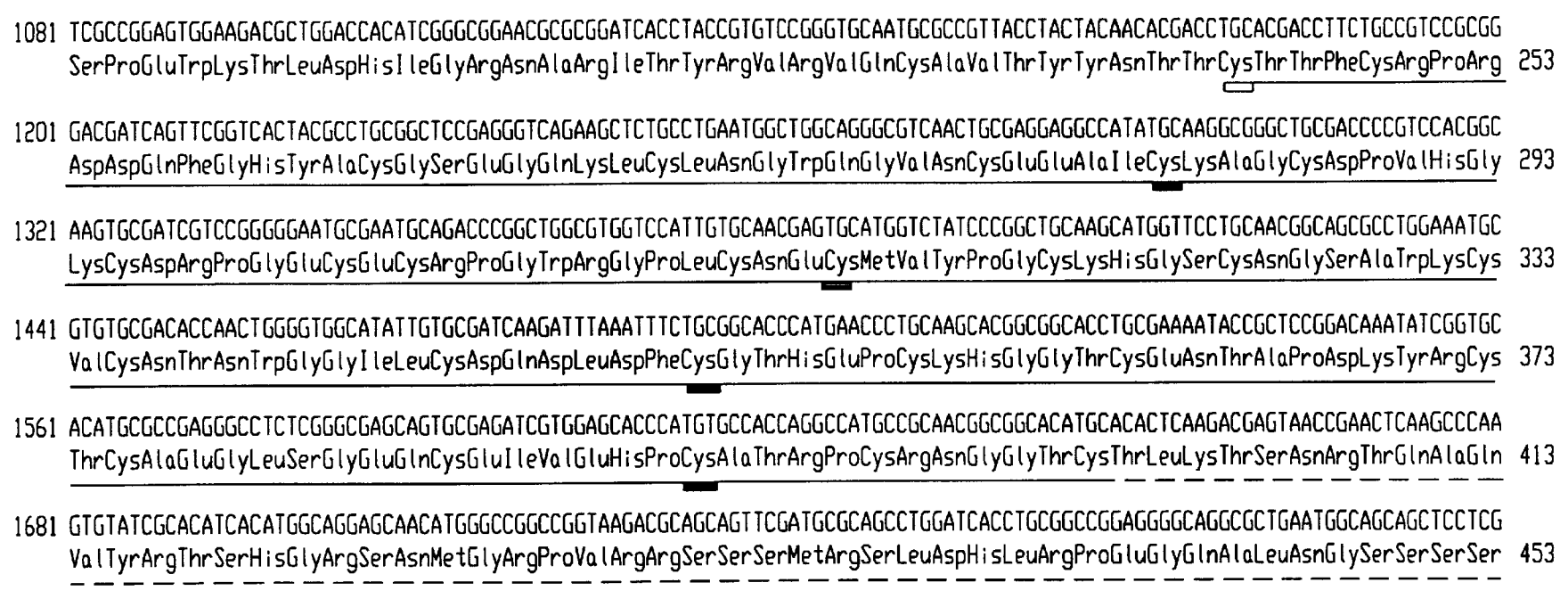
Figure 3C:
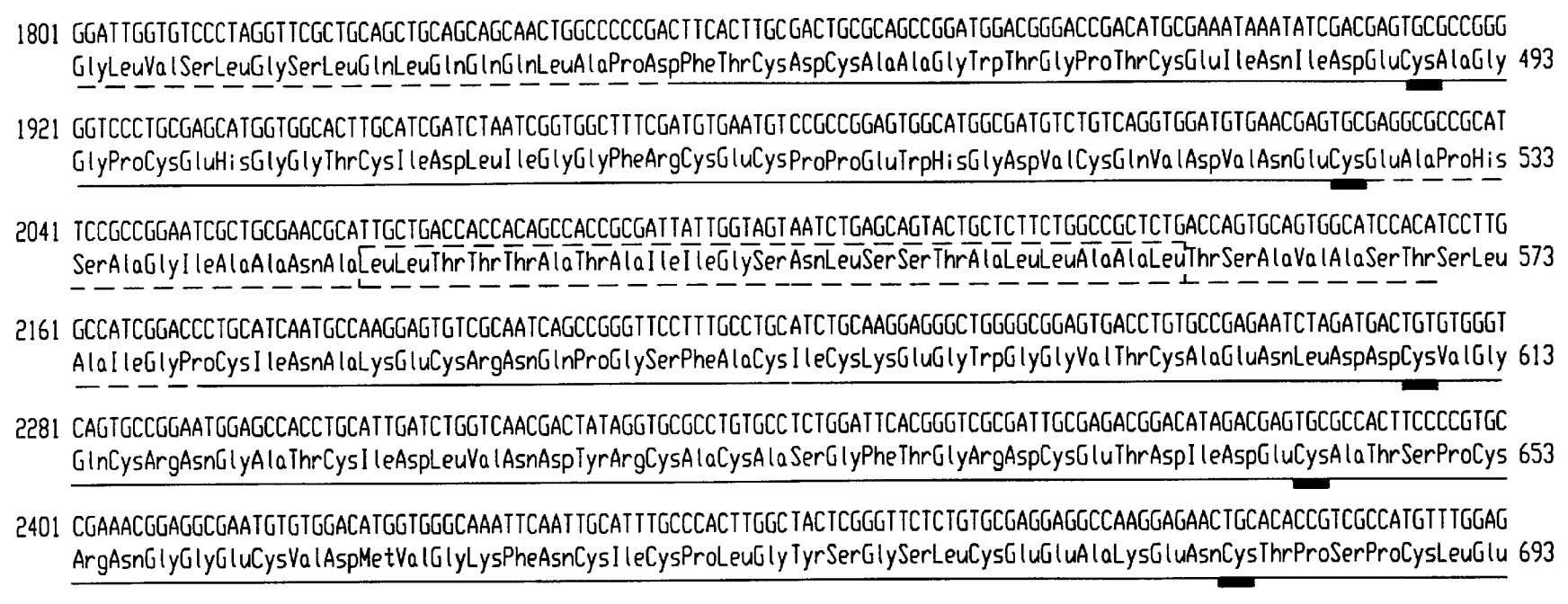
Figure 3E:
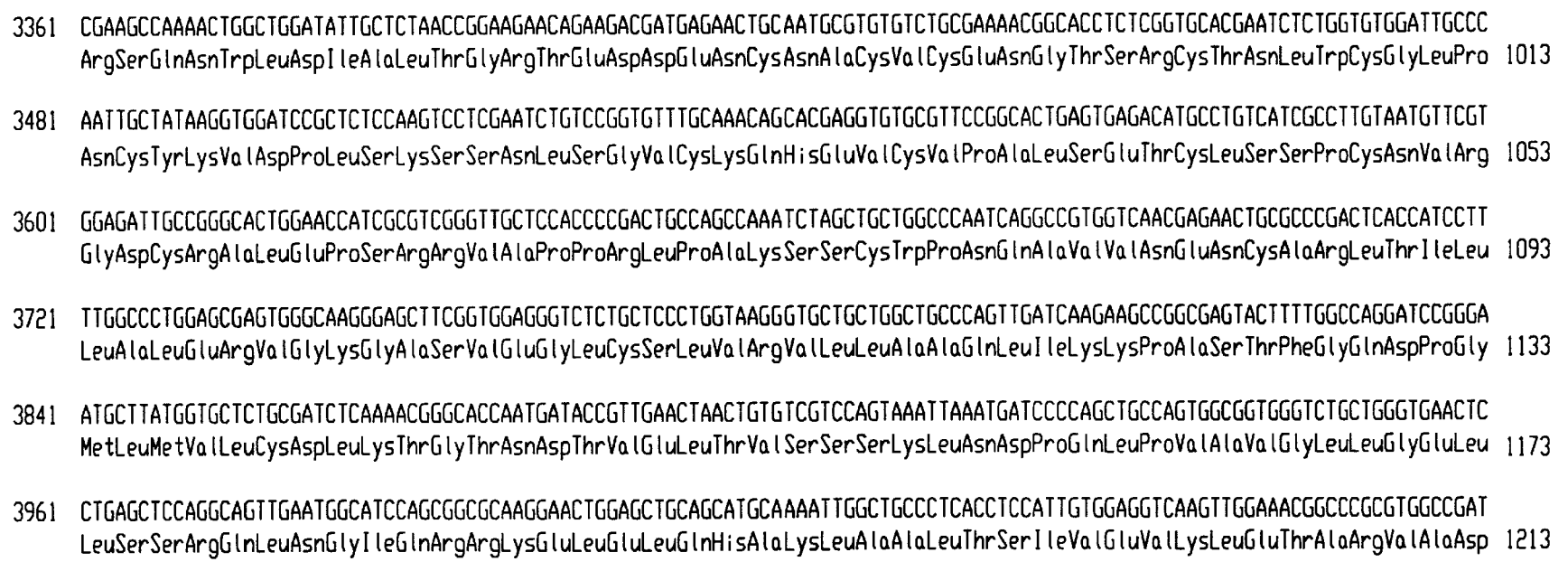
Figure 3F:
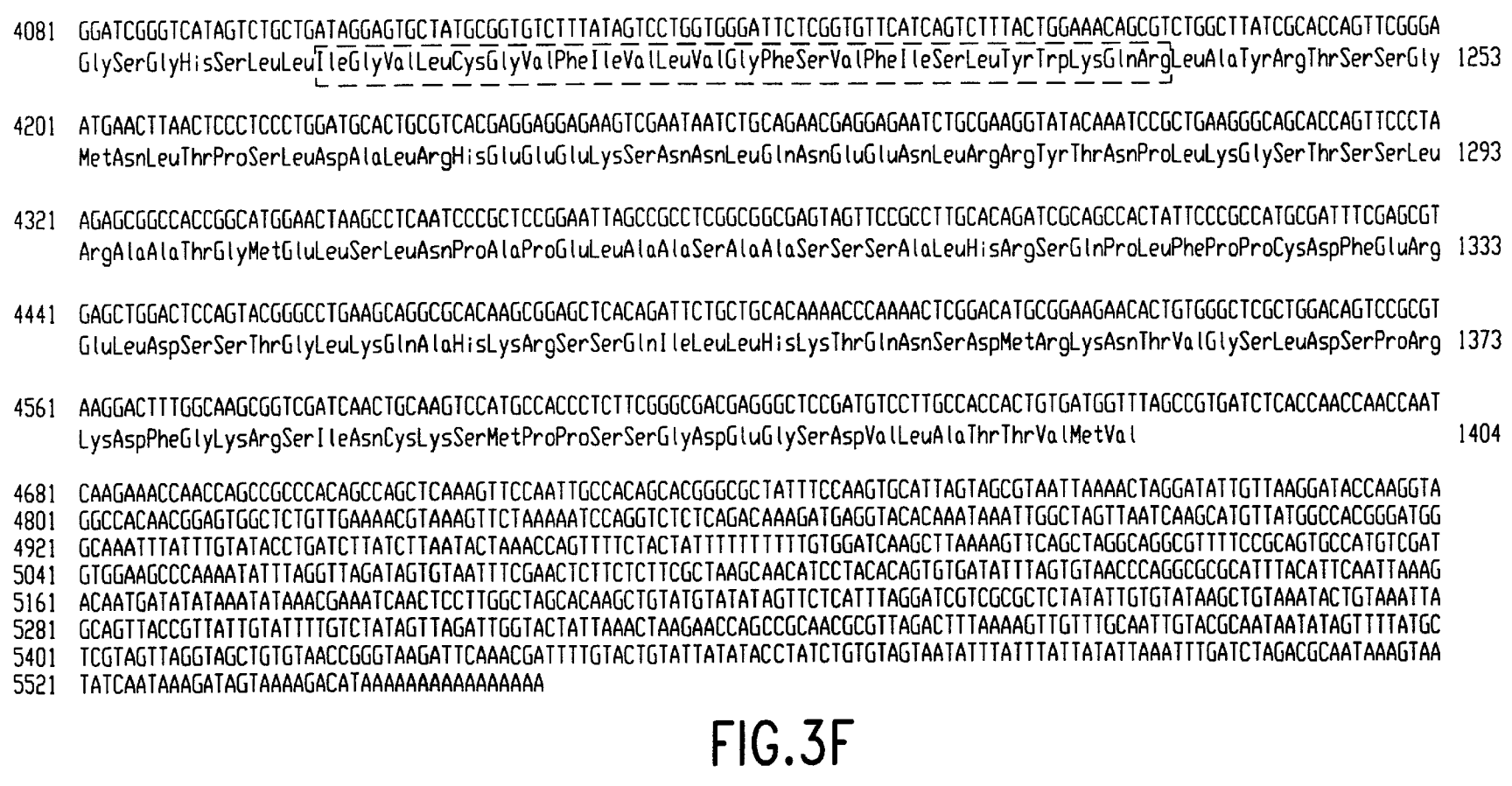

FIGS. 3A–3F. Serrate sequence analysis. The complete 5561 bp sequence (SEQ ID NO:1) derived from cDNAs C1 and C3 is shown. Nucleotide numbering is at left, amino acid numbering of the predicted open reading frame (ORF) is at right. The deduced protein product appears to be a transmembrane protein of 1404 amino acids (SEQ ID NO:2). Hydrophobic regions are denoted inside dashed boxes; amino acids 51 to 80 represent the likely signal peptide; amino acids 542 to 564 represent the potential membrane associated region; amino acids 1221 to 1245 represent the putative transmembrane domain. The first cysteine of each of the fourteen EGF-like repeats is denoted with a solid black box, and each repeat is underlined. The partial EGF-like repeat is considered "degenerate," since the fourth cysteine residue of this repeat has been changed to lysine (shown in boldface type at amino acid position 268). The initial cysteine of this repeat is denoted with an open box (amino acid 284), and the repeat is underlined. Amino acid insertions occur in the fourth, sixth, and tenth EGF-like repeats and are denoted by hatched underlines.

Figure 4A:
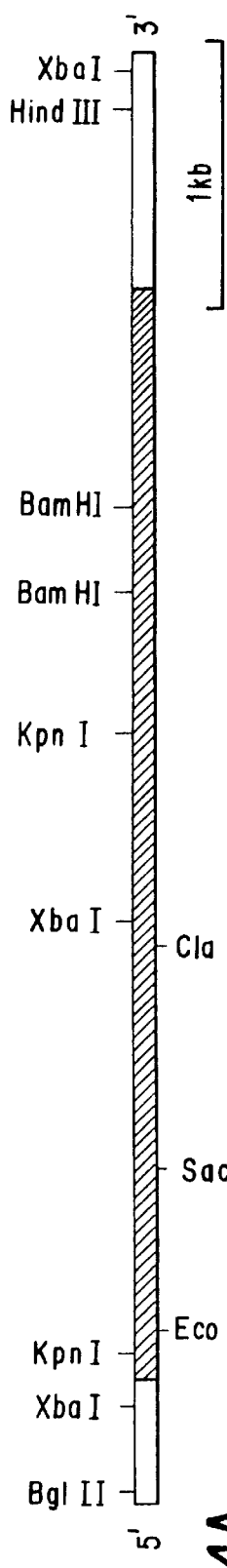
Figure 4B:
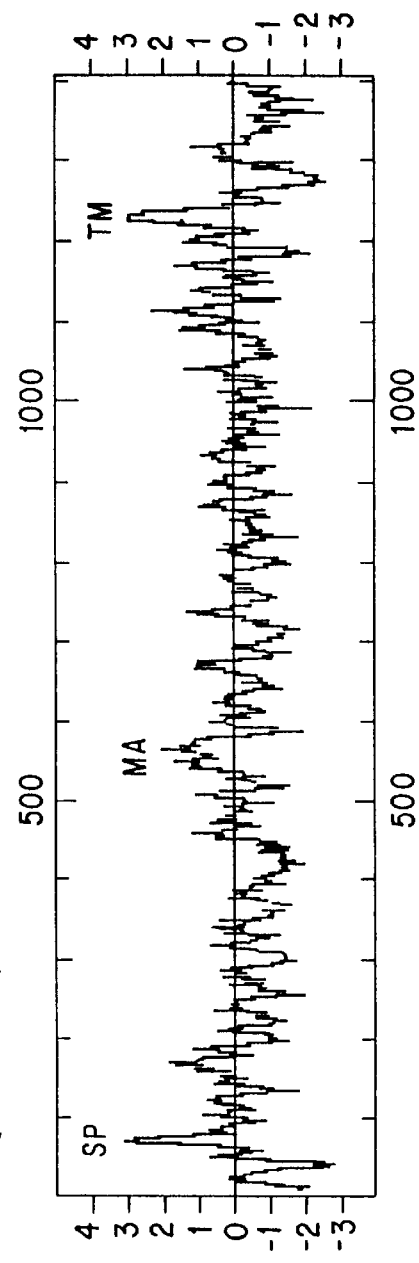
Figure 4C:
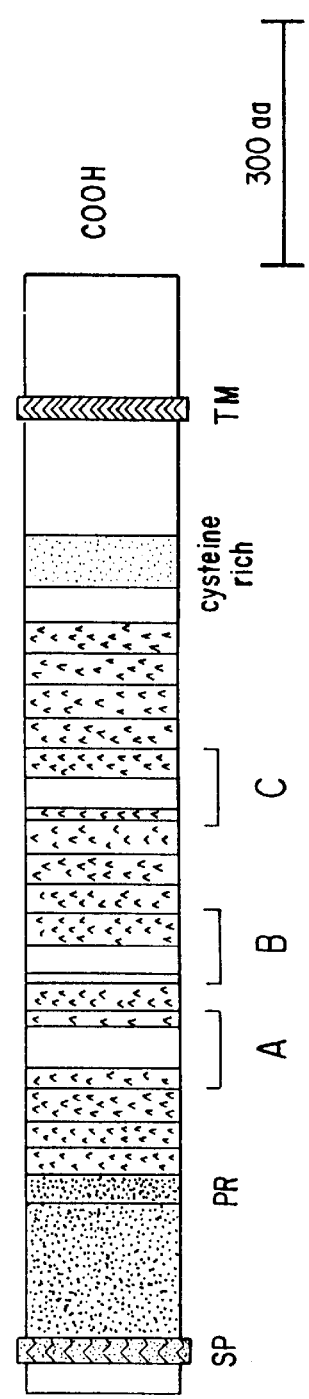

FIGS. 4A–4C. The Serrate transcript and deduced protein product. (a) The composite transcript shown was constructed from the C1 and C3 cDNAs, which overlap by 109 bp. Selected restriction enzyme cleavage sites are shown. The hatched box represents the 4212 bp ORF. Open boxes represent the 442 bp 5'-untranslated leader and 900 bp 3'-trailer sequence. (b) Kyte-Doolittle hydropathy plot of the deduced 1404 amino acid protein. (SP) Putative signal peptide; (MA) potential membrane associated region; (TM) likely transmembrane domain. (c) Cartoon representation of the gross structural features of the predicted Serrate protein. The darkly shaded region, including the partial EGF-like repeat (PR) is ~250 amino acids in length and homologous to the Delta protein. Bracketed EGF-like repeats labelled (A, B, and C) contain insertions of amino acids and thus differ from the canonical EGF-like structure. Other features of the protein include the signal peptide (SP), a cysteine rich region, a transmembrane domain (TM), and an intracellular region of ~160 amino acids.

Figure 5:
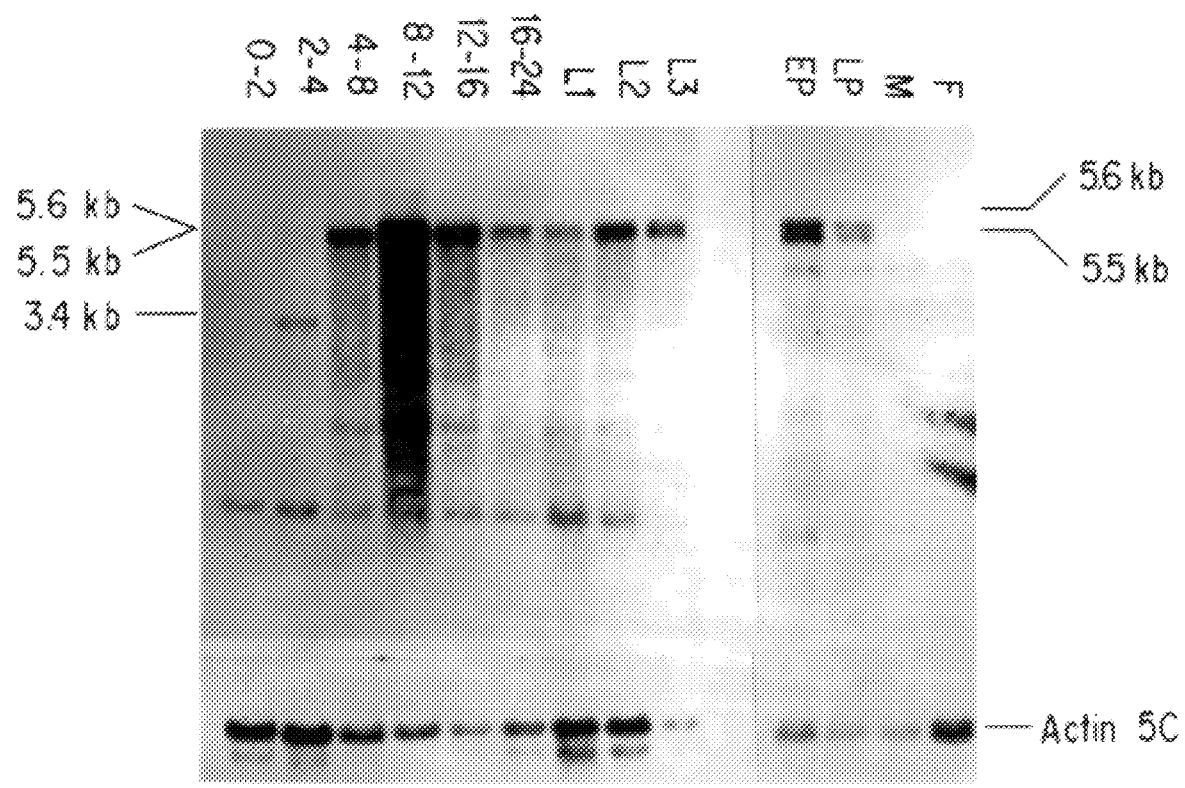

FIG. 5. Temporal profile of Serrate transcript accumulation. Each lane contains five μg of poly(A)⁺ RNA. The stage of the embryonic RNAs is denoted in hours after egg laying; (L1, L2, and L3) RNA from the first, second and third larval instar periods; (EP and LP) early and late pupal stages; (M and F) adult male and female RNAs, respectively. A composite cDNA subclone (constructed from C1 and C3) was used as a hybridization probe. Serrate transcription is represented primarily as a 5.5 kb and 5.6 kb doublet beginning at 4–8 hours of embryogenesis. A transient 3.4 kb transcript is observed only during 2–4 hr of embryogenesis. The pupal and adult RNAs were fractionated on a separate gel for a longer period of time for better resolution. Equivalent loadings of RNA were noted by ethidium bromide staining of the RNA gels and confirmed by subsequent probing with an actin 5C probe shown at bottom; Fyrberg et al., 1983, Cell 33:115–123). Minor bands were not consistently observed in other blots and may reflect other EGF-homologous transcripts FIGS. 6A–6L. Whole-mount in situ Serrate transcripts. Embryos are oriented with anterior to the left and dorsal side up unless otherwise noted. (a) Dorsal view of an early stage 10 embryo (mid-dorsal focal plane). Earliest expression occurs in the ectoderm of the foregut (FG) and presumptive clypeolabrum (CL). (b) Dorsal view of a germ band-extended embryo (late stage 10). Additional expression occurs near the proctodeum (PR), within the eighth (A8) and ninth (A9) abdominal segments, and in the labial and maxillary primordia (arrow). (c) Lateral view of an early stage 11 embryo. The lateral (LE) and ventral (VE) expression patterns are out of register and do not include the tracheal pits (TP). (d) Germ band-extended embryo (mid stage 11) dissected and flattened such that the dorsal surfaces are at the lateral edges. Extensive expression is observed between the labial (LB), maxillary (MX), and mandibular (MN) lobes, and within the hypopharynx (HP) and clypeolabrum (CL). Expression is also apparent in the salivary gland placodes (SP) that have moved to the ventral midline. Note relationship between lateral and ventral patterns and elaboration of expression in the tail region [presumptive telson (TL)]. (e) Germ band-retracting embryo (stage 12; lateral view). Lateral expression (LE) is beginning to coalesce. (f) Lateral view of a germ band-retracted embryo (stage 13). The lateral expression is beginning to extend both dorsally and ventrally in each thoracic and abdominal segment and is most pronounced in the first thoracic segment (T1). A portion of the lateral expression now appears to include the presumptive trachea (T). Ventrally, note different expression (VE) patterns in the thoracic versus abdominal segments. (g) Lateral view of an early stage 14 embryo. Outline of the presumptive trachea (T) is distinct from the overlying epidermal expression. Arrows denote the zigzag pattern of lateral expression. (h) Dissected embryo (stage 14) opened along the dorsal midline and laid flat. Two areas of hindgut expression (HG1 and HG2) are apparent; HGI occurs near the origin of the Malpighian tubules. (i) Ventral view of a stage-16 embryo focusing on the ventral nerve cord (VNC). Earlier expression in the salivary gland placodes (SP in panel d) now constitutes the SD. Expression in the proventriculus (PV) and the maxillary/mandibular region (MX/MN) is slightly out of focus. (j) Dorsomedial focal plane of same embryo as in (i); head involution is nearly complete. The in-pocketings of expression in the thoracic segments (T1, T2, and T3) may represent imaginal disc primordia. Pharyngeal expression (PH) is a combination of clypeolabrum and hypopharyngeal expression noted earlier. (k) Dorsal view of the same embryo as in (i) and (j). Note individual expressing cells in the brain lobes (BC). Expression in the fully differentiated trachea (T) and hindgut (H1) is evident. (l) Flattened preparation of early stage 16 embryo. Expression within the telson (TL) now constitutes a ring around the presumptive anal pads.

Figure 7:
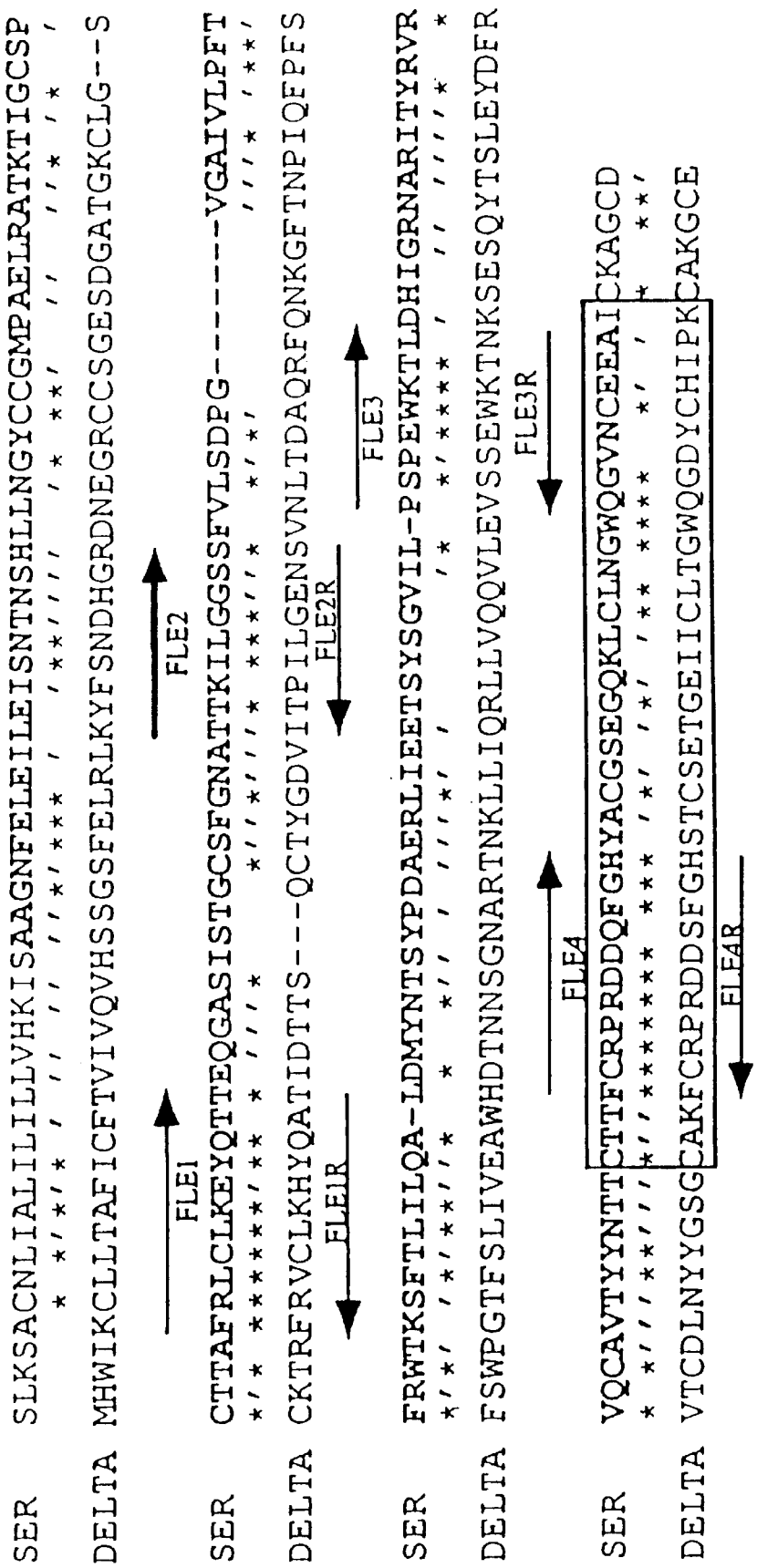

FIG. 7. Amino acid comparison of amino-terminal Serrate-Delta homology. Conserved regions are indicated at the top of the figure (*=identical amino acids; '=conservative changes in sequence). Serrate (see SEQ ID NO:2) is shown above line, Delta (SEQ ID NO:4) below. The sequence begins at Serrate amino acid position 59; the partial EGF-like repeat of both Serrate and Delta is boxed. The Serrate amino acid sequence (amino acids 79–282 of FIG. 3) placed into the chimeric ΔEGF Notch construct and determined to be sufficient for Notch binding is presented in boldface type. The positions of the synthetic degenerate primers (designated FLE1 through FLE4R) are shown; refer to FIG. 8 for nucleotide composition.

Figure 8B:
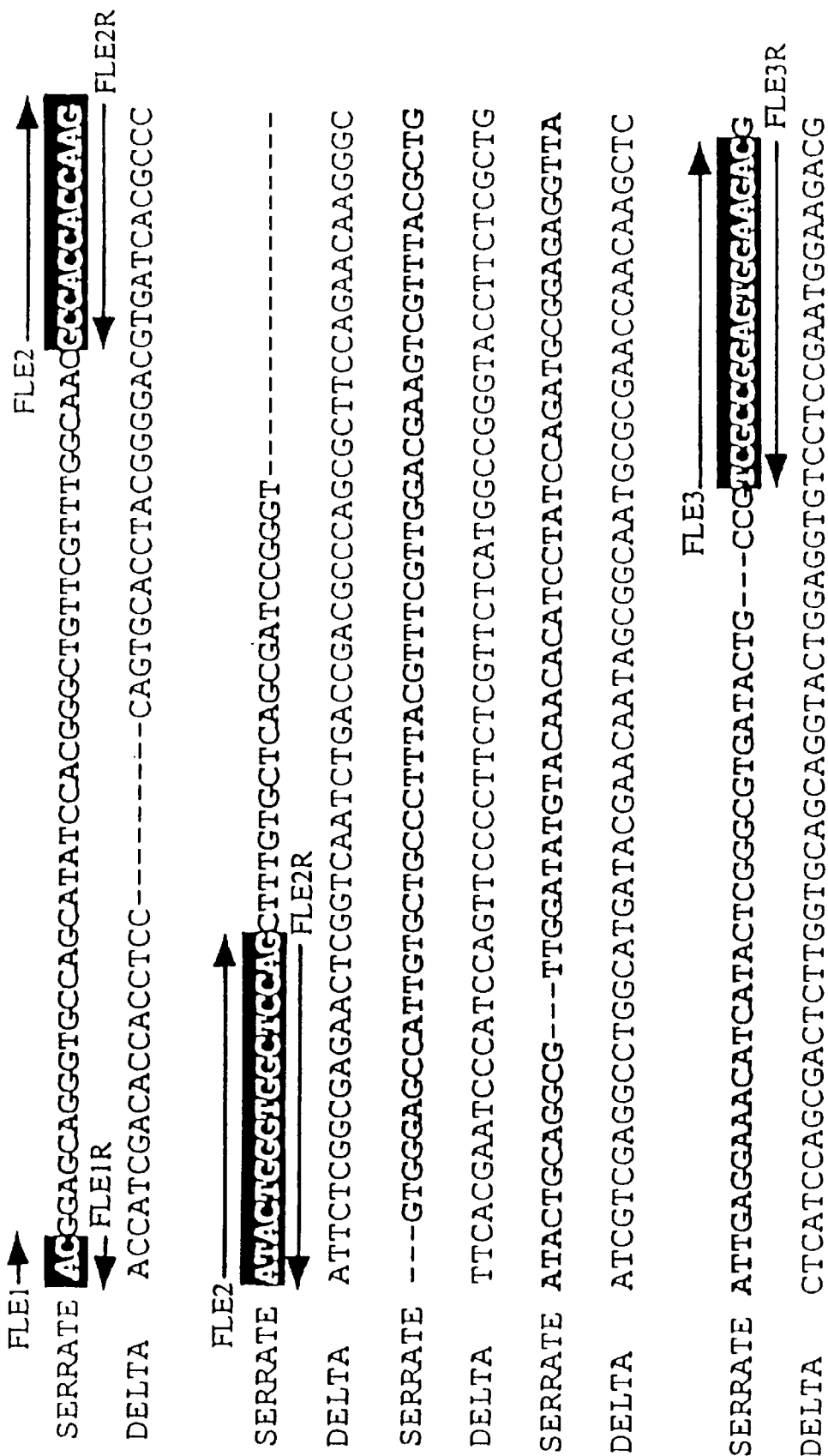
Figure 8C:
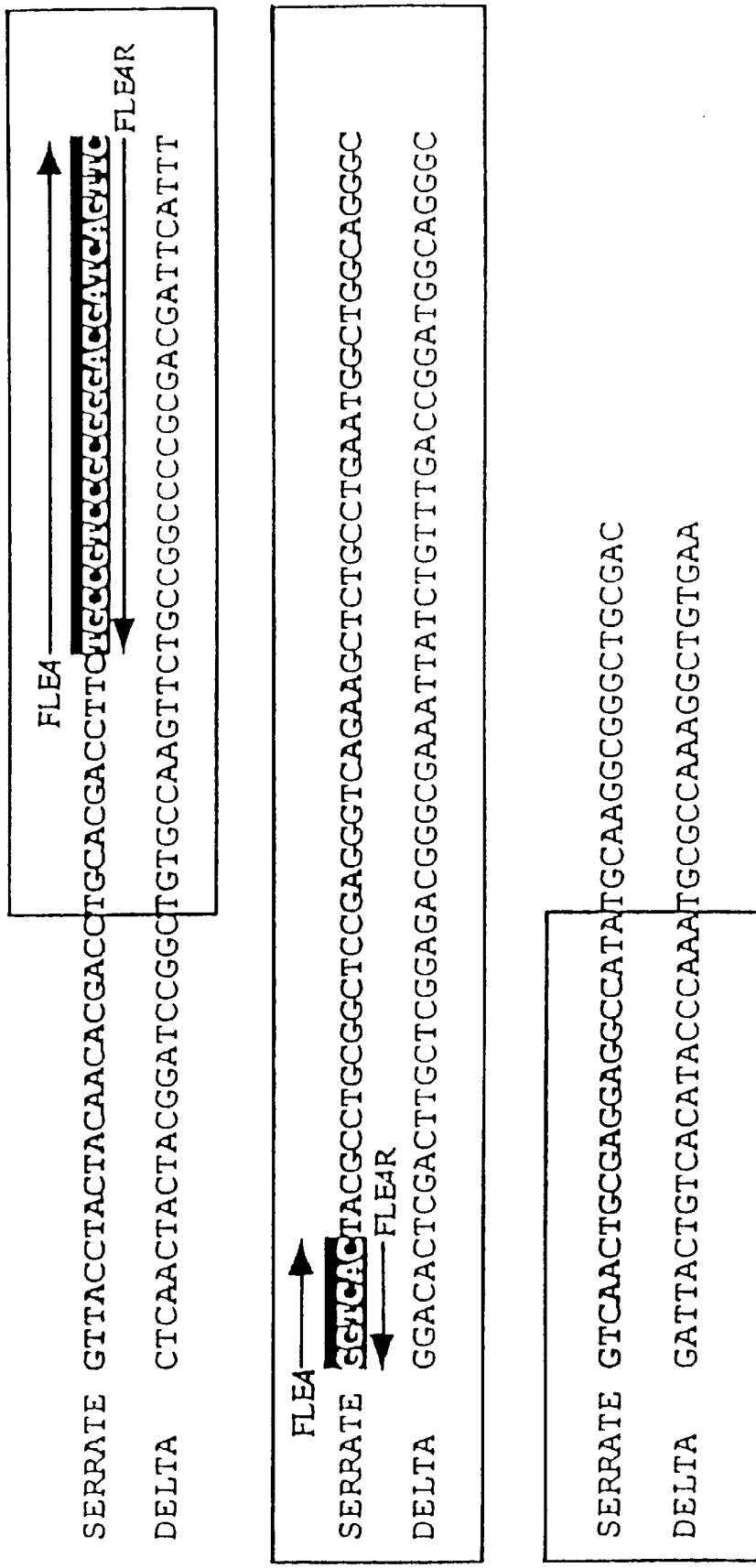

FIGS. 8A–8C. Nucleotide comparison of amino-terminal Serrate-Delta homology. The nucleotide sequence corresponding to the amino acid sequence in FIG. 7 is shown (Serrate sequence: see SEQ ID NO:1; Delta sequence: SEQ ID NO:3). The DNA encoding the partial EGF-repeat is boxed. The Serrate nucleotide sequence (nucleotides 676–1287 of FIG. 3) placed into the chimeric ΔEGF Notch construct determined to be sufficient for Notch binding is presented in boldface type.

FIGS. 9A–9G. Nucleotide sequence (SEQ ID NO:5) and protein sequence (SEQ ID NO:6) of human Serrate cDNA homolog 39.

FIGS. 10A–10E. Preliminary nucleotide sequence (FIGS. 10A–10D; SEQ ID NO:7) and amino acid sequence (FIG. 10E; SEQ ID NO:8) of human Serrate cDNA homolog 15(1). Both the nucleotide and amino acid sequences are partial, with errors. In particular, there appears to be a frameshift after the signal sequence and some error (compression in the reading of the sequence).

FIGS. 11A–11B. Nucleotide sequence (SEQ ID NO:9) of chick Serrate (C-Serrate) cDNA.

FIGS. 12A–12B. Amino acid sequence (SEQ ID NO:10) of C-Serrate (lacking the amino-terminus of the signal sequence). The putative cleavage site following the signal sequence (marking the predicted amino-terminus of the mature protein) is marked with an arrowhead; the DSL domain is indicated by asterisks; the EGF-like repeats (ELRs) are underlined with dashed lines; the cysteine rich region between the ELRs and the transmembrane domain is marked between arrows, and the single transmembrane domain (between amino acids 1042 and 1066) is shown in bold.

FIG. 13. Alignment of the amino terminal sequences of Drosophila melanogaster Delta (SEQ ID NO:4) and Serrate (SEQ ID NO:2) with C-Serrate (SEQ ID NO:10). The region shown extends from the end of the signal sequence to the end of the DSL domain. The DSL domain is indicated. Identical amino acids in all three proteins are boxed.

Figure 14:
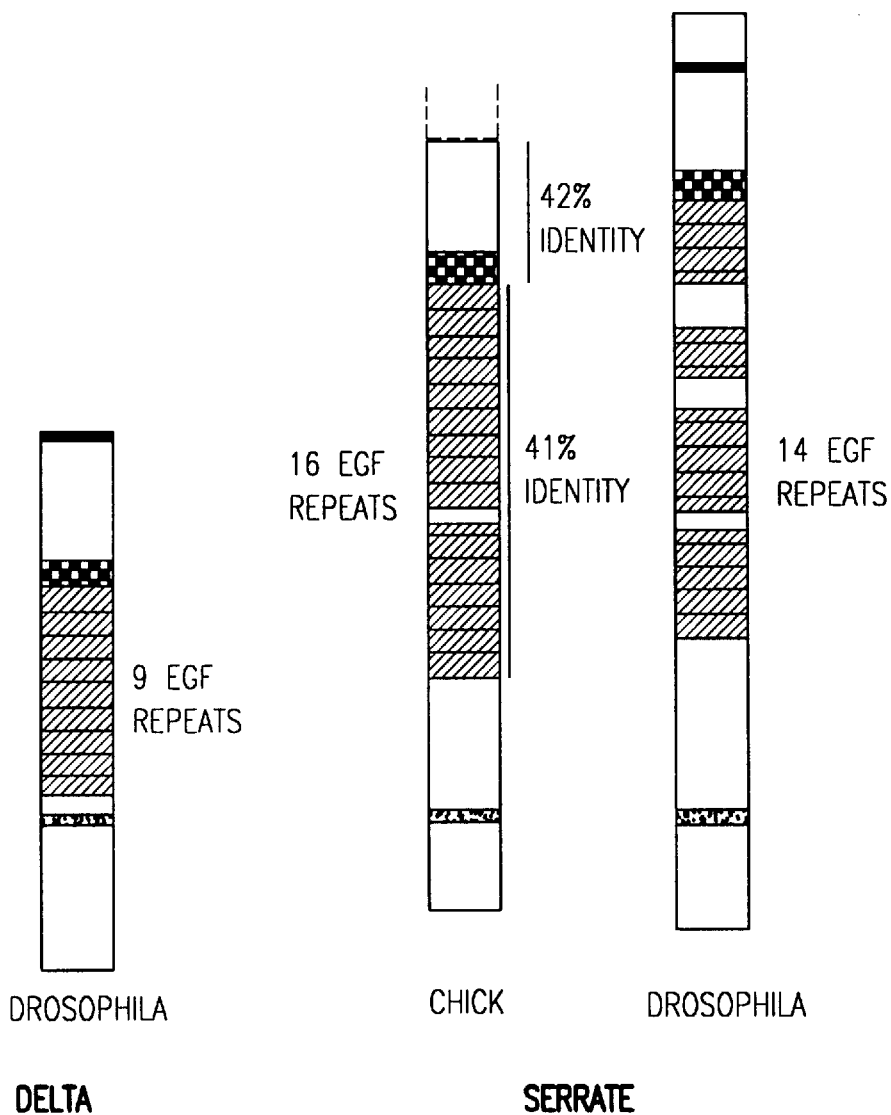

FIG. 14. Diagram showing the domain structures of Drosophila Delta and Drosophila Serrate compared with C-Serrate. The second cysteine-rich region just downstream of the EGF repeats, present only in C-Serrate and Drosophila Serrate, is not shown. Hydrophobic regions are shown in black; DSL domains are checkered and EGF-like repeats are hatched.

5. DETAILED DESCRIPTION OF THE INVENTION

The present invention relates to nucleotide sequences of Serrate genes, and amino acid sequences of their encoded proteins. The invention further relates to fragments and other derivatives, and analogs, of Serrate proteins. Nucleic acids encoding such fragments or derivatives are also within the scope of the invention. The invention provides Serrate genes and their encoded proteins of many different species. The Serrate genes of the invention include Drosophila Serrate and related genes (homologs) in species other than Drosophila. In specific embodiments, the Serrate genes and proteins are from vertebrates, or more particularly, mammals. In a preferred embodiment of the invention, the Serrate protein is a human protein. Production of the foregoing proteins and derivatives, e.g., by recombinant methods, is provided.

The invention relates to Serrate derivatives and analogs of the invention which are functionally active, i.e., they are capable of displaying one or more known functional activities associated with a full-length (wild-type) Serrate protein. Such functional activities include but are not limited to antigenicity [ability to bind (or compete with Serrate for binding) to an anti-Serrate antibody], immunogenicity (ability to generate antibody which binds to Serrate), ability to bind (or compete with Serrate for binding) to Notch or other toporythmic proteins or fragments thereof ("adhesiveness"), ability to bind (or compete with Serrate for binding) to a receptor for Serrate. "Toporythmic proteins" as used herein, refers to the protein products of Notch, Delta, Serrate, Enhancer of split, and Deltex, as well as other members of this interacting gene family which may be identified, e.g., by virtue of the ability of their gene sequences to hybridize, or their homology to Delta, Serrate, or Notch, or the ability of their genes to display phenotypic interactions.

The invention further relates to fragments (and derivatives and analogs thereof) of Serrate which comprise one or more domains of the Serrate protein, including but not limited to the intracellular domain, extracellular domain, transmembrane domain, membrane-associated region, or one or more EGF-like (homologous) repeats of a Serrate protein, or any combination of the foregoing.

Antibodies to Serrate, its derivatives and analogs, are additionally provided.

As demonstrated infra, Serrate plays a critical role in development and other physiological processes, in particular, as a ligand to Notch, which is involved in cell fate (differentiation) determination. In particular, Serrate is believed to play a major role in determining cell fates in the central nervous system. The nucleic acid and amino acid sequences and antibodies thereto of the invention can be used for the detection and quantitation of Serrate mRNA and protein of human and other species, to study expression thereof, to produce Serrate and fragments and other derivatives and analogs thereof, in the study and manipulation of differentiation and other physiological processes. The present invention also relates to therapeutic and diagnostic methods and compositions based on Serrate proteins and nucleic acids. The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof; antibodies thereto; nucleic acids encoding the Serrate proteins, analogs, or derivatives; and Serrate antisense nucleic acids. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, r inhibit, Notch and/or Serrate function (hereinafter "Antagonist Therapeutics") are administered for therapeutic effect. In another embodiment, Therapeutics which promote Notch and/or Serrate function (hereinafter "Agonist Therapeutics") are administered for therapeutic effect.

Disorders of cell fate, in particular hyperproliferative (e.g., cancer) or hypoproliferative disorders, involving aberrant or undesirable levels of expression or activity or localization of Notch and/or Serrate protein can be diagnosed by detecting such levels, as described more fully infra.

In a preferred aspect, a Therapeutic of the invention is a protein consisting of at least a fragment (termed herein "adhesive fragment") of Serrate which mediates binding to a Notch protein or a fragment thereof.

The invention is illustrated by way of examples infra which disclose, inter alia, the cloning of *D. melanogaster* Serrate (Section 6); the construction and recombinant expression of a Serrate chimeric/fusion derivative and production of antibodies thereto (Section 7); the recombinant expression of Serrate, a Serrate fragment lacking the EGF-like repeats present in Serrate, and a chimeric Notch-Serrate derivative, and assays for binding to Notch (Section 8); the cloning of a mouse Serrate homolog (Section 9), the cloning of a Xenopus (frog) Serrate homolog (Section 10), the cloning of a chick Serrate homolog (Section 11), and the cloning of human Serrate homologs (Section 12).

For clarity of disclosure, and not by way of limitation, the detailed description of the invention is divided into the sub-sections which follow.

5.1. ISOLATION OF THE SERRATE GENES

The invention relates to the nucleotide sequences of Serrate nucleic acids. In specific embodiments, Drosophila Serrate nucleic acids comprise the cDNA sequences shown in FIGS. 9A–9G (SEQ ID NO:5), FIGS. 10A–10D (SEQ ID NO:7), FIGS. 11A–11B (SEQ ID NO:9) or FIGS. 3A–3F (SEQ ID NO:1) or the coding regions thereof, or nucleic acids encoding a Serrate protein (e.g., having the sequence of SEQ ID NO:6, 8, 10, or 2). The invention provides nucleic acids consisting of at least 8 nucleotides (i.e., a hybridizable portion) of a Serrate sequence; in other embodiments, the nucleic acids consist of at least 25 (continuous) nucleotides, 50 nucleotides, 100 nucleotides, 150 nucleotides, or 200 nucleotides of a Serrate sequence, or a full-length Serrate coding sequence. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of a Serrate gene. In a specific embodiment, a nucleic acid which is hybridizable to a Serrate nucleic acid (e.g., having sequence SEQ ID NO:5), or to a nucleic acid encoding a Serrate derivative, under conditions of low stringency is provided. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65°–68° C. and reexposed to film. Other conditions of low stringency which may be used are well known in the art (e.g., as employed for cross-species hybridizations).

In another specific embodiment, a nucleic acid which is hybridizable to a Serrate nucleic acid under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

Nucleic acids encoding fragments and derivatives of Serrate proteins (see Section 5.6), and Serrate antisense nucleic acids (see Section 5.11) are additionally provided. As is readily apparent, as used herein, a "nucleic acid encoding a fragment or portion of a Serrate protein" shall be construed as referring to a nucleic acid encoding only the recited fragment or portion of the Serrate protein and not the other contiguous portions of the Serrate protein as a continuous sequence.

Fragments of Serrate nucleic acids comprising regions of homology to other toporythmic proteins are also provided. For example, the region of homology with Delta spans nucleotides 627–1290 of SEQ ID NO:1. The DSL regions (regions of homology with Drosophila Delta and Serrate) of Serrate proteins of other species are also provided. Nucleic acids encoding conserved regions between Delta and Serrate, such as those represented by Serrate amino acids 63–73, 124–134, 149–158, 195–206, 214–219, and 250–259 of SEQ ID NO:2, or by the DSL domains, or by the sequences of SEQ ID NO:20, 14, or 12, are also provided.

Specific embodiments for the cloning of a Serrate gene, presented as a particular example but not by way of limitation, follows:

For expression cloning (a technique commonly known in the art), an expression library is constructed by methods known in the art. For example, mRNA (e.g., human) is isolated, cDNA is made and ligated into an expression vector (e.g., a bacteriophage derivative) such that it is capable of being expressed by the host cell into which it is then introduced. Various screening assays can then be used to select for the expressed Serrate product. In one embodiment, anti-Serrate antibodies can be used for selection.

In another preferred aspect, PCR is used to amplify the desired sequence in a genomic or cDNA library, prior to selection. Oligonucleotide primers representing known Serrate sequences can be used as primers in PCR. In a preferred aspect, the oligonucleotide primers represent at least part of the Serrate conserved segments of strong homology between Serrate and Delta. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp ). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known Serrate nucleotide sequence and the nucleic acid homolog being isolated. For cross species hybridization, low stringency conditions are preferred. For same species hybridization, moderately stringent conditions are preferred. After successful amplification of a segment of a Serrate homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding Serrate proteins may be identified. Such a procedure is presented by way of example in various examples sections infra.

The above-methods are not meant to limit the following general description of methods by which clones of Serrate may be obtained.

Any eukaryotic cell potentially can serve as the nucleic acid source for the molecular cloning of the Serrate gene. The nucleic acid sequences encoding Serrate can be isolated from human, porcine, bovine, feline, avian, equine, canine, as well as additional primate sources, insects, etc. For example, we have amplified fragments of the appropriate size in Drosophila, mouse, Xenopus, and human, by PCR using cDNA libraries with Drosophila Serrate primers. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Serrate (of any species) gene or its specific RNA, or a fragment thereof, e.g., an extracellular domain (see Section 5.6), is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, receptor binding activity, in vitro aggregation activity ("adhesiveness") or antigenic properties as known for Serrate. If an antibody to Serrate is available, the Serrate protein may be identified by binding of labeled antibody to the putatively Serrate synthesizing clones, in an ELISA (enzyme-linked immunosorbent assay)-type procedure.

The Serrate gene can also be identified by mRNA selection by nucleic acid hybridization followed by in vitro translation. In this procedure, fragments are used to isolate complementary mRNAs by hybridization. Such DNA fragments may represent available, purified Serrate DNA of another species (e.g., Drosophila). Immunoprecipitation analysis or functional assays (e.g., aggregation ability in vitro; binding to receptor; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Serrate protein. A radiolabelled Serrate cDNA can be synthesized using the selected mRNA (from the adsorbed polysomes) as a template. The radiolabelled mRNA or cDNA may then be used as a probe to identify the Serrate DNA fragments from among other genomic DNA fragments.

Alternatives to isolating the Serrate genomic DNA include, but are not limited to, chemically synthesizing the gene sequence itself from a known sequence or making cDNA to the mRNA which encodes the Serrate protein. For example, RNA for cDNA cloning of the Serrate gene can be isolated from cells which express Serrate. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pB7322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Serrate gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Serrate gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Serrate sequences provided by the instant invention include those nucleotide sequences encoding substantially the same amino acid sequences as found in native Serrate proteins, and those encoded amino acid sequences with functionally equivalent amino acids, all as described in Section 5.6 infra for Serrate derivatives.

5.2. EXPRESSION OF THE SERRATE GENES

The nucleotide sequence coding for a Serrate protein or a functionally active fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native Serrate gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Serrate gene is expressed. In other specific embodiments, the human Serrate gene is expressed, or a sequence encoding a functionally active portion of human Serrate. In yet another embodiment, a fragment of Serrate comprising the extracellular domain, or other derivative, or analog of Serrate is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Serrate protein or peptide fragment may be regulated by a second nucleic acid sequence so that the Serrate protein or peptide is expressed in a host transformed with the recombinant DNA molecule.

For example, expression of a Serrate protein may be controlled by any promoter/enhancer element known in the art. Promoters which may be used to control toporythmic gene expression include, but are not limited to, the SV40 early promoter region (Bernoist and Chambon, 1981, Nature 290:304– 310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing Serrate gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Serrate gene is inserted within the marker gene sequence of the vector, recombinants containing the Serrate insert can be identified by the absence of the marker gene function. In the third approach, recombinant expression vectors can be identified by assaying the foreign gene product expressed by the recombinant. Such assays can be based, for example, on the physical or functional properties of the Serrate gene product in vitro assay systems, e.g., aggregation (binding) with Notch, binding to a receptor, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Serrate protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian toporythmic protein. Furthermore, different vector/host expression systems may effect processing reactions such as proteolytic cleavages to different extents.

In other specific embodiments, the Serrate protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

5.3. IDENTIFICATION AND PURIFICATION OF THE SERRATE GENE PRODUCTS

In particular aspects, the invention provides amino acid sequences of Serrate, preferably human Serrate, and fragments and derivatives thereof which comprise an antigenic determinant (i.e., can be recognized by an antibody) or which are otherwise functionally active, as well as nucleic acid sequences encoding the foregoing. "Functionally active" material as used herein refers to that material displaying one or more known functional activities associated with a full-length (wild-type) Serrate protein, e.g., binding to Notch or a portion thereof, binding to any other Serrate ligand, antigenicity (binding to an anti-Serrate antibody), etc.

In specific embodiments, the invention provides fragments of a Serrate protein consisting of at least 6 amino acids, 10 amino acids, 50 amino acids, or of at least 75 amino acids. In other embodiments, the proteins comprise or consist essentially of an extracellular domain, DSL domain, epidermal growth factor-like repeat (ELR) domain, one or any combination of ELRs, cysteine-rich region, transmembrane domain, or intracellular (cytoplasmic) domain, or a portion which binds to Notch, or any combination of the foregoing, of a Serrate protein. Fragments, or proteins comprising fragments, lacking some or all of the foregoing regions of a Serrate protein are also provided. Nucleic acids encoding the foregoing are provided.

Once a recombinant which expresses the Serrate gene sequence is identified, the gene product can be analyzed. This is achieved by assays based on the physical or functional properties of the product, including radioactive labelling of the product followed by analysis by gel electrophoresis, immunoassay, etc.

Once the Serrate protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once a Serrate protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In a specific embodiment of the present invention, such Serrate proteins, whether produced by recombinant DNA techniques or by chemical synthetic methods, include but are not limited to those containing, as a primary amino acid sequence, all or part of the amino acid sequence substantially as depicted in FIGS. 3A–3F, 9A–9G, 10E or 12A–12B (SEQ ID NO:2, 6, 8, or 10, respectively), as well as fragments and other derivatives, and analogs thereof.

5.4. STRUCTURE OF THE SERRATE GENE AND PROTEIN

The structure of the Serrate gene and protein can be analyzed by various methods known in the art.

5.4.1. GENETIC ANALYSIS

The cloned DNA or cDNA corresponding to the Serrate gene can be analyzed by methods including but not limited to Southern hybridization (Southern, E. M., 1975, J. Mol. Biol. 98:503–517), northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Patent Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a Serrate-specific probe can allow the detection of the Serrate gene in DNA from various cell types. Methods of amplification other than PCR are commonly known and can also be employed. In one embodiment, Southern hybridization can be used to determine the genetic linkage of Serrate. Northern hybridization analysis can be used to determine the expression of the Serrate gene. Various cell types, at various states of development or activity can be tested for Serrate expression. Examples of such techniques and their results are described in Section 6, infra. The stringency of the hybridization conditions for both Southern and Northern hybridization can be manipulated to ensure detection of nucleic acids with the desired degree of relatedness to the specific Serrate probe used.

Restriction endonuclease mapping can be used to roughly determine the genetic structure of the Serrate gene. In a particular embodiment, cleavage with restriction enzymes can be used to derive the restriction map shown in FIG. 2, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.). The cDNA sequence of a representative Serrate gene comprises the sequence substantially as depicted in FIGS. 9A–9G, and is described in Section 12, infra.

5.4.2. PROTEIN ANALYSIS

The amino acid sequence of the Serrate protein can be derived by deduction from the DNA sequence, or alternatively, by direct sequencing of the protein, e.g., with an automated amino acid sequencer. The amino acid sequence of a representative Serrate protein comprises the sequence substantially as depicted in FIGS. 3A–3F, and detailed in Section 6, infra, with the representative mature protein that shown by amino acid numbers 81–1404.

The Serrate protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Serrate protein and the corresponding regions of the gene sequence which encode such regions. A hydrophilicity profile of the Serrate protein described in the examples section infra is depicted in FIGS. 4A–4C.

Secondary, structural analysis (Chou, P. and Fasman, G., 1974, Biochemistry 13:222) can also be done, to identify regions of Serrate that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. GENERATION OF ANTIBODIES TO SERRATE PROTEINS AND DERIVATIVES THEREOF

According to the invention, Serrate protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to human Serrate are produced. In another embodiment, antibodies to the extracellular domain of Serrate are produced. In another embodiment, antibodies to the intracellular domain of Serrate are produced.

Various procedures known in the art may be used for the production of polyclonal antibodies to a Serrate protein or derivative or analog. In a particular embodiment, rabbit polyclonal antibodies to an epitope of the Serrate protein encoded by a sequence depicted in FIGS. 3A–3F, or a subsequence thereof, can be obtained. For the production of antibody, various host animals can be immunized by injection with the native Serrate protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a Serrate protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for Serrate together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce Serrate-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for Serrate proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a Serrate protein, one may assay generated hybridomas for a product which binds to a Serrate fragment containing such domain. For selection of an antibody specific to human Serrate, one can select on the basis of positive binding to human Serrate and a lack of binding to Drosophila Serrate.

The foregoing antibodies can be used in methods known in the art relating to the localization and activity of the protein sequences of the invention (e.g., see Section 5.7, infra), e.g., for imaging these proteins, measuring levels thereof in appropriate physiological samples, in diagnostic methods, etc.

Antibodies specific to a domain of a Serrate protein are also provided. In a specific embodiment, antibodies which bind to a Notch-binding fragment of Serrate are provided.

In another embodiment of the invention (see infra), anti-Serrate antibodies and fragments thereof containing the binding domain are Therapeutics.

5.6. SERRATE PROTEINS. DERIVATIVES AND ANALOGS

The invention further relates to Serrate proteins, and derivatives (including but not limited to fragments) and analogs of Serrate proteins. Nucleic acids encoding Serrate protein derivatives and protein analogs are also provided. In one embodiment, the Serrate proteins are encoded by the Serrate nucleic acids described in Section 5.1 supra. In particular aspects, the proteins, derivatives, or analogs are of fly, frog, mouse, rat, pig, cow, dog, monkey, or human Serrate proteins.

The production and use of derivatives and analogs related to Serrate are within the scope of the present invention. In a specific embodiment, the derivative or analog is functionally active, i.e., capable of exhibiting one or more functional activities associated with a full-length, wild-type Serrate protein. As one example, such derivatives or analogs which have the desired immunogenicity or antigenicity can be used, for example, in immunoassays, for immunization, for inhibition of Serrate activity, etc. Such molecules which retain, or alternatively inhibit, a desired Serrate property, e.g., binding to Notch or other toporythmic proteins, binding to a cell-surface receptor, can be used as inducers, or inhibitors, respectively, of such property and its physiological correlates. A specific embodiment relates to a Serrate fragment that can be bound by an anti-Serrate antibody but cannot bind to a Notch protein or other toporythmic protein. Derivatives or analogs of Serrate can be tested for the desired activity by procedures known in the art, including but not limited to the assays described in Section 5.7.

In particular, Serrate derivatives can be made by altering Serrate sequences by substitutions, additions or deletions that provide for functionally equivalent molecules. Due to the degeneracy of nucleotide coding sequences, other DNA sequences which encode substantially the same amino acid sequence as a Serrate gene may be used in the practice of the present invention. These include but are not limited to nucleotide sequences comprising all or portions of Serrate genes which are altered by the substitution of different codons that encode a functionally equivalent amino acid residue within the sequence, thus producing a silent change. Likewise, the Serrate derivatives of the invention include, but are not limited to, those containing, as a primary amino acid sequence, all or part of the amino acid sequence of a Serrate protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a Serrate protein consisting of at least 10 (continuous) amino acids of the Serrate protein is provided. In other embodiments, the fragment consists of at least 20 or 50 amino acids of the Serrate protein. In specific embodiments, such fragments are not larger than 35, 100 or 200 amino acids. Derivatives or analogs of Serrate include but are not limited to those peptides which are substantially homologous to Serrate or fragments thereof (e.g., at least 30% identity over an amino acid sequence of identical size) or whose encoding nucleic acid is capable of hybridizing to a coding Serrate sequence.

The Serrate derivatives and analogs of the invention can be produced by various methods known in the art. The manipulations which result in their production can occur at the gene or protein level. For example, the cloned Serrate gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Serrate, care should be taken to ensure that the modified gene remains within the same translational reading frame as Serrate, uninterrupted by translational stop signals, in the gene region where the desired Serrate activity is encoded.

Additionally, the Serrate-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

Manipulations of the Serrate sequence may also be made at the protein level. Included within the scope of the invention are Serrate protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Serrate can be chemically synthesized. For example, a peptide corresponding to a portion of a Serrate protein which comprises the desired domain (see Section 5.6.1), or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the Serrate sequence. Non-classical amino acids include but are not limited to the D-isomers of the common amino acids, a-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nβ-methyl amino acids.

In a specific embodiment, the Serrate derivative is a chimeric, or fusion, protein comprising a Serrate protein or fragment thereof (preferably consisting of at least a domain or motif of the Serrate protein, or at least 10 amino acids of the Serrate protein) joined at its amino- or carboxy-terminus via a peptide bond to an amino acid sequence of a different protein. In one embodiment, such a chimeric protein is produced by recombinant expression of a nucleic acid encoding the protein (comprising a Serrate-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature Serrate protein with a heterologous signal sequence is expressed such that the chimeric protein is expressed and processed by the cell to the mature Serrate protein. As another example, and not by way of limitation, a recombinant molecule can be constructed according to the invention, comprising coding portions of both Serrate and another toporythmic gene, e.g., Delta. The encoded protein of such a recombinant molecule could exhibit properties associated with both Serrate and Delta and portray a novel profile of biological activities, including agonists as well as antagonists. The primary sequence of Serrate and Delta may also be used to predict tertiary structure of the molecules using computer simulation (Hopp and Woods, 1981, Proc. Natl.

Acad. Sci. U.S.A. 78:3824–3828); Serrate/Delta chimeric recombinant genes could be designed in light of correlations between tertiary structure and biological function. Likewise, chimeric genes comprising portions of Serrate fused to any heterologous protein-encoding sequences may be constructed. A specific embodiment relates to a chimeric protein comprising a fragment of Serrate of at least six amino acids. A particular example of the construction and expression of a Notch-Serrate chimera is presented in Section 8 hereof. A particular example of another Serrate fusion protein is presented in Section 7 hereof.

In another specific embodiment, the Serrate derivative is a fragment of Serrate comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region. For example, such a Serrate fragment can comprise one or more regions homologous to Delta, including but not limited to Drosophila Serrate amino acids 63–73, 124–134, 149–158, 195–206, 214–219, 250–259, or 79–282 (or 79–246, excluding the partial EGF-like repeat) (see FIGS. 3A–3F, 7), or portions of Serrate of other species most homologous to the foregoing sequences, or DSL domains or portions thereof.

Other specific embodiments of derivatives and analogs are described in the subsections below and examples sections infra.

5.6.1. DERIVATIVES OF SERRATE CONTAINING ONE OR MORE DOMAINS OF THE PROTEIN

In a specific embodiment, the invention relates to Serrate derivatives and analogs, in particular Serrate fragments and derivatives of such fragments, that comprise, or alternatively consist of, one or more domains of the Serrate protein, including but not limited to the extracellular domain, DSL domain, ELR domain, cysteine rich domain, transmembrane domain, intracellular domain, membrane-associated region, and one or more of the EGF-like repeats (ELR) of the Serrate protein, or any combination of the foregoing. In particular examples relating to the human and chick Serrate proteins, such domains are identified in Examples Section 12 and 11, respectively. In particular examples relating to the Drosophila Serrate protein (see example 6), such domains are identified as follows, with reference to FIGS. 3A–3F: extracellular domain, amino acids numbers (AA) 81–541; transmembrane domain, AA 1221–1245; intracellular domain, AA 1246–1404; membrane-associated region, AA 542–564; ELR (see underscored sequences in FIGS. 3A–3F).

In a specific embodiment, relating to a Serrate protein of a species other than D. melanogaster, the molecules comprising specific fragments of Serrate are those comprising fragments in the respective Serrate protein most homologous to specific fragments of the Drosophila Serrate and/or Delta proteins. In particular embodiments, such a molecule comprises or consists of the amino acid sequences of SEQ ID NO:12, 14 or 20. Alternatively, a fragment comprising a domain of a Serrate homolog can be identified by protein analysis methods as described in Section 5.3.2 or 6.

Serrate derivatives which are Serrate fragments and chimeric/fusion proteins are described by way of example in Sections 7 and 8 infra.

5.6.2. DERIVATIVES OF SERRATE THAT MEDIATE BINDING TO TOPORYTHMIC PROTEIN DOMAINS

The invention also provides for Serrate fragments, and analogs or derivatives of such fragments, which mediate binding to toporythmic proteins (and thus are termed herein "adhesive"), and nucleic acid sequences encoding the foregoing.

In a specific embodiment, the adhesive fragment of Serrate is that comprising the portion of Serrate most homologous to about amino acid numbers 85–283 or 79–282 of the Drosophila Serrate sequence (see FIGS. 3A–3F).

In a particular embodiment, the adhesive fragment of a Serrate protein comprises the DSL domain, or a portion thereof. Subfragments within the DSL domain that mediate binding to Notch can be identified by analysis of constructs expressing deletion mutants.

The ability to bind to a toporythmic protein (preferably Notch) can be demonstrated by in vitro aggregation assays with cells expressing such a toporythmic protein as well as cells expressing Serrate or a Serrate derivative (See Section 5.7). That is, the ability of a Serrate fragment to bind to a Notch protein can be demonstrated by detecting the ability of the Serrate fragment, when expressed on the surface of a first cell, to bind to a Notch protein expressed on the surface of a second cell.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

5.7. ASSAYS OF SERRATE PROTEINS, DERIVATIVES AND ANALOGS

The functional activity of Serrate proteins, derivatives and analogs can be assayed by various methods.

For example, in one embodiment, where one is assaying for the ability to bind or compete with wild-type Serrate for binding to anti-Serrate antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to a toporythmic protein, e.g., Notch, one can carry out an in vitro aggregation assay such as described infra in Section 8.2.1 (see also Fehon et al., 1990, Cell 61:523–534; Rebay et al., 1991, Cell 67:687–699).

In another embodiment, where a receptor for Serrate is identified, receptor binding can be assayed, e.g., by means well-known in the art. In another embodiment, physiological correlates of Serrate binding to cells expressing a Serrate receptor (signal transduction) can be assayed.

In another embodiment, in insect or other model systems, genetic studies can be done to study the phenotypic effect of a Serrate mutant that is a derivative or analog of wild-type Serrate (see Section 6, infra).

Other methods will be known to the skilled artisan and are within the scope of the invention.

5.8. THERAPEUTIC USES

The invention provides for treatment of disorders of cell fate or differentiation by administration of a therapeutic compound of the invention. Such therapeutic compounds (termed herein "Therapeutics") include: Serrate proteins and analogs and derivatives (including fragments) thereof (e.g., as described hereinabove); antibodies thereto (as described hereinabove); nucleic acids encoding the Serrate proteins, analogs, or derivatives (e.g., as described hereinabove); and Serrate antisense nucleic acids. As stated supra, the Antagonist Therapeutics of the invention are those Therapeutics which antagonize, or inhibit, a Serrate function and/or Notch function (since Serrate is a Notch ligand). Such Antagonist Therapeutics are most preferably identified by use of known convenient in vitro assays, e.g., based on their ability to inhibit binding of Serrate to another protein (e.g., a Notch protein), or inhibit any known Notch or Serrate function as preferably assayed in vitro or in cell culture, although genetic assays (e.g., in Drosophila) may also be employed. In a preferred embodiment, the Antagonist Therapeutic is a protein or derivative thereof comprising a functionally active fragment such as a fragment of Serrate which mediates binding to Notch, or an antibody thereto. In other specific embodiments, such an Antagonist Therapeutic is a nucleic acid capable of expressing a molecule comprising a fragment of Serrate which binds to Notch, or a Serrate antisense nucleic acid (see Section 5.11 herein). It should be noted that preferably, suitable in vitro or in vivo assays, as described infra, should be utilized to determine the effect of a specific Therapeutic and whether its administration is indicated for treatment of the affected tissue, since the developmental history of the tissue may determine whether an Antagonist or Agonist Therapeutic is desired.

In addition, the mode of administration, e.g., whether administered in soluble form or administered via its encoding nucleic acid for intracellular recombinant expression, of the Serrate protein or derivative can affect whether it acts as an agonist or antagonist.

In another embodiment of the invention, a nucleic acid containing a portion of a Serrate gene is used, as an Antagonist Therapeutic, to promote Serrate inactivation by homologous recombination (Koller and Smithies, 1989, Proc. Natl. Acad. Sci. USA 86:8932–8935; Zijlstra et al., 1989, Nature 342:435–438).

The Agonist Therapeutics of the invention, as described supra, promote Serrate function. Such Agonist Therapeutics include but are not limited to proteins and derivatives comprising the portions of Notch that mediate binding to Serrate, and nucleic acids encoding the foregoing (which can be administered to express their encoded products in vivo).

Further descriptions and sources of Therapeutics of the inventions are found in Sections 5.1 through 5.7 herein.

Molecules which retain, or alternatively inhibit, a desired Serrate property, e.g., binding to Notch, binding to an intracellular ligand, can be used therapeutically as inducers, or inhibitors, respectively, of such property and its physiological correlates. In a specific embodiment, a peptide (e.g., in the range of 6–50 or 15–25 amino acids; and particularly of about 10, 15, 20 or 25 amino acids) containing the sequence of a portion of Serrate which binds to Notch is used to antagonize Notch function. In a specific embodiment, such an Antagonist Therapeutic is used to treat or prevent human or other malignancies associated with increased Notch expression (e.g., cervical cancer, colon cancer, breast cancer, squamous adenocarcimas (see infra)). Derivatives or analogs of Serrate can be tested for the desired activity by procedures known in the art, including but not limited to the assays described in the examples infra. For example, molecules comprising Serrate fragments which bind to Notch EGF-repeats (ELR) 11 and 12 and which are smaller than a DSL domain, can be obtained and selected by expressing deletion mutants and assaying for binding of the expressed product to Notch by any of the several methods (e.g., in vitro cell aggregation assays, interaction trap system), some of which are described in the Examples Sections infra. In one specific embodiment, peptide libraries can be screened to select a peptide with the desired activity; such screening can be carried out by assaying, e.g., for binding to Notch or a molecule containing the Notch ELR 11 and 12 repeats.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch or Serrate function, for example, in patients where Notch or Serrate protein is lacking, genetically defective, biologically inactive or underactive, or underexpressed; and (2) in diseases or disorders wherein in vitro (or in vivo) assays (see infra) indicate the utility of Serrate agonist administration. The absence or decreased levels in Notch or Serrate function can be readily detected, e.g., by obtaining a patient tissue sample (e.g., from biopsy tissue) and assaying it in vitro for protein levels, structure and/or activity of the expressed Notch or Serrate protein. Many methods standard in the art can be thus employed, including but not limited to immunoassays to detect and/or visualize Notch or Serrate protein (e.g., Western blot, immunoprecipitation followed by sodium dodecyl sulfate polyacrylamide gel electrophoresis, immunocytochemistry, etc.) and/or hybridization assays to detect Notch or Serrate expression by detecting and/or visualizing respectively Notch or Serrate mRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.8.1 through 5.8.3 infra.

In another specific embodiment, a Therapeutic is indicated for use in treating nerve injury or a nervous system degenerative disorder (see Section 5.8.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch or Serrate dominant activated phenotype ("gain of function" mutations.) Administration of an Agonist Therapeutic is indicated in diseases or disorders determined or known to involve a Notch or Serrate dominant negative phenotype ("loss of function" mutations). The functions of various structural domains of the Notch protein have been investigated in vivo, by ectopically expressing a series of Drosophila Notch deletion mutants under the hsp7o heat-shock promoter, as well as eye-specific promoters (see Rebay et al., 1993, Cell 74:319–329). Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. The results indicated that Notch functions as a receptor whose extracellular domain mediates ligand-binding, resulting in the transmission of developmental signals by the cytoplasmic domain. We have shown that Serrate binds to the Notch ELR 11 and 12 (see Section 8 infra).

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch or Serrate function, for example, where the Notch or Serrate protein is overexpressed or overactive; and (2) in diseases or disorders wherein in vitro (or in vivo) assays indicate the utility of Serrate antagonist administration. The increased levels of Notch or Serrate function can be readily detected by methods such as those described above, by quantifying protein and/or RNA. In vitro assays with cells of patient tissue sample or the appropriate cell line or cell type, to determine therapeutic utility, can be carried out as described above.

5.8.1. MALIGNANCIES

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.8.1 and 5.9.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, Medicine, 2d Ed., J. B. Lippincott Co., Philadelphia):

TABLE 1

| MALIGNANCIES AND RELATED DISORDERS |
| --- |
| Leukemia |
| acute leukemia |
| acute lymphocytic leukemia |
| acute myelocytic leukemia |
| myeloblastic |
| promyelocytic |
| myelomonocytic |
| monocytic |
| erythroleukemia |
| chronic leukemia |
| chronic myelocytic (granulocytic) leukemia |
| chronic lymphocytic leukemia |
| Polycythemia vera |
| Lymphoma |
| Hodgkin's disease |
| non-Hodgkin's disease |
| Multiple myeloma |
| Waldenström's macroglobulinemia |
| Heavy chain disease |
| Solid tumors |
| sarcomas and carcinomas |
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon carcinoma |
| pancreatic cancer |
| breast cancer |
| ovarian cancer |
| prostate cancer |
| squamous cell carcinoma |

TABLE 1-continued

MALIGNANCIES AND RELATED DISORDERS basal cell carcinoma
adenocarcinoma
sweat gland carcinoma
sebaceous gland carcinoma
papillary carcinoma
papillary adenocarcinomas
cystadenocarcinomna
medullary carcinoma
bronchogenic carcinoma
renal cell carcinoma
hepatoma
bile duct carcinoma
choriocarcinoma
seminoma
embryonal carcinoma
Wilms' tumor
cervical cancer
testicular tumor
lung carcinoma
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma In specific embodiments, malignancy or dysproliferative changes (such as metaplasias and dysplasias) are treated or prevented in epithelial tissues such as those in the cervix, esophagus, and lung.

Malignancies of the colon and cervix exhibit increased expression of human Notch relative to such non-malignant tissue (see PCT Publication no. WO 94/07474 published Apr. 14, 1994, incorporated by reference herein in its entirety). Thus, in specific embodiments, malignancies or premalignant changes of the colon or cervix are treated or prevented by administering an effective amount of an Antagonist Therapeutic, e.g., a Serrate derivative, that antagonizes Notch function. The presence of increased Notch expression in colon, and cervical cancer suggests that many more cancerous and hyperproliferative conditions exhibit upregulated Notch. Thus, in specific embodiments, various cancers, e.g., breast cancer, squamous adenocarcinoma, seminoma, melanoma, and lung cancer, and premalignant changes therein, as well as other hyperproliferative disorders, can be treated or prevented by administration of an Antagonist Therapeutic that antagonizes Notch function.

5.8.2. NERVOUS SYSTEM DISORDERS

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.8). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.8.3. TISSUE REPAIR AND REGENERATION

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly). In another embodiment, a Therapeutic of the invention is used to treat degenerative or traumatic disorders of the sensory epithelium of the inner ear.

5.9. PROPHYLACTIC USES

5.9.1. MALIGNANCIES

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

In another specific embodiment, an Antagonist Therapeutic of the invention is administered to a human patient to prevent progression to breast, colon, or cervical cancer.

5.9.2. OTHER DISORDERS

In other embodiments, a Therapeutic of the invention can be administered to prevent a nervous system disorder described in Section 5.8.2, or other disorder (e.g., liver cirrhosis, psoriasis, keloids, baldness) described in Section 5.8.3.

5.10. DEMONSTRATION OF THERAPEUTIC OR PROPHYLACTIC UTILITY

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.11. ANTISENSE REGULATION OF SERRATE EXPRESSION

The present invention provides the therapeutic or prophylactic use of nucleic acids of at least six nucleotides that are antisense to a gene or cDNA encoding Serrate or a portion thereof. "Antisense" as used herein refers to a nucleic acid capable of hybridizing to a portion of a Serrate RNA (preferably mRNA) by virtue of some sequence complementarity. Such antisense nucleic acids have utility as Antagonist Therapeutics of the invention, and can be used in the treatment or prevention of disorders as described supra in Section 5.8 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Serrate antisense nucleic acids provided by the instant invention can be used for the treatment of tumors or other disorders, the cells of which tumor type or disorder can be demonstrated (in vitro or in vivo) to express a Serrate gene or a Notch gene. Such demonstration can be by detection of RNA or of protein.

The invention further provides pharmaceutical compositions comprising an effective amount of the Serrate antisense nucleic acids of the invention in a pharmaceutically acceptable carrier, as described infra in Section 5.12. Methods for treatment and prevention of disorders (such as those described in Sections 5.8 and 5.9) comprising administering the pharmaceutical compositions of the invention are also provided.

In another embodiment, the invention is directed to methods for inhibiting the expression of a Serrate nucleic acid sequence in a prokaryotic or eukaryotic cell comprising providing the cell with an effective amount of a composition comprising an antisense Serrate nucleic acid of the invention.

Serrate antisense nucleic acids and their uses are described in detail below.

5.11.1. SERRATE ANTISENSE NUCLEIC ACIDS

The Serrate antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Serrate antisense oligonucleotide is provided, preferably of single-stranded DNA. In a most preferred aspect, such an oligonucleotide comprises a sequence antisense to the sequence encoding an SH3 binding domain or a Notch-binding domain of Serrate, most preferably, of human Serrate. The oligonucleotide may be modified at any position on its structure with substituents generally known in the art.

The Serrate antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, the Serrate antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the Serrate antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Serrate antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Serrate antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a Serrate gene, preferably a human Serrate gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Serrate antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Serrate RNA it may contain and still form a stable duplex (or triplex, as the case may be). One skilled in the art can ascertain a tolerable degree of mismatch by use of standard procedures to determine the melting point of the hybridized complex.

5.11.2. THERAPEUTIC UTILITY OF SERRATE ANTISENSE NUCLEIC ACIDS

The Serrate antisense nucleic acids can be used to treat (or prevent) malignancies or other disorders, of a cell type which has been shown to express Serrate or Notch. In specific embodiments, the malignancy is cervical, breast, or colon cancer, or squamous adenocarcinoma. Malignant, neoplastic, and pre-neoplastic cells which can be tested for such expression include but are not limited to those described supra in Sections 5.8.1 and 5.9.1. In a preferred embodiment, a single-stranded DNA antisense Serrate oligonucleotide is used.

Malignant (particularly, tumor) cell types which express Serrate or Notch RNA can be identified by various methods known in the art. Such methods include but are not limited to hybridization with a Serrate or Notch-specific nucleic acid (e.g. by Northern hybridization, dot blot hybridization, in situ hybridization), observing the ability of RNA from the cell type to be translated in vitro into Notch or Serrate, immunoassay, etc. In a preferred aspect, primary tumor tissue from a patient can be assayed for Notch or Serrate expression prior to treatment, e.g., by immunocytochemistry or in situ hybridization.

Pharmaceutical compositions of the invention (see Section 5.12), comprising an effective amount of a Serrate antisense nucleic acid in a pharmaceutically acceptable carrier, can be administered to a patient having a malignancy which is of a type that expresses Notch or Serrate RNA or protein.

The amount of Serrate antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Serrate antisense nucleic acids are administered via liposomes, microparticles, or microcapsules. In various embodiments of the invention, it may be useful to use such compositions to achieve sustained release of the Serrate antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.12. THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.) In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)). In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, articularly for injectable solutions. Suitable harmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients ay be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.13. DIAGNOSTIC UTILITY

Serrate proteins, analogues, derivatives, and subsequences thereof, Serrate nucleic acids (and sequences complementary thereto), anti-Serrate antibodies, have uses in diagnostics. Such molecules can be used in assays, such as immunoassays, to detect, prognose, diagnose, or monitor various conditions, diseases, and disorders affecting Serrate expression, or monitor the treatment thereof. In particular, such an immunoassay is carried out by a method comprising contacting a sample derived from a patient with an anti-Serrate antibody under conditions such that immunospecific binding can occur, and detecting or measuring the amount of any immunospecific binding by the antibody. In a specific aspect, such binding of antibody, in tissue sections, preferably in conjunction with binding of anti-Notch antibody can be used to detect aberrant Notch and/or Serrate localization or aberrant levels of Notch-Serrate colocalization in a disease state. In a specific embodiment, antibody to Serrate can be used to assay in a patient tissue or serum sample for the presence of Serrate where an aberrant level of Serrate is an indication of a diseased condition. Aberrant levels of Serrate binding ability in an endogenous Notch protein, or aberrant levels of binding ability to Notch (or other Serrate ligand) in an endogenous Serrate protein may be indicative of a disorder of cell fate (e.g., cancer, etc.) By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems sing techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Serrate genes and related nucleic acid sequences and subsequences, including complementary sequences, and other toporythmic gene sequences, can also be used in hybridization assays. Serrate nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Serrate expression and/or activity as described supra. In particular, such a hybridization assay is carried out by a method comprising contacting a sample containing nucleic acid with a nucleic acid probe capable of hybridizing to Serrate DNA or RNA, under conditions such that hybridization can occur, and detecting or measuring any resulting hybridization.

Additionally, since Serrate binds to Notch, Serrate or a binding portion thereof can be used to assay for the presence and/or amounts of Notch in a sample, e.g., in screening for malignancies which exhibit increased Notch expression such as colon and cervical cancers.

6. THE GENE SERRATE ENCODES A PUTATIVE EGF-LIKE TRANSMEMBRANE PROTEIN ESSENTIAL FOR PROPER ECTODERMAL DEVELOPMENT IN DROSOPHILA MELANOGASTER

As described in the example herein (see Fleming et al., 1990, Genes Dev. 4:2188–2201), mutations in the third chromosome gene Serrate are shown to display genetic interactions with specific alleles of the neurogenic locus Notch, which encodes a transmembrane protein with epidermal growth factor homology. The locus Serrate displays a striking phenotypic interaction with a specific Notch allele known to affect postembryonic development. We present the molecular cloning of Serrate and show that it encodes two coordinately-expressed transcripts from a genomic interval greater than 30 kilobases in length. The deduced protein product of 1404 amino acids contains a single transmembrane domain and 14 epidermal growth factor-like repeats. Whole-mount in situ hybridization analysis revealed complex temporal and spatial patterns of RNA expression consistent with the epidermal and neuronal defects observed in mutant embryos.

We demonstrate that the Serrate locus encodes an essential function, the loss of which results in embryonic lethality brought about by the disruption of both neuronal and epidermal tissues. Serrate is likely to represent an element in a network of interacting molecules operating at the cell surface during the differentiation of certain tissues.

6.1. RESULTS

6.1.1. THE SERRATE AND NOTCH GENES INTERACT PHENOTYPICALLY

In the course of genetic crosses designed to detect interactions between the Notch locus and other genes in Drosophila, a dramatic phenotypic interaction was observed between the Notch allele notchoid (nd) and the third chromosome mutation Serrate (designated $Ser^D$ herein). The recessive nd mutation, which is associated with an amino acid substitution in the intracellular portion of the Notch protein (Xu et al., 1990, Genes Dev. 4:464–475), causes wing notches in the adult (see FIG. 1b; compare to wildtype, FIG. 1a). The $Ser^D$ mutation is dominant and in heterozygous condition produces an adult wing blade very similar to that of nd animals (compare FIGS. 1b and 1c). The phenotypic interaction seen in nd/Y; $Ser^D$/+ males is characterized by loss of anterior and posterior wing margins, as well as loss of distal wing blade tissue. Concomitant with this loss, thickening of the L3 and L5 wing veins is observed (see FIG. 1d).

Even though both the $Ser^D$ and nd mutations affect wing blade development, the interaction appears to be synergistic because a novel phenotype is seen, that is, rather than just additive effects. To explore this question of synergy further, we constructed flies carrying genetic duplications of Notch+. Animals carrying an extra copy of Notch+ normally exhibit a Confluens phenotype characterized by wing vein thickening. Surprisingly, animals bearing $Ser^D$ and an extra copy of Notch+ have essentially wild-type wings (FIG. 1e), that is, both the $Ser^D$ wing nicking and the Confluens phenotypes are suppressed in this combination. This interaction was noted using both Dp(1;2)51b (a large genetic duplication of 3C1-2; 3D6 including N+) and CosP479BE [(N+) (86E5-6), a cosmid construct containing only the N+ gene (Ramos et al., 1989, Genetics 123:337:348)].

Because the $Ser^D$ mutation is neomorphic, the interactions observed between $Ser^D$ and Notch mutations might not be representative of interactions normally occurring between these gene products. We therefore examined the phenotypes of nd males heterozygous for Df(3R)Ser$^{+82/24}$ (nd/Y; Df(3R)Ser$^{+82/24}$/+). These animals exhibit a significantly increased mutant wing phenotype as compared to nd alone (not shown). Thus, it appears that Notch and $Ser^D$ mutually influence each other's phenotypic expression.

6.1.2. GENETIC CHARACTERIZATION OF SERRATE

Figure 1D:
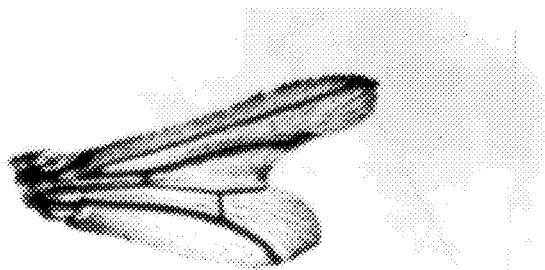
Figure 1E:
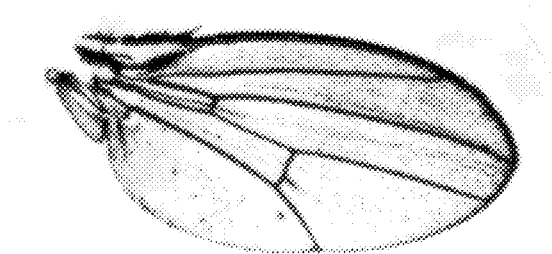
Figure 1F:
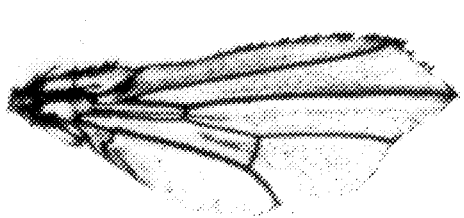

Previous genetic characterizations have demonstrated that the $Ser^D$ mutation maps to the 97F region of the polytene chromosomes and is neomorphic, producing the dominant wing nicking phenotype shown in FIG. 1d (Belt, 1971, Drosophila Inf. Serv. 46:116; P. Lewis, Yale University; unpubl.). The neomorphic nature is demonstrated genetically via the insensitivity of the $Ser^D$ phenotype to the number of wildtype (Ser+) copies present, that is $Ser^D$/+/+ displays a phenotype similar to $Ser^D$/+ and to $Ser^D$/Deficiency (P. Lewis, pers. comm.). Flies with only one copy of wild-type Ser+ (i.e., individuals heterozygous for a wild-type allele over deficiencies) are phenotypically wild-type, demonstrating that reduction of gene product (i.e., haploinsufficiency) is not causing the dominant phenotype. Finally, when the $Ser^D$ mutation is homozygous, viable adults are produced that display a more severe wing phenotype than heterozygous $Ser^D$/+ animals (FIG. 1f). Thus, the expression of the $Ser^D$ wing phenotype appears to be directly related to the expression of a mutant or novel gene product rather than to Ser+ gene dosage.

In an effort to obtain amorphic alleles of Serrate, we used X-ray mutagenesis to produce phenotypic revertants of the dominant mutation (see Section 6.3 for details). All five of the revertants of the $Ser^D$ mutation are lethal when homozygous and, consistent with the deficiency phenotypes, are phenotypically wild-type when heterozygous with a wild-type chromosome. Complementation tests revealed that the $Ser^{revertants}$ are allelic. Moreover, transheterozygotes of nd with two different $Ser^{revertants}$ alleles (nd/Y; $Ser^{rev2-3}$/+ and nd/Y; $Ser^{rev2-11}$/+) exhibit an enhanced mutant wing phenotype as compared to nd mutants, in agreement with the $Ser^D$-Notch interactions noted previously.

These complementation tests were extended to include another dominant mutation, Beaded of Goldschmidt ($Bd^G$), which also maps to the 97F region. Heterozygous adults bearing the $Bd^G$ mutation display a wing nicking phenotype that is more severe than that observed in $Ser^D$ heterozygotes (data not shown). Moreover, the $Bd^G$ mutation, unlike $Ser^D$, is homozygous lethal. Finally, three alleles ($Bd^{43.5}$, $Bd^{862.5}$, and $pll^{11}$) of a lethal complementation group isolated in K. Anderson's laboratory were shown to be allelic to $Bd^G$ (P. Hecht, unpubl.; a complete listing of the alleles used and their descriptions is provided in Section 6.3). Although transheterozygotes of $Ser^D$ and $Bd^G$ are viable, it is interesting to note that Df(3R)Ser$^{+82f4}$ and most of the $Ser^{revertants}$ fail to complement the $Bd^G$ mutation for viability. The exception is the $Ser^{rev2-3}$ allele, which although homozygous lethal, complements $Bd^G$. Despite the exceptional $Ser^{rev2-3}$ allele, these results suggest that the Serrate and Beaded mutations are alleles of the same gene (see also below). Consistent with this idea is the fact that $Ser^{revertant}$ and Bd alleles have similar phenotypes (see also below).

6.1.3. CHARACTERIZATION OF SERRATE MUTANT PHENOTYPES

Several revertants of $Ser^D$, a dominant allele of Serrate, have been isolated (Thomas et al., 1991, Dev. 111:749–761; Fleming et al., 1990, Genes Dev. 4:2188–2201; Speicher et al., 1994, Develop. 120:535–544). In general, such revertants are lethal, displaying larval lethality. However, the exact timing of lethality has been difficult to determine. A combination of expression data, overexpression studies and genetic analyses, including genetic mosaics, indicate that Serrate function is necessary for imaginal development (Speicher et al., 1994, Develop. 120:535–544). Early phenotypic data suggesting that Serrate affects embryonic development (Fleming et al., 1990, Genes Dev. 4:2188–2201), were shown to be due to interactions between Serrate and the genes in the balancer chromosome TM2 (Gu et al., 1995, Develop. 121, in press).

6.1.4. MOLECULAR CHARACTERIZATION OF SERRATE DNA

In an effort to elucidate the molecular nature of the Serrate gene product, DNA from the 97F region was cloned and characterized. A Drosophila genomic clone, previously isolated on the basis of cross hybridization to the EGF-like domain of the Notch gene (Rothberg et al., 1988, Cell 55:1047–1059), was used as an entry point to initiate a chromosomal walk. From this initial clone, eight recombinant phage spanning ~85 kb of genomic DNA were isolated (see FIG. 2). A BamHI site adjacent to the region of EGF homology was arbitrarily chosen as coordinate position zero.

Genomic Southern blots containing mutant and wild-type DNAs were probed with DNA from the individual phage isolates to detect and localize rearrangement breakpoints that might be associated with the various Serrate alleles. Within the first phage isolate, ø10.2, restriction fragment polymorphisms were detected on the original $Ser^D$ chromosome. The polymorphism detected with each of three restriction enzymes (EcoRI, BamHI, and HindIII) was consistent with an insertion of ~5.5 kb of DNA between map coordinates 0 and −3 (FIG. 2). Subsequent Southern analysis using DNA cloned from Ser$^D$ revealed a repeated DNA sequence, suggesting the presence of a mobile insertional element associated with the mutation. In addition to the insertion, the HindIII site at coordinate −2 has been eliminated in the Ser$^D$ chromosome. Because the parental chromosome from which the Ser$^D$ mutation arose is unavailable, we cannot be certain that the noted polymorphisms are causal to the Ser$^D$ phenotype.

Of the five Ser$^{revertant}$ alleles, three (Ser$^{rev2-3}$, Ser$^{rev5-5}$, and Ser$^{rev6-1}$) appeared cytologically normal and did not exhibit DNA polymorphisms detectable by our Southern analyses. The remaining two revertants, Ser$^{rev2-11}$ and Ser$^{rev 3}$, had polymorphic DNA restriction fragments within the cloned region. Ser$^{rev2-11}$ is an inversion of polytene bands 97F to 98C. The 97F breakpoint was localized between coordinates +1.5 to +4, within the region of strongest detectable EGF homology (FIG. 2). Ser$^{rev 3}$ is a reciprocal translocation of chromosomes 3R and 2R, with the 97F breakpoint localized between coordinates +15 and +17 (FIG. 2). In situ hybridization of the cloned wild-type genomic DNAs to polytene chromosomes of Ser$^{rev 3}$ and Ser$^{rev2-11}$ confirmed that the observed DNA polymorphisms represent the 97F breakpoints of these chromosomal rearrangements.

As noted earlier, Ser$^{revertant}$ alleles fail to complement Bd$^G$, suggesting that the Serrate and Bd mutations are alleles of the same gene. As with the Ser$^D$ mutation, the parental chromosome for the Bd$^G$ mutation was not available; hence, unambiguous assignment of mutant phenotypes to DNA polymorphisms cannot be made. Cytological observations of the Bd$^G$ chromosome failed to reveal any visible abnormalities; however, two regions of DNA polymorphism were detectable by Southern analysis. These regions lie between coordinates 0 to +1 and +14 to +17. Investigations of the polymorphism at position 0 to +1 were pursued by cloning the mutant DNA sequences. Preliminary results indicate that the polymorphisms do not result from a small inversion between these two regions but, rather, from a more complex event.

Of the three mutant chromosomes, Bd$^{43.5}$, Bd$^{862.5}$, and pll$^{11}$, only pll$^{11}$ found to have a DNA polymorphism, which was localized between coordinates +17 and +19 (FIG. 2). Genetic and cytological data for the pll$^{11}$ suggest the presence of a very small chromosomal aberration within the 97F region (P. Hecht, pers. comm.), and the molecular data are consistent with this observation. Finally, T(Y:3)R128 is a reciprocal translocation that also breaks within the 97F region (Lindsley et al., 1972, Genetics 71:157–184) and fails to complement Bd$^G$ (P. Hecht, pers. comm.). The DNA breakpoint for this translocation resides at map coordinates +25 to +28 (FIG. 2). Taken together, these findings strengthen the genetic evidence that Serrate and Bd mutations are alleles of the same gene. In summary, of eleven tested chromosomes containing Serrate or Bd mutation, six were shown to have associated DNA rearrangements within a kb region known to contain EGF homologous sequences.

To examine the structure of the Serrate transcription unit, we probed Northern blots containing 2- to 14-hour embryonic poly(A)RNA with the recombinant phages spanning this region (ø10.1, ø1.3 and ø15K; FIG. 2). This analysis revealed the presence of two transcripts of ~5.5 kb and 5.6 kb. We isolated two overlapping cDNA clones, denoted C1 and C3, from an early pupal library (see Section 6.3). Sequence analysis of these cDNAs revealed a perfect overlap of 109 bp for a combined length of 5.6 kb, which is in excellent agreement with the larger of the two transcripts as determined by northern analysis. Genomic probes unique to the 5' end of C3 only detected the larger 5.6 kb transcript. Thus, the size difference between the 5.5 and 5.6 kb transcripts may represent an alteration in the potential protein coding capacity or an alteration of 5' untranslated sequence. The composite 5.6 kb cDNA confirms that the Serrate transcription unit spans ~30 kb of genomic DNA, encompasses the EGF homologous region, and is interrupted by at least five of the six DNA rearrangements that affect Serrate function (FIG. 2). From Southern analysis, at least two introns are apparent; additional introns are likely but not detectable at this level of resolution.

6.1.5. SERRATE ENCODES A PUTATIVE TRANSMEMBRANE PROTEIN WITH 14 EGF-LIKE REPEATS

The complete nucleotide sequence compiled from the cDNAs C1 and C3 is 5561 bp (see FIGS. 3A–3F) and agrees with the transcript sizes determined by northern analysis. Within this sequence there is a single large open reading frame (ORF) of 4329 bp. There are two possible initiator AUG codons at positions 433 and 442. Of these, the second AUG is within a sequence context that agrees with the Drosophila consensus sequence determined for translation initiation [CAAAAUG; (Cavener, 1987, Nucl. Acids Res. 15:1353–1361)]. Predicted codon usage within this ORF is highly consistent with established *Drosophila melanogaster* codon preferences (Beachy et al., 1985, Nature 313:545–550). Assuming that translation starts at the second AUG, the Serrate mRNA contains an untranslated leader sequence of at least 441 base pairs, encodes an expected protein product of 1404 amino acids, and terminates with 908 bp of untranslated 3' sequence (FIG. 4a). However, if translation begins at the first AUG, the protein product is 1443 amino acids.

Hydropathy plots revealed three major hydrophobic regions (FIG. 4b; see also Section 6.3). The first, beginning at amino acid 51, is likely to represent a signal peptide sequence; a potential signal cleavage site occurs at amino acid 80. A second hydrophobic domain runs from amino acid 540 to 560. This region does not have a requisite transmembrane structure and is more likely to be a membrane-associated domain. The third hydrophobic domain (amino acids 1220 to 1245) is bounded by hydrophilic residues and is therefore likely to represent a true transmembrane domain.

The most striking structural feature of the predicted protein is the series of EGF-like repeats (see FIG. 4c). There are 14 copies of this motif with an additional partial or degenerate repeat occurring toward the amino terminus (see below). In addition, at least three of these repeats are interrupted by stretches of amino acids. The first interruption (labelled A in FIG. 4c), which occurs in the fourth complete EGF-like repeat (repeats are numbered beginning from the amino terminus), is ~64 amino acids in length and is enriched for serine residues. The second interruption (labelled B in FIG. 4c), occurring in the sixth repeat, is ~44 amino acids long and has numerous hydrophobic residues. This region represents the putative membrane-associated domain noted earlier. The final interruption (labelled C in FIG. 4c), which occurs in the tenth repeat and is 29 amino acids in length, has an unusual run of threonines [Thr$_{(9)}$ Ala Thr$_{(3)}$].

Within the amino-terminal region of the Serrate protein, considerable structural homology (darkly-shaded region in FIG. 4c) is observed with the main protein product of the Delta locus (Vassin et al., 1987, EMBO J. 6:3431–3440;Kopczynski et al., 1988, Genes Dev. 2:1723–1735). Near the signal peptides for both of these molecules there lies a stretch of ~210 conserved amino acids. Within the first 165 amino acids, there is ~32% identity, which increases to greater than 50% for the remaining 45 amino acids. The latter region corresponds to the partial EGF-like repeat (designated PR in FIG. 4c), which lacks a cysteine residue but retains the other characteristic cysteines and conserved amino acids typically found in the remaining EGF-like repeats. The homology between Serrate and Delta extends beyond these amino-terminal regions, since both of these proteins contain EGF-like repeats.

In addition to the extracellular EGF-like sequences, the predicted Serrate protein contains a small intracellular domain of ~160 amino acids. The internal domain does not contain any significant known structural homologies, although there are numerous potential sites for phosphorylation (Those identified in the putative intracellular region by the SITES program were at amino acid positions 1283, 1292, 1297, 1349, 1365, 1371, 1389, and 1390).

6.1.6. EXPRESSION OF SERRATE RNA

Northern analysis of developmentally staged RNAs revealed that the majority of Serrate expression is represented by two coordinately regulated transcripts of 5.5 kb and 5.6 kb, which first appear 4 to 8 hours into embryogenesis (FIG. 5). These transcripts show peak expression between 8 and 12 hours of embryogenesis and diminish thereafter; however, they continue to be readily detectable throughout development except for the adult stages (FIG. 5). In addition to these major transcripts, a smaller (3.4 kb) transcript is expressed transiently between 2 and 4 hours of embryogenesis (FIG. 5).

We undertook an analysis of the spatial distribution of RNA transcripts from the Serrate locus in order to identify regions of the embryo that may require Serrate function. Using the whole mount in situ method (Tautz and Pfeifle, 1989, Chromosoma 98:81–85) and employing nonradioactive probes that hybridize to both the 5.5 kb and 5.6 kb transcripts, we found that Serrate mRNA accumulates in a dynamic pattern beginning from mid-embryogenesis (late stage 10) and persisting until the latest stages examined (stage 16); (embryonic stages are those of Campos-Ortega and Hartenstein, 1985, *The Embryonic Development of Drosophila Melanogaster*, Springer-Verlag, Berlin). Because the tissue distribution of the two transcripts may be independently regulated, we note that the observed RNA localizations may represent a composite for both transcripts. We also note the possibility of a low level of Serrate RNA in the yolk of pre-gastrulation embryos because faint staining of the yolk was observed consistently. Although this staining was never observed with control probes (see Section 6.3), the presence of yolk staining is known to be a common artifact of the whole-mount in situ technique (Ashburner, 1989, *Drosophila—A laboratory manual*, Cold Spring Harbor Laboratory Press, Cold Spring Harbor, N.Y.). However, if this observation is not artifactual, the observed staining may correspond to the expression of the transient 3.4 kb RNA species observed by the northern analysis of this same developmental stage.

Figure 6A:
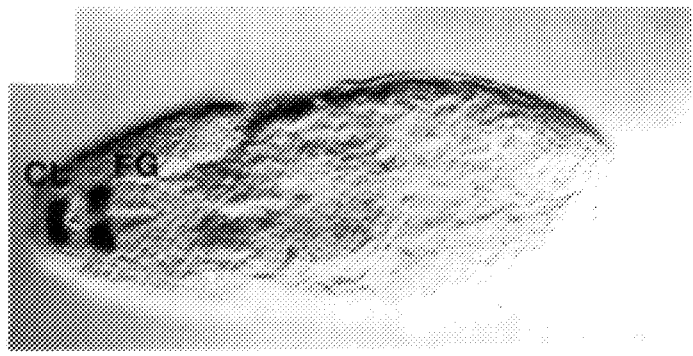
Figure 6B:
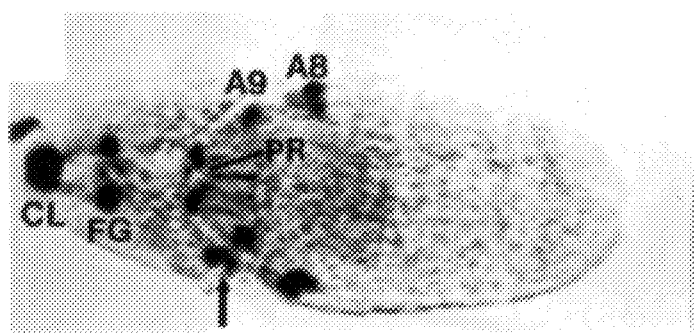
Figure 6C:
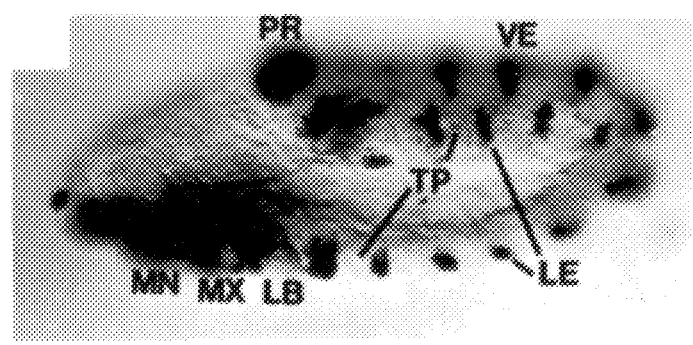

Initial cellular localization was seen in late-stage 10 embryos and consisted of a ring of cells in the foregut. The foregut is formed by the invagination of the stomodeum (the initial event of stage 10); thus, the foregut is actually derived from ectodermal tissue. Shortly thereafter, a bilateral patch of expressing cells appeared in the anterior-most portion of the head, the presumptive clypeolabrum (FIG. 6a). Additional areas of expression appeared abruptly at the end of stage 10 in a group of cells on the lateral edge of abdominal segment 8, followed by cells near the proctodeum and lateral epidermis of abdominal segment 9 (FIG. 6b). Later, during stage 11, expression was detected within cells located at the junction between the labial and maxillary lobes and within cells located near the tracheal pit of the first thoracic segment. The expression pattern progressed to include a group of lateral epidermal cells located between the tracheal pits in each of the thoracic and abdominal segments (FIG. 6c). In addition, each abdominal segment displayed a cluster of cells on either side of the ventral midline.

Figure 6D:
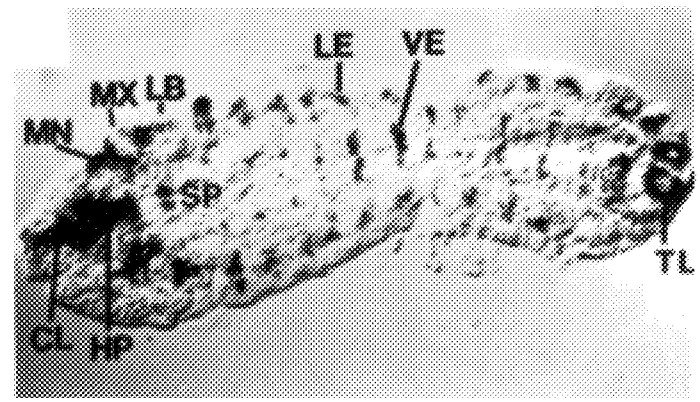
Figure 6E:
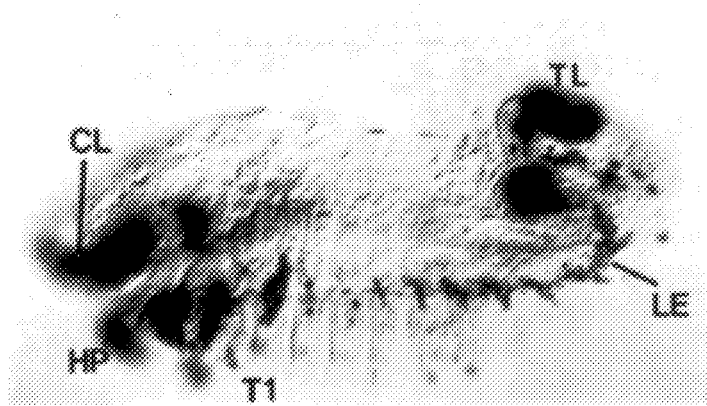
Figure 6F:
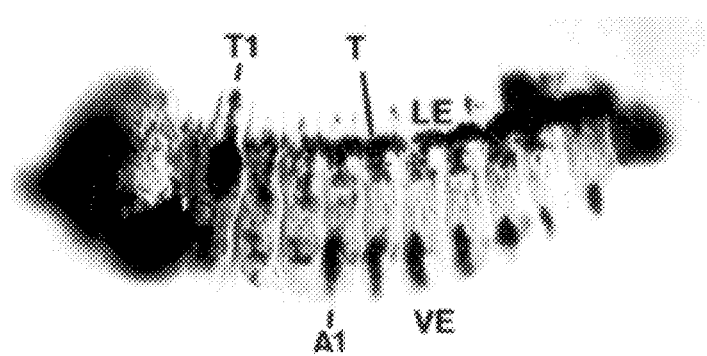
Figure 6G:
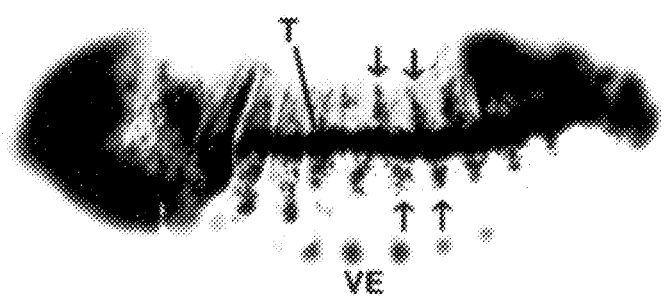
Figure 6H:
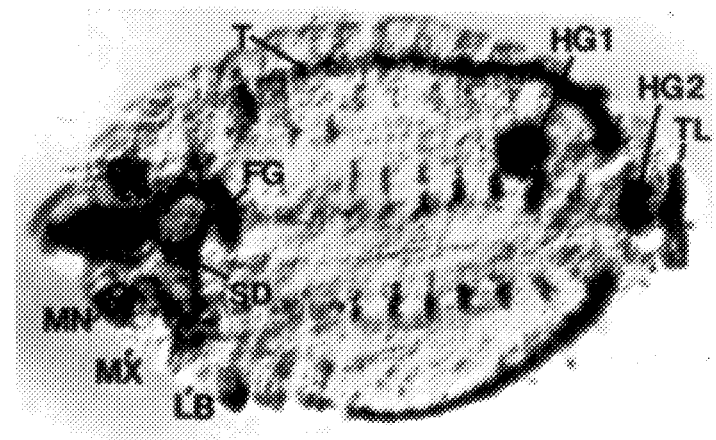
Figure 6I:
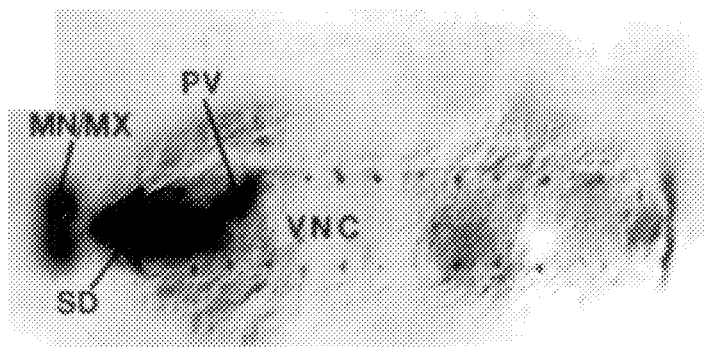
Figure 6J:
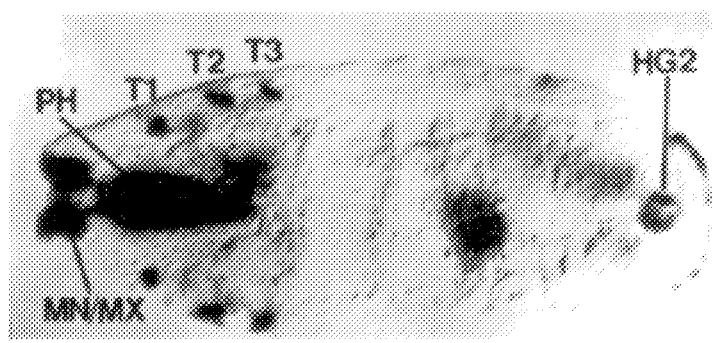

During germ band retraction (stage 12), the lateral epidermal cell patches broadened to form stripes that lie in the middle of each segment. A portion of these cells appeared to coalesce into an internal longitudinal stripe that was coincident with the developing tracheae (see FIGS. 6e, f, g, and h). The cells that remained on the surface extended dorsally and ventrally forming a zig-zag shaped pattern (FIG. 6g, arrows). This surface expression in the thoracic segments was wider, more intense, and extended further dorsally and ventrally than in the abdominal segments (FIG. 6g). Later in embryogenesis (stages 14 and 15) the surface epidermal expression, with the exception of the, first thoracic segment, diminished relative to the tracheal expression. Later, intense expression was observed in what appeared to be ectodermal invaginations located dorsolaterally on the thoracic segments (FIG. 6j). These pockets of cells may correspond to primordia of imaginal discs; in the first thoracic segment they appeared to be closely associated with opening of the anterior spiracle.

Figure 6K:
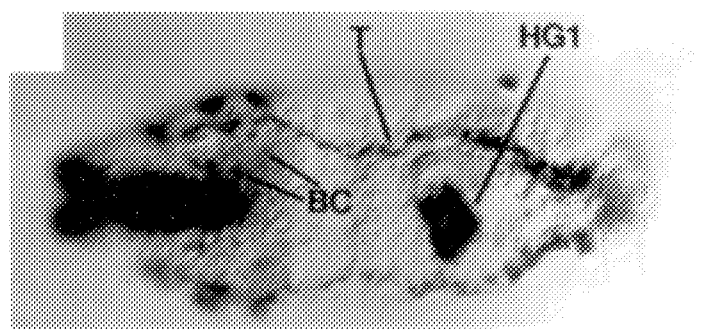
Figure 6L:
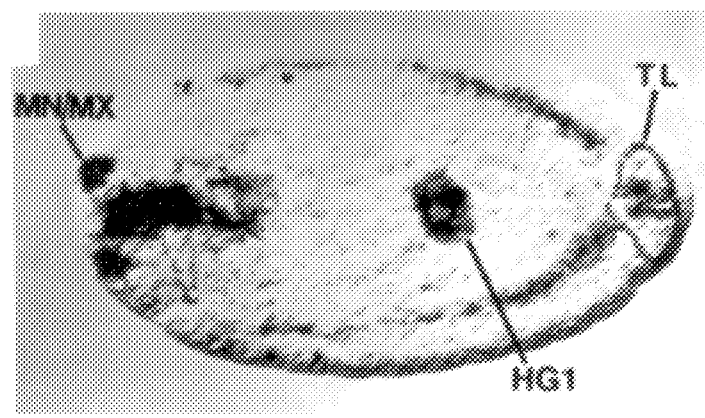

Coincident with the lateral expression, another segmentally reiterated pattern evolved in the ventral epidermis of the trunk. In the extended germ band embryo, this pattern, which consisted of stripes of expressing cells near the anterior border of the abdominal segments, lay out of register with the corresponding lateral expression (FIG. 6c). The pattern in the thorax contrasted with that in the abdomen and consisted of only small clusters of expressing cells in the latero-ventral region (see FIGS. 6f and 6h). The ventral expression was quite intense through stage 13 and dissipated thereafter (FIG. 6l).

Serrate expression was also observed in the ectodermally-derived portions of the gut. The earliest expression was evident in the foregut and persisted throughout embryonic development (FIG. 6a). During germband retraction, a tightly defined, intensely expressing ring of cells lay at the junction with the anterior midgut. The proventriculus develops from this area; however, expression was limited to the ectodermally-derived portion of this composite structure (King, 1988, J. Morph. 196:253–282). Hindgut expression, though appearing later than foregut expression, occurred at an analogous position, that is, where ectoderm meets endoderm. The initial expression in the hindgut was seen at the time of germ band retraction (stage 12) as a wide band of cells where the Malphigian tubules were forming, but never included the tubules themselves. Later still (stage 14), an additional ring of expression appeared in the hindgut approximately mid-way between the insertion point of the Malphigian tubules and the proctodeum (FIG. 6h). Expression at the posterior-most end of the embryo, near the proctodeal opening, initiated early (stage 11) (FIG. 6b). This expression within the telson remained at high levels throughout embryonic development, eventually forming a ring of cells around the presumptive anal pads (FIG. 6l). Within the head region, Serrate expression was temporally and spatially dynamic. The earliest expression occurred in the presumptive clypeolabrum (stage 10; FIG. 6a) and became broader and more intense as development proceeded. Early expression between the labial and maxillary lobes increased along their borders, and expression was also seen in the anterior of the mandibular lobe during stage 12 (FIGS. 6d and 6e). In addition, expression was now observed in the hypopharyngeal region, just posterior to the stomodeum, and at the base of the labial lobes in an area encompassing the salivary gland duct opening (FIG. 6d). There was also low level expression in the dorsal procephalic epidermal region (not shown). By the end of germ band retraction (stage 13), expression encompassed the entire mandibular lobe. As a consequence of the cellular movements associated with head involution (stages 14–16), the expressing cells of the clypeolabrum, hypopharynx and labial lobes combined to form the pharynx. Prior expression in the area of the salivary gland placodes was now limited to the ducts of the developing salivary gland (FIG. 6i). The maxillary and mandibular lobes, which have moved to the anterior-most region of the embryo, expressed intensely at this time (FIG. 6j).

Serrate expression in the central nervous system (CNS) was apparent during stage 12 as a segmentally-reiterated array of single cells along the lateral edge of the ventral nerve cord and within the supraesophogeal ganglia (brain hemispheres). By the end of germ band retraction (stage 13), there were now two cells that appeared to express in each hemisegment of the ventral nerve cord (not shown). However, by stage 15, ventral nerve cord expression was again limited to a single cell per hemisegment (FIG. 6i) while expression in the brain hemispheres remained unchanged (FIG. 6k).

In summary, there are a wide array of tissues that express Serrate mRNA, and the expression pattern is tightly regulated both temporally and spatially. In addition, it should be stressed that at the present level of resolution, Serrate expression appears to be restricted exclusively to cells of ectodermal origin.

6.2. DISCUSSION

Unlike Notch and Delta, the fourteen EGF repeats of Serrate are not completely contiguous. At least three of these repeats contain sizeable interruptions consisting of insertions of long stretches of amino acids. Similarly, interruptions have been noted in two of the thirty EGF-like repeats of the Drosophila gene crumbs (Tepass et al., 1990, Cell 61:787–799). In Serrate, the interruption that occurs in the sixth repeat is particularly intriguing because it consists largely of hydrophobic amino acids. Although hydropathy plots indicate that this region does not conform to known transmembrane regions, it could represent a membrane-associated domain that serves to "tie" the protein back to the membrane. The interruption in the tenth repeat is also unusual in that it bears a stretch of threonines [$Thr_{(9)}$Ala $Thr_{(3)}$]. A similar motif of thirteen contiguous threonine residues is found in the glycoprotein glutactin, a basement membrane protein of Drosophila (Olson et al., 1990, EMBO J. 9:1219–1227).

If the observed genetic interactions between Notch and Serrate had been only with the original $Ser^D$ allele, it could have been argued that this neomorphic mutation is allowing two functionally disparate but structurally similar molecules to interact out of their normal contexts. But because we observe genetic interactions with other Serrate alleles, it is likely that we are observing a manifestation of normal Serrate-Notch interactions.

We have shown that phenotypic revertants of $Ser^D$ behave genetically in a similar fashion to known deficiencies for the locus; that is, they are homozygous lethal during embryogenesis and completely recessive as heterozygotes. We also gathered evidence indicating that the mutation $Bd^G$, which was thought to belong to a distinct complementation group, may in fact be an allele of Serrate.

The embryonic lethal phenotypes of $Ser^{rev2-3}$, $Ser^{rev2-11}$, and $Ser^{rev5-5}$, which are essentially indistinguishable from one another, appear unchanged when in homozygous or hemizygous condition. This latter result genetically defines these alleles genetically as amorphic. However, since the $Ser^{rev2-3}$ allele complements the $Bd^G$ mutation, the $Ser^{rev2-3}$ mutation is probably not a protein null allele.

Consistent with the defects observed in the cuticle and nervous system of $Ser^-$ embryos, Serrate transcripts are localized in complex patterns within these tissues. The abundant and widespread expression of Serrate transcripts in the segments that make up the embryonic head and thorax correlates well with the lack of embryonic head and thoracic structures commonly seen in $Ser^-$ embryos. Likewise, the pattern of Serrate expression in the ventral epidermis of the abdominal segments correlates with the frequently absent or improperly formed denticles. Although Serrate is expressed in a small number of cells within the CNS, the gross morphological defects observed in the CNS of $Ser^-$ embryos may reflect contributions from two components. The first is the loss of Serrate CNS expression itself, and the second may be a consequence of mechanical stresses (e.g., lack of germ band retraction) imposed by an improperly differentiating epidermis.

In the course of examining the embryonic phenotypes associated with Serrate lethal mutations, we noticed their similarity to those produced by several alleles of the gene coding for the Drosophila EGF receptor homolog known as DER, faint little ball or torpedo (Livneh et al., 1985, Cell 40:599–607; Price et al., 1989, Cell 56:1085–1092; Schejter and Shilo, 1989, Cell 56:1093–1104).

6.3. MATERIALS AND METHODS

6.3.1. DROSOPHILA CULTURES AND STRAINS

Cultures were maintained on standard cornmeal/molasses/agar Drosophila medium supplemented with active dry yeast and were raised at 25° C. The red $Ser^D$, $Df(3R)Ser^{+82f24}$, and $Bd^G$ chromosomes were obtained from Peter Lewis. The red $Ser^D$ chromosome was maintained in homozygous condition. The mutations $pll^{11}$, $Bd^{862.5}$, and $B^{43.5}$ were generously provided by Kathryn Anderson. The Notch duplication CosP479 is an ~40 kb P-element cosmid construct inserted into the third chromosome (Ramos et al., 1989, Genetics 123:337–348). Other mutations and chromosomes have been described previously (Lindsley and Grell, 1968, Genetic variations of *Drosophila melanogaster*, Carnegie Inst. Wash. Publ. 627).

6.3.2. MUTAGENESIS

Males aged 3–7 days and homozygous for the red $Ser^D$ chromosome were irradiated with approximately 4500 R (150 kV, 5 mA, 9.2 min exposure; Torrex 150 Source, Torr X-Ray Corp.) and mated immediately to $C(1)A;y/y^2Y611$ or $C(1)Dx;yf/y^2Y611$ virgin females. The $F_1$ males were scored for the absence of he $Ser^D$ wing phenotype and mated to $Gl^{p1-3}$ fz red e/Tm2, red e virgin females to establish balanced $Ser^{rev}$/Tm2, red e stocks.

Mutations used in this study are shown in Table 1.

TABLE I

| Mutation | Origin | Description |
| --- | --- | --- |
| $Ser^D$ | Spontaneous; information (Lindsley and Grell, 1968, Carnegie Inst. Wash. Publ. 627) | heterozygous dominant wing phenotype, homozygous viable; cytologically normal |
| $Bd^G$ | recovered among heat-treated flies (Gottschewski, 1935, Dros. Inf. Serv. 4:14,16) | heterozygous dominant wing phenotype homozygous lethal, cytologically normal |
| $Ser^{rev3}$ | X-ray (this study) | homozygous lethal; reciprocal translocation of 3R (97F) to 2R (57) |
| $Ser^{rev2-3}$ | X-ray (this study) | Homozygous lethal; cytologically normal |
| $Ser^{rev2-11}$ | X-ray (this study) | homozygous lethal; inversion of 97F to 98C |
| $Ser^{rev5-5}$ | X-ray (this study) | homozygous lethal; cytologically normal |
| $Ser^{rev6-1}$ | X-ray (this study) | homozygous lethal; cytologically normal |
| $Bd^{43.5}$ | EMS (K. Anderson, unpubl.) | homozygous lethal; cytologically normal |
| $Bd^{862.5}$ | EMS (K. Anderson, unpubl.) | homozygous lethal; cytologically normal |
| $p11^{11}$ | EMS (K. Anderson, unpubl.) | homozygous lethal; possible small inversion within the 97F interval |
| T(Y:3)R128 | X-ray (Lindsley et al., 1972, Genetics 71: 157-184) | homozygous lethal; reciprocal translocation of 3R (97F) to Y short arm |
| $Df(3R)Ser^{+82124}$ | X-ray (P. Lewis, unpubl.) | deficiency for chromosome bands 97D to 97F-98A1 |

6.3.3. EMBRYONIC PHENOTYPE ANALYSIS

Cuticle preparations were according to the protocol 5of Wieschaus and Nusslein-Volhard (1986, in *Drosophila. A Practical Approach*, (ed. D. B. Roberts), IRL Press, Oxford, pp. 199–227) on embryos aged for a minimum of 24 hours at 25° C. Anti-horseradish peroxidase antibody staining of the embryonic nervous system (Jan and Jan, 1982, Proc. Natl. Acad. Sci. USA 79:2700–2704) was carried out using fluorescein-conjugated antibody (Cappel) as described in Preiss et al. (1988, EMBO J. 7:3917–3927). CNS preparations of $torpedo^{2C82}$ were used for comparison studies.

6.3.4. ISOLATION OF NUCLEIC ACIDS

Genomic DNA was isolated as described in Pirrotta et al. (1983, EMBO J. 2:927–934). Restriction enzyme cleavage, agarose gel electrophoresis, capillary transfer to nitrocellulose and hybridization conditions were carried out according to standard procedures. DNA probes labeled with $^{32}P$ were prepared by random oligonucleotide priming, as described in Feinberg and Vogelstein (1983, Anal. Biochem. 132:6–13).

Stage-specific total RNAs from a Canton-S strain were extracted in guanidinium thiocyanate essentially as described in Chirgwin et al. (1979, Biochem. 18:5294–5299). Pupal and adult RNAs were generously provided by A. Preiss (Preiss et al., 1988, EMBO J. 7:3917–3927). Poly $(A)^+$ RNA was selected by serial passage over oligo(dT)– cellulose (Stratagene) according to Sambrook et al. (1989, *Molecular Cloning: A Laboratory Manual*, 2d Ed., Cold Spring Harbor Laboratory Press, Cold Spring Harbor, N.Y.) and stored in ethanol. RNA was size fractionated in formaldehyde agarose gels and blotted onto Nytran membrane (Schleicher & Schuell) by capillary transfer. RNA was fixed to the membrane via UV crosslinking.

Two Drosophila genomic phage libraries (Preiss et al., 1985, Nature 313:27–32; R. Karess, unpubl.) were screened and recombinant clones were isolated as described in Benton and Davis (1977, Science 196:180–182). cDNAs in λgt10 were isolated from the early pupal library of Poole et al. (1985, Cell 40:37–43). We isolated the C1 cDNA using the genomic EGF-like sequences from coordinates +1.5 to +4 (FIG. 2) as probe. Subsequently, we isolated the C3 cDNA using the 5' 700 bp terminal fragment of the C1 cDNA as probe.

6.3.5. SEQUENCING AND ANALYSIS

The EcoRI cDNA inserts from λgt10 were subcloned directly into Bluescript KS+ and KS– vectors (Stratagene). Single-stranded DNAs were produced according to the manufacturer's instructions. Both strands of the cDNAs were sequenced using the dideoxynucleotide chain-termination procedure (Sanger, et al., 1977, Proc. Natl. Acad. Sci. USA 74:5463–5467) using the Sequenase kit (U. S. Biochemical). Sequence was obtained using the M13 and reverse primers for these vectors. Additional sequence was obtained by generating internal deletions through the use of restriction sites within the Bluescript polylinker and the cDNA inserts. The remaining cDNA sequences that were not accessible by these methods were obtained by using synthetic primers (Research Genetics) complementary to the end of a previously determined sequence.

Sequences were entered by sonic digitizer and overlapping sequence compilation; manipulation, translation, and secondary structure prediction were accomplished by using the Intelligenetics PC-GENE. Open reading frame prediction and plotting were performed using the University of Wisconsin program CODONPREFERENCE (Gribshov et al., 1984, Nucl. Acids Res. 12:539–549). The SITES program (PCGENE) was used to predict the location of the signal sequence, transmembrane domain, EGF-like repeats, and phosphorylation sites.

6.3.6. WHOLE MOUNT IN SITU PROCEDURE

A modification of the whole-mount in situ procedure of D. Tautz (Procedure 84a in Ashburner, 1989, *Drosophila: A Laboratory Manual*, Cold Spring Harbor Laboratory Press, Cold Spring Harbor, N.Y.) was used. The differences were as follows: Proteinase K (Boehringer-Mannheim) treatment was 10 to 14 minutes; 100 μl (rather than 10 μl) of boiled probe was used; after washing the embryos with 1:4 hybridization buffer to PBT, they were washed twice in PBT for 20 minutes, and then twice in 1×PBS, 0.1% BSA (globin free, Sigma), 0.2% Triton-X100 for 20 minutes; the antibody treatment was done in the same PBS, BSA, Triton solution at 4° C. overnight; the embryos were washed four times in the PBS, BSA, Triton solution at room temperature; after the alkaline phosphatase reaction, embryos were dehydrated twice in 70% and 100% ethanol and then cleared in xylenes; the embryos were mounted in Permount (Sigma). Dissected embryos were rehydrated, dissected in PBT, and mounted in 90% glycerol [10% Tris-HCl at pH 8.0, with 0.5% n-propyl-galate (wt/vol; Sigma)].

The probe was made by runoff of a PCR reaction in 50 mM KCl, 10 mM Tris-HCl (pH 8.3), 1.5 mM $MgCl_2$, 0.01% (wt/vol) gelatin, 0.2 mM DATP, 0.2 mM dCTP, 0.2 mM dGTP, 0.15 mM dTTP, and 0.07 mM digoxigenin-11-dUTP (Boehringer Mannheim) using 150 ng of custom synthesized primer and approximately 400 ng of linearized DNA. Probe was synthesized from cDNA coordinates 4826 to 3854; the opposite strand constituted the control probe and was synthesized from coordinates 4458 to 5015 (refer to FIG. 5). The conditions for the PCR thermal cycler were 95° C. for 45 seconds, 55° C. for 30 seconds, and 72° C. for 1 minute, which were run for 30 cycles. The probe was ethanol precipitated twice and resuspended in 300 μl of hybridization solution.

7. EXPRESSION OF A SERRATE FRAGMENT AS A FUSION PROTEIN AND PRODUCTION OF ANTIBODIES THERETO

Mouse anti-Serrate polyclonal antisera were made as follows: A BamHI fragment encoding amino acids 78–425 (FIGS. 3A–3F) was subcloned into the pGEX-1 expression vector (Smith and Johnson, 1988, Gene 67:31–40). Fusion proteins were purified on glutathione-agarose beads (SIGMA), and injected into mice for antibody production. Mouse antisera were precipitated with 50% $(NH_4)_2SO_4$ and resuspended in PBS (150 mM NaCl, 14 mM $Na_2HPO_4$, 6 mM $NaH_2PO_4$) with 0.02% $NaN_3$.

8. EXPRESSION OF SERRATE AND A FRAGMENT AND A CHIMERIC DERIVATIVE THEREOF; IDENTIFICATION OF A NOTCH-BINDING DOMAIN

We describe herein the recombinant expression of Serrate, of a deletion construct (fragment) thereof, and of a chimeric Notch-Serrate fragment, and show that the full-length Serrate and the chimeric derivative are capable of binding to Notch in vitro.

8.1. EXPRESSION OF SERRATE AND OF DERIVATIVES THEREOF

For the Serrate expression construct, a synthetic primer containing an artificial BamHI site immediately 5' to the initiator AUG at position 442 of the Drosophila sequence (all sequence numbers are according to Fleming et al., 1990, Genes & Dev. 4:2188–2201) and homologous through position 464, was used in conjunction with a second primer from position 681–698 to generate a DNA fragment of ~260 base pairs. This fragment was cut with BamHI and KpnI (position 571) and ligated into Bluescript KS+ (Stratagene). This construct, BTSer5'PCR, was checked by sequencing, then cut with KpnI. The Serrate KpnI fragment (571–2981) was inserted and the proper orientation selected, to generate BTSer5'PCR-Kpn. The 5' SacII fragment of BTSer5'PCR-Kpn (SacII sites in Bluescript polylinker and in Serrate (1199)) was isolated and used to replace the 5' SacII fragment of cDNA C1 (Fleming et al., 1990, Genes & Dev. 4:2188–2201), thus regenerating the full length Serrate cDNA minus the 5' untranslated regions. This insert was isolated by a SalI and partial BamHI digestion and shuttled into the BamHI and SalI sites of the metallothionein promoter vector pRmHa-3 (Bunch et al., 1988, Nucl. Acids. Res. 16:1043–1061) to generate the final expression construct, Ser-mtn.

A Serrate deletion expression construct was also made, in which nucleotides 672–1293 (encoding amino acids 77–284) (FIGS. 3A–3F, 7, 8A–8C) were deleted. This deletion construct was made as follows: The Ser-mtn construct was digested with EcoRV, which cuts at nucleotide 672, and with SfiI, which cuts at nucleotide 4073. The linearized vector, lacking the EcoRV-SfiI (672–4073) fragment, was isolated. Plasmid SerFL was then digested with NdeI, which cuts at nucleotide 1289, and treated with mung bean nuclease resulting in the "trimming back" of four bases. The resulting SerFL fragment was then digested with SfiI which cuts at base 4073, and the resulting 1293–4073 fragment was isolated and ligated into the EcoRV-SfiI vector isolated above.

In addition, a Notch-Serrate chimeric construct was made using a clone consisting of Drosophila Notch cDNA with a deletion of all the Notch EGF-like repeats ("AEGF") (see PCT Publication WO 92/19734 published Nov. 12, 1992; Rebay et al., 1991, Cell 67:687–699 (FIGS. 12A–12B, construct no. 25)). An N-terminal region of Serrate with homology to Delta and including the Serrate EGF-like repeats (Serrate nucleotide numbers 676–1287, encoding amino acids 79–282; FIGS. 7, 8A–8C) was placed into the AEGF deletion of Notch. The above constructs were expressed in Drosophila S2 cells. The S2 cell line (Schneider, 1972, J. Embryol. Exp. Morph. 27, 353–365) was grown in M3 medium (prepared by Hazleton Co.) supplemented with 2.5 mg/ml Bacto-Peptone (Difco), 1 mg/ml TC Yeastolate (Difco), 11% heat-inactivated fetal calf serum (FCS) (Hyclone), and 100 U/ml penicillin-100 μg/ml streptomycin-0.25 μg/ml fungizone (Hazleton). Cells growing in log phase at ~2×10⁶ cells/ml were transfected with 20 μg of DNA-calcium phosphate coprecipitate in 1 ml per 5 ml of culture as previously described (Wigler et al., 1979, Proc. Natl. Acad. Sci. USA 78, 1373–1376), with the exception that BES buffer (SIGMA) was used in place of HEPES buffer (Chen and Okayama, 1987, Mol. Cell. Biol. 7, 2745–2752). After 16–18 hr, cells were transferred to conical centrifuge tubes, pelleted in a clinical centrifuge at full speed for 30 seconds, rinsed once with ¼ volume of fresh complete medium, resuspended in their original volume of complete medium, and returned to the original flask. Transfected cells were then allowed to recover for 24 hr before induction. Expression from the metallothionein constructs was induced by the addition of $CUSO_4$ to 0.7 mM.

8.2. AGGREGATION ASSAYS FOR BINDING TO NOTCH

8.2.1. METHODS

Two types of aggregation assays were used. In the first assay, a total of 3 ml of cells (5–10×10⁶ cells/ml) was placed in a 25 ml Erlenmeyer flask and rotated at 40–50 rpm on a rotary shaker for 24–48 hr at room temperature. For these experiments, cells were mixed 1–4 hr after induction began and induction was continued throughout the aggregation period. In the second assay, ~0.6 ml of cells were placed in a 0.6 ml Eppendorf tube (leaving a small bubble) after an overnight induction (12–16 hr) at room temperature and rocked gently for 1–2 hr at 4° C. $Ca^{2+}$ dependence experiments were performed using the latter assay. For $Ca^{2+}$ dependence experiments, cells were first collected and rinsed in balanced saline solution (BSS) with 11% FCS (BSS-FCS; FCS was dialyzed against 0.9% NaCl, 5 mM Tris [pH 7.5]) or in $Ca^{2+}$ free BSS-FCS containing 10 mM EGTA (Snow et al., 1989, Cell 59: 313–323) and then resuspended in the same medium at the original volume.

For viewing by immunofluorescence, cells were collected by centrifugation (3000 rpm for 20 seconds in an Eppendorf microcentrifuge) and fixed in 0.6 ml Eppendorf tubes with 0.5 ml of freshly made 2% paraformaldehyde in PBS for 10 min at room temperature. After fixing, cells were collected by centrifugation, rinsed twice in PBS, and stained for 1 hr in primary antibody in PBS with 0.1% saponin (SIGMA) and 1% normal goat serum (Pocono Rabbit Farm, Canadensis, Pa.). Sera were appropriately diluted (e.g., 1:1000) for this step. Cells were then rinsed once in PBS and stained for 1 hr in specific secondary antibodies (double-labeling grade goat anti-rabbit and goat anti-mouse), in PBS-saponin-normal goat serum. After this incubation, cells were rinsed twice in PBS and mounted on slides in 90% glycerol, 10% 1M Tris (pH 8.0), and 0.5% n-propyl gallate. Cells were viewed under epifluorescence on a Leitz Orthoplan 2 microscope.

Confocal micrographs were taken using the Bio-Rad MRC 500 system connected to a Zeiss Axiovert compound microscope. Images were collected using the BHS and GHS filter sets, aligned using the ALIGN program, and merged using MERGE. Fluorescent bleed-through from the green into the red channel was reduced using the BLEED program (all software provided by Bio-Rad). Photographs were obtained directly from the computer monitor using Kodak Ektar 125 film.

Notch-expressing cells for the assays were obtained similarly, using metallothionein promoter-driven plasmid constructions containing D. melanogaster Notch (see PCT Publication WO 92/19734 published Nov. 12, 1992; Fehon et al., 1990, Cell 61:523–534; Rebay et al., 1991, Cell 67:687–699).

8.2.2. RESULTS

We found that Serrate expressing cells adhere to Notch expressing cells in a calcium dependent manner (see also Rebay et al., 1991, Cell 67:687–699). However, unlike Delta, under the experimental conditions tested, Serrate did not appear to interact homotypically. In addition, we detect no interactions between Serrate and Delta. It is possible that such interactions do occur, but at an affinity such that they are below the level of detection in our assay system.

We have tested a subset of our Notch deletion constructs to map the Serrate-binding domain and have found that Notch EGF-like repeats 11 and 12, in addition to binding to Delta, also mediate interactions with Serrate. In addition, the Serrate-binding function of these repeats also appears to have been conserved in the corresponding two EGF repeats of Xenopus Notch (construct #33ΔCla+XEGF(10–13); see Rebay et al., supra).

We were also able to define the Serrate region which is essential for the Notch/Serrate aggregation. Deleting nucleotides 672–1293 (i.e. amino acids 77–284) eliminated the ability of the Serrate protein to aggregate with Notch. While both cells expressing Notch and cells expressing the Serrate fragments were detected by immunofluorescence with anti-Notch and anti-Serrate antibodies, respectively, these cells did not co-aggregate.

Aggregation assays with cells expressing Notch and cells expressing the chimeric AEGF Notch-Serrate construct showed binding between Notch and the chimeric construct. These experiments thus demonstrated that a fragment of Serrate consisting of amino acids 79–282 (see SEQ ID NO:2) is capable of mediating binding to Notch. Similar experiments with Delta from the laboratory of M. Muskavitch (personal communication) have demonstrated that the homologous region of Delta (without the partial EGF-like repeat) was sufficient to mediate Notch-Delta binding. Therefore, it is likely that the partial EGF-like repeat of Serrate is not essential for this binding to occur.

Work in our laboratory has shown that Notch and Delta proteins interact directly at the molecular level (Fehon et al., 1990, Cell 61:523–534; International Publication No. WO 92/19734 published Nov. 12, 1992; collectively incorporated by reference herein in their entireties), as demonstrated by the specific binding of Notch-expressing cells to Delta-expressing cells in vitro. We have also shown that EGF-like repeats repeats 11 and 12 of Notch are required and sufficient for Notch-Delta-mediated aggregation, and that Delta participates in heterotypic (Delta-Notch) and homotypic (Delta-Delta) interactions mediated by its amino-terminus (id.). Thus, it is conceivable that the Serrate and Delta proteins compete for binding with the Notch protein. Such interplay could underlie the genetic interactions observed between Notch and Serrate.

Notch and Serrate appeared to aggregate less efficiently than Notch and Delta, perhaps because the Notch-Serrate interaction is weaker. For example, when scoring Notch-Delta aggregates, we detect ~40% of all Notch expressing cells in clusters with Delta expressing cells and ~40% of all Delta expressing cells in contact with Notch expressing cells. For Notch-Serrate, we find only ~20% of all Notch expressing cells and -15% of all Serrate expressing cells in aggregates. For the various Notch deletion constructs tested, we consistently detect a reduction in the amount of aggregation between Notch and Serrate as compared to the corresponding Notch-Delta levels, with the possible exception of two constructs which exhibit severely reduced levels of aggregation even with Delta. One trivial explanation for this reduced amount of aggregation could be that our Serrate construct simply does not express as much protein at the cell surface as the Delta construct, thereby diminishing the strength of the interaction. Alternatively, the difference in strength of interaction may indicate a fundamental functional difference between Notch-Delta and Notch-Serrate interactions that may be significant in vivo.

9. ISOLATION AND CHARACTERIZATION OF A MOUSE SERRATE HOMOLOG

A mouse Serrate homolog, termed M-Serrate-1, was isolated as follows:

Mouse Serrate-1 gene

Tissue origin: 10.5-day mouse embryonic RNA

Isolation method:

a) random primed cDNA against above RNA b) PCR of above cDNA using

PCR primer 1: CGI(C/T)TTTGC(C/T)TIAA(A/G)(G/C)AITA(C/T)CA (SEQ ID NO: 11) {encoding RLCCK(H/E)YQ (SEQ ID NO:12)}:

PCR primer 2: TCIATGCAIGTICCICC(A/G)TT (SEQ ID NO:13) {encoding NGGTCID (SEQ ID NO:14)}

Amplification conditions: 50 ng cDNA, 1 μg each primer, 0.2 mM dNTP's, 1.8 U Taq (Perkin-Elmer) in 50 μl of supplied buffer, 40 cycles of: 94° C./30 sec, 45° C./2 min, 72° C./1 min extended by 2 sec each cycle.

Yielded a 1.8 kb fragment which was sequenced at both ends and identified as corresponding to C-Serrate-1

Partial DNA sequence of M-Serrate-1:
From 5' end:

GTCCCGCGTCACTGCCGGGGGACCCTGCAGCTTCGGCTCAGGGTCTACGCCTGTCATCGGG
GGTAACACCTTCAATCTCAAGGCCAGCCGTGGCAACGACCGTAATCGCATCGTACTGCCTT
TCAGTTTCACCTGGCCGAGGTCCTACACTTTGCTGGTGGAG (SEQ ID NO:15)

Protein translation of above:
S R V T A G G P C S F G S G S T P V I G G N T F N - LKASRGNDRNRIVLPFSFTWPRSYTLLVE
(SEQ ID NO:16) (corresponds to amino-terminal sequence upstream of the DSL domain)
From 3' end (but coding strand)

TCTTCTAACGTCTGTGGTCCCCATGGCAAGTGCAAGAGCCAGTCGGCAGGCAAATTCACCT
GTGACTGTAACAAAGGCTTCACCGGCACCTACTGCCATGAAAATATCAACGACTGCGAGAG
CAACCCCTGTAAA (SEQ ID NO:17)

Protein translation of above:
S S N V C G P H G K C K S Q S A G K F T C D C N K G F T-GTYCHENINDCESNPCK (SEQ ID NO:18)
(within tandemly arranged EGF-like repeats)
Expression pattern: The expression pattern was determined to be the same as that observed for C-Serrate-1 (chicken Serrate) (see Section 11 infra), including expression in the developing central nervous system, peripheral nervous system, limb, kidney, lens, and vascular system.

10. ISOLATION AND CHARACTERIZATION OF A XENOPUS SERRATE HOMOLOG

A Xenopus Serrate homolog, termed Xenopus Serrate-1 was isolated as follows:
5 Xenopus Serrate-1 gene
Tissue origin: neurula-stage embryonic RNA
Isolation method:
  a) random primed cDNA against above RNA
  b) PCR using:
Primer 1: CGI(C/T)TTTGC(C/T)TIAA(A/G)(G/C)AITA(C/T)CA (SEQ ID NO:11) {encoding RLCCK(H/E)YQ (SEQ ID NO:12)}:
PCR primer 2: TCIATGCAIGTICCICC(A/G)TT (SEQ ID NO:13) {encoding NGGTCID (SEQ ID NO:14)}
Amplification conditions: 50 ng cDNA, 1 µg each primer, 15 0.2 mM dNTP's, 1.8 U Taq (Perkin-Elmer) in 50 µl of supplied buffer. 40 cycles of: 94° C./30 sec, 45° C./2 min, 72° C./1 min extended by 2 sec each cycle.
Yielded a ~700 bp fragment which was partially sequenced to confirm its relationship to C-Serrate-1.

11. ISOLATION AND CHARACTERIZATION OF A CHICK SERRATE HOMOLOG

In the example herein, we report the cloning and sequence of a chick Serrate homolog, C-Serrate, and of fragments of two chick Notch homologs, C-Notch-1 and C-Notch-2, together with their expression patterns during early embryogenesis. The patterns of transcription of C-Serrate overlaps with that of C-Notch-1 in many regions of the embryo, suggesting that C-Notch-1, like Notch in Drosophila, is a receptor for Serrate. In particular, Notch and Serrate are expressed in the neurogenic regions of the developing central and peripheral nervous system.

Our data show that Serrate, a known ligand of Notch, has been conserved from arthropods to chordates. The overlapping expression patterns suggest conservation of its functional relationship with Notch and imply that development of the chick and in particular of its central nervous system involves the interaction of C-Notch-1 with Serrate at several specific locations.

Materials and Methods

Embryos

White Leghorn chicken eggs were obtained from University Park Farm and incubated at 38° C. Embryos were staged according to Hamburger and Hamilton (1951, J. Exp. Zool. 88:49–92).

Cloning of chicken homologs of Notch

Approximately 1000 base pair PCR fragments of the chicken Notch 1 and Notch 2 genes were amplified from otic explant RNA (see below) using degenerate primers and PCR conditions as outlined in Lardelli and Lendahl (1993, Exp. Cell Res. 204:364–372). The PCR fragment was subcloned into Bluescript KS-, sequenced and used as a template for making a DIG antisense RNA probe (RNA Transcription Kit, Stratagene; DIG RNA labelling mix, Boehringer Mannheim).

Cloning of a chicken homologue of Drosophila Serrate

Otic explants were dissected from embryos of stages 8 to 13. Each otic explant consisted of the two otic cups, a short section of intervening hindbrain and pharynx and the associated head ectoderm and mesenchyme. RNA was extracted using a modification of standard protocols (Sambrook et al., 1989, in Molecular Cloning: A Laboratory Manual, 2nd ed., Cold Spring Harbor Laboratory Press, Cold Spring Harbor, N.Y.) and polyA$^+$ mRNA was isolated from total RNA using the PolyATtract mRNA Isolation System (Promega). First strand cDNA was synthesized using the SuperScript Preamplification System (Gibco).

PCR and degenerate primers were used to amplify a fragment of a chicken gene homologous to the Drosophila gene Serrate from the otic explant cDNA. The primers were designed to recognize peptide motifs found in both the fly Delta and Serrate proteins:
1) primer 1, 5-CGI(T/C)TITGC(T/C)TIAA(G/A)(G/C) AITA(C/T)CA-3'(SEQ ID NO:19), corresponds to the motif RLCLK(E/H)YQ (SEQ ID NO:20) located at the amino-terminus of the fly Delta and Serrate proteins.
2) primer 2, 5'-TCIATGCAIGTICCICC(A/G)TT-3'(SEQ ID NO:13), corresponds to the motif NGGTCID (SEQ ID NO:14) found in several of the EGF-like repeats. The PCR conditions were as follows: 35 cycles of 94° C. for 1 minute, 45° C. for 1.5 minutes and 72° C. for 2 minutes; followed by a final extension step of 72° C. for 10 minutes. A PCR product of approximately 900 base pairs in length was purified, subcloned into Bluescript KS- (Stratagene) and its DNA sequence partially determined to confirm that it was a likely Serrate homolog. It was then used to recover larger cDNA clones by screening two cDNA libraries:

1) a stage 8–13 otic explant random primed cDNA library
2) a stage 17 chick spinal cord oligo dT primed cDNA library Overlapping cDNAs were isolated, and two (termed 9 and 3A.1) that together cover almost the entire coding region of the gene were subcloned into Bluescript KS–. DNA sequence was determined from nested deletion series generated using the double-stranded Nested Deletion Kit (Pharmacia) and Sanger dideoxy chain termination method with the Sequenase enzyme (US Biochemical Corporation). Sequences were aligned and analyzed using Geneworks 2.3 and Intelligenetics. Homology searches were done using the program Sharq.

To obtain the most 5' end of the open reading frame, a number of other PCR based strategies were used including the screening of a number of other libraries (cDNA and genomic) using the method of Lardelli et al. (1994, Mechanisms of Development 46:123–136).

In situ hybridization

Patterns of gene transcription were determined by in situ hybridization using DIG-labelled RNA probes and:

1) a high-stringency wholemount in situ hybridization protocol, and
2) in situ hybridization on cryostat sections based on the protocol of Strahle et al. (1994, Trends in Genet. 10:7).

Results

To obtain insight into the likely role of chick Serrate in the vertebrate embryo, we examined its expression in relation to that of chick Notch, since functional coupling of Notch and Serrate occurs in Drosophila. Two chick Notch homologs were obtained as described below.

C-Notch-1 and C-Notch-2 are apparent counterparts of the rodent Notch-1 and Notch-2 genes, respectively We searched for Notch homologs in the chick by PCR, using cDNA prepared from two-day chick embryos and degenerate primers based on conserved regions common to the known rodent Notch homologs. In this way, we obtained fragments, each approximately 1000 nucleotides long, of two distinct genes, which we have called C-Notch-1 and C-Notch-2. The fragments extend from the third Notch/lin12 repeat up to and including the last five or so EGF-like repeats. EGF-like repeats are present in a large number of proteins, most of which are otherwise unrelated to Notch. The three Notch/lin12 repeats, however, are peculiar to the Notch family of genes and are found in all its known members. C-Notch-1 shows the highest degree of amino-acid identity with rodent Notch1 (Weinmaster et al., 1991, Development 113:199–205), and is expressed in broadly similar domains to rodent Notch1 (see below). Of the rodent Notch genes, C-Notch-2 appears most similar to Notch2 (Weinmaster et al., 1992, Development 116:931–941).

We examined the expression patterns of C-Notch-1 in early embryos by in situ hybridization. C-Notch-1 was expressed in the 1- to 2-day chick embryo in many well-defined domains, including the neural tube, the presomitic mesoderm, the nephrogenic mesoderm (the prospective mesonephros), the nasal placode, the otic placode/vesicle, the lens placode, the epibranchial placodes, the endothelial lining of the vascular system, in the heart, and the apical ectodermal ridges (AER) of the limb buds. These sites match the reported sites of Notch1 expression in rodents at equivalent stages (Table II). Taking the sequence data together with the expression data, we conclude that C-Notch-1 is either the chick ortholog of rodent Notch1, or a very close relative of it.

TABLE II

COMPARISON OF DOMAINS OF RODENT-NOTCH1 AND CHICK NOTCH-1 EXPRESSION THROUGHOUT EMBRYOGENESIS

| Body Region | R-Notch1[a] | C-Notch1 |
| --- | --- | --- |
| primitive streak | + | + |
| Hensen's node | – | – |
| neural tube | + | + |
| retina | + | + |
| lens | + | + |
| otic placode/vesicle | + | + |
| epibranchial placodes | + | + |
| nasal placode | + | + |
| dorsal root ganglia | + | + |
| presomitic mesoderm | + | + |
| somites | + | + |
| notochord | ? | + |
| mesonephric kidney | + | + |
| metanephric kidney | + | + |
| blood vessels | + | + |
| heart | + | + |
| whisker follicles | + | N/A |
| thymus | + | ? |
| toothbuds | + | N/A |
| salivary gland | + | ? |
| limb bud (AER) | ? | + |

[a]from Weinmaster et al., 1991, Development 113:199–205; Franco del Amo et al., 1992, Development 115:737–744; Reaume et al., 1992, Dev. Biol. 154:377–387; Kopan and Weintraub, 1993, J. Cell. Biol. 121:631–641; Lardelli et al., 1994, Mech. of Dev. 46:123–126.

C-Serrate is a homolog of Drosophila Serrate, and codes for a candidate ligand for a receptor belonging to the Notch family In Drosophila, two ligands for Notch are known, encoded by the two related genes Delta and Serrate. The amino-acid sequences corresponding to these genes are homologous at their 5' ends, including a region, the DSL motif, which is necessary and sufficient for in vitro binding to Notch. To isolate a fragment of a chicken homolog of Serrate, we used PCR and degenerate primers designed to recognize sequences on either side of the DSL motif (see Materials and methods). A 900 base pair PCR fragment was recovered and used to screen a library, allowing us to isolate overlapping cDNA clones. The DNA sequence of the cDNA clones revealed an almost complete single open reading frame of 3582 nucleotides, lacking only a few 5' bases. Comparison with the amino acid sequences of Drosophila Delta and Serrate suggests that we are missing only the portion of the coding sequence that encodes part of the signal sequence of the chick Serrate protein.

Translation of the nucleotide sequence (SEQ ID NO:9) (FIGS. 11A–11B) predicts a protein of 1230 amino acids (SEQ ID NO:10) (FIGS. 12A–12B). A hydropathy plot reveals a single hydrophobic region characteristic of a transmembrane domain (Kyte and Doolittle, 1982, J. Mol. Biol. 157:105–132). In addition, the protein has sixteen EGF-like repeats organized in a tandem array in its extracellular domain. Comparison of the chick sequence with sequences of D.melanogaster Delta and Serrate suggests that the clones encode a chicken homolog of Serrate (FIG. 13; FIG. 14). Whereas Drosophila Serrate contains 14 EGF-like repeats with large insertions in repeats 4, 6 and 10, the chicken homolog has an extra two EGF-like repeats and only one small insertion of 16 amino acids in the 10th repeat. Both proteins have a second cysteine-rich region between the EGF-like repeats and the transmembrane domain; the spacing of the cysteines in this region is almost identical in the two proteins (compare $CX_2CXCX_6CX_4CX_{15}CX_5CX_7CX_4CX_5C$ in Drosophila Serrate with $CX_2CXCX_6CX_4CX_9CX_5CX_7CX_4CX_5C$ in C-Serrate). The intracellular domain of C-Serrate bears no significant homology to the intracellular domains of either Drosophila Delta or Serrate.

C-Serrate is expressed in the central nervous system, cranial placodes, nephric mesoderm, vascular system, and limb bud mesenchyme In situ hybridization was to examine the expression of C-Serrate in whole-mount preparations during early embryogenesis, from stage 4 to stage 21, at intervals of roughly 12 hours. Later stages were studied by in situ hybridization on cryosections.

The main sites of early expression of C-Serrate, as seen in whole mounts, can be grouped under five headings: central nervous system, cranial placodes, nephric mesoderm, vascular system, and limb bud mesenchyme.

Central nervous system

The first detectable expression of C-Serrate was seen in the central nervous system at stage 6 (0 somites/24 hrs), within the posterior portion of the neural plate. By stage 10 (9–11 somites/35.5 hrs), a strong stripe of expression was seen in the prospective diencephalon. Additional faint staining was seen in the hindbrain and in the prospective spinal cord.

At stage 13, there were several patches of expression in the neural tube. In the diencephalon, there was a strong triangular stripe of expression that appeared to correspond to neuromere D2. There were two patches (one on either side of the midline) on the floor of the anterior mesencephalon as well as diffuse staining in the dorsal mesencephalon. In the hindbrain and rostral spinal cord, there were two longitudinal stripes of expression on either side of the midline: one along the dorsal edge of the neural tube and a second more ventral one, adjacent to the floor plate. Both were located within the domain of (rat) Notch 1 expression. The anterior limit of the ventral stripe was at the midbrain/hindbrain boundary. The dorsal stripe was continuous with the expression in the dorsal mesencephalon. In the anterior spinal cord, expression was more spotty, the stripes being replaced by isolated scattered cells expressing C-Serrate.

At stage 17 (58 hrs), expression in the diencephalon and midbrain was unchanged. In the hindbrain and spinal cord, there were an additional two longitudinal stripes: one midway along the dorsoventral axis and a second wider more ventral stripe; the anterior limits of these stripes coincided with the anterior border of rhombomere 2. All four longitudinal stripes in the hindbrain continued into the spinal cord of the embryo; decreasing towards its posterior end. These stripes of expression were maintained at least up to and including stage 31 (E7). By stage 21 (84 hrs), additional expression was seen in the cerebral hemispheres and strong expression in a salt and pepper distribution of cells in the optic tectum.

Cranial placodes

It is striking that C-Serrate is expressed in all the cranial placodes—the lens placode, the nasal placode, the otic placode/vesicle and the epibranchial placodes, as well as a patch of cranial ectoderm anterior to the otic placode that may correspond to the trigeminal placode (which is not well-defined morphologically).

In the lens placode, expression was already seen at stage 11, rapidly became very strong, and persisted at least to stage 21. Expression was weaker in the nasal placode and was only detected from stage 13. Again, expression was maintained at least until stage 21.

Likewise for the otic placode, expression began to be visible at stage 10 and was strong by early stage 11 (12–14 somites, 42.5 hours). Curiously, there was a "hole" in the otic expression domain—an anteroventral region of the placode in which the gene was not expressed. Subsequently, as the placode invaginates to form an otic vesicle, the strongest expression was seen at the anterolateral and posteromedial poles. Later still, as the otic vesicle becomes transformed into the membranous labyrinth of the inner ear, C-Serrate expression became restricted to the sensory patches.

The epibranchial expression was seen at stage 13/14 as strong staining in the ectoderm around the dorsal margins of the first and second branchial clefts. It was accompanied by expression of the gene in the deep part of the lining of the clefts and in the endodermal lining of the branchial pouches, where the two epithelia abut one another.

Lastly, a large and strong but transient patch of expression was seen in the cranial ectoderm just anterior and ventral to the ear rudiment at stage 11. From its location, we suspect this to be, or to include, the region of the trigeminal placode.

Nephric mesoderm

Expression was detectable in the cells of the intermediate mesoderm from stage 10 and in older embryos (stage 17 to 21) in the developing mesonephric tubules.

Limb buds

C-Serrate mRNA was localized to a patch of mesenchyme at the distal end of the developing limb bud. This may suggest a role in limb growth.

Other sites

Expression was also seen in the tail bud, allantoic stalk, and possibly other tissues at late stages.

All major sites of C-Serrate expression lie within domains of C-Notch-1 expression The conservation of the DSL domain and adjacent N-terminal region in C-Serrate suggests that it functions as a ligand for a receptor belonging to the Notch family. We thus expected to find sites where C-Serrate expression is accompanied by expression of a Notch gene. At such sites, overlapping or contiguous expression of the two genes can be taken as an indication that cells are communicating by Serrate-Notch signalling. We have compared the expression pattern of C-Serrate, as shown by in situ hybridization, with that of C-Notch-1, to discover what overlaps in fact occur, over a range of stages up to 8 days of incubation (E8). All the observed sites of C-Serrate expression indeed lay within, or very closely adjacent to, domains of expression of C-Notch-1 (Table III).

TABLE III

COMPARISON OF C-NOTCH-1 AND C-SERRATE EXPRESSION AT STAGE 17a

| Body region | C-Notch-1 | C-Serrate |
|---|---|---|
| brain and spinal cord | ++ (almost everywhere) | ++ (specific regions) |
| retina | ++ | − |
| lens | + | ++ |
| otic placode/vesicle | ++ | ++ |
| epibranchial placodes | ++ | ++ |
| nasal placode | ++ | ++ |
| dorsal root ganglia | + | − |
| branchial mesenchyme | − | − |
| branchial ectoderm | + | ++ (furrows) |
| branchial endoderm | + | ++ (tips of pouches) |
| presomitic mesoderm | ++ | − |
| somites | ++ | − |
| notochord | ++ | − |
| mesonephric kidney | ++ | ++ |
| metanephric kidney | ++ | ++ |

TABLE III-continued

COMPARISON OF C-NOTCH-1 AND
C-SERRATE EXPRESSION AT STAGE 17a[a]

| Body region | C-Notch-1 | C-Serrate |
|---|---|---|
| blood vessels | ++ | ++ |
| heart | + | ++ |
| limb bud (stage 21) | ++ (AER) | ++ (distal mesenchyme) |

[a]Hamburger and Hamilton, 1951, J. Exp. Zool. 88:49–92.

Because of the importance of Notch and its partners in insect neurogenesis, it was of particular interest to us to see whether the homologous genes are involved in the development of the vertebrate CNS. C-Serrate is expressed in the CNS, and its pattern of expression shows a remarkable relationship to that of the Notch homologs.

We analyzed transverse sections through the spinal cord of a six day chicken embryo hybridized with C-Notch-1 and C-Serrate antisense RNA probes. C-Notch-1 was expressed throughout the luminal region as described previously; within this region, there were two small patches in which Serrate was strongly expressed.

Discussion

In Drosophila development, cell-cell signalling via the product of the Notch gene plays a cardinal role in the final cell-fate decisions that specify the detailed pattern of differentiated cell types. This signalling pathway, in which the Notch protein has been identified as a transmembrane receptor, is best known for its role in neurogenesis: loss-of-function mutations in Notch or any of a set of other genes required for signal transmission via Notch alter cell fates in the neuroectoderm, causing cells that should have remained epidermal to become neural instead. Notch-dependent signalling is, however, as important in non-neural as in neural tissues. It regulates choices of mode of differentiation in oogenesis, in myogenesis, in formation of the Malpighian tubules and in the gut, for example, as well as in development of the retina, the peripheral sensilla, and the central nervous system. In most of these cases the signal delivered via Notch appears to mediate lateral inhibition, a type of interaction by which a cell that becomes committed to differentiate in a particular way—for example, as a neuroblast—inhibits its immediate neighbors from doing likewise. This forces adjacent cells to behave in contrasting ways, creating a fine-grained pattern of different cell types.

There are, however, good reasons to believe that this is not the only function of signals delivered via Notch. Two direct ligands of Notch have been identified. These are the products of the Delta and Serrate genes. Both of them, like Notch itself, code for transmembrane proteins with tandem arrays of EGF-like repeats in their extracellular domain. Both the Delta and the Serrate protein have been shown to bind to Notch in a cell adhesion assay, and they share a large region of homology at their amino-termini including a motif that is necessary and sufficient for interaction with Notch in vitro, the so-called EBD or DSL domain. Yet despite these biochemical similarities, they seem to have quite different developmental functions. Although Serrate is expressed in many sites in the fly, it is apparently required only in the humeral, wing and halteres disks. When Serrate function is lost by mutation, these structures fail to grow. Studies on the wing disc have indicated that it is specifically the wing margin that depends on Serrate; when Serrate is lacking, this critical signaling region and growth centre fails to form, and when Serrate is expressed ectopically under a GAL4-UAS promoter in the ventral part of the wing disc, ectopic wing margin tissue is induced, leading to ectopic outgrowths. Notch appears to be the receptor for Serrate at the wing margin, since some mutant alleles of Notch cause similar disturbances of wing margin development and allele-specific interactions are seen in the effects of the two genes.

Here we describe the identification and full length sequence of a homolog of the Drosophila gene Serrate, and identification and partial sequence of chick homologs of rat/mouse Notch1 and Notch2.

Within the chick Serrate cDNA there is a single open reading frame predicted to encode a large transmembrane protein with 16 EGF repeats in its extracellular domain. It has a well conserved DSL motif suggesting that it would interact directly with Notch. The intracellular domain of chick Serrate exhibits no homology to anything in the current databases including the intracellular domains of Drosophila Delta and Serrate. It should he pointed out however that the intracellular domains of chick and human Serrate (see Section 12) are almost identical.

The spatial distributions of C-Notch-1 and C-Serrate were investigated during early embryogenesis by in situ hybridization. C-Notch-1 and C-Serrate exhibit dynamic and complex patterns of expression including several regions in which they are coexpressed (CNS, ear, branchial region, lens, heart, nasal placodes and mesonephros). The overlapping expression together with the finding that C-Serrate has a well conserved Notch binding domain suggests that this receptor/ligand interaction has been conserved from Drosophila through to vertebrates.

In Drosophila, the Notch receptor is quite widely distributed and its ligands are found in overlapping but more restricted domains. In the chick a similar situation is observed.

Fly Notch is necessary for many steps in the development of Drosophila; its role in lateral inhibition especially in the development of the central nervous system and peripheral sense organs being the best studied examples. However, Notch is a multifunctional receptor and can interact with different signalling molecules (including Delta and Serrate) and in developmental processes that do not easily fit within the framework of lateral inhibition. While available evidence implicates Delta as the signalling molecule in lateral inhibition there is no data to suggest that Serrate participates in lateral inhibition. Rather, Serrate appears to be necessary for development of the dorsal imaginal discs of the larva; that is, the humeral, haltere and wing discs. In the latter, the best studied of these processes, Serrate and Notch are important for the development of the dorsoventral wing margin, a structure necessary for the organization of wing development as a whole.

That C-Serrate has a significant function can be inferred from the conservation of its sequence, in particular, of its Notch-binding domain. The expression patterns reported for C-Serrate in this paper provide the following information. First, since the Serrate gene is expressed in or next to sites where C-Notch-1 is expressed (possibly in conjunction with other Notch homologs), it is highly probable that C-Serrate exerts its action by binding to C-Notch-1 (or to another chick Notch homolog with a similar expression pattern). Second, the expression in the developing kidney, the vascular system and the limb buds might reflect an involvement in inductive signalling between mesoderm and ectoderm, which plays an important part in the development of all these organs. In the limb buds, for example, C-Serrate is expressed in the distal mesoderm, and C-Notch-1 is expressed in the overlying apical ectodermal ridge, whose maintenance is known to depend on a signal from the mesoderm below. In the cranial placodes, a similar role is possible, but the evidence for inductive signalling is weaker, and C-Serrate may equally be involved in communications between cells within the placodal epithelium, for example, in regulating the specialized modes of differentiation of the placodal cells.

What might C-Serrate's function be within the curiously restricted domains of its expression in the CNS? One possibility is that it is involved in regulating the production of oligodendrocytes, which have likewise been reported to originate from narrow bands of tissue extending along the cranio-caudal axis of the neural tube.

12. ISOLATION AND CHARACTERIZATION OF HUMAN SERRATE HOMOLOGS

Clones for the human Serrate sequence were obtained as described below.

The polymerase chain reaction (PCR) was used to amplify DNA from a human placenta cDNA library. Degenerate oligonucleotide primers used in this reaction were designed based on amino-terminal regions of high homology between Drosophila Serrate and Drosophila Delta (see FIG. 13); this high homology region is in the 5' "DSL" domain, that is believed to code for the Notch-binding portion of Delta and Serrate. Two PCR products were isolated and used, one a 350 base-pair fragment, and one a 1.2 kb fragment. These PCR fragments were labelled with $^{32}$P and used to screen a human fetal brain cDNA library. The library used was a commercial library (available from Stratagene) made from a 17–18 week old fetus, in which the cDNAs were inserted into the EcoRI site of a λ-Zap vector. The 1.2 kb fragment hybridized to a single clone out of 106 screened. We rescued this fragment from the λ DNA by converting the isolated phage λ clone to a plasmid via the manufacturer's instructions, yielding the Serrate-homologous cDNA as an insert in the EcoRI site of the vector Bluescript KS– (Stratagene). This plasmid was termed "pBS39". The isolated cDNA was 6464 bases long and contained a complete open reading frame as well as 5' and 3' untranslated regions (FIGS. 9A–9G). Sequencing was carried out using the Sequenase® sequencing system (U.S. Biochemical Corp.) on 5 and 6% Sequagel acrylamide sequencing gels.

The 350 bp fragment hybridized with two clones, one about 3.1 kb and one about 1.5 kb, called pBS15 and pBS14, respectively. These were isolated, rescued from the λ cDNA, and sequenced as above. pBS14 turned out to contain sequence internal to and identical with pBS15, and was not characterized further. pBS15 contained the start site for the deduced amino acid, and about 3 kb of open reading frame. pBS15 was then labelled with 32P and used to screen another human fetal brain library (from Clontech), made from a week 25–26 fetus, containing the cDNAs cloned into the EcoRI site of λgt11. Three positive clones were identified. To isolate the cDNAs, λgt11 DNA was prepared from a liquid lysate, purified over a DEAE column and cut with EcoRI to isolate the human cDNAs. These isolated fragments were subcloned into the EcoRI site of Bluescript KS–. They were called pBS3-15, pBS3-2, and pBS3-20. Two of these cDNAs contained sequences that partially overlapped with pBS15. One of these, pBS3-2, extended from about bp 1200 of pBS15 to the end of the cDNA, including the polyA tail. pBS20 contained sequences internal to and identical with pBS3-2 and was not characterized further. (pBS3-15 turned out to be a piece of the Bluescript vector.) Alignment of the deduced amino acid sequence (SEQ ID NO:8) of the "complete" cDNA (SEQ ID NO:7) generated on the computer with the deduced amino acid sequence from pBS39 (SEQ ID NO:6) showed a gap of about 160 bases and a frame-shift between the putative signal sequence and the beginning of the DSL domain (FIGS. 10A–10E). This missing region probably resulted from a cloning artifact in the construction of the Stratagene library.

The human Serrate cDNA homolog from pBS39 has thus been completely sequenced and contains the complete coding sequence for the gene product. The nucleotide (SEQ ID NO:5) and protein (SEQ ID NO:6) sequences are shown in FIGS. 9A–9G. The nucleotide sequence of homolog 39 was translated using MacVector software (International Biotechnology Inc., New Haven, Conn.). The coding region consists of nucleotide numbers 371–4024 of SEQ ID NO:5. The Protean protein analysis software program from DNAStar (Madison, Wis.) was used to predict signal peptide and transmembrane regions (based on hydrophobicity). The signal peptide was predicted to consist of amino acids 14–29 of SEQ ID NO:6 (encoded by nucleotide numbers 410–457 of SEQ ID NO:5), whereby the amino terminus of the mature protein was predicted to start with Gly at amino acid number 30. The transmembrane domain was predicted to be amino acid numbers 1069–1091 of SEQ ID NO:6, encoded by nucleotide numbers 3575–3643 of SEQ ID NO:5. The consensus (DSL) domain, the region of homology with Drosophila Delta and Serrate, predicted to mediate binding with Notch (in particular, Notch ELR 11 and 12), spans amino acids 185–233 of SEQ ID NO:6, encoded by nucleotide numbers 923–1069 of SEQ ID NO:5. Epidermal growth factor-like (ELR) repeats in the amino acid sequence were identified by eye; 15 (full-length) ELRs were identified and 3 partial ELRs as follows:

ELR 1: amino acid numbers 234–264

ELR 2: amino acid numbers 265–299

ELR 3: amino acid numbers 300–339

ELR 4: amino acid numbers 340–377

ELR 5: amino acid numbers 378–415

ELR 6: amino acid numbers 416–453

ELR 7: amino acid numbers 454–490

ELR 8: amino acid numbers 491–528

ELR 9: amino acid numbers 529–566

Partial ELR: amino acid numbers 567–598

Partial ELR: amino acid numbers 599–632

ELR 10: amino acid numbers 633–670

ELR 11: amino acid numbers 671–708

ELR 12: amino acid numbers 709–747

ELR 13: amino acid numbers 748–785

ELR 14: amino acid numbers 786–823

ELR 15: amino acid numbers 824–862

Partial ELR: amino acid numbers 863–879

Partial ELR: amino acid numbers 880–896

The total ELR domain is thus amino acid numbers 234–896 (encoded by nucleotide numbers 1070–3058 of SEQ ID NO:5). The extracellular domain is thus predicted to be amino acid numbers 1–1068 of SEQ ID NO:6, encoded by nucleotide numbers 371–3574 of SEQ ID NO:5 (amino acid numbers 30–1068 in the mature protein; encoded by nucleotide numbers 458–3574 of SEQ ID NO:5). The intracellular (cytoplasmic) domain is thus predicted to be amino acid numbers 1092–1218 of SEQ ID NO:6, encoded by nucleotide numbers 3644–4024 of SEQ ID NO:5.

Expression constructs are made using the isolated clone (s). The clone is excised from its vector as an EcoRI restriction fragment(s) and subcloned into the EcoRI restriction site of each of the three pGEX vectors (Glutathione S-Transferase expression vectors; Smith and Johnson, 1988, Gene 7:31–40). This allows for the expression of the human Serrate protein product from the subclone in the correct reading frame.

13. DEPOSIT OF MICROORGANISMS

Bacteria strain XL1-Blue containing plasmid SerFL, containing an EcoRI fragment encoding a full-length Drosophila Serrate, was deposited on Dec. 11, 1991 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 68876.

Plasmid pBS39, containing an EcoRI fragment encoding a full-length human Serrate, was deposited on Feb. 28, 1995 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97068.

Plasmid pBS15, containing a 3.1 kb EcoRI fragment encoding the amino terminus of Human Serrate, cloned into the EcoRI site of Bluescript KS−, was deposited on Mar. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97459.

Plasmid pBS3-2 containing an 3.2 kb EcoRI fragment encoding the carboxy terminus of Human Serrate, cloned into the EcoRI site of Bluescript KS−, was deposited on Mar. 5, 1996 with the American Type Culture Collection, 1201 Parklawn Drive, Rockville, Md. 20852, under the provisions of the Budapest Treaty on the International Recognition of the Deposit of Microorganisms for the Purposes of Patent Procedures, and assigned Accession No. 97460.

The present invention is not to be limited in scope by the microorganisms deposited or the specific embodiments described herein. Indeed, various modifications of the invention in addition to those described herein will become apparent to those skilled in the art from the foregoing description and accompanying figures. Such modifications are intended to fall within the scope of the appended claims. Various references are cited herein, the disclosures of which are incorporated by reference in their entireties.

---

What is claimed is:

1. An isolated nucleic acid comprising a nucleotide sequence encoding a vertebrate Serrate protein, said vertebrate Serrate protein comprising a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8).

2. The nucleic acid of claim 1 which is DNA.

3. An isolated nucleic acid comprising a nucleotide sequence which is the antisense strand to the nucleotide sequence of claim 1.

4. The isolated nucleic acid of claim 1 in which the vertebrate Serrate protein has the amino acid sequence depicted in FIGS. 9A–9G (SEQ ID NO:6).

5. The isolated nucleic acid of claim 1 in which the vertebrate Serrate protein has the amino acid sequence depicted in FIG. 10B (SEQ ID NO:8).

6. The nucleic acid of claim 4 or 5 which is DNA.

7. An isolated nucleic acid comprising a nucleotide sequence that is the antisense strand to the nucleic acid of claim 4 or 5.

8. An isolated nucleic acid comprising a vertebrate Serrate sequence selected from the group consisting of the mouse Serrate sequence of SEQ ID NO:15, the antisense strand to the mouse Serrate sequence of SEQ ID NO:15, the mouse Serrate sequence of SEQ ID NO:17, the antisense strand to the mouse Serrate sequence of SEQ ID NO:17, the chick Serrate sequence depicted in FIGS. 11A–11B (SEQ ID NO:9), the antisense strand to the chick Serrate sequence depicted in FIGS. 11A–11B (SEQ ID NO:9), the human Serrate sequence depicted in FIGS. 9A–9G (SEQ ID NO:5), the antisense strand to the human Serrate sequence depicted in FIGS. 9A–9G (SEQ ID NO:5), the human Serrate sequence depicted in FIGS. 10A–10D (SEQ ID NO:7), and the antisense strand to the human Serrate sequence depicted in FIGS. 10A–10D (SEQ ID NO:7).

9. The isolated nucleic acid of claim 8 in which the vertebrate Serrate sequence is the human Serrate sequence depicted in FIGS. 9A–9G (SEQ ID NO:5).

10. The isolated nucleic acid of claim 8 in which the vertebrate Serrate sequence is the antisense strand to the human Serrate sequence depicted in FIGS. 9A–9G (SEQ ID NO:5).

11. The isolated nucleic acid of claim 8 in which the vertebrate Serrate sequence is the human Serrate sequence depicted in FIGS. 10A–10D (SEQ ID NO:7).

12. The isolated nucleic acid of claim 8 in which the vertebrate Serrate sequence is the antisense strand to the human Serrate sequence depicted in FIGS. 10A–10D (SEQ ID NO:7).

13. The nucleic acid of claim 8 which is an expression vector comprising said Serrate sequence operably linked to a non-native promoter.

14. A recombinant cell containing a recombinant nucleic acid, which nucleic acid (a) hybridizes under high stringency conditions to a vertebrate Serrate sequence selected from the group consisting of the mouse Serrate sequence of SEQ ID NO:15, the antisense strand to the mouse Serrate sequence of SEQ ID NO:15, the mouse Serrate sequence of SEQ ID NO:17, the antisense strand to the mouse Serrate sequence of SEQ ID NO:17, the chick Serrate sequence depicted in FIGS. 11A–11B (SEQ ID NO:9), the antisense strand to the chick Serrate sequence depicted in FIGS. 11A–11B (SEQ ID NO:9), the human Serrate sequence depicted in FIGS. 9A–9G (SEQ ID NO:5), the antisense strand to the human Serrate sequence depicted in FIGS. 9A–9G (SEQ ID NO:5), the human Serrate sequence depicted in FIGS. 10A–10D (SEQ ID NO:7), and the antisense strand to the human Serrate sequence depicted in FIGS. 10A–10D (SEQ ID NO:7), said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 µg/ml denatured salmon sperm DNA, for 48 hours at 65° C., and wash in a buffer consisting of 0.1×SSC, for 45 minutes at 50° C., and (b) encodes, or is the antisense strand of a nucleic acid which encodes, a protein which is able to be bound by an anti-vertebrate Serrate antibody.

15. A method of producing a protein comprising growing the recombinant cell of claim 14 such that the encoded protein is expressed by the cell, and recovering the expressed protein.

16. The recombinant cell of claim 14 in which the recombinant nucleic acid encodes a human Serrate protein.

17. The recombinant cell of claim 14 in which the recombinant nucleic acid encodes a human protein.

18. The recombinant cell of claim 14 in which the anti-vertebrate Serrate antibody does not bind to Drosophila Serrate protein.

19. An isolated nucleic acid, which nucleic acid (a) hybridizes under high stringency conditions to a vertebrate Serrate sequence selected from the group consisting of the mouse Serrate sequence of SEQ ID NO:15, the antisense strand to the mouse Serrate sequence of SEQ ID NO:15, the mouse Serrate sequence of SEQ ID NO:17, the antisense strand to the mouse Serrate sequence of SEQ ID NO:17, the chick Serrate sequence depicted in FIGS. 11A–11B (SEQ ID NO:9), the antisense strand to the chick Serrate sequence depicted in FIGS. 11A–11B (SEQ ID NO:9), the human Serrate sequence depicted in FIGS. 9A–9G (SEQ ID NO:5), the antisense stand to the human Serrate sequence depicted in FIGS. 9A–9G (SEQ ID NO:5), the human Serrate sequence depicted in FIGS. 10A–10D (SEQ ID NO:7), and the antisense strand to the human Serrate sequence depicted in FIGS. 10A–10D (SEQ ID NO:7), said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 µg/ml denatured salmon sperm DNA, for 48 hours at 65° C., and wash in a buffer consisting of 0.1×SSC, for 45 minutes at 50° C., and (b) encodes or is the antisense strand to a nucleic acid which encodes, a protein which is able to be bound by an anti-vertebrate Serrate antibody.

20. The isolated nucleic acid of claim 19 which encodes a human protein.

21. The isolated nucleic acid of claim 19 in which the anti-vertebrate Serrate antibody does not bind to Drosophila Serrate protein.

22. An isolated nucleic acid, which nucleic acid (a) hybridizes under low stringency conditions to a vertebrate Serrate sequence selected from the group consisting of the mouse Serrate sequence of SEQ ID NO:15, the antisense strand to the mouse Serrate sequence of SEQ ID NO:15, the mouse Serrate sequence of SEQ ID NO:17, the antisense strand to the mouse Serrate sequence of SEQ ID NO:17, the chick Serrate sequence depicted in FIGS. 11A–11B (SEQ ID NO:9), the antisense strand to the chick Serrate sequence depicted in FIGS. 11A–11B (SEQ ID NO:9), the human Serrate sequence depicted in FIGS. 9A–9G (SEQ ID NO:5), the antisense stand to the human Serrate sequence depicted in FIGS. 9A–9G (SEQ ID NO:5), the human Serrate sequence depicted in FIGS. 10A–10D (SEQ ID NO:7), and the antisense strand to the human Serrate sequence depicted in FIGS. 10A–10D (SEQ ID NO:7), said low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt/vol) dextran sulfate, for 18–20 hours at 40° C., and wash in a buffer consisting of 2×SSC, 25 mM Tris-HCl (pH 7.4), 5 mM EDTA, and 0.1% SDS, for 1.5 hours at 60° C., and (b) encodes or is the antisense strand to a nucleic acid which encodes, a protein which is able to be bound by an anti-vertebrate Serrate antibody.

23. A recombinant cell containing a recombinant nucleic acid comprising a nucleotide sequence encoding a vertebrate Serrate protein, said vertebrate Serrate protein comprising a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8).

24. A method of producing a vertebrate protein comprising growing the recombinant cell of claim 23 such that the encoded vertebrate protein is expressed by the cell, and recovering the expressed protein.

25. An isolated nucleic acid comprising a nucleotide sequence encoding a fragment of at least 20 amino acids of a vertebrate Serrate protein, said fragment being able to display one or more functional activities of a Serrate protein, said vertebrate Serrate protein having a sequence selected from the group consisting of the mouse Serrate sequence of SEQ ID NO:16, the mouse Serrate sequence of SEQ ID NO:18, the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8).

26. An isolated nucleic acid comprising a fragment of a vertebrate Serrate gene consisting of at least 25 nucleotides of a vertebrate Serrate nucleotide sequence selected from the group consisting of the mouse Serrate sequence of SEQ ID NO:15, the mouse Serrate sequence of SEQ ID NO:17, the chick Serrate sequence depicted in FIGS. 11A–11B (SEQ ID NO:9), the human Serrate sequence depicted in FIGS. 9A–9G (SEQ ID NO:5), and the human Serrate sequence depicted in FIGS. 10A–10D (SEQ ID NO:7).

27. The isolated nucleic acid of claim 26 in which the fragment is of the human Serrate nucleotide sequence depicted in FIGS. 9A–9G (SEQ ID NO:5).

28. An isolated nucleic acid which is the antisense strand to the nucleic acid of claim 27.

29. The isolated nucleic acid of claim 26 in which the fragment is of the human Serrate nucleotide sequence depicted in FIGS. 10A–10D (SEQ ID NO:7).

30. An isolated nucleic acid which is the antisense strand to the nucleic acid of claim 29.

31. A recombinant cell containing a recombinant nucleic acid comprising a fragment of a vertebrate Serrate gene consisting of at least 25 nucleotides of a vertebrate Serrate nucleotide sequence selected from the group consisting of the mouse Serrate sequence of SEQ ID NO:15, the mouse Serrate sequence of SEQ ID NO:17, the chick Serrate sequence depicted in FIGS. 11A–11B (SEQ ID NO:9), the human Serrate sequence depicted in FIGS. 9A–9G (SEQ ID NO:5), and the human Serrate sequence depicted in FIGS. 10A–10D (SEQ ID NO:7).

32. A method of producing a protein comprising growing the recombinant cell of claim 31 such that the encoded protein is expressed by the cell, and recovering the expressed protein.

33. A recombinant cell containing a recombinant oligonucleotide consisting of at least 25 nucleotides, and comprising a sequence which is the antisense strand to at least a portion of an RNA transcript of a vertebrate Serrate gene having a sequence selected from the group consisting of the chick Serrate depicted in FIGS. 11A–11B (SEQ ID NO:9), the human Serrate depicted in FIGS. 9A–9G (SEQ ID NO:5), and the human Serrate depicted in FIGS. 10A–10D (SEQ ID NO:7), and which oligonucleotide hybridizes under high stringency conditions to a sequence-specific portion of the RNA transcript, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C.

34. A method of producing a protein comprising growing the recombinant cell of claim 33 such that the encoded protein is expressed by the cell, and recovering the expressed Serrate protein.

35. An isolated nucleic acid comprising a nucleotide sequence encoding a fragment of at least 20 amino acids of a vertebrate Serrate protein, said protein having a sequence selected from the group consisting of the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8), which fragment (a) is capable of being bound by an anti-vertebrate Serrate antibody; and (b) lacks the transmembrane and intracellular domains of the protein.

36. The isolated nucleic acid of claim 35 in which the vertebrate Serrate protein has the amino acid sequence depicted in FIGS. 9A–9G (SEQ ID NO:6).

37. The isolated nucleic acid of claim 35 in which the vertebrate Serrate protein has the amino acid sequence depicted in FIG. 10E (SEQ ID NO:8).

38. An isolated nucleic acid comprising a nucleotide sequence encoding a fragment of at least 10 amino acids of a vertebrate Serrate protein, said protein having a sequence selected from the group consisting of the chick Serrate sequence depicted in FIGS. 12A–12B (SEQ ID NO:10), the human Serrate sequence depicted in FIGS. 9A–-9G (SEQ ID NO:6), and the human Serrate sequence depicted in FIG. 10E (SEQ ID NO:8), which fragment (a) is capable of being bound by an anti-vertebrate Serrate antibody; and (b) lacks the extracellular domain of the protein.

39. The isolated nucleic acid of claim 38 in which the fragment is of the human Serrate sequence depicted in FIGS. 9A–9G (SEQ ID NO:6).

40. The isolated nucleic acid of claim 38 in which the fragment is of the human Serrate sequence depicted in FIG. 10E (SEQ ID NO:8).

41. An isolated nucleic acid comprising a nucleotide sequence encoding a protein comprising a fragment of at least 20 amino acids of a vertebrate Serrate protein, said vertebrate Serrate protein having a sequence selected from the group consisting of the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8), which fragment is able to bind to a Notch protein the fragment of claim 27.

42. The nucleic acid of claim 41 wherein the vertebrate Serrate fragment is of the human Serrate sequence depicted in FIGS. 9A–9G (SEQ ID NO:6).

43. The nucleic acid of claim 41 wherein the vertebrate Serrate fragment is of the human Serrate sequence depicted in FIG. 10E (SEQ ID NO:8).

44. An isolated nucleic acid comprising a nucleotide sequence encoding a protein comprising a fragment of at least 20 amino acids of the chick Serrate sequence depicted in FIGS. 12A–12B (SEQ ID NO:10), said fragment comprising a domain of the protein selected from the group consisting of the extracellular domain, DSL domain, epidermal growth factor-like repeat domain, cysteine-rich domain, transmembrane domain, and intracellular domain.

45. An isolated oligonucleotide consisting of at least 25 nucleotides, and comprising a sequence which is the antisense strand to at least a portion of an RNA transcript of a vertebrate Serrate gene having a sequence selected from the group consisting of the chick Serrate sequence depicted in FIGS. 11A–11B (SEQ ID NO:9), the human Serrate sequence depicted in FIGS. 9A–9G (SEQ ID NO:5), and the human Serrate sequence depicted in FIGS. 10A–10D (SEQ ID NO:7), and which oligonucleotide hybridizes under high stringency conditions to a sequence-specific portion of the RNA transcript, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C.

46. A pharmaceutical composition comprising the oligonucleotide of claim 45; and a pharmaceutically acceptable carrier.

47. An isolated nucleic acid comprising the human Serrate sequence contained in plasmid pBS39 as deposited with the ATCC and assigned accession number 97068.

48. An isolated nucleic acid, which nucleic acid (a) hybridizes under high stringency conditions to the human Serrate sequence in plasmid pBS39 as deposited with the ATCC and assigned accession number 97068, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

49. The isolated nucleic acid of claim 48 which encodes a human protein.

50. The isolated nucleic acid of claim 48 in which the anti-vertebrate Serrate antibody does not bind to Drosophila Serrate protein.

51. An isolated nucleic acid, which nucleic acid (a) hybridizes under low stringency conditions to the human Serrate sequence in plasmid pBS39 as deposited with the ATCC and assigned accession number 97068. said low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA. 100 μg/ml denatured salmon sperm DNA, and 10% (wt/vol) dextran sulfate, for 18–20 hours at 40° C., and wash in a buffer consisting of 2×SSC, 25 mM Tris-HCl (pH 7.4). 5 mM EDTA, and 0.1% SDS, for 1.5 hours at 60° C., and (b) encodes a protein which is able to be bound by an anti-vertebrate Serrate antibody.

52. An isolated nucleic acid comprising the human Serrate sequence contained in plasmid pBS15 as deposited with the ATCC and assigned accession number 97459.

53. An isolated nucleic acid, which nucleic acid (a) hybridizes under high stringency conditions to the human Serrate sequence in plasmid pBS15 as deposited with the ATCC and assigned accession number 97459, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

54. The isolated nucleic acid of claim 53 which encodes a human protein.

55. The isolated nucleic acid of claim 53 in which the anti-vertebrate Serrate antibody does not bind to Drosophila Serrate protein.

56. An isolated nucleic acid, which nucleic acid (a) hybridizes under low stringency conditions to the human Serrate sequence in plasmid pBS15 as deposited with the ATCC and assigned accession number 97459, said low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt/vol) dextran sulfate, for 18–20 hours at 40° C., and wash in a buffer consisting of 2×SSC, 25 mM Tris-HCl (pH 7.4), 5 mM EDTA, and 0.1% SDS, for 1.5 hours at 60° C., and (b) encodes a protein which is able to be bound by an anti-vertebrate Serrate antibody.

57. An isolated nucleic acid, which nucleic acid hybridizes under high stringency conditions to the human Serrate sequence in plasmid pBS39 as deposited with the ATCC and assigned accession number 97068, or plasmid pBS15 as deposited with the ATCC and assigned accession number 97459, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C.

58. The nucleic acid of claim 57 which encodes a human Serrate protein.

59. The nucleic acid of claim 57 which is an expression vector comprising a nucleotide sequence operably linked to a non-native promoter.

60. A recombinant cell containing a recombinant nucleic acid, which nucleic acid (a) hybridizes under high stringency conditions to the human Serrate sequence in plasmid pBS39 as deposited with the ATCC and assigned accession number 97068, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

61. The recombinant cell of claim 60 in which the recombinant nucleic acid encodes a human protein.

62. The recombinant cell of claim 60 in which the anti-vertebrate Serrate antibody does not bind to Drosophila Serrate protein.

63. A method of producing a protein comprising growing the recombinant cell of claim 60 such that the encoded protein is expressed by the cell, and recovering the expressed protein.

64. A recombinant cell containing a recombinant nucleic acid, which nucleic acid (a) hybridizes under high stringency conditions to the human Serrate sequence in plasmid pBS15 as deposited with the ATCC and assigned accession number 97459, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

65. The recombinant cell of claim 64 in which the recombinant nucleic acid encodes a human protein.

66. The recombinant cell of claim 64 in which the anti-vertebrate Serrate antibody does not bind to Drosophila Serrate protein.

67. A method of producing a protein comprising growing the recombinant cell of claim 64 such that the encoded protein is expressed by the cell, and recovering the expressed protein.

68. A recombinant cell containing a recombinant nucleic acid, which nucleic acid hybridizes under high stringency conditions to the human Serrate sequence in plasmid pBS39 as deposited with the ATCC and assigned accession number 97068, or plasmid pBS15 as deposited with the ATCC and assigned accession number 97459, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C.

69. An isolated nucleic acid comprising the human Serrate sequence contained in plasmid pBS3–2 as deposited with the ATCC and assigned accession number 97460.

70. An isolated nucleic acid, which nucleic acid (a) hybridizes under high stringency conditions to the human Serrate sequence in plasmid pBS3–2 as deposited with the ATCC and assigned accession number 97460, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

71. The isolated nucleic acid of claim 70 which encodes a human protein.

72. The isolated nucleic acid of claim 70 in which the anti-vertebrate Serrate antibody does not bind to Drosophila Serrate protein.

73. The nucleic acid of claim 48, 53, 70, 49, 50, 54, 55, 71, and 72 which is an expression vector comprising a nucleotide sequence operably linked to a non-native promoter.

74. An isolated nucleic acid, which nucleic acid (a) hybridizes under low stringency conditions to the human Serrate sequence in plasmid pBS3–2 as deposited with the ATCC and assigned accession number 97460, said low stringency conditions comprising hybridization in a buffer consisting of 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt/vol) dextran sulfate, for 18–20 hours at 40° C., and wash in a buffer consisting of 2×SSC, 25 mM Tris-HCl (pH 7.4), 5 mM EDTA, and 0.1% SDS, for 1.5 hours at 60° C., and (b) encodes a protein which is able to be bound by an anti-vertebrate Serrate antibody.

75. A recombinant cell containing a recombinant nucleic acid, which nucleic acid (a) hybridizes under high stringency conditions to the human Serrate sequence in plasmid pBS3–2 as deposited with the ATCC and assigned accession number 97460, said high stringency conditions comprising hybridization in a buffer consisting of 6×SSC, 50 mM Tris-HCl (pH 7.5), 1 mM EDTA, 0.02% PVP, 0.02% Ficoll, 0.02% BSA, and 100 μg/ml denatured salmon sperm DNA, for 48 hours at 65° C., and wash in a buffer consisting of 0.1×SSC, for 45 minutes at 50° C., and (b) encodes a protein which is able to be bound by an anti-vertebrate Serrate antibody.

76. The recombinant cell of claim 75 in which the recombinant nucleic acid encodes a human protein.

77. The recombinant cell of claim 75 in which the anti-vertebrate Serrate antibody does not bind to Drosophila Serrate protein.

78. The recombinant cell of claim 60, 64 or 75 in which said recombinant nucleic acid is an expression vector comprising a nucleotide sequence encoding said protein operably linked to a non-native promoter.

79. A method of producing a protein comprising growing the recombinant cell of claim 75 such that the encoded protein is expressed by the cell, and recovering the expressed protein.

80. An isolated nucleic acid comprising a nucleotide sequence encoding a protein, said protein comprising amino acid numbers 30–1218 of SEQ ID NO:6.

81. An isolated nucleic acid encoding a protein, the amino acid sequence of which consists of amino acid numbers 30–1218 of SEQ ID NO:6.

82. A recombinant cell containing an expression vector comprising a nucleotide sequence encoding a protein, the amino acid sequence of which protein consists of amino acid numbers 30–1218 of SEQ ID NO:6, operably linked to a non-native promoter.

83. A recombinant cell containing a recombinant nucleic acid comprising a nucleotide sequence encoding a protein, said protein comprising amino acid numbers 30–1218 of SEQ ID NO:6.

84. The recombinant cell of claim 23 or 83 in which said recombinant nucleic acid is an expression vector comprising said nucleotide sequence operably linked to a non-native promoter.

85. A method of producing a vertebrate Serrate protein comprising growing the recombinant cell of claim 83 such that the encoded vertebrate Serrate protein is expressed by the cell, and recovering the expressed Serrate protein.

86. An isolated nucleic acid comprising a nucleotide sequence encoding a protein which is able to be bound by an antibody that binds to a protein having an amino acid sequence consisting of amino acid numbers 30–1218 of SEQ ID NO:6.

87. The isolated nucleic acid of claim 86 which encodes a human protein.

88. An isolated nucleic acid comprising a nucleotide sequence encoding a protein which is able to be bound by an antibody that binds to a protein encoded by the nucleotide sequence depicted in FIGS. 9A–9G (SEQ ID NO:5).

89. The isolated nucleic acid of claim 88 which encodes a human protein.

90. An isolated nucleic acid comprising a nucleotide sequence encoding a protein comprising a fragment of at least 20 amino acids of the human Serrate sequence depicted in FIGS. 9A–9G (SEQ ID NO:6), said fragment comprising a domain of the protein selected from the group consisting of the extracellular domain, DSL domain, epidermal growth factor-like repeat domain, cysteine-rich domain, transmembrane domain, and intracellular domain.

91. The nucleic acid of claim 1, 90, 80, 4, 86 or 89 which is an expression vector comprising said nucleotide sequence operably linked to a non-native promoter.

92. The nucleic acid of claim 91 wherein the fragment of the human Serrate protein comprises an amino acid sequence selected from the group consisting of amino acid numbers 1–1068, 30–1068, 234–896, 1069–1091, and 1092–1218, as depicted in FIGS. 9A–9G (SEQ ID NO:6).

93. An isolated nucleic acid comprising a nucleotide sequence encoding a protein comprising a fragment of at least 10 amino acids of the human Serrate sequence depicted in FIG. 10E (SEQ ID NO:8), said fragment comprising a domain of the protein selected from the group consisting of the extracellular domain, DSL domain, epidermal growth factor-like repeat domain, cysteine-rich domain, transmembrane domain, and intracellular domain.

94. A recombinant cell containing a recombinant nucleic acid comprising a nucleotide sequence encoding a protein comprising a fragment of at least 20 amino acids of the human Serrate sequence depicted in FIGS. 9A–9G (SEQ ID NO:6), said fragment comprising a domain of the protein selected from the group consisting of the extracellular domain, DSL domain, epidermal growth factor-like repeat domain, cysteine-rich domain, transmembrane domain, and intracellular domain.

95. A method of producing a protein comprising growing the recombinant cell of claim 94 such that the encoded protein is expressed by the cell, and recovering the expressed protein.

96. An isolated nucleic acid comprising a nucleotide sequence encoding a chimeric protein comprising a fragment of at least 20 amino acids of a vertebrate Serrate protein, said vertebrate Serrate protein having a sequence selected from the group consisting of the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8), which fragment is fused via a covalent bond to an amino acid sequence of a second protein, in which the second protein is not a vertebrate Serrate protein.

97. The isolated nucleic acid of claim 96, wherein the vertebrate Serrate fragment of the chimeric protein is of the human Serrate sequence depicted in FIGS. 9A–9G (SEQ ID NO:6).

98. The isolated nucleic acid of claim 96, wherein the vertebrate Serrate fragment of the chimeric protein is of the human Serrate sequence depicted in FIG. 10E (SEQ ID NO:8).

99. The nucleic acid of claim 97 or 98 wherein the chimeric protein is able to display one or more functional activities of a vertebrate Serrate protein.

100. A recombinant cell containing a recombinant nucleic acid comprising a nucleotide sequence encoding a chimeric protein comprising a fragment of at least amino acids of a vertebrate Serrate protein, said vertebrate Serrate protein having a sequence selected from the group consisting of the chick Serrate sequence depicted in FIGS. 12A–12B (SEQ ID NO:10), the human Serrate sequence depicted in FIGS. 9A–9G (SEQ ID NO:6), and the human Serrate sequence depicted in FIG. 10E (SEQ ID NO:8), which fragment is fused via a covalent bond to an amino acid sequence of a second protein, in which the second protein is not a vertebrate Serrate protein.

101. A method of producing a protein comprising growing the recombinant cell of claim 100 such that the encoded protein is expressed by the cell, and recovering the expressed Serrate protein.

102. An isolated nucleic acid comprising a nucleotide sequence encoding the Drosophila Serrate sequence depicted in FIGS. 3A–3F (SEQ ID NO:2).

103. The nucleic acid of claim 88 which is DNA.

104. An isolated nucleic acid comprising a nucleotide sequence that is the antisense strand to the nucleic acid of claim 102.

105. An isolated nucleic acid comprising the Drosophila Serrate sequence contained in plasmid SerFL as deposited with the ATCC and assigned accession number 68876.

106. An isolated nucleic acid comprising a fragment of a Drosophila Serrate gene consisting of at least 25 nucleotides of the Drosophila Serrate nucleotide sequence depicted in FIGS. 3A–3F (SEQ ID NO:1) or the antisense strand thereto.

107. An isolated nucleic acid comprising a nucleotide sequence encoding a protein comprising a fragment of a Drosophila Serrate protein sequence depicted in FIGS. 3A–3F (SEQ ID NO:2), said fragment comprising a domain of the protein selected from the group consisting of the extracellular domain, epidermal growth factor-like repeat domain, membrane-associated region, transmembrane domain, and intracellular domain.

108. A recombinant cell containing a recombinant fragment of a Drosophila gene consisting of at least 25 nucleotides of the Drosophila Serrate nucleotide sequence depicted in FIGS. 3A–3F (SEQ ID NO:1).

109. A method of producing a protein comprising growing the recombinant cell of claim 108 such that a protein encoded by said fragment is expressed by the cell, and recovering the expressed protein.

* * * * *

UNITED STATES PATENT AND TRADEMARK OFFICE
CERTIFICATE OF CORRECTION

PATENT NO. : 5,869,282
DATED : February 9, 1999
INVENTOR(S) : Ish-Horowicz et al.

It is certified that error appears in the above-identified patent and that said Letters Patent is hereby corrected as shown below:

In Claim 5, line 3, "10B" should be "10E".

In Claim 41, lines 9-10, delete "the fragment of claim 27".

In claim 73, line 2, "71, and 72" should be "71, or 72".

In claim 91, line 1, "89which" should be "88 which".

In claim 92, line1, "91" should be "90".

In claim 100, line 3, after "at least" but before "amino", insert "20".

Signed and Sealed this

Third Day of August, 1999

*Attest:*

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 5561 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 442..4656

( x i ) SEQUENCE DESCRIPTION: SEQ ID NO:1:

```
CCGAGTCGAG   CGCCGTGCTT   CGAGCGGTGA   TGAGCCCCTT   TTCTGTCAAC   GCTAAAGATC         60

TACAAAACAT   CAGCGCCTAT   CAAGTGGAAG   TGTCAAGTGT   GAACAAAACA   AAAACGAGAG        120

AAGCACATAC   TAAGGTCCAT   ATAAATAATA   AATAATAATT   GTGTGTGATA   ACAACATTAT        180

CCAAACAAAA   CCAAACAAAA   CGAAGGCAAA   GTGGAGAAAA   TGATACAGCA   TCCAGAGTAC        240

GGCCGTTATT   CAGCTATCCA   GAGCAAGTGT   AGTGTGGCAA   AATAGAAACA   AACAAAGGCA        300

CCAAAATCTG   CATACATGGG   CTAATTAAGG   CTGCCCAGCG   AATTTACATT   TGTGTGGTGC        360

CAATCCAGAG   TGAATCCGAA   ACAAACTCCA   TCTAGATCGC   CAACCAGCAT   CACGCTCGCA        420

AACGCCCCCA   GAATGTACAA   A ATG TTT  AGG AAA CAT  TTT CGG CGA  AAA CCA            471
                           Met Phe  Arg Lys His  Phe Arg Arg  Lys Pro
                             1                    5                    10

GCT ACG TCG  TCG TCG TTG  GAG TCA ACA  ATA GAA TCA  GCA GAC AGC  CTG               519
Ala Thr Ser  Ser Ser Leu  Glu Ser Thr  Ile Glu Ser  Ala Asp Ser  Leu
               1 5                       2 0                       2 5

GGA ATG TCC  AAG AAG ACG  GCG ACA AAA  AGG CAG CGT  CCG AGG CAT  CGG               567
Gly Met Ser  Lys Lys Thr  Ala Thr Lys  Arg Gln Arg  Pro Arg His  Arg
               3 0                       3 5                       4 0
```

| | | | | | | | | | | | | | | | | |
|---|---|---|---|---|---|---|---|---|---|---|---|---|---|---|---|---|
| GTA | CCC | AAA | ATC | GCG | ACC | CTG | CCA | TCG | ACG | ATC | CGC | GAT | TGT | CGA | TCA | 615 |
| Val | Pro | Lys | Ile | Ala | Thr | Leu | Pro | Ser | Thr | Ile | Arg | Asp | Cys | Arg | Ser | |
| | | 45 | | | | | 50 | | | | | 55 | | | | |
| TTA | AAG | TCT | GCC | TGC | AAC | TTA | ATT | GCT | TTA | ATT | TTA | ATA | CTG | TTA | GTC | 663 |
| Leu | Lys | Ser | Ala | Cys | Asn | Leu | Ile | Ala | Leu | Ile | Leu | Ile | Leu | Leu | Val | |
| | 60 | | | | | 65 | | | | | 70 | | | | | |
| CAT | AAG | ATA | TCC | GCA | GCT | GGT | AAC | TTC | GAG | CTG | GAA | ATA | TTA | GAA | ATC | 711 |
| His | Lys | Ile | Ser | Ala | Ala | Gly | Asn | Phe | Glu | Leu | Glu | Ile | Leu | Glu | Ile | |
| 75 | | | | | 80 | | | | | 85 | | | | | 90 | |
| TCA | AAT | ACC | AAC | AGC | CAT | CTA | CTC | AAC | GGC | TAT | TGC | TGC | GGC | ATG | CCA | 759 |
| Ser | Asn | Thr | Asn | Ser | His | Leu | Leu | Asn | Gly | Tyr | Cys | Cys | Gly | Met | Pro | |
| | | | | 95 | | | | | 100 | | | | | 105 | | |
| GCG | GAA | CTT | AGG | GCC | ACC | AAG | ACG | ATA | GGC | TGC | TCG | CCA | TGC | ACG | ACG | 807 |
| Ala | Glu | Leu | Arg | Ala | Thr | Lys | Thr | Ile | Gly | Cys | Ser | Pro | Cys | Thr | Thr | |
| | | | 110 | | | | | 115 | | | | | 120 | | | |
| GCA | TTC | CGG | CTG | TGC | CTG | AAG | GAG | TAC | CAG | ACC | ACG | GAG | CAG | GGT | GCC | 855 |
| Ala | Phe | Arg | Leu | Cys | Leu | Lys | Glu | Tyr | Gln | Thr | Thr | Glu | Gln | Gly | Ala | |
| | | 125 | | | | | 130 | | | | | 135 | | | | |
| AGC | ATA | TCC | ACG | GGC | TGT | TCG | TTT | GGC | AAC | GCC | ACC | ACC | AAG | ATA | CTG | 903 |
| Ser | Ile | Ser | Thr | Gly | Cys | Ser | Phe | Gly | Asn | Ala | Thr | Thr | Lys | Ile | Leu | |
| | 140 | | | | | 145 | | | | | 150 | | | | | |
| GGT | GGC | TCC | AGC | TTT | GTG | CTC | AGC | GAT | CCG | GGT | GTG | GGA | GCC | ATT | GTG | 951 |
| Gly | Gly | Ser | Ser | Phe | Val | Leu | Ser | Asp | Pro | Gly | Val | Gly | Ala | Ile | Val | |
| 155 | | | | | 160 | | | | | 165 | | | | | 170 | |
| CTG | CCC | TTT | ACG | TTT | CGT | TGG | ACG | AAG | TCG | TTT | ACG | CTG | ATA | CTG | CAG | 999 |
| Leu | Pro | Phe | Thr | Phe | Arg | Trp | Thr | Lys | Ser | Phe | Thr | Leu | Ile | Leu | Gln | |
| | | | | 175 | | | | | 180 | | | | | 185 | | |
| GCG | TTG | GAT | ATG | TAC | AAC | ACA | TCC | TAT | CCA | GAT | GCG | GAG | AGG | TTA | ATT | 1047 |
| Ala | Leu | Asp | Met | Tyr | Asn | Thr | Ser | Tyr | Pro | Asp | Ala | Glu | Arg | Leu | Ile | |
| | | | 190 | | | | | 195 | | | | | 200 | | | |
| GAG | GAA | ACA | TCA | TAC | TCG | GGC | GTG | ATA | CTG | CCG | TCG | CCG | GAG | TGG | AAG | 1095 |
| Glu | Glu | Thr | Ser | Tyr | Ser | Gly | Val | Ile | Leu | Pro | Ser | Pro | Glu | Trp | Lys | |
| | | 205 | | | | | 210 | | | | | 215 | | | | |
| ACG | CTG | GAC | CAC | ATC | GGG | CGG | AAC | GCG | CGG | ATC | ACC | TAC | CGT | GTC | CGG | 1143 |
| Thr | Leu | Asp | His | Ile | Gly | Arg | Asn | Ala | Arg | Ile | Thr | Tyr | Arg | Val | Arg | |
| | 220 | | | | | 225 | | | | | 230 | | | | | |
| GTG | CAA | TGC | GCC | GTT | ACC | TAC | TAC | AAC | ACG | ACC | TGC | ACG | ACC | TTC | TGC | 1191 |
| Val | Gln | Cys | Ala | Val | Thr | Tyr | Tyr | Asn | Thr | Thr | Cys | Thr | Thr | Phe | Cys | |
| 235 | | | | | 240 | | | | | 245 | | | | | 250 | |
| CGT | CCG | CGG | GAC | GAT | CAG | TTC | GGT | CAC | TAC | GCC | TGC | GGC | TCC | GAG | GGT | 1239 |
| Arg | Pro | Arg | Asp | Asp | Gln | Phe | Gly | His | Tyr | Ala | Cys | Gly | Ser | Glu | Gly | |
| | | | | 255 | | | | | 260 | | | | | 265 | | |
| CAG | AAG | CTC | TGC | CTG | AAT | GGC | TGG | CAG | GGC | GTC | AAC | TGC | GAG | GAG | GCC | 1287 |
| Gln | Lys | Leu | Cys | Leu | Asn | Gly | Trp | Gln | Gly | Val | Asn | Cys | Glu | Glu | Ala | |
| | | | 270 | | | | | 275 | | | | | 280 | | | |
| ATA | TGC | AAG | GCG | GGC | TGC | GAC | CCC | GTC | CAC | GGC | AAG | TGC | GAT | CGT | CCG | 1335 |
| Ile | Cys | Lys | Ala | Gly | Cys | Asp | Pro | Val | His | Gly | Lys | Cys | Asp | Arg | Pro | |
| | | 285 | | | | | 290 | | | | | 295 | | | | |
| GGG | GAA | TGC | GAA | TGC | AGA | CCC | GGC | TGG | CGT | GGT | CCA | TTG | TGC | AAC | GAG | 1383 |
| Gly | Glu | Cys | Glu | Cys | Arg | Pro | Gly | Trp | Arg | Gly | Pro | Leu | Cys | Asn | Glu | |
| | 300 | | | | | 305 | | | | | 310 | | | | | |
| TGC | ATG | GTC | TAT | CCC | GGC | TGC | AAG | CAT | GGT | TCC | TGC | AAC | GGC | AGC | GCC | 1431 |
| Cys | Met | Val | Tyr | Pro | Gly | Cys | Lys | His | Gly | Ser | Cys | Asn | Gly | Ser | Ala | |
| 315 | | | | | 320 | | | | | 325 | | | | | 330 | |
| TGG | AAA | TGC | GTG | TGC | GAC | ACC | AAC | TGG | GGT | GGC | ATA | TTG | TGC | GAT | CAA | 1479 |
| Trp | Lys | Cys | Val | Cys | Asp | Thr | Asn | Trp | Gly | Gly | Ile | Leu | Cys | Asp | Gln | |
| | | | | 335 | | | | | 340 | | | | | 345 | | |
| GAT | TTA | AAT | TTC | TGC | GGC | ACC | CAT | GAA | CCC | TGC | AAG | CAC | GGC | GGC | ACC | 1527 |
| Asp | Leu | Asn | Phe | Cys | Gly | Thr | His | Glu | Pro | Cys | Lys | His | Gly | Gly | Thr | |
| | | | 350 | | | | | 355 | | | | | 360 | | | |

| | | | | | | | | | | | | | | | | |
|---|---|---|---|---|---|---|---|---|---|---|---|---|---|---|---|---|
| TGC | GAA | AAT | ACC | GCT | CCG | GAC | AAA | TAT | CGG | TGC | ACA | TGC | GCC | GAG | GGC | 1575 |
| Cys | Glu | Asn | Thr | Ala | Pro | Asp | Lys | Tyr | Arg | Cys | Thr | Cys | Ala | Glu | Gly | |
| | | 365 | | | | 370 | | | | 375 | | | | | | |
| CTC | TCG | GGC | GAG | CAG | TGC | GAG | ATC | GTG | GAG | CAC | CCA | TGT | GCC | ACC | AGG | 1623 |
| Leu | Ser | Gly | Glu | Gln | Cys | Glu | Ile | Val | Glu | His | Pro | Cys | Ala | Thr | Arg | |
| 380 | | | | | 385 | | | | | 390 | | | | | | |
| CCA | TGC | CGC | AAC | GGC | GGC | ACA | TGC | ACA | CTC | AAG | ACG | AGT | AAC | CGA | ACT | 1671 |
| Pro | Cys | Arg | Asn | Gly | Gly | Thr | Cys | Thr | Leu | Lys | Thr | Ser | Asn | Arg | Thr | |
| 395 | | | | | 400 | | | | | 405 | | | | | 410 | |
| CAA | GCC | CAA | GTG | TAT | CGC | ACA | TCA | CAT | GGC | AGG | AGC | AAC | ATG | GGC | CGG | 1719 |
| Gln | Ala | Gln | Val | Tyr | Arg | Thr | Ser | His | Gly | Arg | Ser | Asn | Met | Gly | Arg | |
| | | | | 415 | | | | | 420 | | | | | 425 | | |
| CCG | GTA | AGA | CGC | AGC | AGT | TCG | ATG | CGC | AGC | CTG | GAT | CAC | CTG | CGG | CCG | 1767 |
| Pro | Val | Arg | Arg | Ser | Ser | Ser | Met | Arg | Ser | Leu | Asp | His | Leu | Arg | Pro | |
| | | 430 | | | | 435 | | | | 440 | | | | | | |
| GAG | GGG | CAG | GCG | CTG | AAT | GGC | AGC | AGC | TCC | TCG | GGA | TTG | GTG | TCC | CTA | 1815 |
| Glu | Gly | Gln | Ala | Leu | Asn | Gly | Ser | Ser | Ser | Ser | Gly | Leu | Val | Ser | Leu | |
| | | 445 | | | | 450 | | | | 455 | | | | | | |
| GGT | TCG | CTG | CAG | CTG | CAG | CAG | CAA | CTG | GCC | CCC | GAC | TTC | ACT | TGC | GAC | 1863 |
| Gly | Ser | Leu | Gln | Leu | Gln | Gln | Gln | Leu | Ala | Pro | Asp | Phe | Thr | Cys | Asp | |
| 460 | | | | | 465 | | | | | 470 | | | | | | |
| TGC | GCA | GCC | GGA | TGG | ACG | GGA | CCG | ACA | TGC | GAA | ATA | AAT | ATC | GAC | GAG | 1911 |
| Cys | Ala | Ala | Gly | Trp | Thr | Gly | Pro | Thr | Cys | Glu | Ile | Asn | Ile | Asp | Glu | |
| 475 | | | | 480 | | | | | 485 | | | | | 490 | | |
| TGC | GCC | GGG | GGT | CCC | TGC | GAG | CAT | GGT | GGC | ACT | TGC | ATC | GAT | CTA | ATC | 1959 |
| Cys | Ala | Gly | Gly | Pro | Cys | Glu | His | Gly | Gly | Thr | Cys | Ile | Asp | Leu | Ile | |
| | | | | 495 | | | | | 500 | | | | | 505 | | |
| GGT | GGC | TTT | CGA | TGT | GAA | TGT | CCG | CCG | GAG | TGG | CAT | GGC | GAT | GTC | TGT | 2007 |
| Gly | Gly | Phe | Arg | Cys | Glu | Cys | Pro | Pro | Glu | Trp | His | Gly | Asp | Val | Cys | |
| | | | 510 | | | | | 515 | | | | | 520 | | | |
| CAG | GTG | GAT | GTG | AAC | GAG | TGC | GAG | GCG | CCG | CAT | TCC | GCC | GGA | ATC | GCT | 2055 |
| Gln | Val | Asp | Val | Asn | Glu | Cys | Glu | Ala | Pro | His | Ser | Ala | Gly | Ile | Ala | |
| | | 525 | | | | 530 | | | | | 535 | | | | | |
| GCG | AAC | GCA | TTG | CTG | ACC | ACC | ACA | GCC | ACC | GCG | ATT | ATT | GGT | AGT | AAT | 2103 |
| Ala | Asn | Ala | Leu | Leu | Thr | Thr | Thr | Ala | Thr | Ala | Ile | Ile | Gly | Ser | Asn | |
| | 540 | | | | | 545 | | | | | 550 | | | | | |
| CTG | AGC | AGT | ACT | GCT | CTT | CTG | GCC | GCT | CTG | ACC | AGT | GCA | GTG | GCA | TCC | 2151 |
| Leu | Ser | Ser | Thr | Ala | Leu | Leu | Ala | Ala | Leu | Thr | Ser | Ala | Val | Ala | Ser | |
| 555 | | | | | 560 | | | | | 565 | | | | | 570 | |
| ACA | TCC | TTG | GCC | ATC | GGA | CCC | TGC | ATC | AAT | GCC | AAG | GAG | TGT | CGC | AAT | 2199 |
| Thr | Ser | Leu | Ala | Ile | Gly | Pro | Cys | Ile | Asn | Ala | Lys | Glu | Cys | Arg | Asn | |
| | | | | 575 | | | | 580 | | | | | 585 | | | |
| CAG | CCG | GGT | TCC | TTT | GCC | TGC | ATC | TGC | AAG | GAG | GGC | TGG | GGC | GGA | GTG | 2247 |
| Gln | Pro | Gly | Ser | Phe | Ala | Cys | Ile | Cys | Lys | Glu | Gly | Trp | Gly | Gly | Val | |
| | | | 590 | | | | | 595 | | | | | 600 | | | |
| ACC | TGT | GCC | GAG | AAT | CTA | GAT | GAC | TGT | GTG | GGT | CAG | TGC | CGG | AAT | GGA | 2295 |
| Thr | Cys | Ala | Glu | Asn | Leu | Asp | Asp | Cys | Val | Gly | Gln | Cys | Arg | Asn | Gly | |
| | | 605 | | | | 610 | | | | | 615 | | | | | |
| GCC | ACC | TGC | ATT | GAT | CTG | GTC | AAC | GAC | TAT | AGG | TGC | GCC | TGT | GCC | TCT | 2343 |
| Ala | Thr | Cys | Ile | Asp | Leu | Val | Asn | Asp | Tyr | Arg | Cys | Ala | Cys | Ala | Ser | |
| | | 620 | | | | 625 | | | | | 630 | | | | | |
| GGA | TTC | ACG | GGT | CGC | GAT | TGC | GAG | ACG | GAC | ATA | GAC | GAG | TGC | GCC | ACT | 2391 |
| Gly | Phe | Thr | Gly | Arg | Asp | Cys | Glu | Thr | Asp | Ile | Asp | Glu | Cys | Ala | Thr | |
| 635 | | | | | 640 | | | | | 645 | | | | | 650 | |
| TCC | CCG | TGC | CGA | AAC | GGA | GGC | GAA | TGT | GTG | GAC | ATG | GTG | GGC | AAA | TTC | 2439 |
| Ser | Pro | Cys | Arg | Asn | Gly | Gly | Glu | Cys | Val | Asp | Met | Val | Gly | Lys | Phe | |
| | | | | 655 | | | | | 660 | | | | | 665 | | |
| AAT | TGC | ATT | TGC | CCA | CTT | GGC | TAC | TCG | GGT | TCT | CTG | TGC | GAG | GAG | GCC | 2487 |
| Asn | Cys | Ile | Cys | Pro | Leu | Gly | Tyr | Ser | Gly | Ser | Leu | Cys | Glu | Glu | Ala | |
| | | | 670 | | | | | 675 | | | | | 680 | | | |

| | | | | | | | | | | | | | | | | |
|---|---|---|---|---|---|---|---|---|---|---|---|---|---|---|---|---|
| AAG | GAG | AAC | TGC | ACA | CCG | TCG | CCA | TGT | TTG | GAG | GGT | CAC | TGC | CTC | AAC | 2535 |
| Lys | Glu | Asn | Cys | Thr | Pro | Ser | Pro | Cys | Leu | Glu | Gly | His | Cys | Leu | Asn | |
| | | 685 | | | | 690 | | | | | 695 | | | | | |
| ACG | CCC | GAA | GGA | TAC | TAC | TGC | CAT | TGT | CCA | CCG | GAT | CGC | GCC | GGA | AAG | 2583 |
| Thr | Pro | Glu | Gly | Tyr | Tyr | Cys | His | Cys | Pro | Pro | Asp | Arg | Ala | Gly | Lys | |
| | 700 | | | | | 705 | | | | | 710 | | | | | |
| CAC | TGC | GAG | CAA | CTG | CGT | CCG | CTC | TGC | TCC | CAG | CCG | CCC | TGC | AAC | GAG | 2631 |
| His | Cys | Glu | Gln | Leu | Arg | Pro | Leu | Cys | Ser | Gln | Pro | Pro | Cys | Asn | Glu | |
| 715 | | | | 720 | | | | | 725 | | | | | 730 | | |
| GGC | TGC | TTC | GCC | AAT | GTC | AGC | CTA | GCG | ACG | TCA | GCG | ACA | ACG | ACG | ACG | 2679 |
| Gly | Cys | Phe | Ala | Asn | Val | Ser | Leu | Ala | Thr | Ser | Ala | Thr | Thr | Thr | Thr | |
| | | | | 735 | | | | | 740 | | | | | 745 | | |
| ACA | ACC | ACC | ACA | ACG | GCG | ACA | ACG | ACA | AGG | AAG | ATG | GCC | AAG | CCA | AGC | 2727 |
| Thr | Thr | Thr | Thr | Thr | Ala | Thr | Thr | Thr | Arg | Lys | Met | Ala | Lys | Pro | Ser | |
| | | | 750 | | | | | 755 | | | | | 760 | | | |
| GGA | TTG | CCC | TGC | AGC | GGA | CAC | GGC | AGC | TGC | GAG | ATG | AGC | GAC | GTG | GGC | 2775 |
| Gly | Leu | Pro | Cys | Ser | Gly | His | Gly | Ser | Cys | Glu | Met | Ser | Asp | Val | Gly | |
| | | 765 | | | | | 770 | | | | | 775 | | | | |
| ACC | TTC | TGC | AAA | TGC | CAT | GTG | GGC | CAC | ACC | GGC | ACC | TTC | TGC | GAG | CAC | 2823 |
| Thr | Phe | Cys | Lys | Cys | His | Val | Gly | His | Thr | Gly | Thr | Phe | Cys | Glu | His | |
| | 780 | | | | | 785 | | | | | 790 | | | | | |
| AAT | CTC | AAC | GAA | TGC | TCG | CCG | AAT | CCT | TGT | CGA | AAT | GGG | GGA | ATT | TGC | 2871 |
| Asn | Leu | Asn | Glu | Cys | Ser | Pro | Asn | Pro | Cys | Arg | Asn | Gly | Gly | Ile | Cys | |
| 795 | | | | 800 | | | | | 805 | | | | | 810 | | |
| CTT | GAC | GGC | GAC | GGC | GAT | TTT | ACA | TGC | GAG | TGC | ATG | TCG | GGC | TGG | ACA | 2919 |
| Leu | Asp | Gly | Asp | Gly | Asp | Phe | Thr | Cys | Glu | Cys | Met | Ser | Gly | Trp | Thr | |
| | | | | 815 | | | | | 820 | | | | | 825 | | |
| GGT | AAA | CGC | TGC | TCG | GAG | CGC | GCT | ACA | GGT | TGT | TAT | GCC | GGT | CAG | TGC | 2967 |
| Gly | Lys | Arg | Cys | Ser | Glu | Arg | Ala | Thr | Gly | Cys | Tyr | Ala | Gly | Gln | Cys | |
| | | | 830 | | | | | 835 | | | | | 840 | | | |
| CAG | AAT | GGT | GGT | ACC | TGC | ATG | CCT | GGA | GCC | CCG | GAC | AAG | GCT | CTG | CAG | 3015 |
| Gln | Asn | Gly | Gly | Thr | Cys | Met | Pro | Gly | Ala | Pro | Asp | Lys | Ala | Leu | Gln | |
| | | 845 | | | | | 850 | | | | | 855 | | | | |
| CCG | CAT | TGC | CGC | TGT | GCG | CCA | GGT | TGG | ACT | GGT | CTG | TTT | TGC | GCC | GAG | 3063 |
| Pro | His | Cys | Arg | Cys | Ala | Pro | Gly | Trp | Thr | Gly | Leu | Phe | Cys | Ala | Glu | |
| | 860 | | | | | 865 | | | | | 870 | | | | | |
| GCT | ATT | GAC | CAG | TGT | CGC | GGG | CAG | CCG | TGC | CAC | AAT | GGC | GGA | ACG | TGC | 3111 |
| Ala | Ile | Asp | Gln | Cys | Arg | Gly | Gln | Pro | Cys | His | Asn | Gly | Gly | Thr | Cys | |
| 875 | | | | 880 | | | | | 885 | | | | | 890 | | |
| GAG | TCG | GGA | GCG | GGC | TGG | TTC | CGC | TGC | GTC | TGC | GCT | CAG | GGA | TTC | TCT | 3159 |
| Glu | Ser | Gly | Ala | Gly | Trp | Phe | Arg | Cys | Val | Cys | Ala | Gln | Gly | Phe | Ser | |
| | | | | 895 | | | | | 900 | | | | | 905 | | |
| GGT | CCA | GAC | TGC | CGC | ATC | AAT | GTG | AAC | GAG | TGC | TCG | CCA | CAG | CCT | TGC | 3207 |
| Gly | Pro | Asp | Cys | Arg | Ile | Asn | Val | Asn | Glu | Cys | Ser | Pro | Gln | Pro | Cys | |
| | | | 910 | | | | | 915 | | | | | 920 | | | |
| CAG | GGC | GGT | GCC | ACC | TGC | ATC | GAC | GGA | ATC | GGT | GGA | TAC | AGC | TGC | ATC | 3255 |
| Gln | Gly | Gly | Ala | Thr | Cys | Ile | Asp | Gly | Ile | Gly | Gly | Tyr | Ser | Cys | Ile | |
| | | 925 | | | | | 930 | | | | | 935 | | | | |
| TGC | CCA | CCA | GGA | AGG | CAT | GGA | TTG | CGG | TGT | GAA | ATT | TTG | CTC | TCC | GAT | 3303 |
| Cys | Pro | Pro | Gly | Arg | His | Gly | Leu | Arg | Cys | Glu | Ile | Leu | Leu | Ser | Asp | |
| 940 | | | | | 945 | | | | | 950 | | | | | | |
| CCC | AAG | TCC | GCC | TGC | CAG | AAC | GCA | AGC | AAC | ACT | ATC | TCT | CCG | TAT | ACA | 3351 |
| Pro | Lys | Ser | Ala | Cys | Gln | Asn | Ala | Ser | Asn | Thr | Ile | Ser | Pro | Tyr | Thr | |
| 955 | | | | 960 | | | | | 965 | | | | | 970 | | |
| GCT | CTA | AAC | CGA | AGC | CAA | AAC | TGG | CTG | GAT | ATT | GCT | CTA | ACC | GGA | AGA | 3399 |
| Ala | Leu | Asn | Arg | Ser | Gln | Asn | Trp | Leu | Asp | Ile | Ala | Leu | Thr | Gly | Arg | |
| | | | | 975 | | | | | 980 | | | | | 985 | | |
| ACA | GAA | GAC | GAT | GAG | AAC | TGC | AAT | GCG | TGT | GTC | TGC | GAA | AAC | GGC | ACC | 3447 |
| Thr | Glu | Asp | Asp | Glu | Asn | Cys | Asn | Ala | Cys | Val | Cys | Glu | Asn | Gly | Thr | |
| | | | 990 | | | | | 995 | | | | | 1000 | | | |

| | | | | | | | | | | | | | | | | |
|---|---|---|---|---|---|---|---|---|---|---|---|---|---|---|---|---|
| TCT | CGG | TGC | ACG | AAT | CTC | TGG | TGT | GGA | TTG | CCC | AAT | TGC | TAT | AAG | GTG | 3495 |
| Ser | Arg | Cys | Thr | Asn | Leu | Trp | Cys | Gly | Leu | Pro | Asn | Cys | Tyr | Lys | Val | |
| | | 1005 | | | | 1010 | | | | 1015 | | | | | | |
| GAT | CCG | CTC | TCC | AAG | TCC | TCG | AAT | CTG | TCC | GGT | GTT | TGC | AAA | CAG | CAC | 3543 |
| Asp | Pro | Leu | Ser | Lys | Ser | Ser | Asn | Leu | Ser | Gly | Val | Cys | Lys | Gln | His | |
| | 1020 | | | | 1025 | | | | | 1030 | | | | | | |
| GAG | GTG | TGC | GTT | CCG | GCA | CTG | AGT | GAG | ACA | TGC | CTG | TCA | TCG | CCT | TGT | 3591 |
| Glu | Val | Cys | Val | Pro | Ala | Leu | Ser | Glu | Thr | Cys | Leu | Ser | Ser | Pro | Cys | |
| 1035 | | | | 1040 | | | | | 1045 | | | | | 1050 | | |
| AAT | GTT | CGT | GGA | GAT | TGC | CGG | GCA | CTG | GAA | CCA | TCG | CGT | CGG | GTT | GCT | 3639 |
| Asn | Val | Arg | Gly | Asp | Cys | Arg | Ala | Leu | Glu | Pro | Ser | Arg | Arg | Val | Ala | |
| | | | | 1055 | | | | | 1060 | | | | | 1065 | | |
| CCA | CCC | CGA | CTG | CCA | GCC | AAA | TCT | AGC | TGC | TGG | CCC | AAT | CAG | GCC | GTG | 3687 |
| Pro | Pro | Arg | Leu | Pro | Ala | Lys | Ser | Ser | Cys | Trp | Pro | Asn | Gln | Ala | Val | |
| | | 1070 | | | | | 1075 | | | | | 1080 | | | | |
| GTC | AAC | GAG | AAC | TGC | GCC | CGA | CTC | ACC | ATC | CTT | TTG | GCC | CTG | GAG | CGA | 3735 |
| Val | Asn | Glu | Asn | Cys | Ala | Arg | Leu | Thr | Ile | Leu | Leu | Ala | Leu | Glu | Arg | |
| | | | 1085 | | | | | 1090 | | | | | 1095 | | | |
| GTG | GGC | AAG | GGA | GCT | TCG | GTG | GAG | GGT | CTC | TGC | TCC | CTG | GTA | AGG | GTG | 3783 |
| Val | Gly | Lys | Gly | Ala | Ser | Val | Glu | Gly | Leu | Cys | Ser | Leu | Val | Arg | Val | |
| 1100 | | | | | 1105 | | | | | 1110 | | | | | | |
| CTG | CTG | GCT | GCC | CAG | TTG | ATC | AAG | AAG | CCG | GCG | AGT | ACT | TTT | GGC | CAG | 3831 |
| Leu | Leu | Ala | Ala | Gln | Leu | Ile | Lys | Lys | Pro | Ala | Ser | Thr | Phe | Gly | Gln | |
| 1115 | | | | | 1120 | | | | | 1125 | | | | | 1130 | |
| GAT | CCG | GGA | ATG | CTT | ATG | GTG | CTC | TGC | GAT | CTC | AAA | ACG | GGC | ACC | AAT | 3879 |
| Asp | Pro | Gly | Met | Leu | Met | Val | Leu | Cys | Asp | Leu | Lys | Thr | Gly | Thr | Asn | |
| | | | | 1135 | | | | | 1140 | | | | | 1145 | | |
| GAT | ACC | GTT | GAA | CTA | ACT | GTG | TCG | TCC | AGT | AAA | TTA | AAT | GAT | CCC | CAG | 3927 |
| Asp | Thr | Val | Glu | Leu | Thr | Val | Ser | Ser | Ser | Lys | Leu | Asn | Asp | Pro | Gln | |
| | | | | 1150 | | | | | 1155 | | | | | 1160 | | |
| CTG | CCA | GTG | GCG | GTG | GGT | CTG | CTG | GGT | GAA | CTC | CTG | AGC | TCC | AGG | CAG | 3975 |
| Leu | Pro | Val | Ala | Val | Gly | Leu | Leu | Gly | Glu | Leu | Leu | Ser | Ser | Arg | Gln | |
| | | 1165 | | | | | 1170 | | | | | 1175 | | | | |
| TTG | AAT | GGC | ATC | CAG | CGG | CGC | AAG | GAA | CTG | GAG | CTG | CAG | CAT | GCA | AAA | 4023 |
| Leu | Asn | Gly | Ile | Gln | Arg | Arg | Lys | Glu | Leu | Glu | Leu | Gln | His | Ala | Lys | |
| | | 1180 | | | | | 1185 | | | | | 1190 | | | | |
| TTG | GCT | GCC | CTC | ACC | TCC | ATT | GTG | GAG | GTC | AAG | TTG | GAA | ACG | GCC | CGC | 4071 |
| Leu | Ala | Ala | Leu | Thr | Ser | Ile | Val | Glu | Val | Lys | Leu | Glu | Thr | Ala | Arg | |
| 1195 | | | | | 1200 | | | | | 1205 | | | | | 1210 | |
| GTG | GCC | GAT | GGA | TCG | GGT | CAT | AGT | CTG | CTG | ATA | GGA | GTG | CTA | TGC | GGT | 4119 |
| Val | Ala | Asp | Gly | Ser | Gly | His | Ser | Leu | Leu | Ile | Gly | Val | Leu | Cys | Gly | |
| | | | | 1215 | | | | | 1220 | | | | | 1225 | | |
| GTC | TTT | ATA | GTC | CTG | GTG | GGA | TTC | TCG | GTG | TTC | ATC | AGT | CTT | TAC | TGG | 4167 |
| Val | Phe | Ile | Val | Leu | Val | Gly | Phe | Ser | Val | Phe | Ile | Ser | Leu | Tyr | Trp | |
| | | | | 1230 | | | | | 1235 | | | | | 1240 | | |
| AAA | CAG | CGT | CTG | GCT | TAT | CGC | ACC | AGT | TCG | GGA | ATG | AAC | TTA | ACT | CCC | 4215 |
| Lys | Gln | Arg | Leu | Ala | Tyr | Arg | Thr | Ser | Ser | Gly | Met | Asn | Leu | Thr | Pro | |
| | | 1245 | | | | | 1250 | | | | | 1255 | | | | |
| TCC | CTG | GAT | GCA | CTG | CGT | CAC | GAG | GAG | GAG | AAG | TCG | AAT | AAT | CTG | CAG | 4263 |
| Ser | Leu | Asp | Ala | Leu | Arg | His | Glu | Glu | Glu | Lys | Ser | Asn | Asn | Leu | Gln | |
| | 1260 | | | | | 1265 | | | | | 1270 | | | | | |
| AAC | GAG | GAG | AAT | CTG | CGA | AGG | TAT | ACA | AAT | CCG | CTG | AAG | GGC | AGC | ACC | 4311 |
| Asn | Glu | Glu | Asn | Leu | Arg | Arg | Tyr | Thr | Asn | Pro | Leu | Lys | Gly | Ser | Thr | |
| 1275 | | | | | 1280 | | | | | 1285 | | | | | 1290 | |
| AGT | TCC | CTA | AGA | GCG | GCC | ACC | GGC | ATG | GAA | CTA | AGC | CTC | AAT | CCC | GCT | 4359 |
| Ser | Ser | Leu | Arg | Ala | Ala | Thr | Gly | Met | Glu | Leu | Ser | Leu | Asn | Pro | Ala | |
| | | | | 1295 | | | | | 1300 | | | | | 1305 | | |
| CCG | GAA | TTA | GCC | GCC | TCG | GCG | GCG | AGT | AGT | TCC | GCC | TTG | CAC | AGA | TCG | 4407 |
| Pro | Glu | Leu | Ala | Ala | Ser | Ala | Ala | Ser | Ser | Ser | Ala | Leu | His | Arg | Ser | |
| | | | 1310 | | | | | 1315 | | | | | 1320 | | | |

| | | | | | | | | | | | | | | | |
|---|---|---|---|---|---|---|---|---|---|---|---|---|---|---|---|
| CAG | CCA | CTA | TTC | CCG | CCA | TGC | GAT | TTC | GAG | CGT | GAG | CTG | GAC | TCC | AGT | 4455
| Gln | Pro | Leu<br>1325 | Phe | Pro | Pro | Cys | Asp<br>1330 | Phe | Glu | Arg | Glu<br>1335 | Leu | Asp | Ser | Ser |

```
CAG  CCA  CTA  TTC  CCG  CCA  TGC  GAT  TTC  GAG  CGT  GAG  CTG  GAC  TCC  AGT      4455
Gln  Pro  Leu  Phe  Pro  Pro  Cys  Asp  Phe  Glu  Arg  Glu  Leu  Asp  Ser  Ser
          1325                     1330                1335

ACG  GGC  CTG  AAG  CAG  GCG  CAC  AAG  CGG  AGC  TCA  CAG  ATT  CTG  CTG  CAC      4503
Thr  Gly  Leu  Lys  Gln  Ala  His  Lys  Arg  Ser  Ser  Gln  Ile  Leu  Leu  His
     1340                     1345                     1350

AAA  ACC  CAA  AAC  TCG  GAC  ATG  CGG  AAG  AAC  ACT  GTG  GGC  TCG  CTG  GAC      4551
Lys  Thr  Gln  Asn  Ser  Asp  Met  Arg  Lys  Asn  Thr  Val  Gly  Ser  Leu  Asp
1355                     1360                     1365                     1370

AGT  CCG  CGT  AAG  GAC  TTT  GGC  AAG  CGG  TCG  ATC  AAC  TGC  AAG  TCC  ATG      4599
Ser  Pro  Arg  Lys  Asp  Phe  Gly  Lys  Arg  Ser  Ile  Asn  Cys  Lys  Ser  Met
                    1375                     1380                     1385

CCA  CCC  TCT  TCG  GGC  GAC  GAG  GGC  TCC  GAT  GTC  CTT  GCC  ACC  ACT  GTG      4647
Pro  Pro  Ser  Ser  Gly  Asp  Glu  Gly  Ser  Asp  Val  Leu  Ala  Thr  Thr  Val
               1390                     1395                1400

ATG  GTT  TAG  CCGTGATCTC  ACCAACCAAC  CAATCAAGAA  ACCAACCAGC                       4696
Met  Val  *
          1405
```

| | | | | | |
|---|---|---|---|---|---|
| CGCCCACAGC | CAGCTCAAAG | TTCCAATTGC | CACAGCACGG | GCGCTATTTC | CAAGTGCATT | 4756
| AGTAGCGTAA | TTAAAACTAG | GATATTGTTA | AGGATACCAA | GGTAGGCCAC | AACGGAGTGG | 4816
| CTCTGTTGAA | AACGTAAAGT | TCTAAAAATC | CAGGTCTCTC | AGACAAAGAT | GAGGTACACA | 4876
| AATAAATTGG | CTAGTTAATC | AAGCATGTTA | TGGCCACGGG | ATGGGCAAAT | TTATTTGTAT | 4936
| ACCTGATCTT | ATCTTAATAC | TAAACCAGTT | TTCTACTATT | TTTTTTTGT | GGATCAAGCT | 4996
| TAAAAGTTCA | GCTAGGCAGG | CGTTTTCCGC | AGTGCCATGT | CGATGTGGAA | GCCCAAAATA | 5056
| TTTAGGTTAG | ATAGTGTAAT | TTCGAACTCT | TCTCTTCGCT | AAGCAACATC | CTACACAGTG | 5116
| TGATATTTAG | TGTAACCCAG | GCGCGCATTT | ACATTCAATT | AAAGACAATG | ATATATAAAT | 5176
| ATAAACGAAA | TCAACTCCTT | GGCTAGCACA | AGCTGTATGT | ATATAGTTCT | CATTTAGGAT | 5236
| CGTCGCGCTC | TATATTGTGT | ATAAGCTGTA | AATACTGTAA | ATTAGCAGTT | ACCGTTATTG | 5296
| TATTTTGTCT | ATAGTTAGAT | TGGTACTATT | AAACTAAGAA | CCAGCCGCAA | CGCGTTAGAC | 5356
| TTTAAAAGTT | GTTTGCAATT | GTACGCAATA | ATATAGTTTT | ATGCTCGTAG | TTAGGTAGCT | 5416
| GTGTAACCGG | GTAAGATTCA | AACGATTTTG | TACTGTATTA | TATACCTATC | TGTGTAGTAA | 5476
| TATTTATTTA | TTATATTAAA | TTTGATCTAG | ACGCAATAAA | GTAATATCAA | TAAAGATAGT | 5536
| AAAAGACATA | AAAAAAAAAA | AAAAA | | | | 5561

( 2 ) INFORMATION FOR SEQ ID NO:2:

( i ) SEQUENCE CHARACTERISTICS:
        ( A ) LENGTH: 1404 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Phe  Arg  Lys  His  Phe  Arg  Arg  Lys  Pro  Ala  Thr  Ser  Ser  Ser  Leu
  1              5                       10                      15

Glu  Ser  Thr  Ile  Glu  Ser  Ala  Asp  Ser  Leu  Gly  Met  Ser  Lys  Lys  Thr
               20                      25                      30

Ala  Thr  Lys  Arg  Gln  Arg  Pro  Arg  His  Arg  Val  Pro  Lys  Ile  Ala  Thr
          35                      40                      45

Leu  Pro  Ser  Thr  Ile  Arg  Asp  Cys  Arg  Ser  Leu  Lys  Ser  Ala  Cys  Asn
     50                      55                      60

Leu  Ile  Ala  Leu  Ile  Leu  Ile  Leu  Leu  Val  His  Lys  Ile  Ser  Ala  Ala
```

```
             65                      70                      75                      80

Gly  Asn  Phe  Glu  Leu  Glu  Ile  Leu  Glu  Ile  Ser  Asn  Thr  Asn  Ser  His
                         85                      90                      95

Leu  Leu  Asn  Gly  Tyr  Cys  Cys  Gly  Met  Pro  Ala  Glu  Leu  Arg  Ala  Thr
                    100                 105                      110

Lys  Thr  Ile  Gly  Cys  Ser  Pro  Cys  Thr  Thr  Ala  Phe  Arg  Leu  Cys  Leu
               115                      120                 125

Lys  Glu  Tyr  Gln  Thr  Thr  Glu  Gln  Gly  Ala  Ser  Ile  Ser  Thr  Gly  Cys
          130                      135                      140

Ser  Phe  Gly  Asn  Ala  Thr  Thr  Lys  Ile  Leu  Gly  Gly  Ser  Ser  Phe  Val
145                      150                      155                           160

Leu  Ser  Asp  Pro  Gly  Val  Gly  Ala  Ile  Val  Leu  Pro  Phe  Thr  Phe  Arg
                    165                      170                      175

Trp  Thr  Lys  Ser  Phe  Thr  Leu  Ile  Leu  Gln  Ala  Leu  Asp  Met  Tyr  Asn
                    180                      185                      190

Thr  Ser  Tyr  Pro  Asp  Ala  Glu  Arg  Leu  Ile  Glu  Glu  Thr  Ser  Tyr  Ser
               195                      200                      205

Gly  Val  Ile  Leu  Pro  Ser  Pro  Glu  Trp  Lys  Thr  Leu  Asp  His  Ile  Gly
          210                      215                      220

Arg  Asn  Ala  Arg  Ile  Thr  Tyr  Arg  Val  Arg  Val  Gln  Cys  Ala  Val  Thr
225                           230                      235                      240

Tyr  Tyr  Asn  Thr  Thr  Cys  Thr  Thr  Phe  Cys  Arg  Pro  Arg  Asp  Asp  Gln
                    245                      250                      255

Phe  Gly  His  Tyr  Ala  Cys  Gly  Ser  Glu  Gly  Gln  Lys  Leu  Cys  Leu  Asn
               260                      265                      270

Gly  Trp  Gln  Gly  Val  Asn  Cys  Glu  Glu  Ala  Ile  Cys  Lys  Ala  Gly  Cys
          275                      280                      285

Asp  Pro  Val  His  Gly  Lys  Cys  Asp  Arg  Pro  Gly  Glu  Cys  Glu  Cys  Arg
     290                      295                      300

Pro  Gly  Trp  Arg  Gly  Pro  Leu  Cys  Asn  Glu  Cys  Met  Val  Tyr  Pro  Gly
305                      310                      315                           320

Cys  Lys  His  Gly  Ser  Cys  Asn  Gly  Ser  Ala  Trp  Lys  Cys  Val  Cys  Asp
                    325                      330                      335

Thr  Asn  Trp  Gly  Gly  Ile  Leu  Cys  Asp  Gln  Asp  Leu  Asn  Phe  Cys  Gly
               340                      345                      350

Thr  His  Glu  Pro  Cys  Lys  His  Gly  Gly  Thr  Cys  Glu  Asn  Thr  Ala  Pro
          355                      360                      365

Asp  Lys  Tyr  Arg  Cys  Thr  Cys  Ala  Glu  Gly  Leu  Ser  Gly  Glu  Gln  Cys
     370                      375                      380

Glu  Ile  Val  Glu  His  Pro  Cys  Ala  Thr  Arg  Pro  Cys  Arg  Asn  Gly  Gly
385                      390                      395                           400

Thr  Cys  Thr  Leu  Lys  Thr  Ser  Asn  Arg  Thr  Gln  Ala  Gln  Val  Tyr  Arg
                    405                      410                      415

Thr  Ser  His  Gly  Arg  Ser  Asn  Met  Gly  Arg  Pro  Val  Arg  Arg  Ser  Ser
               420                      425                      430

Ser  Met  Arg  Ser  Leu  Asp  His  Leu  Arg  Pro  Glu  Gly  Gln  Ala  Leu  Asn
          435                      440                      445

Gly  Ser  Ser  Ser  Ser  Gly  Leu  Val  Ser  Leu  Gly  Ser  Leu  Gln  Leu  Gln
     450                      455                      460

Gln  Gln  Leu  Ala  Pro  Asp  Phe  Thr  Cys  Asp  Cys  Ala  Ala  Gly  Trp  Thr
465                      470                      475                           480

Gly  Pro  Thr  Cys  Glu  Ile  Asn  Ile  Asp  Glu  Cys  Ala  Gly  Gly  Pro  Cys
                    485                      490                      495
```

-continued

| | | | | | | | | | | | | | | | |
|---|---|---|---|---|---|---|---|---|---|---|---|---|---|---|---|
| Glu | His | Gly | Gly | Thr | Cys | Ile | Asp | Leu | Ile | Gly | Gly | Phe | Arg | Cys | Glu |
| | | | 500 | | | | 505 | | | | 510 | | | | |
| Cys | Pro | Pro | Glu | Trp | His | Gly | Asp | Val | Cys | Gln | Val | Asp | Val | Asn | Glu |
| | | | 515 | | | | 520 | | | | 525 | | | | |
| Cys | Glu | Ala | Pro | His | Ser | Gly | Ile | Ala | Ala | Asn | Ala | Leu | Leu | Thr | |
| | 530 | | | | 535 | | | | 540 | | | | | | |
| Thr | Thr | Ala | Thr | Ala | Ile | Ile | Gly | Ser | Asn | Leu | Ser | Ser | Thr | Ala | Leu |
| 545 | | | | | 550 | | | | 555 | | | | | | 560 |
| Leu | Ala | Ala | Leu | Thr | Ser | Ala | Val | Ala | Ser | Thr | Ser | Leu | Ala | Ile | Gly |
| | | | | 565 | | | | | 570 | | | | | 575 | |
| Pro | Cys | Ile | Asn | Ala | Lys | Glu | Cys | Arg | Asn | Gln | Pro | Gly | Ser | Phe | Ala |
| | | | 580 | | | | | 585 | | | | | 590 | | |
| Cys | Ile | Cys | Lys | Glu | Gly | Trp | Gly | Gly | Val | Thr | Cys | Ala | Glu | Asn | Leu |
| | | 595 | | | | | 600 | | | | | 605 | | | |
| Asp | Asp | Cys | Val | Gly | Gln | Cys | Arg | Asn | Gly | Ala | Thr | Cys | Ile | Asp | Leu |
| | 610 | | | | | 615 | | | | | 620 | | | | |
| Val | Asn | Asp | Tyr | Arg | Cys | Ala | Cys | Ala | Ser | Gly | Phe | Thr | Gly | Arg | Asp |
| 625 | | | | | 630 | | | | | 635 | | | | | 640 |
| Cys | Glu | Thr | Asp | Ile | Asp | Glu | Cys | Ala | Thr | Ser | Pro | Cys | Arg | Asn | Gly |
| | | | | 645 | | | | | 650 | | | | | 655 | |
| Gly | Glu | Cys | Val | Asp | Met | Val | Gly | Lys | Phe | Asn | Cys | Ile | Cys | Pro | Leu |
| | | | | 660 | | | | 665 | | | | | 670 | | |
| Gly | Tyr | Ser | Gly | Ser | Leu | Cys | Glu | Ala | Lys | Glu | Asn | Cys | Thr | Pro | |
| | | 675 | | | | | 680 | | | | | 685 | | | |
| Ser | Pro | Cys | Leu | Glu | Gly | His | Cys | Leu | Asn | Thr | Pro | Glu | Gly | Tyr | Tyr |
| | 690 | | | | | 695 | | | | | 700 | | | | |
| Cys | His | Cys | Pro | Pro | Asp | Arg | Ala | Gly | Lys | His | Cys | Glu | Gln | Leu | Arg |
| 705 | | | | | 710 | | | | | 715 | | | | | 720 |
| Pro | Leu | Cys | Ser | Gln | Pro | Pro | Cys | Asn | Glu | Gly | Cys | Phe | Ala | Asn | Val |
| | | | | 725 | | | | | 730 | | | | | 735 | |
| Ser | Leu | Ala | Thr | Ser | Ala | Thr | Thr | Thr | Thr | Thr | Thr | Thr | Thr | Thr | Ala |
| | | | | 740 | | | | | 745 | | | | | 750 | |
| Thr | Thr | Thr | Arg | Lys | Met | Ala | Lys | Pro | Ser | Gly | Leu | Pro | Cys | Ser | Gly |
| | | | 755 | | | | | 760 | | | | | 765 | | |
| His | Gly | Ser | Cys | Glu | Met | Ser | Asp | Val | Gly | Thr | Phe | Cys | Lys | Cys | His |
| | 770 | | | | | 775 | | | | | 780 | | | | |
| Val | Gly | His | Thr | Gly | Thr | Phe | Cys | Glu | His | Asn | Leu | Asn | Glu | Cys | Ser |
| 785 | | | | | 790 | | | | | 795 | | | | | 800 |
| Pro | Asn | Pro | Cys | Arg | Asn | Gly | Gly | Ile | Cys | Leu | Asp | Gly | Asp | Gly | Asp |
| | | | | 805 | | | | | 810 | | | | | 815 | |
| Phe | Thr | Cys | Glu | Cys | Met | Ser | Gly | Trp | Thr | Gly | Lys | Arg | Cys | Ser | Glu |
| | | | 820 | | | | | 825 | | | | | 830 | | |
| Arg | Ala | Thr | Gly | Cys | Tyr | Ala | Gly | Gln | Cys | Gln | Asn | Gly | Gly | Thr | Cys |
| | | | 835 | | | | | 840 | | | | | 845 | | |
| Met | Pro | Gly | Ala | Pro | Asp | Lys | Ala | Leu | Gln | Pro | His | Cys | Arg | Cys | Ala |
| | 850 | | | | | 855 | | | | | 860 | | | | |
| Pro | Gly | Trp | Thr | Gly | Leu | Phe | Cys | Ala | Glu | Ala | Ile | Asp | Gln | Cys | Arg |
| 865 | | | | | 870 | | | | | 875 | | | | | 880 |
| Gly | Gln | Pro | Cys | His | Asn | Gly | Gly | Thr | Cys | Glu | Ser | Gly | Ala | Gly | Trp |
| | | | | 885 | | | | | 890 | | | | | 895 | |
| Phe | Arg | Cys | Val | Cys | Ala | Gln | Gly | Phe | Ser | Gly | Pro | Asp | Cys | Arg | Ile |
| | | | 900 | | | | | 905 | | | | | 910 | | |
| Asn | Val | Asn | Glu | Cys | Ser | Pro | Gln | Pro | Cys | Gln | Gly | Gly | Ala | Thr | Cys |
| | | | 915 | | | | | 920 | | | | | 925 | | |

```
Ile Asp Gly Ile Gly Gly Tyr Ser Cys Ile Cys Pro Pro Gly Arg His
    930             935             940
Gly Leu Arg Cys Glu Ile Leu Leu Ser Asp Pro Lys Ser Ala Cys Gln
945             950             955                         960
Asn Ala Ser Asn Thr Ile Ser Pro Tyr Thr Ala Leu Asn Arg Ser Gln
                965             970                     975
Asn Trp Leu Asp Ile Ala Leu Thr Gly Arg Thr Glu Asp Asp Glu Asn
            980             985                 990
Cys Asn Ala Cys Val Cys Glu Asn Gly Thr Ser Arg Cys Thr Asn Leu
        995             1000            1005
Trp Cys Gly Leu Pro Asn Cys Tyr Lys Val Asp Pro Leu Ser Lys Ser
        1010            1015            1020
Ser Asn Leu Ser Gly Val Cys Lys Gln His Glu Val Cys Val Pro Ala
1025            1030            1035                    1040
Leu Ser Glu Thr Cys Leu Ser Ser Pro Cys Asn Val Arg Gly Asp Cys
            1045            1050            1055
Arg Ala Leu Glu Pro Ser Arg Arg Val Ala Pro Pro Arg Leu Pro Ala
            1060            1065            1070
Lys Ser Ser Cys Trp Pro Asn Gln Ala Val Val Asn Glu Asn Cys Ala
        1075            1080            1085
Arg Leu Thr Ile Leu Leu Ala Leu Glu Arg Val Gly Lys Gly Ala Ser
        1090            1095            1100
Val Glu Gly Leu Cys Ser Leu Val Arg Val Leu Leu Ala Ala Gln Leu
1105            1110            1115                    1120
Ile Lys Lys Pro Ala Ser Thr Phe Gly Gln Asp Pro Gly Met Leu Met
            1125            1130            1135
Val Leu Cys Asp Leu Lys Thr Gly Thr Asn Asp Thr Val Glu Leu Thr
            1140            1145            1150
Val Ser Ser Ser Lys Leu Asn Asp Pro Gln Leu Pro Val Ala Val Gly
            1155            1160            1165
Leu Leu Gly Glu Leu Leu Ser Ser Arg Gln Leu Asn Gly Ile Gln Arg
1170            1175            1180
Arg Lys Glu Leu Glu Leu Gln His Ala Lys Leu Ala Ala Leu Thr Ser
1185            1190            1195                    1200
Ile Val Glu Val Lys Leu Glu Thr Ala Arg Val Ala Asp Gly Ser Gly
            1205            1210            1215
His Ser Leu Leu Ile Gly Val Leu Cys Gly Val Phe Ile Val Leu Val
            1220            1225            1230
Gly Phe Ser Val Phe Ile Ser Leu Tyr Trp Lys Gln Arg Leu Ala Tyr
            1235            1240            1245
Arg Thr Ser Ser Gly Met Asn Leu Thr Pro Ser Leu Asp Ala Leu Arg
        1250            1255            1260
His Glu Glu Glu Lys Ser Asn Asn Leu Gln Asn Glu Glu Asn Leu Arg
1265            1270            1275                    1280
Arg Tyr Thr Asn Pro Leu Lys Gly Ser Thr Ser Ser Leu Arg Ala Ala
                1285            1290            1295
Thr Gly Met Glu Leu Ser Leu Asn Pro Ala Pro Glu Leu Ala Ala Ser
            1300            1305            1310
Ala Ala Ser Ser Ser Ala Leu His Arg Ser Gln Pro Leu Phe Pro Pro
            1315            1320            1325
Cys Asp Phe Glu Arg Glu Leu Asp Ser Ser Thr Gly Leu Lys Gln Ala
        1330            1335            1340
His Lys Arg Ser Ser Gln Ile Leu Leu His Lys Thr Gln Asn Ser Asp
```

-continued

```
                1345                        1350                        1355                        1360
Met Arg Lys Asn Thr Val Gly Ser Leu Asp Ser Pro Arg Lys Asp Phe
                            1365                        1370                        1375
Gly Lys Arg Ser Ile Asn Cys Lys Ser Met Pro Pro Ser Ser Gly Asp
                1380                        1385                        1390
Glu Gly Ser Asp Val Leu Ala Thr Thr Val Met Val
                1395                        1400                    1405
```

( 2 ) INFORMATION FOR SEQ ID NO:3:

( i ) SEQUENCE CHARACTERISTICS:
        ( A ) LENGTH: 707 amino acids
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..708

( x i ) SEQUENCE DESCRIPTION: SEQ ID NO:3:

```
ATG CAT TGG ATT AAA TGT TTA TTA ACA GCA TTC ATT TGC TTC ACA GTC        48
Met His Trp Ile Lys Cys Leu Leu Thr Ala Phe Ile Cys Phe Thr Val
 1               5                  10                  15

ATC GTG CAG GTT CAC AGT TCC GGC AGC TTT GAG TTG CGC CTG AAG TAC        96
Ile Val Gln Val His Ser Ser Gly Ser Phe Glu Leu Arg Leu Lys Tyr
            20                  25                  30

TTC AGC AAC GAT CAC GGG CGG GAC AAC GAG GGT CGC TGC TGC AGC GGG       144
Phe Ser Asn Asp His Gly Arg Asp Asn Glu Gly Arg Cys Cys Ser Gly
        35                  40                  45

GAG TCG GAC GGA GCG ACG GGC AAG TGC CTG GGC AGC TGC AAG ACG CGG       192
Glu Ser Asp Gly Ala Thr Gly Lys Cys Leu Gly Ser Cys Lys Thr Arg
    50                  55                  60

TTT CGC GTC TGC CTA AAG CAC TAC CAG GCC ACC ATC GAC ACC ACC TCC       240
Phe Arg Val Cys Leu Lys His Tyr Gln Ala Thr Ile Asp Thr Thr Ser
 65                  70                  75                  80

CAG TGC ACC TAC GGG GAC GTG ATC ACG CCC ATT CTC GGC GAG AAC TCG       288
Gln Cys Thr Tyr Gly Asp Val Ile Thr Pro Ile Leu Gly Glu Asn Ser
                85                  90                  95

GTC AAT CTG ACC GAC GCC CAG CGC TTC CAG AAC AAG GGC TTC ACG AAT       336
Val Asn Leu Thr Asp Ala Gln Arg Phe Gln Asn Lys Gly Phe Thr Asn
            100                 105                 110

CCC ATC CAG TTC CCC TTC TCG TTC TCA TGG CCG GGT ACC TTC TCG CTG       384
Pro Ile Gln Phe Pro Phe Ser Phe Ser Trp Pro Gly Thr Phe Ser Leu
        115                 120                 125

ATC GTC GAG GCC TGG CAT GAT ACG AAC AAT AGC GGC AAT GCG CGA ACC       432
Ile Val Glu Ala Trp His Asp Thr Asn Asn Ser Gly Asn Ala Arg Thr
    130                 135                 140

AAC AAG CTC CTC ATC CAG CGA CTC TTG GTG CAG CAG GTA CTG GAG GTG       480
Asn Lys Leu Leu Ile Gln Arg Leu Leu Val Gln Gln Val Leu Glu Val
145                 150                 155                 160

TCC TCC GAA TGG AAG ACG AAC AAG TCG GAA TCG CAG TAC ACG TCG CTG       528
Ser Ser Glu Trp Lys Thr Asn Lys Ser Glu Ser Gln Tyr Thr Ser Leu
                165                 170                 175

GAG TAC GAT TTC CGT GTC ACC TGC GAT CTC AAC TAC TAC GGA TCC GGC       576
Glu Tyr Asp Phe Arg Val Thr Cys Asp Leu Asn Tyr Tyr Gly Ser Gly
            180                 185                 190

TGT GCC AAG TTC TGC CGG CCC CGC GAC GAT TCA TTT GGA CAC TCG ACT       624
Cys Ala Lys Phe Cys Arg Pro Arg Asp Asp Ser Phe Gly His Ser Thr
        195                 200                 205
```

|     |     |     |     |     |     |     |     |     |     |     |     |     |     |     |
| --- | --- | --- | --- | --- | --- | --- | --- | --- | --- | --- | --- | --- | --- | --- |
| TGC | TCG | GAG | ACG | GGC | GAA | ATT | ATC | TGT | TTG | ACC | GGA | TGG | CAG | GGC | GAT |
| Cys | Ser | Glu | Thr | Gly | Glu | Ile | Ile | Cys | Leu | Thr | Gly | Trp | Gln | Gly | Asp |
| 210 |     |     |     |     |     | 215 |     |     |     |     | 220 |     |     |     |

672

|     |     |     |     |     |     |     |     |     |     |
| --- | --- | --- | --- | --- | --- | --- | --- | --- | --- |
| TAC | TGT | CAC | ATA | CCC | AAA | TGC | GCC | AAA | GGC | TGT | GAA |
| Tyr | Cys | His | Ile | Pro | Lys | Cys | Ala | Lys | Gly | Cys | Glu |
| 225 |     |     |     | 230 |     |     |     |     | 235 |     |     |

708

( 2 ) INFORMATION FOR SEQ ID NO:4:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | His | Trp | Ile | Lys | Cys | Leu | Leu | Thr | Ala | Phe | Ile | Cys | Phe | Thr | Val |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ile | Val | Gln | Val | His | Ser | Ser | Gly | Ser | Phe | Glu | Leu | Arg | Leu | Lys | Tyr |
|     |     |     | 20 |     |     |     |     | 25 |     |     |     |     | 30 |     |     |
| Phe | Ser | Asn | Asp | His | Gly | Arg | Asp | Asn | Glu | Gly | Arg | Cys | Cys | Ser | Gly |
|     |     | 35 |     |     |     |     | 40 |     |     |     |     | 45 |     |     |     |
| Glu | Ser | Asp | Gly | Ala | Thr | Gly | Lys | Cys | Leu | Gly | Ser | Cys | Lys | Thr | Arg |
|     | 50 |     |     |     |     | 55 |     |     |     |     | 60 |     |     |     |     |
| Phe | Arg | Val | Cys | Leu | Lys | His | Tyr | Gln | Ala | Thr | Ile | Asp | Thr | Thr | Ser |
| 65 |     |     |     |     | 70 |     |     |     |     | 75 |     |     |     |     | 80 |
| Gln | Cys | Thr | Tyr | Gly | Asp | Val | Ile | Thr | Pro | Ile | Leu | Gly | Glu | Asn | Ser |
|     |     |     |     | 85 |     |     |     |     | 90 |     |     |     |     | 95 |     |
| Val | Asn | Leu | Thr | Asp | Ala | Gln | Arg | Phe | Gln | Asn | Lys | Gly | Phe | Thr | Asn |
|     |     |     | 100 |     |     |     |     | 105 |     |     |     |     | 110 |     |     |
| Pro | Ile | Gln | Phe | Pro | Phe | Ser | Phe | Ser | Trp | Pro | Gly | Thr | Phe | Ser | Leu |
|     |     | 115 |     |     |     |     | 120 |     |     |     |     | 125 |     |     |     |
| Ile | Val | Glu | Ala | Trp | His | Asp | Thr | Asn | Asn | Ser | Gly | Asn | Ala | Arg | Thr |
|     | 130 |     |     |     |     | 135 |     |     |     |     | 140 |     |     |     |     |
| Asn | Lys | Leu | Leu | Ile | Gln | Arg | Leu | Leu | Val | Gln | Gln | Val | Leu | Glu | Val |
| 145 |     |     |     |     | 150 |     |     |     |     | 155 |     |     |     |     | 160 |
| Ser | Ser | Glu | Trp | Lys | Thr | Asn | Lys | Ser | Glu | Ser | Gln | Tyr | Thr | Ser | Leu |
|     |     |     |     | 165 |     |     |     |     | 170 |     |     |     |     | 175 |     |
| Glu | Tyr | Asp | Phe | Arg | Val | Thr | Cys | Asp | Leu | Asn | Tyr | Tyr | Gly | Ser | Gly |
|     |     |     | 180 |     |     |     |     | 185 |     |     |     |     | 190 |     |     |
| Cys | Ala | Lys | Phe | Cys | Arg | Pro | Arg | Asp | Asp | Ser | Phe | Gly | His | Ser | Thr |
|     |     | 195 |     |     |     |     | 200 |     |     |     |     | 205 |     |     |     |
| Cys | Ser | Glu | Thr | Gly | Glu | Ile | Ile | Cys | Leu | Thr | Gly | Trp | Gln | Gly | Asp |
|     | 210 |     |     |     |     | 215 |     |     |     |     | 220 |     |     |     |     |
| Tyr | Cys | His | Ile | Pro | Lys | Cys | Ala | Lys | Gly | Cys | Glu |     |     |     |     |
| 225 |     |     |     | 230 |     |     |     |     | 235 |     |     |     |     |     |     |

( 2 ) INFORMATION FOR SEQ ID NO:5:

( i ) SEQUENCE CHARACTERISTICS:
        ( A ) LENGTH: 6464 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 371..4027

( x i ) SEQUENCE DESCRIPTION: SEQ ID NO:5:

```
GAATTCCCCT CCCCCCTTTT TCCATGCAGC TGATCTAAAA GGGAATAAAA GGCTGCGCAT         60

AATCATAATA ATAAAAGAAG GGGAGCGCGA GAGAAGGAAA GAAAGCCGGG AGGTGGAAGA        120

GGAGGGGGAG CGTCTCAAAG AAGCGATCAG AATAATAAAA GGAGGCCGGG CTCTTTGCCT        180

TCTGGAACGG GCCGCTCTTG AAAGGGCTTT TGAAAAGTGG TGTTGTTTTC CAGTCGTGCA        240

TGCTCCAATC GGCGGAGTAT ATTAGAGCCG GGACGCGGCC GCAGGGGCAG CGGCGACGGC        300

AGCACCGGCG GCAGCACCAG CGCGAACAGC AGCGGCGGCG TCCCGAGTGC CCGCGGCGGC        360

GCGCGCAGCG ATG CGT TCC CCA CGG ACA CGC GGC CGG TCC GGG CGC CCC          409
           Met Arg Ser Pro Arg Thr Arg Gly Arg Ser Gly Arg Pro
             1               5                      10
```

```
CTA AGC CTC CTG CTC GCC CTG CTC TGT GCC CTG CGA GCC AAG GTG TGT         457
Leu Ser Leu Leu Leu Ala Leu Leu Cys Ala Leu Arg Ala Lys Val Cys
     15                  20                  25
```

```
GGG GCC TCG GGT CAG TTC GAG TTG GAG ATC CTG TCC ATG CAG AAC GTG         505
Gly Ala Ser Gly Gln Phe Glu Leu Glu Ile Leu Ser Met Gln Asn Val
 30              35                  40                      45
```

```
AAC GGG GAG CTG CAG AAC GGG AAC TGC TGC GGC GGC GCC CGG AAC CCG         553
Asn Gly Glu Leu Gln Asn Gly Asn Cys Cys Gly Gly Ala Arg Asn Pro
                 50                  55                  60
```

```
GGA GAC CGC AAG TGC ACC CGC GAC GAG TGT GAC ACA TAC TTC AAA GTG         601
Gly Asp Arg Lys Cys Thr Arg Asp Glu Cys Asp Thr Tyr Phe Lys Val
             65                  70                  75
```

```
TGC CTC AAG GAG TAT CAG TCC CGC GTC ACG GCC GGG GGG CCC TGC AGC         649
Cys Leu Lys Glu Tyr Gln Ser Arg Val Thr Ala Gly Gly Pro Cys Ser
         80                  85                  90
```

```
TTC GGC TCA GGG TCC ACG CCT GTC ATC GGG GGC AAC ACC TTC AAC CTC         697
Phe Gly Ser Gly Ser Thr Pro Val Ile Gly Gly Asn Thr Phe Asn Leu
     95                 100                 105
```

```
AAG GCC AGC CGC GGC AAC GAC CCG AAC CGC ATC GTG CTG CCT TTC AGT         745
Lys Ala Ser Arg Gly Asn Asp Pro Asn Arg Ile Val Leu Pro Phe Ser
110                 115                 120                     125
```

```
TTC GCC TGG CCG AGG TCC TAT ACG TTG CTT GTG GAG GCG TGG GAT TCC         793
Phe Ala Trp Pro Arg Ser Tyr Thr Leu Leu Val Glu Ala Trp Asp Ser
                130                 135                 140
```

```
AGT AAT GAC ACC GTT CAA CCT GAC AGT ATT ATT GAA AAG GCT TCT CAC         841
Ser Asn Asp Thr Val Gln Pro Asp Ser Ile Ile Glu Lys Ala Ser His
            145                 150                 155
```

```
TCG GGC ATG ATC AAC CCC AGC CGG CAG TGG CAG ACG CTG AAG CAG AAC         889
Ser Gly Met Ile Asn Pro Ser Arg Gln Trp Gln Thr Leu Lys Gln Asn
        160                 165                 170
```

```
ACG GGC GTT GCC CAC TTT GAG TAT CAG ATC CGC GTG ACC TGT GAT GAC         937
Thr Gly Val Ala His Phe Glu Tyr Gln Ile Arg Val Thr Cys Asp Asp
    175                 180                 185
```

```
TAC TAC TAT GGC TTT GGC TGT AAT AAG TTC TGC CGC CCC AGA GAT GAC         985
Tyr Tyr Tyr Gly Phe Gly Cys Asn Lys Phe Cys Arg Pro Arg Asp Asp
190                 195                 200                 205
```

```
TTC TTT GGA CAC TAT GCC TGT GAC CAG AAT GGC AAC AAA ACT TGC ATG        1033
Phe Phe Gly His Tyr Ala Cys Asp Gln Asn Gly Asn Lys Thr Cys Met
                210                 215                 220
```

```
GAA GGC TGG ATG GGC CCC GAA TGT AAC AGA GCT ATT TGC CGA CAA GGC        1081
Glu Gly Trp Met Gly Pro Glu Cys Asn Arg Ala Ile Cys Arg Gln Gly
            225                 230                 235
```

```
TGC AGT CCT AAG CAT GGG TCT TGC AAA CTC CCA GGT GAC TGC AGG TGC        1129
Cys Ser Pro Lys His Gly Ser Cys Lys Leu Pro Gly Asp Cys Arg Cys
        240                 245                 250
```

```
CAG TAC GGC TGG CAA GGC CTG TAC TGT GAT AAG TGC ATC CCA CAC CCG        1177
Gln Tyr Gly Trp Gln Gly Leu Tyr Cys Asp Lys Cys Ile Pro His Pro
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 255 |     |     |     |     | 260 |     |     |     |     |     | 265 |     |     |     |      |
| GGA | TGC | GTC | CAC | GGC | ATC | TGT | AAT | GAG | CCC | TGG | CAG | TGC | CTC | TGT | GAG | 1225 |
| Gly | Cys | Val | His | Gly | Ile | Cys | Asn | Glu | Pro | Trp | Gln | Cys | Leu | Cys | Glu |      |
| 270 |     |     |     | 275 |     |     |     |     | 280 |     |     |     |     |     | 285 |      |
| ACC | AAC | TGG | GGC | GGC | CAG | CTC | TGT | GAC | AAA | GAT | CTC | AAT | TAC | TGT | GGG | 1273 |
| Thr | Asn | Trp | Gly | Gly | Gln | Leu | Cys | Asp | Lys | Asp | Leu | Asn | Tyr | Cys | Gly |      |
|     |     |     |     | 290 |     |     |     |     | 295 |     |     |     |     | 300 |     |      |
| ACT | CAT | CAG | CCG | TGT | CTC | AAC | GGG | GGA | ACT | TGT | AGC | AAC | ACA | GGC | CCT | 1321 |
| Thr | His | Gln | Pro | Cys | Leu | Asn | Gly | Gly | Thr | Cys | Ser | Asn | Thr | Gly | Pro |      |
|     |     |     | 305 |     |     |     |     | 310 |     |     |     |     | 315 |     |     |      |
| GAC | AAA | TAT | CAG | TGT | TCC | TGC | CCT | GAG | GGG | TAT | TCA | GGA | CCC | AAC | TGT | 1369 |
| Asp | Lys | Tyr | Gln | Cys | Ser | Cys | Pro | Glu | Gly | Tyr | Ser | Gly | Pro | Asn | Cys |      |
|     |     | 320 |     |     |     |     | 325 |     |     |     |     | 330 |     |     |     |      |
| GAA | ATT | GCT | GAG | CAC | GCC | TGC | CTC | TCT | GAT | CCC | TGT | CAC | AAC | AGA | GGC | 1417 |
| Glu | Ile | Ala | Glu | His | Ala | Cys | Leu | Ser | Asp | Pro | Cys | His | Asn | Arg | Gly |      |
|     | 335 |     |     |     |     | 340 |     |     |     |     | 345 |     |     |     |     |      |
| AGC | TGT | AAG | GAG | ACC | TCC | CTG | GGC | TTT | GAG | TGT | GAG | TGT | TCC | CCA | GGC | 1465 |
| Ser | Cys | Lys | Glu | Thr | Ser | Leu | Gly | Phe | Glu | Cys | Glu | Cys | Ser | Pro | Gly |      |
| 350 |     |     |     |     | 355 |     |     |     |     | 360 |     |     |     |     | 365 |      |
| TGG | ACC | GGC | CCC | ACA | TGC | TCT | ACA | AAC | ATT | GAT | GAC | TGT | TCT | CCT | AAT | 1513 |
| Trp | Thr | Gly | Pro | Thr | Cys | Ser | Thr | Asn | Ile | Asp | Asp | Cys | Ser | Pro | Asn |      |
|     |     |     |     | 370 |     |     |     |     | 375 |     |     |     |     | 380 |     |      |
| AAC | TGT | TCC | CAC | GGG | GGC | ACC | TGC | CAG | GAC | CTG | GTT | AAC | GGA | TTT | AAG | 1561 |
| Asn | Cys | Ser | His | Gly | Gly | Thr | Cys | Gln | Asp | Leu | Val | Asn | Gly | Phe | Lys |      |
|     |     |     | 385 |     |     |     |     | 390 |     |     |     |     | 395 |     |     |      |
| TGT | GTG | TGC | CCC | CCA | CAG | TGG | ACT | GGG | AAA | ACG | TGC | CAG | TTA | GAT | GCA | 1609 |
| Cys | Val | Cys | Pro | Pro | Gln | Trp | Thr | Gly | Lys | Thr | Cys | Gln | Leu | Asp | Ala |      |
|     |     |     | 400 |     |     |     |     | 405 |     |     |     |     | 410 |     |     |      |
| AAT | GAA | TGT | GAG | GCC | AAA | CCT | TGT | GTA | AAC | GCC | AAA | TCC | TGT | AAG | AAT | 1657 |
| Asn | Glu | Cys | Glu | Ala | Lys | Pro | Cys | Val | Asn | Ala | Lys | Ser | Cys | Lys | Asn |      |
|     |     | 415 |     |     |     |     | 420 |     |     |     |     | 425 |     |     |     |      |
| CTC | ATT | GCC | AGC | TAC | TAC | TGC | GAC | TGT | CTT | CCC | GGC | TGG | ATG | GGT | CAG | 1705 |
| Leu | Ile | Ala | Ser | Tyr | Tyr | Cys | Asp | Cys | Leu | Pro | Gly | Trp | Met | Gly | Gln |      |
| 430 |     |     |     |     | 435 |     |     |     |     | 440 |     |     |     |     | 445 |      |
| AAT | TGT | GAC | ATA | AAT | ATT | AAT | GAC | TGC | CTT | GGC | CAG | TGT | CAG | AAT | GAC | 1753 |
| Asn | Cys | Asp | Ile | Asn | Ile | Asn | Asp | Cys | Leu | Gly | Gln | Cys | Gln | Asn | Asp |      |
|     |     |     |     | 450 |     |     |     |     | 455 |     |     |     |     | 460 |     |      |
| GCC | TCC | TGT | CGG | GAT | TTG | GTT | AAT | GGT | TAT | CGC | TGT | ATC | TGT | CCA | CCT | 1801 |
| Ala | Ser | Cys | Arg | Asp | Leu | Val | Asn | Gly | Tyr | Arg | Cys | Ile | Cys | Pro | Pro |      |
|     |     |     | 465 |     |     |     |     | 470 |     |     |     |     | 475 |     |     |      |
| GGC | TAT | GCA | GGC | GAT | CAC | TGT | GAG | AGA | GAC | ATC | GAT | GAA | TGT | GCC | AGC | 1849 |
| Gly | Tyr | Ala | Gly | Asp | His | Cys | Glu | Arg | Asp | Ile | Asp | Glu | Cys | Ala | Ser |      |
|     |     | 480 |     |     |     |     | 485 |     |     |     |     | 490 |     |     |     |      |
| AAC | CCC | TGT | TTG | AAT | GGG | GGT | CAC | TGT | CAG | AAT | GAA | ATC | AAC | AGA | TTC | 1897 |
| Asn | Pro | Cys | Leu | Asn | Gly | Gly | His | Cys | Gln | Asn | Glu | Ile | Asn | Arg | Phe |      |
|     | 495 |     |     |     |     | 500 |     |     |     |     | 505 |     |     |     |     |      |
| CAG | TGT | CTG | TGT | CCC | ACT | GGT | TTC | TCT | GGA | AAC | CTC | TGT | CAG | CTG | GAC | 1945 |
| Gln | Cys | Leu | Cys | Pro | Thr | Gly | Phe | Ser | Gly | Asn | Leu | Cys | Gln | Leu | Asp |      |
| 510 |     |     |     |     | 515 |     |     |     |     | 520 |     |     |     |     | 525 |      |
| ATC | GAT | TAT | TGT | GAG | CCT | AAT | CCC | TGC | CAG | AAC | GGT | GCC | CAG | TGC | TAC | 1993 |
| Ile | Asp | Tyr | Cys | Glu | Pro | Asn | Pro | Cys | Gln | Asn | Gly | Ala | Gln | Cys | Tyr |      |
|     |     |     |     | 530 |     |     |     |     | 535 |     |     |     |     | 540 |     |      |
| AAC | CGT | GCC | AGT | GAC | TAT | TTC | TGC | AAG | TGC | CCC | GAG | GAC | TAT | GAG | GGC | 2041 |
| Asn | Arg | Ala | Ser | Asp | Tyr | Phe | Cys | Lys | Cys | Pro | Glu | Asp | Tyr | Glu | Gly |      |
|     |     |     |     | 545 |     |     |     |     | 550 |     |     |     |     | 555 |     |      |
| AAG | AAC | TGC | TCA | CAC | CTG | AAA | GAC | CAC | TGC | CGC | ACG | ACC | CCC | TGT | GAA | 2089 |
| Lys | Asn | Cys | Ser | His | Leu | Lys | Asp | His | Cys | Arg | Thr | Thr | Pro | Cys | Glu |      |
|     |     |     |     | 560 |     |     |     |     | 565 |     |     |     |     | 570 |     |      |
| GTG | ATT | GAC | AGC | TGC | ACA | GTG | GCC | ATG | GCT | TCC | AAC | GAC | ACA | CCT | GAA | 2137 |
| Val | Ile | Asp | Ser | Cys | Thr | Val | Ala | Met | Ala | Ser | Asn | Asp | Thr | Pro | Glu |      |

|     |     |     |     |     |     | 575 |     |     |     |     |     | 580 |     |     |     |     |     | 585 |     |     |      |
|-----|-----|-----|-----|-----|-----|-----|-----|-----|-----|-----|-----|-----|-----|-----|-----|-----|-----|-----|-----|-----|------|

```
              5 7 5                                   5 8 0                                  5 8 5
GGG  GTG  CGG  TAT  ATT  TCC  TCC  AAC  GTC  TGT  GGT  CCT  CAC  GGG  AAG  TGC                        2185
Gly  Val  Arg  Tyr  Ile  Ser  Ser  Asn  Val  Cys  Gly  Pro  His  Gly  Lys  Cys
590                      595                     600                     605

AAG  AGT  CAG  TCG  GGA  GGC  AAA  TTC  ACC  TGT  GAC  TGT  AAC  AAA  GGC  TTC                        2233
Lys  Ser  Gln  Ser  Gly  Gly  Lys  Phe  Thr  Cys  Asp  Cys  Asn  Lys  Gly  Phe
                    610                      615                     620

ACG  GGA  ACA  TAC  TGC  CAT  GAA  AAT  ATT  AAT  GAC  TGT  GAG  AGC  AAC  CCT                        2281
Thr  Gly  Thr  Tyr  Cys  His  Glu  Asn  Ile  Asn  Asp  Cys  Glu  Ser  Asn  Pro
               625                      630                     635

TGT  AGA  AAC  GGT  GGC  ACT  TGC  ATC  GAT  GGT  GTC  AAC  TCC  TAC  AAG  TGC                        2329
Cys  Arg  Asn  Gly  Gly  Thr  Cys  Ile  Asp  Gly  Val  Asn  Ser  Tyr  Lys  Cys
          640                      645                     650

ATC  TGT  AGT  GAC  GGC  TGG  GAG  GGG  GCC  TAC  TGT  GAA  ACC  AAT  ATT  AAT                        2377
Ile  Cys  Ser  Asp  Gly  Trp  Glu  Gly  Ala  Tyr  Cys  Glu  Thr  Asn  Ile  Asn
     655                      660                     665

GAC  TGC  AGC  CAG  AAC  CCC  TGC  CAC  AAT  GGG  GGC  ACG  TGT  CGC  GAC  CTG                        2425
Asp  Cys  Ser  Gln  Asn  Pro  Cys  His  Asn  Gly  Gly  Thr  Cys  Arg  Asp  Leu
670                      675                     680                     685

GTC  AAT  GAC  TTC  TAC  TGT  GAC  TGT  AAA  AAT  GGG  TGG  AAA  GGA  AAG  ACC                        2473
Val  Asn  Asp  Phe  Tyr  Cys  Asp  Cys  Lys  Asn  Gly  Trp  Lys  Gly  Lys  Thr
                    690                      695                     700

TGC  CAC  TCA  CGT  GAC  AGT  CAG  TGT  GAT  GAG  GCC  ACG  TGC  AAC  AAC  GGT                        2521
Cys  His  Ser  Arg  Asp  Ser  Gln  Cys  Asp  Glu  Ala  Thr  Cys  Asn  Asn  Gly
               705                      710                     715

GGC  ACC  TGC  TAT  GAT  GAG  GGG  GAT  GCT  TTT  AAG  TGC  ATG  TGT  CCT  GGC                        2569
Gly  Thr  Cys  Tyr  Asp  Glu  Gly  Asp  Ala  Phe  Lys  Cys  Met  Cys  Pro  Gly
          720                      725                     730

GGC  TGG  GAA  GGA  ACA  ACC  TGT  AAC  ATA  GCC  CGA  AAC  AGT  AGC  TGC  CTG                        2617
Gly  Trp  Glu  Gly  Thr  Thr  Cys  Asn  Ile  Ala  Arg  Asn  Ser  Ser  Cys  Leu
     735                      740                     745

CCC  AAC  CCC  TGC  CAT  AAT  GGG  GGC  ACA  TGT  GTG  GTC  AAC  GGC  GAG  TCC                        2665
Pro  Asn  Pro  Cys  His  Asn  Gly  Gly  Thr  Cys  Val  Val  Asn  Gly  Glu  Ser
750                      755                     760                     765

TTT  ACG  TGC  GTC  TGC  AAG  GAA  GGC  TGG  GAG  GGG  CCC  ATC  TGT  GCT  CAG                        2713
Phe  Thr  Cys  Val  Cys  Lys  Glu  Gly  Trp  Glu  Gly  Pro  Ile  Cys  Ala  Gln
                    770                      775                     780

AAT  ACC  AAT  GAC  TGC  AGC  CCT  CAT  CCC  TGT  TAC  AAC  AGC  GGC  ACC  TGT                        2761
Asn  Thr  Asn  Asp  Cys  Ser  Pro  His  Pro  Cys  Tyr  Asn  Ser  Gly  Thr  Cys
               785                      790                     795

GTG  GAT  GGA  GAC  AAC  TGG  TAC  CGG  TGC  GAA  TGT  GCC  CCG  GGT  TTT  GCT                        2809
Val  Asp  Gly  Asp  Asn  Trp  Tyr  Arg  Cys  Glu  Cys  Ala  Pro  Gly  Phe  Ala
          800                      805                     810

GGG  CCC  GAC  TGC  AGA  ATA  AAC  ATC  AAT  GAA  TGC  CAG  TCT  TCA  CCT  TGT                        2857
Gly  Pro  Asp  Cys  Arg  Ile  Asn  Ile  Asn  Glu  Cys  Gln  Ser  Ser  Pro  Cys
     815                      820                     825

GCC  TTT  GGA  GCG  ACC  TGT  GTG  GAT  GAG  ATC  AAT  GGC  TAC  CGG  TGT  GTC                        2905
Ala  Phe  Gly  Ala  Thr  Cys  Val  Asp  Glu  Ile  Asn  Gly  Tyr  Arg  Cys  Val
830                      835                     840                     845

TGC  CCT  CCA  GGG  CAC  AGT  GGT  GCC  AAG  TGC  CAG  GAA  GTT  TCA  GGG  AGA                        2953
Cys  Pro  Pro  Gly  His  Ser  Gly  Ala  Lys  Cys  Gln  Glu  Val  Ser  Gly  Arg
                    850                      855                     860

CCT  TGC  ATC  ACC  ATG  GGG  AGT  GTG  ATA  CCA  GAT  GGG  GCC  AAA  TGG  GAT                        3001
Pro  Cys  Ile  Thr  Met  Gly  Ser  Val  Ile  Pro  Asp  Gly  Ala  Lys  Trp  Asp
               865                      870                     875

GAT  GAC  TGT  AAT  ACC  TGC  CAG  TGC  CTG  AAT  GGA  CGG  ATC  GCC  TGC  TCA                        3049
Asp  Asp  Cys  Asn  Thr  Cys  Gln  Cys  Leu  Asn  Gly  Arg  Ile  Ala  Cys  Ser
          880                      885                     890

AAG  GTC  TGG  TGT  GGC  CCT  CGA  CCT  TGC  CTG  CTC  CAC  AAA  GGG  CAC  AGC                        3097
Lys  Val  Trp  Cys  Gly  Pro  Arg  Pro  Cys  Leu  Leu  His  Lys  Gly  His  Ser
```

```
                895                            900                            905
GAG  TGC  CCC  AGC  GGG  CAG  AGC  TGC  ATC  CCC  ATC  CTG  GAC  GAC  CAG  TGC     3145
Glu  Cys  Pro  Ser  Gly  Gln  Ser  Cys  Ile  Pro  Ile  Leu  Asp  Asp  Gln  Cys
910            915                      920                            925

TTC  GTC  CAC  CCC  TGC  ACT  GGT  GTG  GGC  GAG  TGT  CGG  TCT  TCC  AGT  CTC     3193
Phe  Val  His  Pro  Cys  Thr  Gly  Val  Gly  Glu  Cys  Arg  Ser  Ser  Ser  Leu
                    930                      935                           940

CAG  CCG  GTG  AAG  ACA  AAG  TGC  ACC  TCT  GAC  TCC  TAT  TAC  CAG  GAT  AAC     3241
Gln  Pro  Val  Lys  Thr  Lys  Cys  Thr  Ser  Asp  Ser  Tyr  Tyr  Gln  Asp  Asn
               945                      950                      955

TGT  GCG  AAC  ATC  ACA  TTT  ACC  TTT  AAC  AAG  GAG  ATG  ATG  TCA  CCA  GGT     3289
Cys  Ala  Asn  Ile  Thr  Phe  Thr  Phe  Asn  Lys  Glu  Met  Met  Ser  Pro  Gly
          960                      965                      970

CTT  ACT  ACG  GAG  CAC  ATT  TGC  AGT  GAA  TTG  AGG  AAT  TTG  AAT  ATT  TTG     3337
Leu  Thr  Thr  Glu  His  Ile  Cys  Ser  Glu  Leu  Arg  Asn  Leu  Asn  Ile  Leu
     975                      980                      985

AAG  AAT  GTT  TCC  GCT  GAA  TAT  TCA  ATC  TAC  ATC  GCT  TGC  GAG  CCT  TCC     3385
Lys  Asn  Val  Ser  Ala  Glu  Tyr  Ser  Ile  Tyr  Ile  Ala  Cys  Glu  Pro  Ser
990            995                      1000                         1005

CCT  TCA  GCG  AAC  AAT  GAA  ATA  CAT  GTG  GCC  ATT  TCT  GCT  GAA  GAT  ATA     3433
Pro  Ser  Ala  Asn  Asn  Glu  Ile  His  Val  Ala  Ile  Ser  Ala  Glu  Asp  Ile
                    1010                     1015                        1020

CGG  GAT  GAT  GGG  AAC  CCG  ATC  AAG  GAA  ATC  ACT  GAC  AAA  ATA  ATC  GAT     3481
Arg  Asp  Asp  Gly  Asn  Pro  Ile  Lys  Glu  Ile  Thr  Asp  Lys  Ile  Ile  Asp
               1025                     1030                      1035

CTT  GTT  ACT  AAA  CGT  GAT  GGA  AAC  AGC  TCG  CTG  ATT  GCT  GCC  GTT  GAA     3529
Leu  Val  Thr  Lys  Arg  Asp  Gly  Asn  Ser  Ser  Leu  Ile  Ala  Ala  Val  Glu
          1040                     1045                     1050

GAA  GTA  AGA  GTT  CAG  AGG  CGG  CCT  CTG  AAG  AAC  AGA  ACA  GAT  TTC  CTT     3577
Glu  Val  Arg  Val  Gln  Arg  Arg  Pro  Leu  Lys  Asn  Arg  Thr  Asp  Phe  Leu
     1055                     1060                     1065

GTT  CCC  TTG  CTG  AGC  TCT  GTC  TTA  ACT  GTG  GCT  TGG  ATC  TGT  TGC  TTG     3625
Val  Pro  Leu  Leu  Ser  Ser  Val  Leu  Thr  Val  Ala  Trp  Ile  Cys  Cys  Leu
1070                     1075                     1080                        1085

GTG  ACG  GCC  TTC  TAC  TGG  TGC  CTG  CGG  AAG  CGG  CGG  AAG  CCG  GGC  AGC     3673
Val  Thr  Ala  Phe  Tyr  Trp  Cys  Leu  Arg  Lys  Arg  Arg  Lys  Pro  Gly  Ser
                    1090                     1095                       1100

CAC  ACA  CAC  TCA  GCC  TCT  GAG  GAC  AAC  ACC  ACC  AAC  AAC  GTG  CGG  GAG     3721
His  Thr  His  Ser  Ala  Ser  Glu  Asp  Asn  Thr  Thr  Asn  Asn  Val  Arg  Glu
               1105                     1110                     1115

CAG  CTG  AAC  CAG  ATC  AAA  AAC  CCC  ATT  GAG  AAA  CAT  GGG  GCC  AAC  ACG     3769
Gln  Leu  Asn  Gln  Ile  Lys  Asn  Pro  Ile  Glu  Lys  His  Gly  Ala  Asn  Thr
          1120                     1125                     1130

GTC  CCC  ATC  AAG  GAT  TAC  GAG  AAC  AAG  AAC  TCC  AAA  ATG  TCT  AAA  ATA     3817
Val  Pro  Ile  Lys  Asp  Tyr  Glu  Asn  Lys  Asn  Ser  Lys  Met  Ser  Lys  Ile
     1135                     1140                     1145

AGG  ACA  CAC  AAT  TCT  GAA  GTA  GAA  GAG  GAC  GAC  ATG  GAC  AAA  CAC  CAG     3865
Arg  Thr  His  Asn  Ser  Glu  Val  Glu  Glu  Asp  Asp  Met  Asp  Lys  His  Gln
1150                     1155                     1160                        1165

CAG  AAA  GCC  CGG  TTT  GCC  AAG  CAG  CCG  GCG  TAC  ACG  CTG  GTA  GAC  AGA     3913
Gln  Lys  Ala  Arg  Phe  Ala  Lys  Gln  Pro  Ala  Tyr  Thr  Leu  Val  Asp  Arg
                    1170                     1175                       1180

GAA  GAG  AAG  CCC  CCC  AAC  GGC  ACG  CCG  ACA  AAA  CAC  CCA  AAC  TGG  ACA     3961
Glu  Glu  Lys  Pro  Pro  Asn  Gly  Thr  Pro  Thr  Lys  His  Pro  Asn  Trp  Thr
               1185                     1190                     1195

AAC  AAA  CAG  GAC  AAC  AGA  GAC  TTG  GAA  AGT  GCC  CAG  AGC  TTA  AAC  CGA     4009
Asn  Lys  Gln  Asp  Asn  Arg  Asp  Leu  Glu  Ser  Ala  Gln  Ser  Leu  Asn  Arg
          1200                     1205                     1210

ATG  GAG  TAC  ATC  GTA  TAG  CAGACCGCGG  GCACTGCCGC  CGCTAGGTAG                   4057
Met  Glu  Tyr  Ile  Val   *
```

```
       1 2 1 5
AGTCTGAGGG  CTTGTAGTTC  TTTAAACTGT  CGTGTCATAC  TCGAGTCTGA  GGCCGTTGCT    4117
GACTTAGAAT  CCCTGTGTTA  ATTTAGTTTG  ACAAGCTGGC  TTACACTGGC  AATGGTAGTT    4177
CTGTGGTTGG  CTGGGAAATC  GAGTGGCGCA  TCTCACAGCT  ATGCAAAAAG  CTAGTCAACA    4237
GTACCCCTGG  TTGTGTGTCC  CCTTGCAGCC  GACACGGTCT  CGGATCAGGC  TCCCAGGAGC    4297
TGCCCAGCCC  CCTGGTACTT  TGAGCTCCCA  CTTCTGCCAG  ATGTCTAATG  GTGATGCAGT    4357
CTTAGATCAT  AGTTTTATTT  ATATTATTG   ACTCTTGAGT  TGTTTTGTA   TATTGGTTTT    4417
ATGATGACGT  ACAAGTAGTT  CTGTATTTGA  AAGTGCCTTT  GCAGCTCAGA  ACCACAGCAA    4477
CGATCACAAA  TGACTTTATT  ATTTATTTTT  TTTAATTGTA  TTTTTGTTGT  TGGGGAGGG     4537
GAGACTTTGA  TGTCAGCAGT  TGCTGGTAAA  ATGAAGAATT  TAAAGAAAAA  ATGTCCAAAA    4597
GTAGAACTTT  GTATAGTTAT  GTAAATAATT  CTTTTTATT   AATCACTGTG  TATATTTGAT    4657
TTATTAACTT  AATAATCAAG  AGCCTTAAAA  CATCATTCCT  TTTTATTTAT  ATGTATGTGT    4717
TTAGAATTGA  AGGTTTTTGA  TAGCATTGTA  AGCGTATGGC  TTTATTTTTT  TGAACTCTTC    4777
TCATTACTTG  TTGCCTATAA  GCCAAAAAGG  AAAGGGTGTT  TTGAAAATAG  TTTATTTTAA    4837
AACAATAGGA  TGGGCTACAC  GTACATAGGT  AAATAATAGC  ACCGTACTGG  TTATGATGAT    4897
GAAAATAACT  GGAAACTTGA  AAGCTTGTGG  TAATGGCAGA  TAAAGATGGT  TCACCTGGGA    4957
AATTAAAACT  TGAATGGTTG  TACAGAAAAG  CACAGAGTGG  AATGCACATC  AATGACAGTA    5017
AGGGAGTTAG  TTCTAGGAAC  AGCTCCTGAA  CAGTAAGATT  CCCGCAATAG  TCTCCGCCTC    5077
GTTCGTCTAT  GGTATGCATC  CCATTCATTT  TCTTCTTCTG  ATTATTGTCA  TCTTTCCCTT    5137
TGCCAAATGG  GCAGTTATTG  TTTCAGGGAG  AGAAGCTGCT  CATTGGCCAA  TCATTCTGGT    5197
GTGCAGTGCT  CCATCGGATT  CTACATGTCC  AACAAGGCAT  GTCTGGATGA  TGCAATGTCT    5257
GTCTGACCCC  CGGAATTCCG  TGCAGAGACA  ACATTCTAGA  CAGATATACA  CTTTTTATTA    5317
TTAACAAACT  TTGGCCACAA  CCTTTGATGT  ATAAATTGCC  GGATTTCCCC  AGTCCTTTCA    5377
TTGTGGCTTT  GGACAGGAGC  AGGCTCACTT  GTCTGCTTCA  GGCTGCCTTT  CTCTTGGGTT    5437
GCACCTCAGT  TCTTACTTAT  TTATTTATTT  TGAGTGGAGC  ATAGGGCCT   CTTCCAAAAT    5497
GGGTAGAGCT  CAGGGGCTTT  CTTATTGAAA  TGGTCACATG  ATAAAAACGG  GCTGAAAAAG    5557
GAGAGTTCCA  GGAGAAAAGC  CCAGAAAAGG  CCCCTCCTCA  GAAGACAGCC  TTTAAGCCTC    5617
TTGCTTACTG  AAGGAAGCCC  CACCTTCTAG  CACTGAGGCC  GGGTCTGATC  TTCCAGAGGA    5677
GTTGGAGGAG  TCCATGAGAA  TGGCCACCAT  TCTTGCTTGC  TGCTGCTGAT  GTTGCAGTTT    5737
TGAGAGAACA  GCGGGATCCT  TGTTGTCCTC  TAGAGACTTG  AGTCTGTCAC  TGACATTTTT    5797
TCAGTTCCTT  TGCTCATAGA  CCATACGAGG  AATTAGTGAT  GTGTCAGTTG  AGAGTTCACA    5857
ATCTCATTGT  TCATTTAATT  CACTTTAAAG  TTGTCAATTT  CTGTGTGAGT  AACCTGTAAA    5917
AGACACCTTT  CCAGAAGAGT  TTTGCCGTCT  GTTTGAAAAA  AAAATCTTTA  TAAACTTTCC    5977
TAAGTATCTG  GATTTGGATT  CCTTATTTGG  AGAGAAAATG  TACCCTGTCT  CCACCAAAAA    6037
TACAAAAATT  AGCCAGGCTT  GGTGGTGCAC  ACCGGTAATC  CCAGCAACTC  TGGAGACTAA    6097
GGCAGGAAGA  ATCGCTTGAC  CCAGGAGGGT  CGAGGCTACA  ATGAGTTGAA  ACCGCGCCAC    6157
TGCACTCCAG  CCTGGGCGAC  AGTGCGAGGC  CCTGTCTCAA  AAATAAAATA  AATAAATAA    6217
ATAAATTAGC  CAGATACTGT  GTGCACGCCT  GCAGTCCCAG  CTATTCTGGA  AGCTGAGGTG    6277
GGAAGATGGT  TAAGCCTGAG  AGGACAAAGC  TGCAGTGAGT  CATGTTTGCA  TCACTGCACT    6337
CCAGCCTGGG  TGACAGAGCA  AGACCCTGTC  TAAAAAACAA  AAACAGGCCG  GGTGTGGTGG    6397
```

| CTCATGCCTG | CCATCCCAGT | GCTTTGGGAG | GCAGAGGTTG | GCATAATCCC | AGCGCTCTGG | 6457 |
|---|---|---|---|---|---|---|
| GAATTCC | | | | | | 6464 |

(2) INFORMATION FOR SEQ ID NO:6:

(i) SEQUENCE CHARACTERISTICS:
        (A) LENGTH: 1218 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Ser Pro Arg Thr Arg Gly Arg Ser Gly Arg Pro Leu Ser Leu
 1               5                  10                  15
Leu Leu Ala Leu Leu Cys Ala Leu Arg Ala Lys Val Cys Gly Ala Ser
                20                  25                  30
Gly Gln Phe Glu Leu Glu Ile Leu Ser Met Gln Asn Val Asn Gly Glu
            35                  40                  45
Leu Gln Asn Gly Asn Cys Cys Gly Gly Ala Arg Asn Pro Gly Asp Arg
        50                  55                  60
Lys Cys Thr Arg Asp Glu Cys Asp Thr Tyr Phe Lys Val Cys Leu Lys
 65                  70                  75                  80
Glu Tyr Gln Ser Arg Val Thr Ala Gly Gly Pro Cys Ser Phe Gly Ser
                85                  90                  95
Gly Ser Thr Pro Val Ile Gly Gly Asn Thr Phe Asn Leu Lys Ala Ser
            100                 105                 110
Arg Gly Asn Asp Pro Asn Arg Ile Val Leu Pro Phe Ser Phe Ala Trp
        115                 120                 125
Pro Arg Ser Tyr Thr Leu Leu Val Glu Ala Trp Asp Ser Ser Asn Asp
    130                 135                 140
Thr Val Gln Pro Asp Ser Ile Ile Glu Lys Ala Ser His Ser Gly Met
145                 150                 155                 160
Ile Asn Pro Ser Arg Gln Trp Gln Thr Leu Lys Gln Asn Thr Gly Val
                165                 170                 175
Ala His Phe Glu Tyr Gln Ile Arg Val Thr Cys Asp Asp Tyr Tyr Tyr
            180                 185                 190
Gly Phe Gly Cys Asn Lys Phe Cys Arg Pro Arg Asp Asp Phe Phe Gly
        195                 200                 205
His Tyr Ala Cys Asp Gln Asn Gly Asn Lys Thr Cys Met Glu Gly Trp
    210                 215                 220
Met Gly Pro Glu Cys Asn Arg Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
        275                 280                 285
Gly Gly Gln Leu Cys Asp Lys Asp Leu Asn Tyr Cys Gly Thr His His Gln
    290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
```

|     |     |     |     |     |     | 340 |     |     |     |     |     | 345 |     |     |     |     |     | 350 |     |     |
| --- | --- | --- | --- | --- | --- | --- | --- | --- | --- | --- | --- | --- | --- | --- | --- | --- | --- | --- | --- | --- |

Glu Thr Ser Leu Gly Phe Glu Cys Ser Pro Gly Trp Thr Gly
         355             360             365

Pro Thr Cys Ser Thr Asn Ile Asp Asp Cys Ser Pro Asn Asn Cys Ser
    370             375             380

His Gly Gly Thr Cys Gln Asp Leu Val Asn Gly Phe Lys Cys Val Cys
385             390             395                         400

Pro Pro Gln Trp Thr Gly Lys Thr Cys Gln Leu Asp Ala Asn Glu Cys
            405             410             415

Glu Ala Lys Pro Cys Val Asn Ala Lys Ser Cys Lys Asn Leu Ile Ala
            420             425             430

Ser Tyr Tyr Cys Asp Cys Leu Pro Gly Trp Met Gly Gln Asn Cys Asp
        435             440             445

Ile Asn Ile Asn Asp Cys Leu Gly Gln Cys Gln Asn Asp Ala Ser Cys
    450             455             460

Arg Asp Leu Val Asn Gly Tyr Arg Cys Ile Cys Pro Pro Gly Tyr Ala
465             470             475                         480

Gly Asp His Cys Glu Arg Asp Ile Asp Glu Cys Ala Ser Asn Pro Cys
            485             490             495

Leu Asn Gly Gly His Cys Gln Asn Glu Ile Asn Arg Phe Gln Cys Leu
            500             505             510

Cys Pro Thr Gly Phe Ser Gly Asn Leu Cys Gln Leu Asp Ile Asp Tyr
        515             520             525

Cys Glu Pro Asn Pro Cys Gln Asn Gly Ala Gln Cys Tyr Asn Arg Ala
    530             535             540

Ser Asp Tyr Phe Cys Lys Cys Pro Glu Asp Tyr Glu Gly Lys Asn Cys
545             550             555                         560

Ser His Leu Lys Asp His Cys Arg Thr Thr Pro Cys Glu Val Ile Asp
            565             570             575

Ser Cys Thr Val Ala Met Ala Ser Asn Asp Thr Pro Glu Gly Val Arg
            580             585             590

Tyr Ile Ser Ser Asn Val Cys Gly Pro His Gly Lys Cys Lys Ser Gln
        595             600             605

Ser Gly Gly Lys Phe Thr Cys Asp Cys Asn Lys Gly Phe Thr Gly Thr
    610             615             620

Tyr Cys His Glu Asn Ile Asn Asp Cys Glu Ser Asn Pro Cys Arg Asn
625             630             635                         640

Gly Gly Thr Cys Ile Asp Gly Val Asn Ser Tyr Lys Cys Ile Cys Ser
            645             650             655

Asp Gly Trp Glu Gly Ala Tyr Cys Glu Thr Asn Ile Asn Asp Cys Ser
            660             665             670

Gln Asn Pro Cys His Asn Gly Gly Thr Cys Arg Asp Leu Val Asn Asp
        675             680             685

Phe Tyr Cys Asp Cys Lys Asn Gly Trp Lys Gly Lys Thr Cys His Ser
    690             695             700

Arg Asp Ser Gln Cys Asp Glu Ala Thr Cys Asn Asn Gly Gly Thr Cys
705             710             715                         720

Tyr Asp Glu Gly Asp Ala Phe Lys Cys Met Cys Pro Gly Gly Trp Glu
            725             730             735

Gly Thr Thr Cys Asn Ile Ala Arg Asn Ser Ser Cys Leu Pro Asn Pro
            740             745             750

Cys His Asn Gly Gly Thr Cys Val Val Asn Gly Glu Ser Phe Thr Cys
        755             760             765

```
Val Cys Lys Glu Gly Trp Glu Gly Pro Ile Cys Ala Gln Asn Thr Asn
    770             775                 780

Asp Cys Ser Pro His Pro Cys Tyr Asn Ser Gly Thr Cys Val Asp Gly
785             790             795                         800

Asp Asn Trp Tyr Arg Cys Glu Cys Ala Pro Gly Phe Ala Gly Pro Asp
                805             810                     815

Cys Arg Ile Asn Ile Asn Glu Cys Gln Ser Pro Cys Ala Phe Gly
            820             825             830

Ala Thr Cys Val Asp Glu Ile Asn Gly Tyr Arg Cys Val Cys Pro Pro
        835             840             845

Gly His Ser Gly Ala Lys Cys Gln Glu Val Ser Gly Arg Pro Cys Ile
    850             855             860

Thr Met Gly Ser Val Ile Pro Asp Gly Ala Lys Trp Asp Asp Cys
865             870             875                     880

Asn Thr Cys Gln Cys Leu Asn Gly Arg Ile Ala Cys Ser Lys Val Trp
            885             890             895

Cys Gly Pro Arg Pro Cys Leu Leu His Lys Gly His Ser Glu Cys Pro
            900             905             910

Ser Gly Gln Ser Cys Ile Pro Ile Leu Asp Asp Gln Cys Phe Val His
        915             920             925

Pro Cys Thr Gly Val Gly Glu Cys Arg Ser Ser Leu Gln Pro Val
    930             935             940

Lys Thr Lys Cys Thr Ser Asp Ser Tyr Tyr Gln Asp Asn Cys Ala Asn
945             950             955                         960

Ile Thr Phe Thr Phe Asn Lys Glu Met Met Ser Pro Gly Leu Thr Thr
                965             970                     975

Glu His Ile Cys Ser Glu Leu Arg Asn Leu Asn Ile Leu Lys Asn Val
            980             985             990

Ser Ala Glu Tyr Ser Ile Tyr Ile Ala Cys Glu Pro Ser Pro Ser Ala
        995             1000            1005

Asn Asn Glu Ile His Val Ala Ile Ser Ala Glu Asp Ile Arg Asp Asp
    1010            1015            1020

Gly Asn Pro Ile Lys Glu Ile Thr Asp Lys Ile Ile Asp Leu Val Thr
1025            1030            1035                        1040

Lys Arg Asp Gly Asn Ser Ser Leu Ile Ala Ala Val Glu Glu Val Arg
                1045            1050            1055

Val Gln Arg Arg Pro Leu Lys Asn Arg Thr Asp Phe Leu Val Pro Leu
                1060            1065            1070

Leu Ser Ser Val Leu Thr Val Ala Trp Ile Cys Cys Leu Val Thr Ala
        1075            1080            1085

Phe Tyr Trp Cys Leu Arg Lys Arg Arg Lys Pro Gly Ser His Thr His
    1090            1095            1100

Ser Ala Ser Glu Asp Asn Thr Thr Asn Asn Val Arg Glu Gln Leu Asn
1105            1110            1115                        1120

Gln Ile Lys Asn Pro Ile Glu Lys His Gly Ala Asn Thr Val Pro Ile
            1125            1130            1135

Lys Asp Tyr Glu Asn Lys Asn Ser Lys Met Ser Lys Ile Arg Thr His
            1140            1145            1150

Asn Ser Glu Val Glu Glu Asp Asp Met Asp Lys His Gln Gln Lys Ala
        1155            1160            1165

Arg Phe Ala Lys Gln Pro Ala Tyr Thr Leu Val Asp Arg Glu Glu Lys
    1170            1175            1180

Pro Pro Asn Gly Thr Pro Thr Lys His Pro Asn Trp Thr Asn Lys Gln
1185            1190            1195                        1200
```

Asp Asn Arg Asp Leu Glu Ser Ala Gln Ser Leu Asn Arg Met Glu Tyr
            1205                    1210                    1215

Ile Val ( 2 ) INFORMATION FOR SEQ ID NO:7:

( i ) SEQUENCE CHARACTERISTICS:
        ( A ) LENGTH: 4463 amino acids
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:7:

```
GGCCGGGGCC  GGGCGGGCGG  GTCGCGGGGG  CAATGCGGGC  GCAGGGCCGG  GGGCGCCTTC      60
CCCGGCGGCT  GCTGCTGCTG  CTGGCGCTCT  GGGTGCAGGC  GGCGCGGCCC  ATGGGCTATT     120
TCGAGCTGCA  GCTGAGCGCG  CTGCGGAACG  TGAACGGGGA  GCTGCTGAGC  GGCGCCTGCT     180
GTGACGGCGA  CGGCCGGACA  ACGCGCGCGG  GGGCTGCGG   CCACGACGAG  TGCGACACCG     240
CTCCTTTACC  CTCATCGTGG  AGGCCTGGGA  CTGGGACAAC  GATACCACCC  CGAATGAGGA     300
GCTGCTGATC  GAGCGAGTGT  CGCATGCCGG  CATGATCAAC  CCGGAGGACC  GCTGGAAGAG     360
CCTGCACTTC  AGCGGCCACG  TGGCGCACCT  GGAGCTGCAG  ATCCGCGTGC  GCTGCGACGA     420
GAACTACTAC  AGCGCCACTT  GCAACAAGTT  CTGCCGGCCC  CGCAATGACT  TTTTCGGCCA     480
CTACACCTGC  GACCAGTACG  GCAACAAGGC  CTGCATGGAC  GGCTGGATGG  GCAAGGAGTG     540
CAAGGAAGCT  GTGTGTAAAC  AAGGGTGTAA  TTTGCTCCAC  GGGGGATGCA  CCGTGCCTGG     600
GGAGTGCAGG  TGCAGCTACG  GCTGGCAAGG  GAGGTTCTGC  GATGAGTGTG  TCCCCTACCC     660
CGGCTGCGTG  CATGGCAGTT  GTGTGGAGCC  CTGGCAGTGC  AACTGTGAGA  CCAACTGGGG     720
CGGCCTGCTC  TGTGACAAAG  ACCTGAACTA  CTGTGGCAGC  CACCACCCCT  GCACCAACGG     780
AGGCACGTGC  ATCAACGCCG  AGCCTGACCA  GTACCGCTGC  ACCTGCCCTG  ACGGCTACTC     840
GGGCAGGAAC  TGTGAGAAGG  CTGAGCACGC  CTGCACCTCC  AACCCGTGTG  CCAACGGGGG     900
CTCTTGCCAT  GAGGTGCCGT  CCGGCTTCGA  ATGCCACTGC  CCATCGGGCT  GGAGCGGGCC     960
CACCTGTGCC  CTTGACATCG  ATGAGTGTGC  TTCGAACCCG  TGTGCGGCCG  GTGGCACCTG    1020
TGTGGACCAG  GTGGACGGCT  TTGAGTGCAT  CTGCCCCGAG  CAGTGGGTGG  GGGCCACCTG    1080
CCAGCTGGAC  GCCAATGAGT  GTGAAGGGAA  GCCATGCCTT  AACGCTTTTT  CTTGCAAAAA    1140
CCTGATTGGC  GGCTATTACT  GTGATTGCAT  CCCGGGCTGG  AAGGGCATCA  ACTGCCATAT    1200
CAACGTCAAC  GACTGTCGCG  GCAGTGTCA   GCATGGGGGC  ACCTGCAAGG  ACCTGGTGAA    1260
CGGGTACCAG  TGTGTGTGCC  CACGGGGCTT  CGGAGGCCGG  CATTGCGAGC  TGGAACGAGA    1320
CAAGTGTGCC  AGCAGCCCCT  GCCACAGCGG  CGGCCTCTGC  GAGGACCTGG  CCGACGGCTT    1380
CCACTGCCAC  TGCCCCCAGG  GCTTCTCCGG  GCCTCTCTGT  GAGGTGGATG  TCGACCTTTG    1440
TGAGCCAAGC  CCCTGCCGGA  ACGGCGCTCG  CTGCTATAAC  CTGGAGGGTG  ACTATTACTG    1500
CGCCTGCCCT  GATGACTTTG  GTGGCAAGAA  CTGCTCCGTG  CCCCGCGAGC  CGTGCCCTGG    1560
CGGGGCCTGC  AGAGTGATCG  ATGGCTGCGG  GTCAGACGCG  GGGCCTGGA   TGCCTGGCAC    1620
AGCAGCCTCC  GGCGTGTGTG  GCCCCCATGG  ACGCTGCGTC  AGCCAGCCAG  GGGCAACTT     1680
TTCCTGCATC  TGTGACAGTG  GCTTTACTGG  CACCTACTGC  CATGAGAACA  TTGACGACTG    1740
CCTGGGCCAG  CCCTGCCGCA  ATGGGGGCAC  ATGCATCGAT  GAGGTGGACG  CCTTCCGCTG    1800
CTTCTGCCCC  AGCGGTTGGG  AGGGCGAGCT  CTGCGACACC  AATCCCAACG  ACTGCCTTCC    1860
```

```
CGATCCCTGC CACAGCCGCG GCCGCTGCTA CGACCTGGTC AATGACTTCT ACTGTGCGTG    1920
CGACGACGGC TGGAAGGGCA AGACCTGCCA CTCACGCGAG TTCCAGTGCG ATGCCTACAC    1980
CTGCAGCAAC GGTGGCACCT GCTACGACAG CGGCGACACC TTCCGCTGCG CCTGCCCCCC    2040
CGGCTGGAAG GGCAGCACCT GCGCCGTCGC CAAGAACAGC AGCTGCCTGC CCAACCCCTG    2100
TGTGAATGGT GGCACCTGCG TGGGCAGCGG GGCCTCCTTC TCCTGCATCT GCCGGGACGG    2160
CTGGGAGGGT CGTACTTGCA CTCACAATAC CAACGACTGC AACCCTCTGC CTTGCTACAA    2220
TGGTGGCATC TGTGTTGACG GCGTCAACTG GTTCCGCTGC GAGTGTGCAC CTGGCTTCGC    2280
GGGGCCTGAC TGCCGCATCA ACATCGACGA GTGCCAGTCC TCGCCCTGTG CCTACGGGGC    2340
CACGTGTGTG GATGAGATCA ACGGGTATCG CTGTAGCTGC CCACCCGGCC GAGCCGGCCC    2400
CCGGTGCCAG GAAGTGATCG GGTTCGGGAG ATCCTGCTGG TCCGGGGCA CTCCGTTCCC    2460
ACACGGAAGC TCCTGGGTGG AAGACTGCAA CAGCTGCCGC TGCCTGGATG GCCGCCGTGA    2520
CTGCAGCAAG GTGTGGTGCG GATGGAAGCC TTGTCTGCTG GCCGGCCAGC CCGAGGCCCT    2580
GAGCGCCCAG TGCCCACTGG GGCAAAGGTG CCTGGAGAAG GCCCAGGCC AGTGTCTGCG    2640
ACCACCCTGT GAGGCCTGGG GGGAGTGCGG CGCAGAAGAG CCACCGAGCA CCCCCTGCCT    2700
GCCACGCTCC GGCCACCTGG ACAATAACTG TGCCCGCCTC ACCTTGCATT TCAACCGTGA    2760
CCACGTGCCC CAGGGCACCA CGGTGGGCGC CATTTGCTCC GGGATCCGCT CCCTGCCAGC    2820
CACAAGGGCT GTGGCACGGG ACCGCCTGCT GGTGTTGCTT TGCGACCGGG CGTCCTCGGG    2880
GGCCAGTGCT GTGGAGGTGG CCGTGTCCTT CAGCCCTGCC AGGGACCTGC CTGACAGCAG    2940
CCTGATCCAG GGCGCGGCCC ACGCCATCGT GGCCGCCATC ACCCAGCGGG GAACAGCTC    3000
ACTGCTCCTG GCTGTCACCG AGGTCAAGGT GGAGACGGTT GTTACGGGCG GCTCTTCCAC    3060
AGGTCTGCTG GTGCCTGTGC TGTGTGGTGC CTTCAGCGTG CTGTGGCTGG CGTGCGTGGT    3120
CCTGTGCGTG TGGTGGACAC AAGCGCAGGA AAGAGCGGGA GAGGAGCCGG CTGCCGCGGG    3180
AGGAGAGCGC CAACAACCAG TGGGCCCCGC TCAACCCCAT CCGCAACCCC ATTGAGCNNC    3240
CGGGGGCACA AGGACGTGCT CTACCAGTGC AAGAACTTCA CNCCGCCGCC GCGCAGGNCG    3300
AGGNCTNCCG GNCCGNCNGC ACNCNNCAGG GAGGATGAGG AGGACGGGAT CTGGGCCNCN    3360
GTGAGGAGGA CTCCTGGAGG CNNAGAAGTT CCTCTCACAC AAATTCACCA AAGATCCTGG    3420
CCGCTCGCCG GGAGNCGNCC ACTGCNCAGG CCAAAGTGGA CAACCGCNCN GTCAGGAGCA    3480
TCAATGAGGC CCGCTACNCG CAAGGGAAGT AGGGCGGCTG CAGCTGGGCC GGGACCCAGG    3540
GCCTCGGTGG GAGCCATGCC GTCTGCCGGN CCCGAGCCGA GGCATGTGCA TAGTTTCTTT    3600
ATTTTGTGTA AAAAAACCAC CAAAAACAAA AACCAAATGT TTATTTTCTA CGTTTCTTTA    3660
ACCTTGTATA AATTATTCAG TAACTGTCAG GCTGAAACAA TGGAGTATTC TCGGATAGTT    3720
GCTATTTTTG TTAAAGTTTC TCTCGCGTGG CACTCGCTGT ATGGAAAGGA GAGAGCAAAA    3780
GGGTGTCTGA CGTCGTCACC AAATCGTAGC GTTTGTTACC AGAGGTTGTG CACTGTTTAC    3840
AGAATGTTGG TTTTATTCCT CACTCGGGTT TCTCTGTGCT CCAGGCCAAA GTGCCGGTGA    3900
GACCCATGGC TGTGTTGGTG TGGCCCATGG CTGTTGGTGG GACCCTGTGG CTGATGGTGT    3960
GGCCTGTGGC TGTCGGTGGG ACTCGTGGCT GTCAATGGGA CCTGTGGCTG TCGGTGGGAC    4020
CTACGGTGGT CGGTGGGACC CTGGTTATTG ATGTGGCCCT GGCTGCCGGC ACGGCCCGTG    4080
GCTGTTGACG CACCTGTGGT TGTTAGTGGG GCCTGAGGTC ATCGGCGTGG CCCAAGGCCG    4140
GCAGGTCAAC CTCGCGCTTG CTGGCCAGTC CACCCTGCCT GCCGTCTGTG CTTCCTCCTG    4200
CCCAGAACGC CGCTCCAGCG TACTCTCCAC TGTGCTTTCA GAAGTGCCCT TCCTGCTGNG    4260
```

```
CAGTTCTCCC ATCCTGGACG GCGGCAGTAT TGAAGCTCGT GACAAGTGCC TTCACACAGA    4320

CCCCTCGCAA CTGTCCACGC GTGCCGTGGC ACCAGGCGCT GCCCACCTGC CGGCCCCGGC    4380

CGCCCCTCCT CGTGAAAGTG CATTTTTGTA AATGTGTACA TATTAAAGGA AGCACTCTGT    4440

ATAAAAAAAA AAAACCGGAA TTCC                                          4464
```

( 2 ) INFORMATION FOR SEQ ID NO:8:

( i ) SEQUENCE CHARACTERISTICS:
        ( A ) LENGTH: 1065 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:8:

```
Met Ile Asn Pro Glu Asp Arg Trp Lys Ser Leu His Phe Ser Gly His
 1               5                  10                  15

Val Ala His Leu Glu Leu Gln Ile Arg Val Arg Cys Asp Glu Asn Tyr
                20                  25                  30

Tyr Ser Ala Thr Cys Asn Lys Phe Cys Arg Pro Arg Asn Asp Phe Phe
            35                  40                  45

Gly His Tyr Thr Cys Asp Gln Tyr Gly Asn Lys Ala Cys Met Asp Gly
        50                  55                  60

Trp Met Gly Lys Glu Cys Lys Glu Ala Val Cys Lys Gln Gly Cys Asn
 65                  70                  75                  80

Leu Leu His Gly Gly Cys Thr Val Pro Gly Glu Cys Arg Cys Ser Tyr
                85                  90                  95

Gly Trp Gln Gly Arg Phe Cys Asp Glu Cys Val Pro Tyr Pro Gly Cys
            100                 105                 110

Val His Gly Ser Cys Val Glu Pro Trp Gln Cys Asn Cys Glu Thr Asn
        115                 120                 125

Trp Gly Gly Leu Leu Cys Asp Lys Asp Leu Asn Tyr Cys Gly Ser His
    130                 135                 140

His Pro Cys Thr Asn Gly Gly Thr Cys Ile Asn Ala Glu Pro Asp Gln
145                 150                 155                 160

Tyr Arg Cys Thr Cys Pro Asp Gly Tyr Ser Gly Arg Asn Cys Glu Lys
                165                 170                 175

Ala Glu His Ala Cys Thr Ser Asn Pro Cys Ala Asn Gly Gly Ser Cys
            180                 185                 190

His Glu Val Pro Ser Gly Phe Glu Cys His Cys Pro Ser Gly Trp Ser
        195                 200                 205

Gly Pro Thr Cys Ala Leu Asp Ile Asp Glu Cys Ala Ser Asn Pro Cys
    210                 215                 220

Ala Ala Gly Gly Thr Cys Val Asp Gln Val Asp Gly Phe Glu Cys Ile
225                 230                 235                 240

Cys Pro Glu Gln Trp Val Gly Ala Thr Cys Gln Leu Asp Ala Asn Glu
                245                 250                 255

Cys Glu Gly Lys Pro Cys Leu Asn Ala Phe Ser Cys Lys Asn Leu Ile
            260                 265                 270

Gly Gly Tyr Tyr Cys Asp Cys Ile Pro Gly Trp Lys Gly Ile Asn Cys
        275                 280                 285

His Ile Asn Val Asn Asp Cys Arg Gly Gln Cys Gln His Gly Gly Thr
    290                 295                 300

Cys Lys Asp Leu Val Asn Gly Tyr Gln Cys Val Cys Pro Arg Gly Phe
```

```
            305                    310                    315                    320
Gly Gly Arg His Cys Glu Leu Glu Arg Asp Lys Cys Ala Ser Ser Pro
                325                    330                    335
Cys His Ser Gly Gly Leu Cys Glu Asp Leu Ala Asp Gly Phe His Cys
                340                    345                    350
His Cys Pro Gln Gly Phe Ser Gly Pro Leu Cys Glu Val Asp Val Asp
                355                    360                    365
Leu Cys Glu Pro Ser Pro Cys Arg Asn Gly Ala Arg Cys Tyr Asn Leu
370                    375                    380
Glu Gly Asp Tyr Tyr Cys Ala Cys Pro Asp Asp Phe Gly Gly Lys Asn
385                    390                    395                    400
Cys Ser Val His Arg Glu Pro Cys Pro Gly Gly Ala Cys Arg Val Ile
                405                    410                    415
Asp Gly Cys Gly Ser Asp Ala Gly Pro Gly Met Pro Gly Thr Ala Ala
            420                    425                    430
Ser Gly Val Cys Gly Pro His Gly Arg Cys Val Ser Gln Pro Gly Gly
            435                    440                    445
Asn Phe Ser Cys Ile Cys Asp Ser Gly Phe Thr Gly Thr Tyr Cys His
450                    455                    460
Glu Asn Ile Asp Asp Cys Leu Gly Gln Pro Cys Arg Asn Gly Gly Thr
465                    470                    475                    480
Cys Ile Asp Glu Val Asp Ala Phe Arg Cys Phe Cys Pro Ser Gly Trp
                485                    490                    495
Glu Gly Glu Leu Cys Asp Thr Asn Pro Asn Asp Cys Leu Pro Asp Pro
            500                    505                    510
Cys His Ser Arg Gly Arg Cys Tyr Asp Leu Val Asn Asp Phe Tyr Cys
        515                    520                    525
Ala Cys Asp Asp Gly Trp Lys Gly Lys Thr Cys His Ser Arg Glu Phe
    530                    535                    540
Gln Cys Asp Ala Tyr Thr Cys Ser Asn Gly Gly Thr Cys Tyr Asp Ser
545                    550                    555                    560
Gly Asp Thr Phe Arg Cys Ala Cys Pro Pro Gly Trp Lys Gly Ser Thr
                565                    570                    575
Cys Ala Val Ala Lys Asn Ser Ser Cys Leu Pro Asn Pro Cys Val Asn
            580                    585                    590
Gly Gly Thr Cys Val Gly Ser Gly Ala Ser Phe Ser Cys Ile Cys Arg
        595                    600                    605
Asp Gly Trp Glu Gly Arg Thr Cys Thr His Asn Thr Asn Asp Cys Asn
    610                    615                    620
Pro Leu Pro Cys Tyr Asn Gly Gly Ile Cys Val Asp Gly Val Asn Trp
625                    630                    635                    640
Phe Arg Cys Glu Cys Ala Pro Gly Phe Ala Gly Pro Asp Cys Arg Ile
                645                    650                    655
Asn Ile Asp Glu Cys Gln Ser Ser Pro Cys Ala Tyr Gly Ala Thr Cys
            660                    665                    670
Val Asp Glu Ile Asn Gly Tyr Arg Cys Ser Cys Pro Pro Gly Arg Ala
        675                    680                    685
Gly Pro Arg Cys Gln Glu Val Ile Gly Phe Gly Arg Ser Cys Trp Ser
    690                    695                    700
Arg Gly Thr Pro Phe Pro His Gly Ser Ser Trp Val Glu Asp Cys Asn
705                    710                    715                    720
Ser Cys Arg Cys Leu Asp Gly Arg Arg Asp Cys Ser Lys Val Trp Cys
                725                    730                    735
```

| Gly | Trp | Lys | Pro 740 | Cys | Leu | Leu | Ala | Gln 745 | Pro | Glu | Ala | Leu 750 | Ser | Ala |
|---|---|---|---|---|---|---|---|---|---|---|---|---|---|---|
| Gln | Cys | Pro 755 | Leu | Gly | Gln | Arg | Cys 760 | Leu | Glu | Lys | Ala | Pro 765 | Gly | Gln | Cys |
| Leu | Arg 770 | Pro | Pro | Cys | Glu | Ala 775 | Trp | Gly | Glu | Cys | Gly 780 | Ala | Glu | Glu | Pro |
| Pro 785 | Ser | Thr | Pro | Cys | Leu 790 | Pro | Arg | Ser | Gly | His 795 | Leu | Asp | Asn | Asn | Cys 800 |
| Ala | Arg | Leu | Thr | Leu 805 | His | Phe | Asn | Arg | Asp 810 | His | Val | Pro | Gln | Gly 815 | Thr |
| Thr | Val | Gly | Ala 820 | Ile | Cys | Ser | Gly | Ile 825 | Arg | Ser | Leu | Pro | Ala 830 | Thr | Arg |
| Ala | Val | Ala 835 | Arg | Asp | Arg | Leu | Leu 840 | Val | Leu | Leu | Cys | Asp 845 | Arg | Ala | Ser |
| Ser | Gly 850 | Ala | Ser | Ala | Val | Glu 855 | Val | Ala | Val | Ser | Phe 860 | Ser | Pro | Ala | Arg |
| Asp 865 | Leu | Pro | Asp | Ser | Ser 870 | Leu | Ile | Gln | Asp | Ala 875 | Ala | His | Ala | Ile | Val 880 |
| Ala | Ala | Ile | Thr | Gln 885 | Arg | Gly | Asn | Ser | Ser 890 | Leu | Leu | Leu | Ala | Val 895 | Thr |
| Glu | Val | Lys | Val 900 | Glu | Thr | Val | Val | Thr 905 | Gly | Gly | Ser | Ser | Thr 910 | Gly | Leu |
| Leu | Val | Pro 915 | Val | Leu | Cys | Gly | Ala 920 | Phe | Ser | Val | Leu | Trp 925 | Leu | Ala | Cys |
| Val | Val 930 | Leu | Cys | Val | Trp | Trp 935 | Thr | Gln | Ala | Gln | Glu 940 | Arg | Ala | Gly | Glu |
| Glu 945 | Pro | Ala | Ala | Ala | Gly 950 | Gly | Glu | Arg | Gln | Gln 955 | Pro | Val | Gly | Pro | Ala 960 |
| Gln | Pro | His | Pro | Gln 965 | Pro | His | His | Ala | Ala 970 | Gly | Gly | Thr | Arg | Thr 975 | Cys |
| Ser | Thr | Ser | Ala 980 | Arg | Thr | Ser | Ser | Arg 985 | Arg | Arg | Ala | Gly | Arg 990 | Gly | Leu |
| Pro | Pro | Arg 995 | Arg | His | His | His | Gly 1000 | Arg | Met | Arg | Arg | Thr 1005 | Gly | Ser | Gly |
| Pro | Pro | Pro 1010 | Gly | Gly | Leu | Leu 1015 | Glu | Ala | Ala | Lys | Phe 1020 | Leu | Ser | His | Lys |
| Phe 1025 | Thr | Lys | Asp | Pro | Gly 1030 | Arg | Ser | Pro | Gly | Gly 1035 | Gly | His | Cys | Cys | Gly 1040 |
| Gln | Ser | Gly | Gln | Pro 1045 | Pro | Pro | Gln | Glu | His 1050 | Gln | Gln | Gly | Pro | Leu 1055 | Leu |
| Ala | Arg | Ser | Arg 1060 | Arg | Arg | Ala | Ala | Gly 1065 | | | | | | | |

( 2 ) INFORMATION FOR SEQ ID NO:9:

( i ) SEQUENCE CHARACTERISTICS:
        ( A ) LENGTH: 3582 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..3582

( x i ) SEQUENCE DESCRIPTION: SEQ ID NO:9:

| | | | | | | | | | | | | | | | | |
|---|---|---|---|---|---|---|---|---|---|---|---|---|---|---|---|---|
|CAG|GTG|GCG|TCA|GCA|TCG|GGA|CAG|TTC|GAG|CTG|GAG|ATC|TTA|TCC|GTG|48|
|Gln|Val|Ala|Ser|Ala|Ser|Gly|Gln|Phe|Glu|Leu|Glu|Ile|Leu|Ser|Val| |
|1| | |  |5| | | | |10| | | | |15| | |
|CAG|AAT|GTG|AAC|GGC|GTG|CTG|CAG|AAC|GGG|AAC|TGC|TGC|GAC|GGC|ACT|96|
|Gln|Asn|Val|Asn|Gly|Val|Leu|Gln|Asn|Gly|Asn|Cys|Cys|Asp|Gly|Thr| |
| | | |20| | | | |25| | | | |30| | | |
|CGA|AAC|CCC|GGA|GAT|AAA|AAG|TGC|ACC|AGA|GAT|GAG|TGT|GAC|ACC|TAC|144|
|Arg|Asn|Pro|Gly|Asp|Lys|Lys|Cys|Thr|Arg|Asp|Glu|Cys|Asp|Thr|Tyr| |
| | |35| | | | |40| | | | |45| | | | |
|TTT|AAA|GTT|TGC|CTG|AAG|GAG|TAC|CAG|TCG|CGG|GTC|ACT|GCT|GGC|GGC|192|
|Phe|Lys|Val|Cys|Leu|Lys|Glu|Tyr|Gln|Ser|Arg|Val|Thr|Ala|Gly|Gly| |
| |50| | | | |55| | | | |60| | | | | |
|CCT|TGC|AGC|TTC|GGA|TCC|AAA|TCC|ACC|CCT|GTC|ATC|GGC|GGG|AAT|ACC|240|
|Pro|Cys|Ser|Phe|Gly|Ser|Lys|Ser|Thr|Pro|Val|Ile|Gly|Gly|Asn|Thr| |
|65| | | | |70| | | | |75| | | | |80| |
|TTC|AAT|TTA|AAG|TAC|AGC|CGG|AAT|AAT|GAA|AAG|AAC|CGG|ATT|GTT|ATC|288|
|Phe|Asn|Leu|Lys|Tyr|Ser|Arg|Asn|Asn|Glu|Lys|Asn|Arg|Ile|Val|Ile| |
| | | | |85| | | | |90| | | | |95| | |
|CCT|TTC|ACG|TTC|GCC|TGG|CCG|AGA|TCC|TAC|ACG|TTG|CTT|GTT|GAG|GCA|336|
|Pro|Phe|Thr|Phe|Ala|Trp|Pro|Arg|Ser|Tyr|Thr|Leu|Leu|Val|Glu|Ala| |
| | | | |100| | | |105| | | | |110| | | |
|TGG|GAT|TAC|AAT|GAT|AAC|TCT|ACT|AAT|CCC|GAT|CGC|ATA|ATT|GAG|AAG|384|
|Trp|Asp|Tyr|Asn|Asp|Asn|Ser|Thr|Asn|Pro|Asp|Arg|Ile|Ile|Glu|Lys| |
| | | |115| | | | |120| | | | |125| | | |
|GCA|TCC|CAC|TCT|GGC|ATG|ATC|AAT|CCA|AGC|CGT|CAG|TGG|CAG|ACG|TTG|432|
|Ala|Ser|His|Ser|Gly|Met|Ile|Asn|Pro|Ser|Arg|Gln|Trp|Gln|Thr|Leu| |
| | |130| | | | |135| | | | |140| | | | |
|AAA|CAT|AAC|ACA|GGA|GCT|GCC|CAC|TTT|GAG|TAT|CAA|ATC|CGT|GTG|ACT|480|
|Lys|His|Asn|Thr|Gly|Ala|Ala|His|Phe|Glu|Tyr|Gln|Ile|Arg|Val|Thr| |
|145| | | | |150| | | | |155| | | | |160| |
|TGC|GCA|GAA|CAT|TAC|TAT|GGC|TTT|GGA|TGC|AAC|AAG|TTT|TGT|CGA|CCG|528|
|Cys|Ala|Glu|His|Tyr|Tyr|Gly|Phe|Gly|Cys|Asn|Lys|Phe|Cys|Arg|Pro| |
| | | | |165| | | | |170| | | | |175| | |
|AGA|GAT|GAC|TTC|TTC|ACT|CAC|CAT|ACC|TGT|GAC|CAG|AAT|GGC|AAC|AAA|576|
|Arg|Asp|Asp|Phe|Phe|Thr|His|His|Thr|Cys|Asp|Gln|Asn|Gly|Asn|Lys| |
| | | |180| | | | |185| | | | |190| | | |
|ACC|TGC|TTG|GAA|GGC|TGG|ACG|GGA|CCA|GAA|TGC|AAC|AAA|GCT|ATT|TGT|624|
|Thr|Cys|Leu|Glu|Gly|Trp|Thr|Gly|Pro|Glu|Cys|Asn|Lys|Ala|Ile|Cys| |
| | |195| | | | |200| | | | |205| | | | |
|CGT|CAG|GGA|TGT|AGC|CCC|AAG|CAT|GGT|TCT|TGC|ACA|GTT|CCA|GGA|GAG|672|
|Arg|Gln|Gly|Cys|Ser|Pro|Lys|His|Gly|Ser|Cys|Thr|Val|Pro|Gly|Glu| |
|210| | | | |215| | | | |220| | | | | | |
|TGC|AGG|TGT|CAG|TAT|GGA|TGG|CAA|GGC|CAG|TAC|TGT|GAT|AAG|TGC|ATT|720|
|Cys|Arg|Cys|Gln|Tyr|Gly|Trp|Gln|Gly|Gln|Tyr|Cys|Asp|Lys|Cys|Ile| |
|225| | | | |230| | | | |235| | | | |240| |
|CCA|CAC|CCG|GGA|TGT|GTC|CAT|GGC|ACT|TGC|ATT|GAA|CCA|TGG|CAG|TGC|768|
|Pro|His|Pro|Gly|Cys|Val|His|Gly|Thr|Cys|Ile|Glu|Pro|Trp|Gln|Cys| |
| | | | |245| | | | |250| | | | |255| | |
|CTC|TGT|GAA|ACC|AAC|TGG|GGT|GGT|CAG|CTC|TGT|GAC|AAA|GAC|CTG|AAC|816|
|Leu|Cys|Glu|Thr|Asn|Trp|Gly|Gly|Gln|Leu|Cys|Asp|Lys|Asp|Leu|Asn| |
| | |260| | | | |265| | | | |270| | | | |
|TAC|TGT|GGA|ACC|CAC|CCA|CCC|TGT|TTG|AAT|GGT|GGT|ACC|TGC|AGC|AAC|864|
|Tyr|Cys|Gly|Thr|His|Pro|Pro|Cys|Leu|Asn|Gly|Gly|Thr|Cys|Ser|Asn| |
| | |275| | | | |280| | | | |285| | | | |
|ACT|GGC|CCC|GAT|AAA|TAC|CAG|TGT|TCC|TGC|CCT|GAG|GGT|TAC|TCA|GGA|912|
|Thr|Gly|Pro|Asp|Lys|Tyr|Gln|Cys|Ser|Cys|Pro|Glu|Gly|Tyr|Ser|Gly| |
| |290| | | | |295| | | | |300| | | | | |
|CAG|AAC|TGT|GAA|ATA|GCG|GAG|CAT|GCG|TGC|CTC|TCT|GAT|CCG|TGC|CAC|960|
|Gln|Asn|Cys|Glu|Ile|Ala|Glu|His|Ala|Cys|Leu|Ser|Asp|Pro|Cys|His| |
|305| | | | |310| | | | |315| | | | |320| |

-continued

| | | | | | | | | | | | | | | | |
|---|---|---|---|---|---|---|---|---|---|---|---|---|---|---|---|
| AAC | GGA | GGA | AGC | TGC | CTA | GAA | ACG | TCT | ACA | GGA | TTT | GAA | TGT | GTG | TGT | 1008 |
| Asn | Gly | Gly | Ser | Cys 325 | Leu | Glu | Thr | Ser 330 | Thr | Gly | Phe | Glu | Cys 335 | Val | Cys | |
| GCA | CCT | GGC | TGG | GCT | GGA | CCA | ACT | TGC | ACT | GAT | AAT | ATT | GAT | GAT | TGT | 1056 |
| Ala | Pro | Gly | Trp 340 | Ala | Gly | Pro | Thr | Cys 345 | Thr | Asp | Asn | Ile | Asp 350 | Asp | Cys | |
| TCT | CCA | AAT | CCC | TGT | GGT | CAT | GGA | GGA | ACT | TGC | CAA | GAT | CTA | GTT | GAT | 1104 |
| Ser | Pro | Asn 355 | Pro | Cys | Gly | His | Gly 360 | Gly | Thr | Cys | Gln | Asp 365 | Leu | Val | Asp | |
| GGA | TTT | AAG | TGT | ATT | TGC | CCA | CCT | CAG | TGG | ACT | GGC | AAA | ACA | TGC | CAG | 1152 |
| Gly | Phe 370 | Lys | Cys | Ile | Cys | Pro 375 | Pro | Gln | Trp | Thr | Gly 380 | Lys | Thr | Cys | Gln | |
| CTA | GAT | GCG | AAT | GAA | TGT | GAG | GGC | AAA | CCC | TGT | GTC | AAT | GCC | AAC | TCC | 1200 |
| Leu 385 | Asp | Ala | Asn | Glu | Cys 390 | Glu | Gly | Lys | Pro | Cys 395 | Val | Asn | Ala | Asn | Ser 400 | |
| TGC | AGG | AAC | TTG | ATT | GGC | AGC | TAC | TAT | TGT | GAC | TGC | ATT | ACT | GGC | TGG | 1248 |
| Cys | Arg | Asn | Leu | Ile 405 | Gly | Ser | Tyr | Tyr | Cys 410 | Asp | Cys | Ile | Thr | Gly 415 | Trp | |
| TCT | GGC | CAC | AAC | TGT | GAT | ATA | AAT | ATT | AAT | GAT | TGT | CGT | GGA | CAA | TGT | 1296 |
| Ser | Gly | His | Asn 420 | Cys | Asp | Ile | Asn | Ile 425 | Asn | Asp | Cys | Arg | Gly 430 | Gln | Cys | |
| CAG | AAT | GGA | GGA | TCC | TGT | CGG | GAC | TTG | GTT | AAT | GGT | TAT | CGG | TGC | ATC | 1344 |
| Gln | Asn | Gly 435 | Gly | Ser | Cys | Arg | Asp 440 | Leu | Val | Asn | Gly | Tyr 445 | Arg | Cys | Ile | |
| TGT | TCA | CCT | GGC | TAT | GCA | GGA | GAT | CAC | TGT | GAG | AAA | GAC | ATC | AAT | GAA | 1392 |
| Cys | Ser 450 | Pro | Gly | Tyr | Ala | Gly 455 | Asp | His | Cys | Glu | Lys 460 | Asp | Ile | Asn | Glu | |
| TGT | GCA | AGT | AAC | CCT | TGC | ATG | AAT | GGG | GGT | CAC | TGC | CAG | GAT | GAA | ATC | 1440 |
| Cys 465 | Ala | Ser | Asn | Pro | Cys 470 | Met | Asn | Gly | Gly | His 475 | Cys | Gln | Asp | Glu | Ile 480 | |
| AAT | GGA | TTC | CAA | TGT | CTG | TGT | CCT | GCT | GGT | TTC | TCA | GGA | AAC | CTC | TGT | 1488 |
| Asn | Gly | Phe | Gln | Cys 485 | Leu | Cys | Pro | Ala | Gly 490 | Phe | Ser | Gly | Asn | Leu 495 | Cys | |
| CAG | CTG | GAT | ATA | GAC | TAC | TGT | GAG | CCA | AAC | CCT | TGC | CAG | AAC | GGT | GCC | 1536 |
| Gln | Leu | Asp | Ile 500 | Asp | Tyr | Cys | Glu | Pro 505 | Asn | Pro | Cys | Gln | Asn 510 | Gly | Ala | |
| CAG | TGC | TTC | AAT | CTT | GCT | ATG | GAC | TAT | TTC | TGT | AAC | TGC | CCT | GAA | GAT | 1584 |
| Gln | Cys | Phe 515 | Asn | Leu | Ala | Met | Asp 520 | Tyr | Phe | Cys | Asn | Cys 525 | Pro | Glu | Asp | |
| TAC | GAA | GGC | AAG | AAC | TGC | TCC | CAC | CTG | AAA | GAT | CAC | TGC | CGC | ACA | ACT | 1632 |
| Tyr | Glu 530 | Gly | Lys | Asn | Cys | Ser 535 | His | Leu | Lys | Asp | His 540 | Cys | Arg | Thr | Thr | |
| CCT | TGT | GAA | GTA | ATC | GAC | AGC | TGT | ACA | GTG | GCA | GTG | GCT | TCT | AAC | AGC | 1680 |
| Pro 545 | Cys | Glu | Val | Ile | Asp 550 | Ser | Cys | Thr | Val | Ala 555 | Val | Ala | Ser | Asn | Ser 560 | |
| ACA | CCA | GAA | GGA | GTT | CGT | TAC | ATT | TCT | TCA | AAT | GTC | TGT | GGT | CCT | CAT | 1728 |
| Thr | Pro | Glu | Gly | Val 565 | Arg | Tyr | Ile | Ser | Ser 570 | Asn | Val | Cys | Gly | Pro 575 | His | |
| GGA | AAA | TGC | AAG | AGC | CAA | GCA | GGT | GGA | AAA | TTC | ACC | TGT | GAA | TGC | AAC | 1776 |
| Gly | Lys | Cys 580 | Lys | Ser | Gln | Ala | Gly 585 | Gly | Lys | Phe | Thr | Cys 590 | Glu | Cys | Asn | |
| AAA | GGA | TTC | ACT | GGC | ACC | TAC | TGT | CAT | GAG | AAT | ATC | AAT | GAC | TGT | GAG | 1824 |
| Lys | Gly | Phe 595 | Thr | Gly | Thr | Tyr | Cys 600 | His | Glu | Asn | Ile | Asn 605 | Asp | Cys | Glu | |
| AGC | AAC | CCC | TGT | AAA | AAT | GGT | GGC | ACT | TGT | ATT | GAC | GGT | GTA | AAC | TCC | 1872 |
| Ser | Asn | Pro 610 | Cys | Lys | Asn | Gly | Gly 615 | Thr | Cys | Ile | Asp | Gly 620 | Val | Asn | Ser | |
| TAC | AAA | TGT | ATT | TGT | AGT | GAT | GGA | TGG | GAA | GGA | ACA | TAT | TGT | GAA | ACA | 1920 |
| Tyr | Lys | Cys 625 | Ile | Cys | Ser | Asp | Gly 630 | Trp | Glu | Gly | Thr | Tyr 635 | Cys | Glu | Thr 640 | |

-continued

| | | | | | | | | | | | | | | | | |
|---|---|---|---|---|---|---|---|---|---|---|---|---|---|---|---|---|
| AAT | ATT | AAT | GAC | TGC | AGT | AAA | AAC | CCC | TGC | CAC | AAT | GGA | GGA | ACT | TGC | 1968 |
| Asn | Ile | Asn | Asp | Cys | Ser | Lys | Asn | Pro | Cys | His | Asn | Gly | Gly | Thr | Cys | |
| | | | | 645 | | | | | 650 | | | | | 655 | | |
| CGA | GAC | TTG | GTC | AAT | GAC | TTC | TTC | TGT | GAA | TGT | AAA | AAT | GGG | TGG | AAA | 2016 |
| Arg | Asp | Leu | Val | Asn | Asp | Phe | Phe | Cys | Glu | Cys | Lys | Asn | Gly | Trp | Lys | |
| | | | 660 | | | | | 665 | | | | | 670 | | | |
| GGA | AAA | ACT | TGC | CAC | TCT | CGT | GAC | AGC | CAG | TGT | GAT | GAG | GCA | ACA | TGC | 2064 |
| Gly | Lys | Thr | Cys | His | Ser | Arg | Asp | Ser | Gln | Cys | Asp | Glu | Ala | Thr | Cys | |
| | | 675 | | | | | 680 | | | | | 685 | | | | |
| AAT | AAT | GGA | GGA | ACA | TGT | TAT | GAT | GAG | GGG | GAC | ACT | TTC | AAG | TGC | ATG | 2112 |
| Asn | Asn | Gly | Gly | Thr | Cys | Tyr | Asp | Glu | Gly | Asp | Thr | Phe | Lys | Cys | Met | |
| | 690 | | | | | 695 | | | | | 700 | | | | | |
| TGT | CCT | GCA | GGA | TGG | GAA | GGA | GCC | ACT | TGT | AAT | ATA | GCA | AGG | AAC | AGC | 2160 |
| Cys | Pro | Ala | Gly | Trp | Glu | Gly | Ala | Thr | Cys | Asn | Ile | Ala | Arg | Asn | Ser | |
| 705 | | | | | 710 | | | | | 715 | | | | | 720 | |
| AGC | TGC | CTG | CCA | AAC | CCC | TGT | CAC | AAT | GGT | GGT | ACC | TGT | GTA | GTT | AGT | 2208 |
| Ser | Cys | Leu | Pro | Asn | Pro | Cys | His | Asn | Gly | Gly | Thr | Cys | Val | Val | Ser | |
| | | | | 725 | | | | | 730 | | | | | 735 | | |
| GGG | GAT | TCT | TTC | ACT | TGT | GTC | TGC | AAG | GAG | GGC | TGG | GAA | GGA | CCG | ACA | 2256 |
| Gly | Asp | Ser | Phe | Thr | Cys | Val | Cys | Lys | Glu | Gly | Trp | Glu | Gly | Pro | Thr | |
| | | | 740 | | | | | 745 | | | | | 750 | | | |
| TGT | ACT | CAG | AAC | ACA | AAT | GAC | TGC | AGT | CCT | CAT | CCT | TGT | TAC | AAC | AGT | 2304 |
| Cys | Thr | Gln | Asn | Thr | Asn | Asp | Cys | Ser | Pro | His | Pro | Cys | Tyr | Asn | Ser | |
| | | 755 | | | | | 760 | | | | | 765 | | | | |
| GGT | ACT | TGT | GTG | GAT | GGA | GAC | AAC | TGG | TAC | CGC | TGT | GAG | TGC | GCT | CCC | 2352 |
| Gly | Thr | Cys | Val | Asp | Gly | Asp | Asn | Trp | Tyr | Arg | Cys | Glu | Cys | Ala | Pro | |
| | 770 | | | | | 775 | | | | | 780 | | | | | |
| GGC | TTC | GCA | GGT | CCC | GAC | TGT | AGG | ATC | AAC | ATC | AAT | GAA | TGT | CAG | TCT | 2400 |
| Gly | Phe | Ala | Gly | Pro | Asp | Cys | Arg | Ile | Asn | Ile | Asn | Glu | Cys | Gln | Ser | |
| 785 | | | | | 790 | | | | | 795 | | | | | 800 | |
| TCA | CCC | TGT | GCC | TTT | GGG | GCT | ACT | TGT | GTG | GAT | GAA | ATT | AAT | GGG | TAC | 2448 |
| Ser | Pro | Cys | Ala | Phe | Gly | Ala | Thr | Cys | Val | Asp | Glu | Ile | Asn | Gly | Tyr | |
| | | | | 805 | | | | | 810 | | | | | 815 | | |
| CGT | TGC | ATT | TGT | CCA | CCG | GGT | CGC | AGT | GGT | CCA | GGA | TGC | CAG | GAA | GTT | 2496 |
| Arg | Cys | Ile | Cys | Pro | Pro | Gly | Arg | Ser | Gly | Pro | Gly | Cys | Gln | Glu | Val | |
| | | | 820 | | | | | 825 | | | | | 830 | | | |
| ACA | GGG | AGG | CCT | TGC | TTT | ACC | AGT | ATT | CGA | GTA | ATG | CCA | GAC | GGT | GCT | 2544 |
| Thr | Gly | Arg | Pro | Cys | Phe | Thr | Ser | Ile | Arg | Val | Met | Pro | Asp | Gly | Ala | |
| | | 835 | | | | | 840 | | | | | 845 | | | | |
| AAG | TGG | GAT | GAT | GAC | TGT | AAT | ACT | TGT | CAG | TGT | TTG | AAT | GGA | AAA | GTC | 2592 |
| Lys | Trp | Asp | Asp | Asp | Cys | Asn | Thr | Cys | Gln | Cys | Leu | Asn | Gly | Lys | Val | |
| | 850 | | | | | 855 | | | | | 860 | | | | | |
| ACC | TGT | TCT | AAG | GTT | TGG | TGT | GGT | CCT | CGA | CCT | TGT | ATA | ATA | CAT | GCC | 2640 |
| Thr | Cys | Ser | Lys | Val | Trp | Cys | Gly | Pro | Arg | Pro | Cys | Ile | Ile | His | Ala | |
| 865 | | | | | 870 | | | | | 875 | | | | | 880 | |
| AAA | GGT | CAT | AAT | GAA | TGC | CCA | GCT | GGA | CAC | GCT | TGT | GTT | CCT | GTT | AAA | 2688 |
| Lys | Gly | His | Asn | Glu | Cys | Pro | Ala | Gly | His | Ala | Cys | Val | Pro | Val | Lys | |
| | | | | 885 | | | | | 890 | | | | | 895 | | |
| GAA | GAC | CAT | TGT | TTC | ACT | CAT | CCT | TGT | GCT | GCA | GTG | GGT | GAA | TGC | TGG | 2736 |
| Glu | Asp | His | Cys | Phe | Thr | His | Pro | Cys | Ala | Ala | Val | Gly | Glu | Cys | Trp | |
| | | | 900 | | | | | 905 | | | | | 910 | | | |
| CCT | TCT | AAT | CAG | CAG | CCT | GTG | AAG | ACC | AAA | TGC | AAT | TCT | GAT | TCT | TAT | 2784 |
| Pro | Ser | Asn | Gln | Gln | Pro | Val | Lys | Thr | Lys | Cys | Asn | Ser | Asp | Ser | Tyr | |
| | | 915 | | | | | 920 | | | | | 925 | | | | |
| TAC | CAA | GAT | AAT | TGT | GCC | AAC | ATC | ACC | TTC | ACC | TTT | AAT | AAG | GAA | ATG | 2832 |
| Tyr | Gln | Asp | Asn | Cys | Ala | Asn | Ile | Thr | Phe | Thr | Phe | Asn | Lys | Glu | Met | |
| | | 930 | | | | | 935 | | | | | 940 | | | | |
| ATG | GCA | CCA | GGC | CTT | ACC | ACG | GAG | CAC | ATT | TGC | AGT | GAA | TTG | AGG | AAT | 2880 |
| Met | Ala | Pro | Gly | Leu | Thr | Thr | Glu | His | Ile | Cys | Ser | Glu | Leu | Arg | Asn | |
| 945 | | | | | 950 | | | | | 955 | | | | | 960 | |

| | | | | | | | | | | | | | | | | |
|---|---|---|---|---|---|---|---|---|---|---|---|---|---|---|---|---|
| CTG | AAT | ATC | CTG | AAG | AAT | GTT | TCT | GCT | GAA | TAT | TCC | ATC | TAT | ATT | ACC | 2928 |
| Leu | Asn | Ile | Leu | Lys 965 | Asn | Val | Ser | Ala | Glu 970 | Tyr | Ser | Ile | Tyr | Ile 975 | Thr | |
| TGT | GAG | CCT | TCA | CAC | TTG | GCA | AAT | AAT | GAA | ATA | CAT | GTT | GCT | ATT | TCT | 2976 |
| Cys | Glu | Pro | Ser 980 | His | Leu | Ala | Asn | Asn 985 | Glu | Ile | His | Val | Ala 990 | Ile | Ser | |
| GCT | GAA | GAT | ATA | GGA | GAA | GAT | GAA | AAC | CCA | ATC | AAG | GAA | ATC | ACA | GAT | 3024 |
| Ala | Glu | Asp 995 | Ile | Gly | Glu | Asp | Glu | Asn 1000 | Pro | Ile | Lys | Glu 1005 | Ile | Thr | Asp | |
| AAG | ATT | ATT | GAC | CTT | GTC | AGT | AAG | CGT | GAT | GGA | AAC | AAC | ACA | CTA | ATT | 3072 |
| Lys | Ile 1010 | Ile | Asp | Leu | Val | Ser 1015 | Lys | Arg | Asp | Gly | Asn 1020 | Asn | Thr | Leu | Ile | |
| GCT | GCA | GTC | GCA | GAA | GTC | AGA | GTA | CAA | AGG | CGA | CCA | GTT | AAG | AAC | AAA | 3120 |
| Ala | Ala 1025 | Val | Ala | Glu | Val 1030 | Arg | Val | Gln | Arg | Arg 1035 | Pro | Val | Lys | Asn | Lys 1040 | |
| ACA | GAT | TTC | TTG | GTG | CCA | TTA | CTG | AGC | TCA | GTC | TTA | ACA | GTA | GCC | TGG | 3168 |
| Thr | Asp | Phe | Leu | Val 1045 | Pro | Leu | Leu | Ser | Ser 1050 | Val | Leu | Thr | Val | Ala 1055 | Trp | |
| ATC | TGC | TGT | CTG | GTA | ACT | GTT | TTC | TAT | TGG | TGC | ATT | CAA | AAG | CGC | AGA | 3216 |
| Ile | Cys | Cys | Leu 1060 | Val | Thr | Val | Phe | Tyr 1065 | Trp | Cys | Ile | Gln | Lys 1070 | Arg | Arg | |
| AAG | CAG | AGC | AGC | CAT | ACT | CAC | ACA | GCA | TCT | GAT | GAC | AAC | ACC | ACC | AAC | 3264 |
| Lys | Gln | Ser 1075 | Ser | His | Thr | His | Thr 1080 | Ala | Ser | Asp | Asp | Asn 1085 | Thr | Thr | Asn | |
| AAC | GTA | AGG | GAG | CAG | CTG | AAT | CAG | ATT | AAA | AAC | CCC | ATA | GAG | AAA | CAC | 3312 |
| Asn | Val 1090 | Arg | Glu | Gln | Leu | Asn 1095 | Gln | Ile | Lys | Asn | Pro 1100 | Ile | Glu | Lys | His | |
| GGA | GCA | AAT | ACT | GTT | CCA | ATT | AAA | GAC | TAT | GAA | AAC | AAA | AAC | TCT | AAA | 3360 |
| Gly | Ala | Asn | Thr 1105 | Val | Pro | Ile | Lys 1110 | Asp | Tyr | Glu | Asn 1115 | Lys | Asn | Ser | Lys 1120 | |
| ATC | GCC | AAA | ATA | AGG | ACG | CAC | AAT | TCA | GAA | GTG | GAG | GAA | GAT | GAC | ATG | 3408 |
| Ile | Ala | Lys | Ile | Arg 1125 | Thr | His | Asn | Ser | Glu 1130 | Val | Glu | Glu | Asp | Asp 1135 | Met | |
| GAC | AAA | CAC | CAG | CAA | AAG | GCC | CGG | TTT | GCC | AAG | CAG | CCA | GCG | TAC | ACT | 3456 |
| Asp | Lys | His | Gln | Gln 1140 | Lys | Ala | Arg | Phe | Ala 1145 | Lys | Gln | Pro | Ala | Tyr 1150 | Thr | |
| TTG | GTA | GAC | AGA | GAT | GAA | AAG | CCA | CCC | AAC | AGC | ACA | CCC | ACA | AAA | CAC | 3504 |
| Leu | Val | Asp | Arg 1155 | Asp | Glu | Lys | Pro | Pro 1160 | Asn | Ser | Thr | Pro | Thr 1165 | Lys | His | |
| CCA | AAC | TGG | ACA | AAT | AAA | CAG | GAC | AAC | AGA | GAC | TTG | GAA | AGT | GCA | CAA | 3552 |
| Pro | Asn | Trp | Thr 1170 | Asn | Lys | Gln | Asp | Asn 1175 | Arg | Asp | Leu | Glu | Ser 1180 | Ala | Gln | |
| AGT | TTA | AAT | AGA | ATG | GAG | TAC | ATT | GTA | TAG | | | | | | | 3582 |
| Ser | Leu | Asn 1185 | Arg | Met | Glu | Tyr 1190 | Ile | Val | * | | | | | | | |

( 2 ) INFORMATION FOR SEQ ID NO:10:

( i ) SEQUENCE CHARACTERISTICS:
        ( A ) LENGTH: 1193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Gln | Val | Ala | Ser | Ala | Ser | Gly | Gln | Phe | Glu | Leu | Glu | Ile | Leu | Ser | Val |
| 1 | | | | 5 | | | | | 10 | | | | | 15 | |
| Gln | Asn | Val | Asn | Gly | Val | Leu | Gln | Asn | Gly | Asn | Cys | Cys | Asp | Gly | Thr |
| | | | 20 | | | | | 25 | | | | | 30 | | |
| Arg | Asn | Pro | Gly | Asp | Lys | Lys | Cys | Thr | Arg | Asp | Glu | Cys | Asp | Thr | Tyr |
| | | 35 | | | | | 40 | | | | | 45 | | | |

| | | | | | | | | | | | | | | |
|---|---|---|---|---|---|---|---|---|---|---|---|---|---|---|
| Phe | Lys | Val | Cys | Leu | Lys | Glu | Tyr | Gln | Ser | Arg | Val | Thr | Ala | Gly | Gly |
| | 50 | | | | | 55 | | | | | 60 | | | | |
| Pro | Cys | Ser | Phe | Gly | Ser | Lys | Ser | Thr | Pro | Val | Ile | Gly | Gly | Asn | Thr |
| 65 | | | | | 70 | | | | | 75 | | | | | 80 |
| Phe | Asn | Leu | Lys | Tyr | Ser | Arg | Asn | Asn | Glu | Lys | Asn | Arg | Ile | Val | Ile |
| | | | | 85 | | | | | 90 | | | | | 95 | |
| Pro | Phe | Thr | Phe | Ala | Trp | Pro | Arg | Ser | Tyr | Thr | Leu | Leu | Val | Glu | Ala |
| | | | 100 | | | | | 105 | | | | | 110 | | |
| Trp | Asp | Tyr | Asn | Asp | Asn | Ser | Thr | Asn | Pro | Asp | Arg | Ile | Ile | Glu | Lys |
| | | 115 | | | | | 120 | | | | | 125 | | | |
| Ala | Ser | His | Ser | Gly | Met | Ile | Asn | Pro | Ser | Arg | Gln | Trp | Gln | Thr | Leu |
| | 130 | | | | | 135 | | | | | 140 | | | | |
| Lys | His | Asn | Thr | Gly | Ala | Ala | His | Phe | Glu | Tyr | Gln | Ile | Arg | Val | Thr |
| 145 | | | | | 150 | | | | | 155 | | | | | 160 |
| Cys | Ala | Glu | His | Tyr | Tyr | Gly | Phe | Gly | Cys | Asn | Lys | Phe | Cys | Arg | Pro |
| | | | | 165 | | | | | 170 | | | | | 175 | |
| Arg | Asp | Asp | Phe | Phe | Thr | His | His | Thr | Cys | Asp | Gln | Asn | Gly | Asn | Lys |
| | | | 180 | | | | | 185 | | | | | 190 | | |
| Thr | Cys | Leu | Glu | Gly | Trp | Thr | Gly | Pro | Glu | Cys | Asn | Lys | Ala | Ile | Cys |
| | | 195 | | | | | 200 | | | | | 205 | | | |
| Arg | Gln | Gly | Cys | Ser | Pro | Lys | His | Gly | Ser | Cys | Thr | Val | Pro | Gly | Glu |
| | 210 | | | | | 215 | | | | | 220 | | | | |
| Cys | Arg | Cys | Gln | Tyr | Gly | Trp | Gln | Gly | Gln | Tyr | Cys | Asp | Lys | Cys | Ile |
| 225 | | | | | 230 | | | | | 235 | | | | | 240 |
| Pro | His | Pro | Gly | Cys | Val | His | Gly | Thr | Cys | Ile | Glu | Pro | Trp | Gln | Cys |
| | | | | 245 | | | | | 250 | | | | | 255 | |
| Leu | Cys | Glu | Thr | Asn | Trp | Gly | Gly | Gln | Leu | Cys | Asp | Lys | Asp | Leu | Asn |
| | | | 260 | | | | | 265 | | | | | 270 | | |
| Tyr | Cys | Gly | Thr | His | Pro | Pro | Cys | Leu | Asn | Gly | Gly | Thr | Cys | Ser | Asn |
| | | 275 | | | | | 280 | | | | | 285 | | | |
| Thr | Gly | Pro | Asp | Lys | Tyr | Gln | Cys | Ser | Cys | Pro | Glu | Gly | Tyr | Ser | Gly |
| | 290 | | | | | 295 | | | | | 300 | | | | |
| Gln | Asn | Cys | Glu | Ile | Ala | Glu | His | Ala | Cys | Leu | Ser | Asp | Pro | Cys | His |
| 305 | | | | | 310 | | | | | 315 | | | | | 320 |
| Asn | Gly | Gly | Ser | Cys | Leu | Glu | Thr | Ser | Thr | Gly | Phe | Glu | Cys | Val | Cys |
| | | | | 325 | | | | | 330 | | | | | 335 | |
| Ala | Pro | Gly | Trp | Ala | Gly | Pro | Thr | Cys | Thr | Asp | Asn | Ile | Asp | Asp | Cys |
| | | | 340 | | | | | 345 | | | | | 350 | | |
| Ser | Pro | Asn | Pro | Cys | Gly | His | Gly | Gly | Thr | Cys | Gln | Asp | Leu | Val | Asp |
| | | 355 | | | | | 360 | | | | | 365 | | | |
| Gly | Phe | Lys | Cys | Ile | Cys | Pro | Pro | Gln | Trp | Thr | Gly | Lys | Thr | Cys | Gln |
| | 370 | | | | | 375 | | | | | 380 | | | | |
| Leu | Asp | Ala | Asn | Glu | Cys | Glu | Gly | Lys | Pro | Cys | Val | Asn | Ala | Asn | Ser |
| 385 | | | | | 390 | | | | | 395 | | | | | 400 |
| Cys | Arg | Asn | Leu | Ile | Gly | Ser | Tyr | Tyr | Cys | Asp | Cys | Ile | Thr | Gly | Trp |
| | | | | 405 | | | | | 410 | | | | | 415 | |
| Ser | Gly | His | Asn | Cys | Asp | Ile | Asn | Ile | Asn | Asp | Cys | Arg | Gly | Gln | Cys |
| | | | 420 | | | | | 425 | | | | | 430 | | |
| Gln | Asn | Gly | Gly | Ser | Cys | Arg | Asp | Leu | Val | Asn | Gly | Tyr | Arg | Cys | Ile |
| | | 435 | | | | | 440 | | | | | 445 | | | |
| Cys | Ser | Pro | Gly | Tyr | Ala | Gly | Asp | His | Cys | Glu | Lys | Asp | Ile | Asn | Glu |
| | 450 | | | | | 455 | | | | | 460 | | | | |
| Cys | Ala | Ser | Asn | Pro | Cys | Met | Asn | Gly | Gly | His | Cys | Gln | Asp | Glu | Ile |

|     |     |     |     | 465 |     |     |     | 470 |     |     |     | 475 |     |     |     | 480 |
| --- | --- | --- | --- | --- | --- | --- | --- | --- | --- | --- | --- | --- | --- | --- | --- | --- |
| Asn | Gly | Phe | Gln | Cys | Leu | Cys | Pro | Ala | Gly | Phe | Ser | Gly | Asn | Leu | Cys |
|     |     |     |     |     | 485 |     |     |     | 490 |     |     |     | 495 |     |     |
| Gln | Leu | Asp | Ile | Asp | Tyr | Cys | Glu | Pro | Asn | Pro | Cys | Gln | Asn | Gly | Ala |
|     |     |     |     | 500 |     |     |     | 505 |     |     |     | 510 |     |     |     |
| Gln | Cys | Phe | Asn | Leu | Ala | Met | Asp | Tyr | Phe | Cys | Asn | Cys | Pro | Glu | Asp |
|     |     |     |     | 515 |     |     |     | 520 |     |     |     | 525 |     |     |     |
| Tyr | Glu | Gly | Lys | Asn | Cys | Ser | His | Leu | Lys | Asp | His | Cys | Arg | Thr | Thr |
|     | 530 |     |     |     |     | 535 |     |     |     |     | 540 |     |     |     |     |
| Pro | Cys | Glu | Val | Ile | Asp | Ser | Cys | Thr | Val | Ala | Val | Ala | Ser | Asn | Ser |
| 545 |     |     |     |     | 550 |     |     |     |     | 555 |     |     |     |     | 560 |
| Thr | Pro | Glu | Gly | Val | Arg | Tyr | Ile | Ser | Ser | Asn | Val | Cys | Gly | Pro | His |
|     |     |     |     |     | 565 |     |     |     |     | 570 |     |     |     | 575 |     |
| Gly | Lys | Cys | Lys | Ser | Gln | Ala | Gly | Gly | Lys | Phe | Thr | Cys | Glu | Cys | Asn |
|     |     |     | 580 |     |     |     |     | 585 |     |     |     |     | 590 |     |     |
| Lys | Gly | Phe | Thr | Gly | Thr | Tyr | Cys | His | Glu | Asn | Ile | Asn | Asp | Cys | Glu |
|     |     |     | 595 |     |     |     | 600 |     |     |     |     | 605 |     |     |     |
| Ser | Asn | Pro | Cys | Lys | Asn | Gly | Gly | Thr | Cys | Ile | Asp | Gly | Val | Asn | Ser |
|     | 610 |     |     |     |     | 615 |     |     |     |     | 620 |     |     |     |     |
| Tyr | Lys | Cys | Ile | Cys | Ser | Asp | Gly | Trp | Glu | Gly | Thr | Tyr | Cys | Glu | Thr |
| 625 |     |     |     |     | 630 |     |     |     |     | 635 |     |     |     |     | 640 |
| Asn | Ile | Asn | Asp | Cys | Ser | Lys | Asn | Pro | Cys | His | Asn | Gly | Gly | Thr | Cys |
|     |     |     |     | 645 |     |     |     |     | 650 |     |     |     |     | 655 |     |
| Arg | Asp | Leu | Val | Asn | Asp | Phe | Phe | Cys | Glu | Cys | Lys | Asn | Gly | Trp | Lys |
|     |     |     | 660 |     |     |     |     | 665 |     |     |     |     | 670 |     |     |
| Gly | Lys | Thr | Cys | His | Ser | Arg | Asp | Ser | Gln | Cys | Asp | Glu | Ala | Thr | Cys |
|     |     | 675 |     |     |     |     | 680 |     |     |     |     | 685 |     |     |     |
| Asn | Asn | Gly | Gly | Thr | Cys | Tyr | Asp | Glu | Gly | Asp | Thr | Phe | Lys | Cys | Met |
|     | 690 |     |     |     |     | 695 |     |     |     |     | 700 |     |     |     |     |
| Cys | Pro | Ala | Gly | Trp | Glu | Gly | Ala | Thr | Cys | Asn | Ile | Ala | Arg | Asn | Ser |
| 705 |     |     |     |     | 710 |     |     |     |     | 715 |     |     |     |     | 720 |
| Ser | Cys | Leu | Pro | Asn | Pro | Cys | His | Asn | Gly | Gly | Thr | Cys | Val | Val | Ser |
|     |     |     |     | 725 |     |     |     |     | 730 |     |     |     |     | 735 |     |
| Gly | Asp | Ser | Phe | Thr | Cys | Val | Cys | Lys | Glu | Gly | Trp | Glu | Gly | Pro | Thr |
|     |     |     | 740 |     |     |     |     | 745 |     |     |     |     | 750 |     |     |
| Cys | Thr | Gln | Asn | Thr | Asn | Asp | Cys | Ser | Pro | His | Pro | Cys | Tyr | Asn | Ser |
|     |     | 755 |     |     |     |     | 760 |     |     |     |     | 765 |     |     |     |
| Gly | Thr | Cys | Val | Asp | Gly | Asp | Asn | Trp | Tyr | Arg | Cys | Glu | Cys | Ala | Pro |
|     | 770 |     |     |     |     | 775 |     |     |     |     | 780 |     |     |     |     |
| Gly | Phe | Ala | Gly | Pro | Asp | Cys | Arg | Ile | Asn | Ile | Asn | Glu | Cys | Gln | Ser |
| 785 |     |     |     |     | 790 |     |     |     |     | 795 |     |     |     |     | 800 |
| Ser | Pro | Cys | Ala | Phe | Gly | Ala | Thr | Cys | Val | Asp | Glu | Ile | Asn | Gly | Tyr |
|     |     |     |     | 805 |     |     |     |     | 810 |     |     |     |     | 815 |     |
| Arg | Cys | Ile | Cys | Pro | Pro | Gly | Arg | Ser | Gly | Pro | Gly | Cys | Gln | Glu | Val |
|     |     |     | 820 |     |     |     |     | 825 |     |     |     |     | 830 |     |     |
| Thr | Gly | Arg | Pro | Cys | Phe | Thr | Ser | Ile | Arg | Val | Met | Pro | Asp | Gly | Ala |
|     |     | 835 |     |     |     |     | 840 |     |     |     |     | 845 |     |     |     |
| Lys | Trp | Asp | Asp | Asp | Cys | Asn | Thr | Cys | Gln | Cys | Leu | Asn | Gly | Lys | Val |
| 850 |     |     |     |     | 855 |     |     |     |     | 860 |     |     |     |     |     |
| Thr | Cys | Ser | Lys | Val | Trp | Cys | Gly | Pro | Arg | Pro | Cys | Ile | Ile | His | Ala |
| 865 |     |     |     |     | 870 |     |     |     |     | 875 |     |     |     |     | 880 |
| Lys | Gly | His | Asn | Glu | Cys | Pro | Ala | Gly | His | Ala | Cys | Val | Pro | Val | Lys |
|     |     |     |     | 885 |     |     |     |     | 890 |     |     |     |     | 895 |     |

| | | | | | | | | | | | | | |
|---|---|---|---|---|---|---|---|---|---|---|---|---|---|
| Glu | Asp | His | Cys<br>900 | Phe | Thr | His | Pro<br>905 | Cys | Ala | Ala | Val | Gly<br>910 | Glu | Cys | Trp |
| Pro | Ser | Asn<br>915 | Gln | Gln | Pro | Val | Lys<br>920 | Thr | Lys | Cys | Asn<br>925 | Ser | Asp | Ser | Tyr |
| Tyr | Gln<br>930 | Asp | Asn | Cys | Ala | Asn<br>935 | Ile | Thr | Phe | Thr | Phe<br>940 | Asn | Lys | Glu | Met |
| Met<br>945 | Ala | Pro | Gly | Leu | Thr<br>950 | Thr | Glu | His | Ile | Cys<br>955 | Ser | Glu | Leu | Arg | Asn<br>960 |
| Leu | Asn | Ile | Leu | Lys<br>965 | Asn | Val | Ser | Ala | Glu<br>970 | Tyr | Ser | Ile | Tyr | Ile<br>975 | Thr |
| Cys | Glu | Pro | Ser<br>980 | His | Leu | Ala | Asn | Asn<br>985 | Glu | Ile | His | Val | Ala<br>990 | Ile | Ser |
| Ala | Glu | Asp | Ile<br>995 | Gly | Glu | Asp | Glu<br>1000 | Asn | Pro | Ile | Lys | Glu<br>1005 | Ile | Thr | Asp |
| Lys | Ile<br>1010 | Ile | Asp | Leu | Val | Ser<br>1015 | Lys | Arg | Asp | Gly | Asn<br>1020 | Asn | Thr | Leu | Ile |
| Ala<br>1025 | Ala | Val | Ala | Glu | Val<br>1030 | Arg | Val | Gln | Arg | Arg<br>1035 | Pro | Val | Lys | Asn | Lys<br>1040 |
| Thr | Asp | Phe | Leu | Val<br>1045 | Pro | Leu | Leu | Ser | Ser<br>1050 | Val | Leu | Thr | Val | Ala<br>1055 | Trp |
| Ile | Cys | Cys | Leu | Val<br>1060 | Thr | Val | Phe | Tyr | Trp<br>1065 | Cys | Ile | Gln | Lys<br>1070 | Arg | Arg |
| Lys | Gln | Ser | Ser<br>1075 | His | Thr | His | Thr<br>1080 | Ala | Ser | Asp | Asp | Asn<br>1085 | Thr | Thr | Asn |
| Asn | Val<br>1090 | Arg | Glu | Gln | Leu | Asn<br>1095 | Gln | Ile | Lys | Asn | Pro<br>1100 | Ile | Glu | Lys | His |
| Gly<br>1105 | Ala | Asn | Thr | Val | Pro<br>1110 | Ile | Lys | Asp | Tyr | Glu<br>1115 | Asn | Lys | Asn | Ser | Lys<br>1120 |
| Ile | Ala | Lys | Ile | Arg<br>1125 | Thr | His | Asn | Ser | Glu<br>1130 | Val | Glu | Glu | Asp | Asp<br>1135 | Met |
| Asp | Lys | His | Gln<br>1140 | Gln | Lys | Ala | Arg | Phe<br>1145 | Ala | Lys | Gln | Pro | Ala<br>1150 | Tyr | Thr |
| Leu | Val | Asp | Arg<br>1155 | Asp | Glu | Lys | Pro<br>1160 | Pro | Asn | Ser | Thr | Pro<br>1165 | Thr | Lys | His |
| Pro | Asn<br>1170 | Trp | Thr | Asn | Lys | Gln<br>1175 | Asp | Asn | Arg | Asp | Leu<br>1180 | Glu | Ser | Ala | Gln |
| Ser<br>1185 | Leu | Asn | Arg | Met | Glu<br>1190 | Tyr | Ile | Val |

( 2 ) INFORMATION FOR SEQ ID NO:11:

( i ) SEQUENCE CHARACTERISTICS:
        ( A ) LENGTH: 22 amino acids
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 3
        ( D ) OTHER INFORMATION: /mod_base=i ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base (B) LOCATION: 18
(D) OTHER INFORMATION: /mod_base=i (xi) SEQUENCE DESCRIPTION: SEQ ID NO:11:

CGNYTTTGCY TNAARSANTA YCA                23

(2) INFORMATION FOR SEQ ID NO:12:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 6
(D) OTHER INFORMATION: /label=A
/ note= "X=histidine or glutamic acid"

(xi) SEQUENCE DESCRIPTION: SEQ ID NO:12:

Arg Leu Cys Cys Lys Xaa Tyr Gln
1               5

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: modified_base
(B) LOCATION: 3
(D) OTHER INFORMATION: /mod_base=i (ix) FEATURE:
(A) NAME/KEY: modified_base
(B) LOCATION: 9
(D) OTHER INFORMATION: /mod_base=i (ix) FEATURE:
(A) NAME/KEY: modified_base
(B) LOCATION: 12
(D) OTHER INFORMATION: /mod_base=i (ix) FEATURE:
(A) NAME/KEY: modified_base
(B) LOCATION: 15
(D) OTHER INFORMATION: /mod_base=i (xi) SEQUENCE DESCRIPTION: SEQ ID NO:13:

TCNATGCANG TNCCNCCRTT                20

(2) INFORMATION FOR SEQ ID NO:14:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:14:

Asn Gly Gly Thr Cys Ile Asp
1               5

( 2 ) INFORMATION FOR SEQ ID NO:15:

( i ) SEQUENCE CHARACTERISTICS:
        ( A ) LENGTH: 163 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 2..163

( x i ) SEQUENCE DESCRIPTION: SEQ ID NO:15:

```
G TCC CGC GTC ACT GCC GGG GGA CCC TGC AGC TTC GGC TCA GGG TCT        46
  Ser Arg Val Thr Ala Gly Gly Pro Cys Ser Phe Gly Ser Gly Ser
  1               5                   10                  15

ACG CCT GTC ATC GGG GGT AAC ACC TTC AAT CTC AAG GCC AGC CGT GGC      94
Thr Pro Val Ile Gly Gly Asn Thr Phe Asn Leu Lys Ala Ser Arg Gly
                20                  25                  30

AAC GAC CGT AAT CGC ATC GTA CTG CCT TTC AGT TTC ACC TGG CCG AGG      142
Asn Asp Arg Asn Arg Ile Val Leu Pro Phe Ser Phe Thr Trp Pro Arg
                35                  40                  45

TCC TAC ACT TTG CTG GTG GAG                                          163
Ser Tyr Thr Leu Leu Val Glu
                50
```

( 2 ) INFORMATION FOR SEQ ID NO:16:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ser Arg Val Thr Ala Gly Gly Pro Cys Ser Phe Gly Ser Gly Ser Thr
1               5                   10                  15

Pro Val Ile Gly Gly Asn Thr Phe Asn Leu Lys Ala Ser Arg Gly Asn
                20                  25                  30

Asp Arg Asn Arg Ile Val Leu Pro Phe Ser Phe Thr Trp Pro Arg Ser
                35                  40                  45

Tyr Thr Leu Leu Val Glu
                50
```

( 2 ) INFORMATION FOR SEQ ID NO:17:

( i ) SEQUENCE CHARACTERISTICS:
        ( A ) LENGTH: 135 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 1..135

( x i ) SEQUENCE DESCRIPTION: SEQ ID NO:17:

```
TCT TCT AAC GTC TGT GGT CCC CAT GGC AAG TGC AAG AGC CAG TCG GCA      48
Ser Ser Asn Val Cys Gly Pro His Gly Lys Cys Lys Ser Gln Ser Ala
1               5                   10                  15

GGC AAA TTC ACC TGT GAC TGT AAC AAA GGC TTC ACC GGC ACC TAC TGC      96
Gly Lys Phe Thr Cys Asp Cys Asn Lys Gly Phe Thr Gly Thr Tyr Cys
```

```
                          20                       25                       30
CAT  GAA  AAT  ATC  AAC  GAC  TGC  GAG  AGC  AAC  CCC  TGT  AAA                    135
His  Glu  Asn  Ile  Asn  Asp  Cys  Glu  Ser  Asn  Pro  Cys  Lys
               35                       40                       45
```

(2) INFORMATION FOR SEQ ID NO:18:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:18:

```
Ser  Ser  Asn  Val  Cys  Gly  Pro  His  Gly  Lys  Cys  Lys  Ser  Gln  Ser  Ala
 1                   5                        10                       15

Gly  Lys  Phe  Thr  Cys  Asp  Cys  Asn  Lys  Gly  Phe  Thr  Gly  Thr  Tyr  Cys
               20                       25                       30

His  Glu  Asn  Ile  Asn  Asp  Cys  Glu  Ser  Asn  Pro  Cys  Lys
               35                       40                  45
```

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 3
        (D) OTHER INFORMATION: /mod_base=i (ix) FEATURE:
        (A) NAME/KEY: modified_base
        (B) LOCATION: 6
        (D) OTHER INFORMATION: /mod_base=i (ix) FEATURE:
        (A) NAME/KEY: modified_base
        (B) LOCATION: 12
        (D) OTHER INFORMATION: /mod_base=i (ix) FEATURE:
        (A) NAME/KEY: modified_base
        (B) LOCATION: 18
        (D) OTHER INFORMATION: /mod_base=i (xi) SEQUENCE DESCRIPTION: SEQ ID NO:19:

```
CGN YTNTGC Y TNAARSAN-
TA  Y CA                                                                            23
```

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label=A
            / note= "X=glutamic acid or histidine"

(xi) SEQUENCE DESCRIPTION: SEQ ID NO:20:

```
Arg Leu Cys Leu Lys Xaa Tyr Gln
1               5
```